(12) United States Patent
Yu et al.

(10) Patent No.: US 11,798,653 B2
(45) Date of Patent: Oct. 24, 2023

(54) METHODS FOR DETERMINING TREATMENT FOR CANCER PATIENTS

(71) Applicant: MEDIMMUNE, LLC, Gaithersburg, MD (US)

(72) Inventors: Li Yu, Gaithersburg, MD (US); Harry Yang, Gaithersburg, MD (US); Mohammed Dar, Gaithersburg, MD (US); Lorin Roskos, Gaithersburg, MD (US); Jean-Charles Soria, Gaithersburg, MD (US); Charles Ferte, Gaithersburg, MD (US); Wei Zhao, Gaithersburg, MD (US); Aline Gendrin Brokmann, Cambridge (GB); Jolyon Faria, Cambridge (GB); Pralay Mukhopadhyay, Wilmington, DE (US); Ikbel Achour, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 846 days.

(21) Appl. No.: 16/657,375

(22) Filed: Oct. 18, 2019

(65) Prior Publication Data

US 2020/0126636 A1    Apr. 23, 2020

Related U.S. Application Data

(60) Provisional application No. 62/854,566, filed on May 30, 2019, provisional application No. 62/747,420, filed on Oct. 18, 2018.

(51) Int. Cl.
*G16B 40/20* (2019.01)
*G16B 5/20* (2019.01)
(Continued)

(52) U.S. Cl.
CPC ............... *G16B 40/20* (2019.02); *G06N 5/01* (2023.01); *G06N 20/20* (2019.01); *G16B 5/20* (2019.02);
(Continued)

(58) Field of Classification Search
CPC .. G16H 10/00–80/00; G06Q 10/00–2250/905; G06N 3/00–99/007
See application file for complete search history.

(56) References Cited

U.S. PATENT DOCUMENTS

| 6,682,736 B1 | 1/2004 | Hanson et al. |
| 7,109,003 B2 | 9/2006 | Hanson et al. |

(Continued)

FOREIGN PATENT DOCUMENTS

| CA | 2843369 A1 * | 2/2013 | ........... C12Q 1/6881 |
| CN | 106202968 A * | 12/2016 | ............. G16H 50/20 |

(Continued)

OTHER PUBLICATIONS

Morrow et al., "A simple risk index for rapid initial triage of patients with ST-elevation myocardial infarction: an InTIME II substudy," The Lancet 2001, 358: 1571-75. (Year: 2001).*

(Continued)

*Primary Examiner* — Jonathon A. Szumny
(74) *Attorney, Agent, or Firm* — McDonnell Boehnen Hulbert & Berghoff LLP

(57) ABSTRACT

Methods for determining treatments for cancer patients are disclosed.

11 Claims, 83 Drawing Sheets

(51) Int. Cl.
*G06N 20/20* (2019.01)
*G16H 50/20* (2018.01)
*G16H 50/50* (2018.01)
*G16H 50/30* (2018.01)
*G06N 5/01* (2023.01)
*G16H 20/40* (2018.01)
*A61K 38/00* (2006.01)
*C07K 16/28* (2006.01)
*G01N 33/574* (2006.01)

(52) U.S. Cl.
CPC ............ *G16H 50/20* (2018.01); *G16H 50/30* (2018.01); *G16H 50/50* (2018.01); *A61K 38/00* (2013.01); *C07K 16/2818* (2013.01); *G01N 33/57484* (2013.01); *G16H 20/40* (2018.01)

(56) References Cited

U.S. PATENT DOCUMENTS

| | | | |
|---|---|---|---|
| 7,132,281 B2 | 11/2006 | Hanson et al. | |
| 7,411,057 B2 | 8/2008 | Hanson et al. | |
| 7,807,797 B2 | 10/2010 | Hanson et al. | |
| 7,824,679 B2 | 11/2010 | Hanson et al. | |
| 8,143,379 B2 | 3/2012 | Hanson et al. | |
| 8,491,895 B2 | 7/2013 | Hanson et al. | |
| 8,779,108 B2 | 7/2014 | Queva et al. | |
| 9,493,565 B2 | 11/2016 | Queva et al. | |
| 9,938,576 B1 * | 4/2018 | Sadee | C12Q 1/6883 |
| 10,289,464 B1 * | 5/2019 | DeLozier | G06F 11/0778 |
| 10,400,039 B2 | 9/2019 | Queva et al. | |
| 10,810,512 B1 * | 10/2020 | Wubbels | G16H 50/20 |
| 2004/0110221 A1 * | 6/2004 | Twine | C12Q 1/6886 435/7.23 |
| 2006/0024757 A1 * | 2/2006 | Hussa | G01N 33/6887 800/21 |
| 2006/0188878 A1 * | 8/2006 | Dressman | A61P 35/00 435/6.12 |
| 2006/0195269 A1 | 8/2006 | Yeatman et al. | |
| 2010/0284915 A1 | 11/2010 | Dai et al. | |
| 2014/0304197 A1 * | 10/2014 | Jaiswal | G06F 21/6209 706/12 |
| 2016/0102358 A1 * | 4/2016 | Xu | C12Q 1/6886 506/9 |
| 2016/0153878 A1 * | 6/2016 | Candon | G01N 33/558 422/520 |
| 2017/0140297 A1 * | 5/2017 | Karumanchi | G06Q 10/063 |
| 2017/0248603 A1 | 8/2017 | Hodi et al. | |
| 2017/0281071 A1 * | 10/2017 | Ford | A61B 5/4088 |
| 2017/0298443 A1 * | 10/2017 | Dai | G01N 33/57484 |
| 2018/0011106 A1 * | 1/2018 | Staudt | G16B 25/10 |
| 2018/0357360 A1 * | 12/2018 | Braun | C12Q 1/6876 |
| 2019/0080253 A1 * | 3/2019 | Lokare | G06N 3/08 |
| 2020/0090796 A1 * | 3/2020 | Krishnan | G06N 5/01 |
| 2020/0210767 A1 * | 7/2020 | Do | G06V 10/454 |
| 2021/0200616 A1 * | 7/2021 | Xu | G06F 3/0617 |
| 2021/0366618 A1 * | 11/2021 | Schoedl | G16H 50/30 |

FOREIGN PATENT DOCUMENTS

| | | | | |
|---|---|---|---|---|
| CN | 107480686 A * | 12/2017 | ............ | G06K 9/6259 |
| WO | WO-2007041820 A2 * | 4/2007 | ......... | G01N 30/8675 |
| WO | WO-2011128820 A2 * | 10/2011 | ............ | C12Q 1/6886 |
| WO | WO-2013119869 A1 * | 8/2013 | ............ | C12Q 1/6883 |
| WO | WO-2014022826 A2 * | 2/2014 | ............ | C12Q 1/6886 |
| WO | 2015077414 A1 | 5/2015 | | |
| WO | WO-2016094330 A2 * | 6/2016 | ....... | G01N 33/57423 |
| WO | WO-2017132749 A1 * | 8/2017 | ............ | C12Q 1/6841 |
| WO | 2017210502 A1 | 12/2017 | | |
| WO | WO 2018/129301 | 7/2018 | | |
| WO | WO-2018124854 A1 * | 7/2018 | ............ | G06F 17/18 |
| WO | WO-2020023671 A1 * | 1/2020 | ............ | G06N 20/00 |

OTHER PUBLICATIONS

Bertsimas et al., "Applied Informatics Decision Support Tool for Mortality Predictions in Patients With Cancer," Published online on ascopubs.org/journal/cci on Jun. 7, 2018. (Year: 2018).*

Quirina et al., "Can Machine-learning Techniq ues Be Used for 5-year Survival Prediction of Patients With Chondrosarcoma," Clin Orthop Relat Res (2018) 476:2040-2048. (Year: 2018).*

Motivala et al., "Changes in Myocardial Infarction Guideline Adherence as a Function of Patient Risk," Journal of the American College of Cardiology vol. 58, No. 17, 2011. (Year: 2011).*

Azar et al., "Decision tree classifiers for automated medical diagnosis," Neural Comput & Applic (2013) 23:2387-2403. (Year: 2013).*

Paul et al., "Deep Feature Transfer Learning in Combination with Traditional Features Predicts Survival Among Patients with Lung Adenocarcinoma," tomography.org | vol. 2 No. 4 | Dec. 2016. (Year: 2016).*

Elfiky et al., "Development and Application of a Machine Learning Approach to Assess Short-term Mortality Risk Among Patients With Cancer Starting Chemotherapy," JAMA Network Open. 2018;1(3):e180926 (Year: 2018).*

Rajan et al., "Effect of primary prophylactic G-CSF use on systemic therapy administration for elderly breast cancer patients," Breast Cancer Res Treat (2011) 130:255-266. (Year: 2011).*

Martin-Perez et al., "Impact of hyperkalaemia definition on incidence assessment: implications for epidemiological research based on a large cohort study in newly diagnosed heart," BMC Family Practice (2016) 17:51. (Year: 2016).*

Bertsimas et al., "Optimal classification trees," Mach Learn (2017) 106:1039-1082. (Year: 2017).*

Das et al., "Predicting Lung Radiotherapy-Induced Pneumonitis Using a Model Combining Parametric Lyman Probit With Nonparametric Decision Trees," Int. J. Radiation Oncology Biol. Phys., vol. 68, No. 4, pp. 1212-1221, 2007 (Year: 2007).*

Ploquin et al., "Prediction of early death among patients enrolled in phase I trials: development and validation of a new model based on platelet count and albumin," British Journal of Cancer (2012) 107, 1025-103. (Year: 2012).*

Huiling Zhang, "Predictors of In-Hospital Mortality Among Acute Myocardial Infarction Patients in a Large Health Care System," Thesis presented to the School of Public Health University of North Texas Jul. 2001. (Year: 2001).*

Gogi et al., "Prognosis of Liver Disease: Using Machine Learning Algorithms," International Conference on Recent Innovations in Electrical, Electronics & Communication Engineering—(ICRIEECE). (Year: 2018).*

Lee et al., "Risk of Myocardial Infarction in Anticoagulated Patients With Atrial Fibrillation," Journal of t h e American College of Cardiology vol. 72 , No. 1, 2018. (Year: 2018).*

Mantarro et al., "Risk of severe cardiotoxicity following treatment with trastuzumab: a meta-analysis of randomized and cohort studies of 29,000 women with breast cancer," Intern Emerg Med (2016) 11:123-140 (Year: 2016).*

Weijer et al, "The duty to exclude: excluding people at undue risk from research," Clin. Invest. Med., vol. 17:2, pp. 115-122. (Year: 1994).*

Neda et al., "The evaluation and management of drug effects on cardiac conduction (PR and QRS Intervals) in clinical development," American Heart Journal Apr. 2013, pp. 489-500. (Year: 2013).*

Hijazi et al., "The novel biomarker-based ABC (age, biomarkers, clinical history)—bleeding risk score for patients with atrial fibrillation: a derivation and validation study," Lancet 2016; 387: 2302-11 Published Online Apr. 4, 2016 (Year: 2016).*

Harshdeep Singh, "Understanding Gradient Boosting Machines," https://towardsdatascience.com/understanding-gradient-boosting-machines-9be756fe76ab, 2016. (Year: 2016).*

Tenzer et al., "Prospective study for the development of a machine learning algorithm as a diagnostic tool foreosinophilic esophagitis,"

(56) References Cited

OTHER PUBLICATIONS

Journal of Pediatric Gastroenterology and Nutrition, suppl. Supplement 2 63: S9-S10. Lippincott Williams and Wilkins. (Oct. 2016) (Year: 2016).*
Bertsimas et al., "Applied Informatics Decision Support Tool for Mortality Predictions in Patients With Cancer," Published online on ascopubs.org/journal/cci on Jun. 7, 2018 (including Data Supplement). (Year: 2018).*
Arkenau, H-T., et al., "Prospective validation of a prognostic score to improve patient selection for oncology phase I trials", J Clin Oncol. 27(16):2692-6, (Jun. 2009), Epub Mar. 2009.
Bellmunt, J., et al., "Pembrolizumab as Second-Line Therapy for Advanced Urothelial Carcinoma", N Engl J Med., 376 (11):1015-26, (Mar. 2017), Epub Feb. 2017.
Bigot, F., et al., "Prospective validation of a prognostic score for patients in immunotherapy phase I trials: The Gustave Roussy Immune Score (GRIm-Score)", Eur J Cancer. 84:212-8, (Oct. 2017), Epub Aug. 2017.
Borghaei, H., et al. "Nivolumab versus Docetaxel in Advanced Nonsquamous Non-Small-Cell Lung Cancer", N Engl J Med., 373(17):1627-39, (Nov. 2015), Epub Oct. 2015.
Bowen, RC, et al., "Neutrophil-to-lymphocyte ratio as prognostic indicator in gastrointestinal cancers: a systematic review and meta-analysis", Oncotarget., 8(19):32171-89, (May 2017), Epub Mar. 2017.
Caliskan, A., et al., "Semantics derived automatically from language corpora contain human-like biases", Science, 356 (6334):183-186, Apr. 2017.
Champiat, S., et al., "Hyperprogressive disease: recognizing a novel pattern to improve patient management", Nat Rev Clin Oncol., 15(12):748-62, Dec. 2018.
Chen, T., et al., "XGBoost: A Scalable Tree Boosting System. Proceedings of the 22nd ACM SIGKDD International Conference on Knowledge Discovery and Data Mining (KDD)",785-794, Aug. 2016.
Chen T., et al., "R Package 'xgboost'", https://cran.r-project.org/web/packages/xgboost/xgboost.pdf, Mar. 2019.
Ding, Y., et al., "Prognostic value of neutrophil-to-lymphocyte ratio in melanoma: Evidence from a PRISMA-compliant meta-analysis", Medicine (Baltimore), 97(30):e11446, Epub Jul. 2018.
Ferris, RL., et al., "Nivolumab for Recurrent Squamous-Cell Carcinoma of the Head and Neck", N Engl J Med., 375 (19):1856-67, (Nov. 2016) Epub Oct. 2016.
Freis P, et al., "Prognostic factors in neuroendocrine carcinoma: biological markers are more useful than histomorphological markers", Sci Rep., 7:40609, Jan. 2017.
Friedman, J., et al., "Additive logistic regression: a statistical view of boosting (with discussion and a rejoinder by the authors)", The annals of statistics, 28(2), 337-407, Apr. 2000.
Friedman, J., "Greedy function approximation: a gradient boosting machine", Annals of Statistics, pp. 2001; 1189-1232, Oct. 2001.
Fukui, T., et al., "Activity of Nivolumab and Utility of Neutrophil-to-Lymphocyte Ratio as a Predictive Biomarker for Advanced Non-Small-Cell Lung Cancer: A Prospective Observational Study", Clin Lung Cancer., 20(3):208-14 e2, Epub May 2018.
Garon, EB, et al., "Five-Year Overall Survival for Patients With Advanced NonSmall-Cell Lung Cancer Treated With Pembrolizumab: Results From the Phase I KEYNOTE-001 Study", J Clin Oncol., JCO1900934, Epub Jun. 2019.
Gupta D, et al., "Pretreatment serum albumin as a predictor of cancer survival: a systematic review of the epidemiological literature", Nutr J, 9:69, Apr. 2010.
Kazandjian, DG., et al., "Exploration of baseline derived neutrophil to lymphocyte ratio (dNLR) and lactate dehydrogenase (LDH) in patients (pts) with metastatic non-small cell lung cancer (mNSCLC) treated with immune checkpoint inhibitors (ICI) or cytotoxic chemotherapy (CCT)", 36(15_suppl):3035, Epub Jun. 2018.
Khunger M., et al., "Post-treatment changes in hematological parameters predict response to nivolumab monotherapy in non-small cell lung cancer patients", PLoS One, 13(10):e0197743, Oct. 2018.
Luo M., et al., "High pretreatment serum gamma-glutamyl transpeptidase predicts an inferior outcome in nasopharyngeal carcinoma", Oncotarget, 8(40):67651-6, (Sep. 2017), Epub Jun. 2017.
Mezquita L., et al., "Association of the Lung Immune Prognostic Index With Immune Checkpoint Inhibitor Outcomes in Patients With Advanced Non-Small Cell Lung Cancer", JAMA Oncol., 4(3):351-357, (Jan. 2018) Epub Mar. 2018.
Minami S., et al., "Gustave Roussy Immune Score and Royal Marsden Hospital Prognostic Score Are Biomarkers of Immune-Checkpoint Inhibitor for Non-Small Cell Lung Cancer", World J Oncol., 10(2):90-100, Apr. 2019.
Mok TSK, et al., "Pembrolizumab versus chemotherapy for previously untreated, PD-L1-expressing, locally advanced or metastatic non-small-cell lung cancer (KEYNOTE-042): a randomised, open-label, controlled, phase 3 trial", Lancet. 393(10183):1819-30, (May 2019), Epub Apr. 2019.
Mulkey F, et al., "Analysis of early mortality in randomized clinical trials evaluating anti-PD-1/PD-L1 antibodies: A systematic analysis by the United States Food and Drug Administration (FDA)", 37(15_suppl):2516, May 2019.
Petrelli F., et al., "Prognostic role of lactate dehydrogenase in solid tumors: a systematic review and meta-analysis of 76 studies", Acta Oncol., 54(7):961-70, (Jul. 2015), May 2015.
Powles T., et al., "Atezolizumab versus chemotherapy in patients with platinum-treated locally advanced or metastatic urothelial carcinoma (IMvigor211): a multicentre, open-label, phase 3 randomised controlled trial", Lancet., 391 (10122):748-57, (Feb. 2018), Dec. 2018.
Rizvi N., et al., "Durvalumab with or without tremelimumab vs platinum-based chemotherapy as first-line treatment for metastatic non-small cell lung cancer: MYSTIC", ESMO Immuno-Oncology Congress, Geneva, Switzerland. Abstract LBA6 [oral presentation], Dec. 2018.
Sacdalan DB, et al., "Prognostic utility of baseline neutrophil-to-lymphocyte ratio in patients receiving immune checkpoint inhibitors: a review and meta-analysis", Onco Targets Ther., 11:955-65, Feb. 2018.
Shitara K, et al., "Pembrolizumab versus paclitaxel for previously treated, advanced gastric or gastro-oesophageal junction cancer (KEYNOTE-061): a randomised, open-label, controlled, phase 3 trial", Lancet, 392(10142):123-33, (Jul. 2018), Epub Jun. 2018.
Socinski MA, et al., "Atezolizumab for First-Line Treatment of Metastatic Nonsquamous NSCLC", N Engl J Med., 378 (24):2288-301, Jun. 2018.
Tham T., et al., "Neutrophil-to-lymphocyte ratio as a prognostic indicator in head and neck cancer: A systematic review and meta-analysis", Head Neck, 40(11):2546-57, (Nov. 2018), Epub May 2018.
Varga A, et al.,"Applicability of the Lung Immune Prognostic Index (LIPI) in patients with metastatic solid tumors when treated with Immune Checkpoint Inhibitors (ICI) in early clinical trials", Ann Oncol., 30(Supplement 1), Feb. 2019.
Wheler J., et al., "Survival of 1,181 patients in a phase I clinic: the MD Anderson Clinical Center for targeted therapy experience", Clin Cancer Res., 18(10):2922-9, (May 2012), Mar. 2012.
Winquist E., et al., "Early mortality with immune checkpoint inhibitors (IOs) in solid tumors: An inconvenient truth?", J Clin Oncol., 36 (suppl; abstr 12121), (Jun. 2018), Epub May 2018.
Yu Y., et al., "Pretreatment neutrophil to lymphocyte ratio in determining the prognosis of head and neck cancer: a meta-analysis", BMC Cancer, 18(1):383, Apr. 2018.
The International Search Report of the International Searching Authority for International Application No. PCT/US2019/056974; dated Feb. 14, 2020 (4 pages).
Wikipedia—"Gradient Boosting" Sep. 19, 2018, pp. 1-8.
Abdel-Rahman (Expert Opinion on Drug Safety vol. 14 pp. 1507-1518 published 2015) (Year: 2015).
Botticelli (Oncotarget vol. 8 pp. 8890-8899 published 2017). (Year: 2017).
Hopkins (British Journal of Cancer vol. 117 pp. 913-920 published 2017) (Year: 2017).
Office Action, U.S. Appl. No. 16/657,359, dated Jan. 30, 2023.

(56) References Cited

OTHER PUBLICATIONS

Powles (Journal of Clinical Oncology vol. 35 issue 15, published 2017; abstract only) (Year: 2017).
Ziemer (Journal of Hepatology vol. 66 pp. 657-665 published 2017) . (Year: 2017).

* cited by examiner

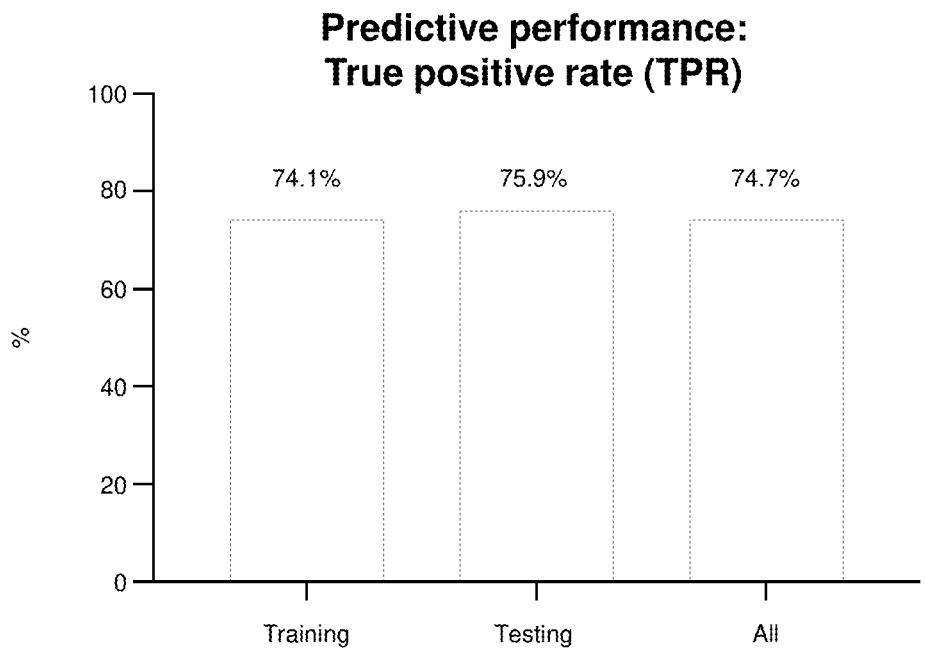

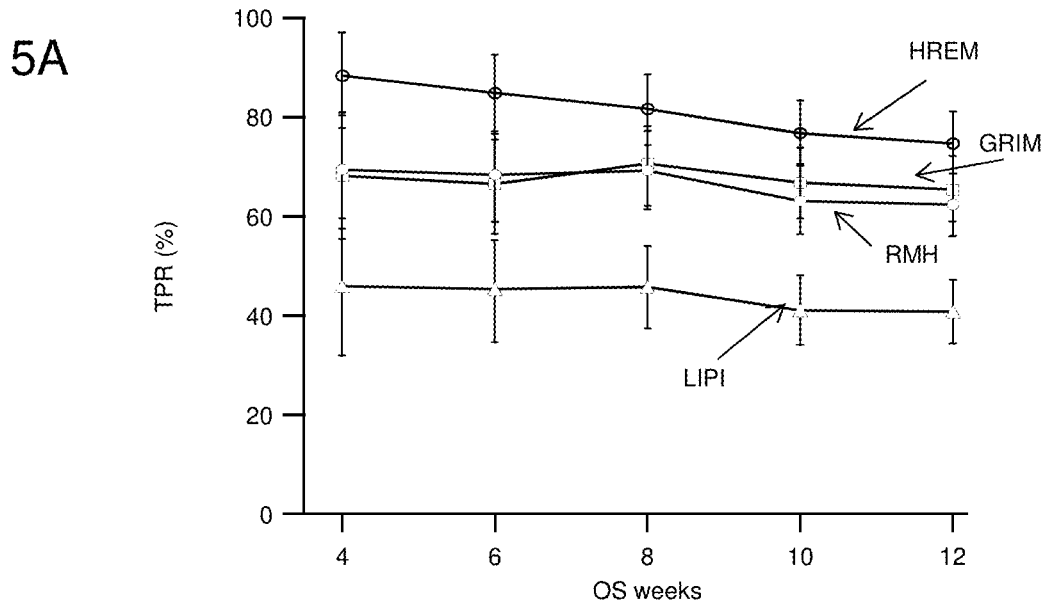
5A
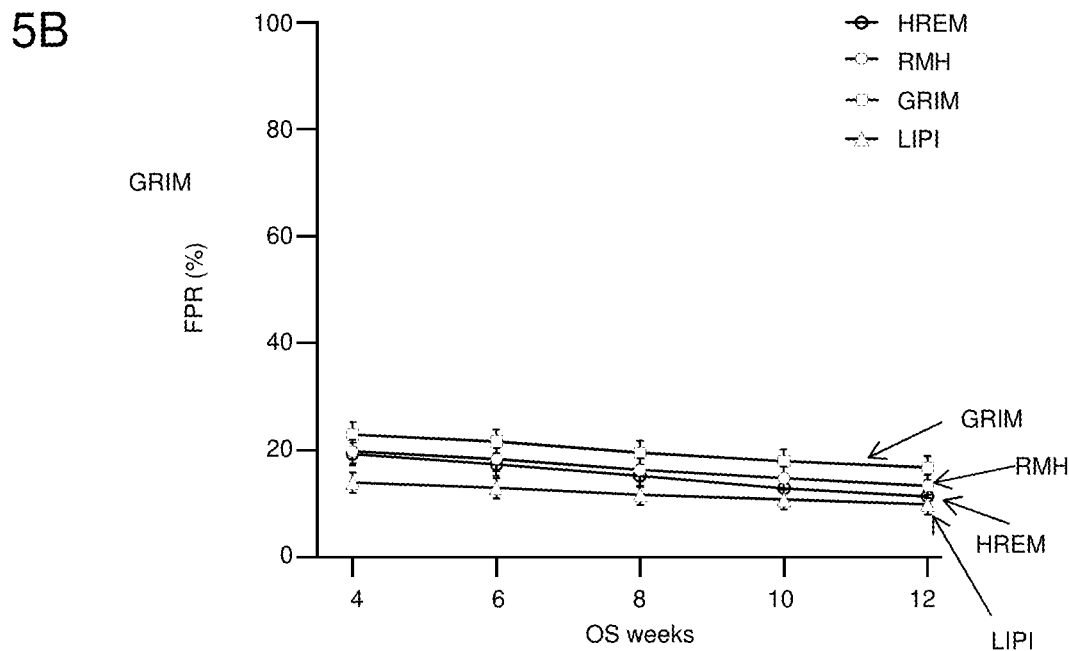
5B

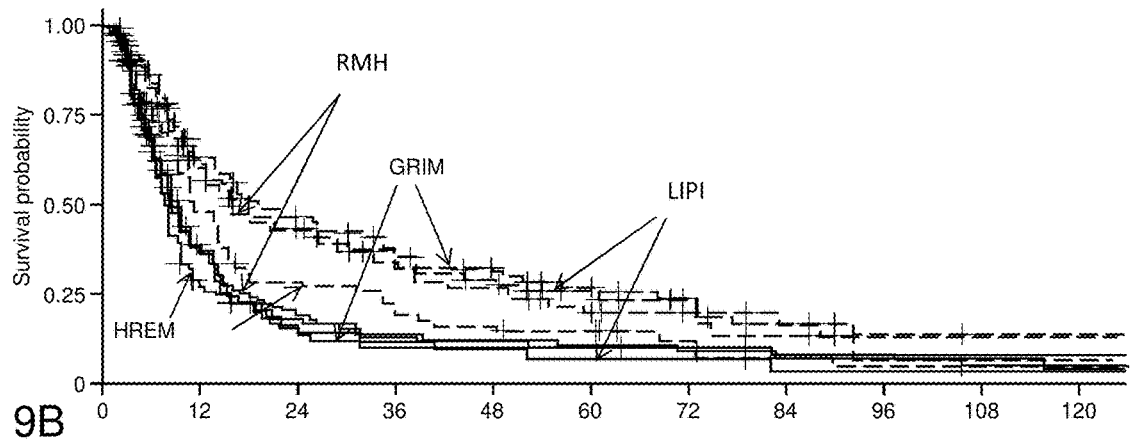
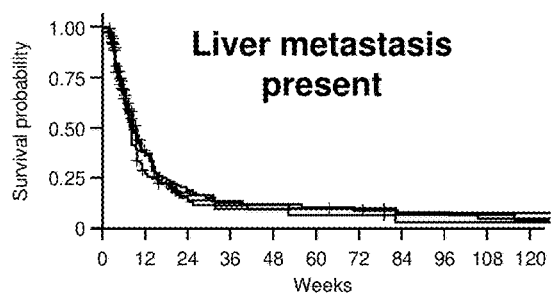
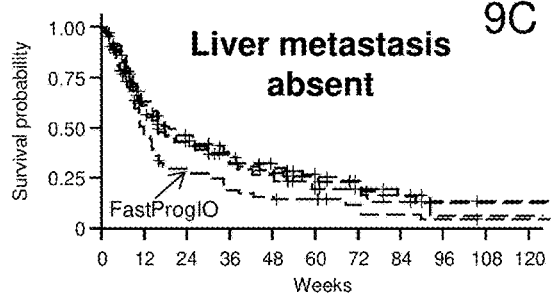
| Score | Liver mets present | | Liver mets absent | | p-value |
|---|---|---|---|---|---|
| | N | Median survival, weeks (95% CI) | N | Median survival, weeks (95% CI) | |
| HREM | 110 | 7.6 (6.4, 9.3) | 96 | 11.1 (9.3, 14.6) | 0.0433 |
| RMH | 116 | 9.6 (7.6, 11.0) | 93 | 16.4 (11.0, 28.9) | 0.0009 |
| GRIM | 103 | 8.3 (7.1, 10.9) | 127 | 19.7 (14.6, 33.4) | <0.0001 |
| LIPI | 62 | 8.3 (6.3, 11.9) | 77 | 17.7 (12.1, 29.9) | <0.0001 |
Figure 9

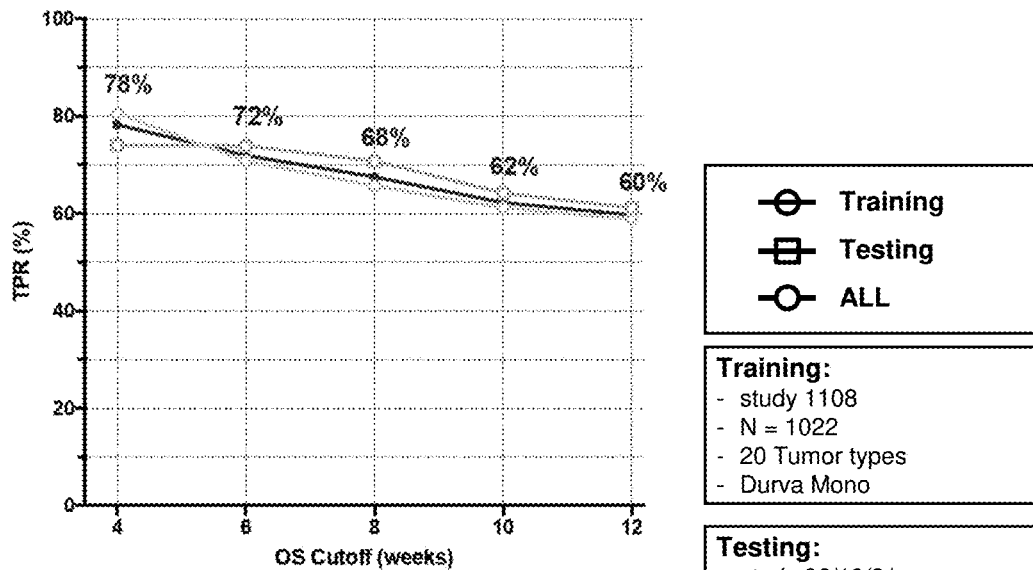
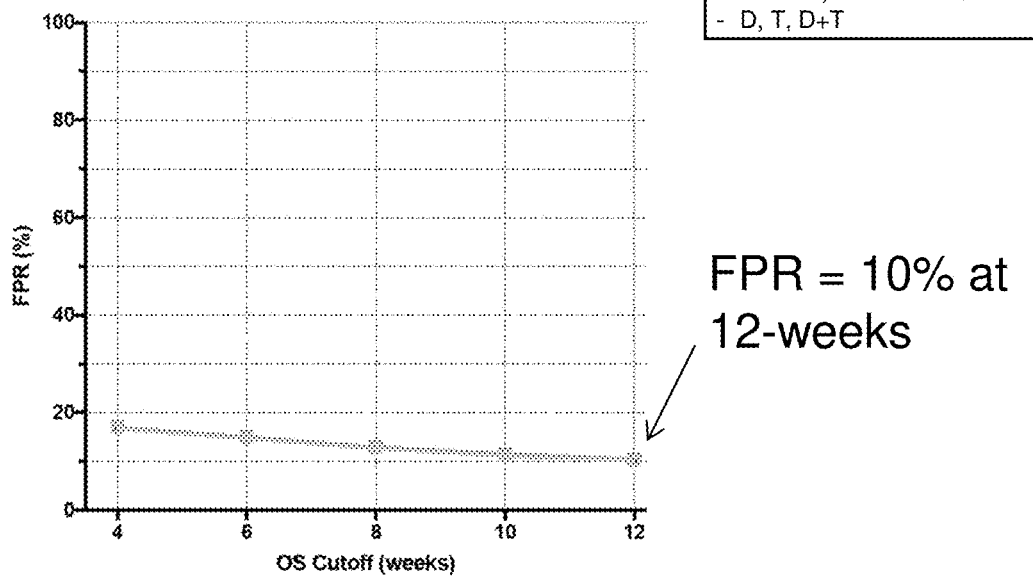
Figure 15

| F1 model predicted | N | Median survival time (weeks, 95% CI) |
|---|---|---|
| HREM | 324 | 9.4 (8.3, 10.9) |
| Non-HREM | 1358 | 62.3 (56.7, 67.4) |
| All | 1682 | 47.1 (41.7, 51.7) |

| Score | N | Median survival time (95% CI) | p-Value (against F1 Model) |
|---|---|---|---|
| F1 model | 324 | 9.4 (8.3 – 10.9) | - |
| RMH | 373 | 12.0 (10.6, 14.4) | 0.0023 |
| GRIM | 399 | 12.7 (10.6, 14.3) | 0.0014 |
| LIPI | 233 | 11.7 (9.7, 14.3) | 0.0501 |

Overall survival of F1 model predicted fast progressors

Median survival time (weeks)

| Score | N | Liver mets: pos Median survival time (wks, 95% CI) | N | Liver mets: neg Median survival time (wks, 95% CI) | p-Value |
|---|---|---|---|---|---|
| F1 model | 176 | 8.0 (6.7 - 9.7) | 148 | 11.0 (9.3 - 14.1) | 0.0020 |
| RMH | 207 | 10.6 (8.4 - 12.7) | 166 | 15.4 (11.3 - 19.0) | 0.0185 |
| GRIM | 184 | 9.3 (7.6 - 11.0) | 215 | 17.0 (12.9 - 22.1) | <0.0001 |
| LIPI | 112 | 9.6 (6.7, 12.7) | 121 | 15.4 (11.0 - 20.7) | 0.0072 |

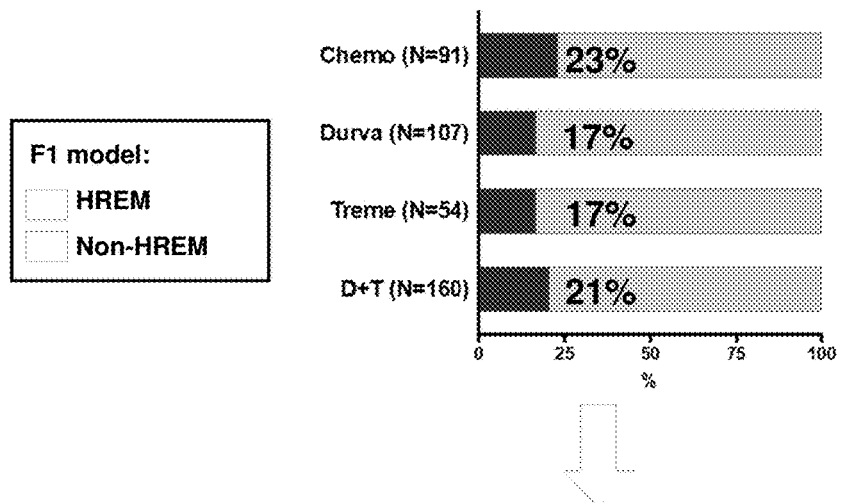
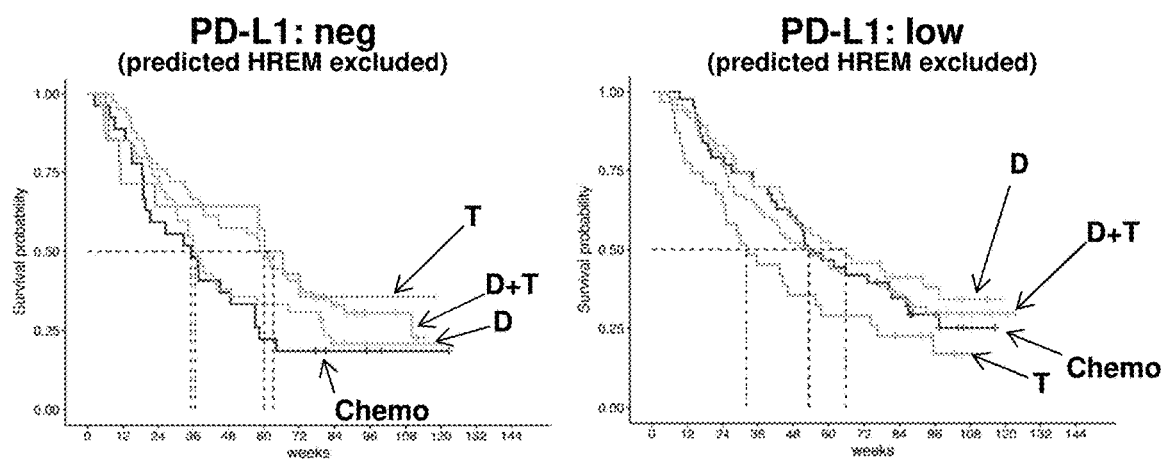
Figure 22

```
┌─────────────────────────────────────────────────────────────────┐
│ OBTAIN A GRADIENT BOOSTING MACHINE LEARNING MODEL, WHEREIN THE  │
│ GRADIENT BOOSTING MACHINE LEARNING MODEL WAS TRAINED ON MODEL   │
│ TRAINING DATA, WHEREIN THE MODEL TRAINING DATA INVOLVES A FIRST SET │
│ OF CANCER PATIENTS THAT UNDERWENT CANCER TREATMENTS, WHEREIN    │
│ THE MODEL TRAINING DATA ASSOCIATES (I) RESULTS FROM LABORATORY  │
│ TESTS CONDUCTED ON THE FIRST SET OF CANCER PATIENTS AND TUMOR   │
│ TYPES OF THE FIRST SET OF CANCER PATIENTS WITH (II) WHETHER     │
│ INDIVIDUALS FROM THE FIRST SET OF CANCER PATIENTS DIED WITHIN A │ ← 7300
│ THRESHOLD NUMBER OF WEEKS FROM INITIATION OF THE CANCER         │
│ TREATMENTS, WHEREIN TRAINING THE GRADIENT BOOSTING MACHINE      │
│ LEARNING MODEL INVOLVED: (I) TRAINING A SEQUENTIAL SERIES OF DECISION │
│ TREES UNTIL A STOPPING CONDITION WAS REACHED, WHEREIN EACH      │
│ SUBSEQUENT DECISION TREE OF THE SEQUENTIAL SERIES OF DECISION   │
│ TREES WAS CONSTRUCTED BASED ON RESIDUAL VALUES OF ITS PRECEDING │
│ DECISION TREE OF THE SEQUENTIAL SERIES OF DECISION TREES, AND (II) │
│ DETERMINING AN ADDITIVE FUNCTION OF THE SEQUENTIAL SERIES OF    │
│ DECISION TREES                                                  │
└─────────────────────────────────────────────────────────────────┘
                                  │
                                  ▼
┌─────────────────────────────────────────────────────────────────┐
│ OBTAIN RESULTS FROM THE LABORATORY TESTS AS CONDUCTED ON A      │ ← 7302
│                     FURTHER CANCER PATIENT                      │
└─────────────────────────────────────────────────────────────────┘
                                  │
                                  ▼
┌─────────────────────────────────────────────────────────────────┐
│         OBTAIN A TUMOR TYPE OF THE FURTHER CANCER PATIENT       │ ← 7304
└─────────────────────────────────────────────────────────────────┘
                                  │
                                  ▼
┌─────────────────────────────────────────────────────────────────┐
│ APPLY THE GRADIENT BOOSTING MACHINE LEARNING MODEL TO RESULTS   │
│ FROM THE LABORATORY TESTS AS CONDUCTED ON A FURTHER CANCER      │ ← 7306
│   PATIENT AND THE TUMOR TYPE OF THE FURTHER CANCER PATIENT      │
└─────────────────────────────────────────────────────────────────┘
                                  │
                                  ▼
┌─────────────────────────────────────────────────────────────────┐
│ RECEIVE, FROM THE GRADIENT BOOSTING MACHINE LEARNING MODEL, A   │
│ PREDICTION OF WHETHER THE FURTHER CANCER PATIENT DIES WITHIN THE│ ← 7308
│                   THRESHOLD NUMBER OF WEEKS                     │
└─────────────────────────────────────────────────────────────────┘
```

Figure 73

METHODS FOR DETERMINING TREATMENT FOR CANCER PATIENTS

This application is claims benefit under 35 U.S.C. § 119(e) of the following U.S. Provisional Application Nos. 62/854,566 filed May 30, 2019, and 62/747,420 filed Oct. 18, 2018. Each of the above listed applications is incorporated by reference herein in its entirety for all purposes.

FIELD OF THE INVENTION

The present invention generally relates to methods of treating patients for cancer.

BACKGROUND OF THE INVENTION

Development of new anticancer therapeutics, such as immuno-oncology therapeutics (TO), drugs targeting DNA damage repair systems, and the like, requires extensive investments of time and resources to identify potentially effective candidate drugs. However, before such candidates can be added to the existing armamentarium of approved anticancer therapies, they must be proven to be both safe and effective in clinical trials. The initial step in this process is to conduct phase I clinical trials, which are designed to focus on drug safety.

These phase I clinical trials recruit patients who may potentially benefit from taking part in the trial, oftentimes because standard of care treatments for these patients have failed. In many clinical trials, irrespective of the type of treatment being tested or its intended indication, a subset of the participants is unable to complete the study due to a variety of reasons. For example, some patients may enter clinical trials with significantly advanced underlying disease or may have secondary or other unrelated pathological conditions to their cancer.

In the context of IO phase I clinical trials, such as PD-1 or PD-L1 (PDx) studies as monotherapies, nearly 20% of patients recruited to participate die within 2-3 months of beginning the study, even though ideally most trials of this type last much longer than 2-3 months. Therefore, to participate in an IO phase I clinical trial, patients should have a life expectancy of greater than 24 weeks and not be at risk of early mortality (EM; defined as a life expectancy of less than 24 weeks). An EM phenomenon has been observed in many randomized clinical trials comparing ICIs with active comparator arms in advanced or metastatic cancer patients, even with overall benefit ultimately favoring ICI therapy (Champiat, et al. 2018). While the precise etiology of this phenomenon is not clearly established, it is characterized by what seems to be disproportionately higher mortality in the early treatment period where survival is favored in the control arm, followed by subsequent benefit in overall survival (OS) favoring the ICI treatment arm. This is often reflected in the clinical data by the "crossing of the Kaplan-Meier curves" suggesting a subpopulation of patients at a higher risk of EM whose advanced rate of tumour growth may require the cytotoxic tumour-debulking effect of chemotherapy.

Accordingly, it is of great therapeutic interest to better predict the risk of early mortality for a given patient to better inform the appropriate treatment for their individual clinical state. An unexpected rapid disease progression or exacerbation of another underlying pathological condition in a significantly large number of patients participating in a phase I clinical trial can diminish the ability to detect early efficacy signals of the therapeutic being tested, delay dose escalation due to premature patient dropout, confound analysis of predictive biomarkers of efficacy, and dilute efficacy versus comparators in randomized trials. This can also prevent patients from getting potentially life-extending therapeutic intervention outside of a phase I clinical trial. If such patients were to receive therapeutic intervention that corrects or alleviates the underlying condition, they may then be able to fully benefit from trial participation. Therefore, improved prognostic methodologies for predicting EM in patients for anticancer therapeutic clinical trials are needed.

Immune checkpoint inhibitors (ICIs) are profoundly changing the treatment of many types of cancer, including melanoma, non-small cell lung cancer (NSCLC), renal cell carcinoma (RCC), squamous cell carcinoma of the head and neck (SCCHN), urothelial carcinoma (UC), and Hodgkin's lymphoma, and have been associated with long-lasting tumour responses. To aid in this objective, herein is presented a novel prognostic score, Immune Immediacy Index (3i score), that uses pre-treatment measurements of routinely collected blood-based factors to predict a patient's risk of early mortality, and to optimize the benefit:risk profile for treatment of patients with ICI.

SUMMARY OF THE INVENTION

As described below, in a first aspect, the present disclosure provides a method of treating a patient having cancer, comprising: a) determining concentrations of multiple clinicopathological markers of the patient; b) providing, to a gradient boosting machine learning model, the determined concentrations of the multiple clinicopathological markers; c) receiving, from the gradient boosting machine learning model, a prediction of whether the patient is likely to die within a period of 12 weeks; and d) administering an anticancer therapeutic to the patient if the prediction indicates that the patient is not likely to die within the period of 12 weeks.

In one embodiment of the first aspect, the multiple clinicopathological markers comprise one or more of age, albumin (g/L), alanine phosphatases (U/L), alanine amino transferase (U/L), aspartate amino transferase (U/L), basophils ($10^3/\mu L$), basophils/Leukocytes (%), bilirubin ($\mu mol/L$), Body Mass Index, calcium (mmol/L), chloride (mmol/L), eosinophils ($10^3/\mu L$), eosinophils/leukocytes (%), gamma-glutamyl transferase (U/L), glucose (mmol/L), hematocrit (%), hemoglobin (g/L), potassium (mmol/L), lactate dehydrogenase (U/L), liver metastasis (yes/no), lymphocytes ($10^3/\mu L$), lymphocytes/leukocytes (%), magnesium (mmol/L), monocytes ($10^3/\mu L$), monocytes/leukocytes (%), neutrophils ($10^3/\mu L$), neutrophils/leukocytes (%), neutrophils/lymphocytes (%), platelets ($10^3/\mu L$), protein (g/L), gender, sodium (mmol/L), thyrotropin (mU/L), tumor size, uric acid (mmol/L), and leukocytes ($10^3/\mu L$).

In another embodiment of the first aspect, the multiple clinicopathological markers comprise neutrophils/leukocytes (%), neutrophils ($10^3/\mu L$), albumin (g/L), lactate dehydrogenase (U/L), aspartate amino transferase (U/L), and/or gamma-glutamyl transferase (U/L).

In one embodiment of the first aspect, the method further comprises taking a sample from the patient.

In one embodiment of the first aspect, the sample comprises a tissue biopsy, cerebrospinal fluid, lymph, whole blood, serum, a blood cell, urine, sweat, tears, saliva, and/or feces.

In one embodiment of the first aspect, a concentration of one or more of the multiple clinicopathological markers is determined from the sample taken from the patient.

In one embodiment of the first aspect, the anticancer therapeutic comprises cisplatin, gemcitabine, methotrexate, vinblastine, doxorubicin, cisplatin (MVAC), carboplatin, a taxane, temozolomide, dacarbazine, vinflunine, docetaxel, paclitaxel, nab-paclitaxel, Vemurafenib, Erlotinib, Afatinib, Cetuximab, Bevacizumab, Gefitinib, and/or Pemetrexed.

In one embodiment of the first aspect, the anticancer therapeutic comprises an immune checkpoint inhibitor.

In one embodiment of the first aspect, the immune checkpoint inhibitor comprises an anti-CTLA-4 antibody, an anti-PD-1 antibody, and/or an anti-PD-L1 antibody.

In one embodiment of the first aspect, the anti-CTLA-4 antibody is tremelimumab or ipilimumab.

In one embodiment of the first aspect, the anti-PD-1 antibody is REGN2810, SHR1210, IBI308, PDR001, nivolumab, pembrolizumab, Anti-PD-1, BGB-A317, BCD-100, or JS001.

In one embodiment of the first aspect, the anti-PD-L1 antibody comprises durvalumab, avelumab, atezolizumab, or KNO35.

In a further embodiment of the first aspect, the method further includes determining a cancer type of the patient and also providing, to the gradient boosting machine learning model, the determined cancer type.

In a second aspect, the present disclosure provides a method of treating a patient having cancer, comprising: a) determining concentrations of multiple clinicopathological markers of the patient; b) providing, to a gradient boosting machine learning model, the determined concentrations of the multiple clinicopathological markers; c) receiving, from the gradient boosting machine learning model, a prediction of whether the patient has poor immune fitness; and d) administering an anticancer therapeutic to the patient if the prediction indicates that the patient does not have poor immune fitness.

In one embodiment of the second aspect, the method further includes e) reducing in the patient at least one of a rate of cancer cell division, tumor growth, tumor size, tumor density, or rate of tumor metastasis.

In a third aspect, the present disclosure provides a method of treating a patient having cancer, comprising: a) determining concentrations of multiple clinicopathological markers of the patient; b) providing, to a gradient boosting machine learning model, the determined concentrations of the multiple clinicopathological markers; c) receiving, from the gradient boosting machine learning model, a prediction of whether the patient has poor immune fitness; d) administering a therapeutic to the patient to boost the patient's immune fitness if the prediction indicates that the patient has poor immune fitness; e) determining second concentrations of multiple clinicopathological markers of the patient; f) providing, to a gradient boosting machine learning model, the determined second concentrations of the multiple clinicopathological markers; g) receiving, from the gradient boosting machine learning model, a second prediction of whether the patient has poor immune fitness; and h) administering an anticancer therapeutic to the patient if the prediction indicates that the patient does not have poor immune fitness.

In a fourth aspect, the present disclosure provides a method of conducting a clinical trial for an anticancer therapeutic, comprising: a) identifying a candidate participant for a clinical trial, wherein the candidate participant has cancer; b) determining concentrations of multiple clinicopathological markers of the patient; c) providing, to a gradient boosting machine learning model, the determined concentrations of the multiple clinicopathological markers; d) receiving, from the gradient boosting machine learning model, a prediction of whether the patient has a likelihood of death within a period of 12 weeks; and e) including the patient in the clinical trial for the anticancer therapeutic if the prediction indicates that the patient does not have a likelihood of death within the period of 12 weeks.

In one embodiment of the fourth aspect, the anticancer therapeutic is an immune checkpoint inhibitor.

In a fifth aspect, the present disclosure provides a method of predicting the effectiveness of treating a cancer patient with an immune checkpoint inhibitor, comprising: a) determining concentrations of multiple clinicopathological markers of the patient; b) providing, to a gradient boosting machine learning model, the determined concentrations of the multiple clinicopathological markers; c) receiving, from the gradient boosting machine learning model, a prediction of whether the patient lacks immune fitness, wherein a prediction indicating that the patient does not lack immune fitness predicts that the patient may be more effectively treated with an immune checkpoint inhibitor (ICI) than a patient predicted to lack immune fitness.

In a sixth aspect, the present disclosure provides a method of determining a treatment regimen for a cancer patient, comprising: a) determining concentrations of multiple clinicopathological markers of the patient; b) providing, to a gradient boosting machine learning model, the determined concentrations of the multiple clinicopathological markers; c) receiving, from the gradient boosting machine learning model, a prediction of whether the patient lacks immune fitness, wherein a prediction indicating that the patient does not lack immune fitness suggests a treatment regimen including an immune checkpoint inhibitor (ICI), and wherein a prediction indicating the patient lacks immune fitness suggests a treatment regimen without an immune checkpoint inhibitor (ICI).

In a seventh aspect, a computing system includes computer memory configured to store model training data, wherein the model training data involves a first set of cancer patients that underwent cancer treatments, wherein the model training data associates (i) results from laboratory tests conducted on the first set of cancer patients and tumor types of the first set of cancer patients with (ii) whether individuals from the first set of cancer patients died within a threshold number of weeks from initiation of the cancer treatments. The computing system also includes one or more processors in communication with the computer memory and configured to execute program instructions to: (i) train, based on the model training data, a sequential series of decision trees until a stopping condition is reached, wherein each subsequent decision tree of the sequential series of decision trees is constructed based on residual values of its preceding decision tree of the sequential series of decision trees; and (ii) generate a gradient boosting machine learning model as an additive function of the sequential series of decision trees, wherein the gradient boosting machine learning model predicts whether a further cancer patient dies within the threshold number of weeks based on the additive function applied to results from the laboratory tests as conducted on the further cancer patient and a tumor type of the further cancer patient.

In an eighth aspect, a computer implemented method involves obtaining model training data, wherein the model training data involves a first set of cancer patients that underwent cancer treatments, wherein the model training data associates (i) results from laboratory tests conducted on the first set of cancer patients and tumor types of the first set of cancer patients with (ii) whether individuals from the first set of cancer patients died within a threshold number of weeks from initiation of the cancer treatments. The computer implemented method also involves training, based on the model training data, a sequential series of decision trees until a stopping condition is reached, and wherein each subsequent decision tree of the sequential series of decision trees is constructed based on residual values of its preceding decision tree of the sequential series of decision trees. The computer implemented method also involves generating a gradient boosting machine learning model as an additive function of the sequential series of decision trees, wherein the gradient boosting machine learning model predicts whether a further cancer patient dies within the threshold number of weeks based on the additive function applied to results from the laboratory tests as conducted on the further cancer patient and a tumor type of the further cancer patient.

In a ninth aspect, an article of manufacture includes a non-transitory computer-readable medium, having stored thereon program instructions that, upon execution by a computing device, cause the computing device to perform the operations of the eighth aspect.

In a tenth aspect, a computing system involves computer memory configured to store a gradient boosting machine learning model, wherein the gradient boosting machine learning model was trained on model training data, wherein the model training data involves a first set of cancer patients that underwent cancer treatments, wherein the model training data associates (i) results from laboratory tests conducted on the first set of cancer patients and tumor types of the first set of cancer patients with (ii) whether individuals from the first set of cancer patients died within a threshold number of weeks from initiation of the cancer treatments, wherein training the gradient boosting machine learning model involved: (i) training a sequential series of decision trees until a stopping condition was reached, wherein each subsequent decision tree of the sequential series of decision trees was constructed based on residual values of its preceding decision tree of the sequential series of decision trees, and (ii) determining an additive function of the sequential series of decision trees. The computing system also involves one or more processors in communication with the computer memory and configured to execute program instructions to: (i) obtain results from the laboratory tests as conducted on a further cancer patient; (ii) obtain a tumor type of the further cancer patient; (iii) apply the gradient boosting machine learning model to results from the laboratory tests as conducted on the further cancer patient and the tumor type of the further cancer patient; and (iv) receive, from the gradient boosting machine learning model, a prediction of whether the further cancer patient dies within the threshold number of weeks.

In an eleventh aspect, a computer-implemented method involves obtaining a gradient boosting machine learning model, wherein the gradient boosting machine learning model was trained on model training data, wherein the model training data involves a first set of cancer patients that underwent cancer treatments, wherein the model training data associates (i) results from laboratory tests conducted on the first set of cancer patients and tumor types of the first set of cancer patients with (ii) whether individuals from the first set of cancer patients died within a threshold number of weeks from initiation of the cancer treatments, wherein training the gradient boosting machine learning model involved: (i) training a sequential series of decision trees until a stopping condition was reached, wherein each subsequent decision tree of the sequential series of decision trees was constructed based on residual values of its preceding decision tree of the sequential series of decision trees, and (ii) determining an additive function of the sequential series of decision trees. The computer-implemented method also involves obtaining results from the laboratory tests as conducted on a further cancer patient. The computer-implemented method also involves obtaining a tumor type of the further cancer patient. The computer-implemented method also involves applying the gradient boosting machine learning model to results from the laboratory tests as conducted on a further cancer patient and the tumor type of the further cancer patient. The computer-implemented method also involves receiving, from the gradient boosting machine learning model, a prediction of whether the further cancer patient dies within the threshold number of weeks.

In a twelfth aspect, an article of manufacture includes a non-transitory computer-readable medium, having stored thereon program instructions that, upon execution by a computing device, cause the computing device to perform the operations of the eleventh aspect.

Other features and advantages of the invention will be apparent from the detailed description, and the claims.

BRIEF DESCRIPTION OF THE DRAWINGS/FIGURES

FIG. 1A illustrates overall survival of patients enrolled in a Phase I immuno-oncology trial (Durvalumab study 1108 (2L+ UC cohort)). The chart illustrates that about ~20% of patients died early in the Phase I I/O clinical trial despite meeting eligibility criteria. FIG. 1B depicts published prognostic scores for estimating life expectancy based on retrospective studies. These scores were developed to identify patients likely to have short survival times. dNLR, derived neutrophils/(leukocytes minus neutrophils) ratio; LDH, lactate dehydrogenase; LLN, lower limit of normal; NLR, neutrophil-to-lymphocyte ratio; ULN, upper limit of normal. Arkenau, J Clin Oncol 2009; Bigot, Eur J Cancer 2017; Mezquita, JAMA Oncol 2018.

FIG. 2 illustrates the schema for development of the High Risk of Early Mortality (HREM) prognostic score. Briefly, data from all patients enrolled in three Phase I trials (NCT01693562, NCT02000947, NCT02261220) were separated into 2 pools (training data and testing data). The training data were used for building a model with 10× cross-validation. The testing data were then applied to the model and the results compared to those derived using the RMH, GRIM, and LIPI prognostic scores (see FIG. 1).

FIG. 3A shows the proportion of patients with an overall survival (OS) score of 8 weeks or less (i.e., patients with high risk of early mortality). FIG. 3B shows the proportion of patients with an overall survival (OS) score of 12 weeks or less (i.e., patients with high risk of early mortality). Study sites with an enrollment of seven or more patients were included (n=55 sites). Selection of the study sites may be improved by identifying patients with high risk of early mortality by determining whether the sites tend to recruit patients more or less likely to have EM.

FIG. 4 shows the HREM Score (FIG. 4A) and associated predictive performance of identifying patients (FIG. 4B) with overall survival (OS)≤12 Weeks. The true positive rate (TPR) averaged about 75% for training and testing groups. The false positive rate (FPR) was controlled to around 10%.

FIG. 5 shows the time-dependent TPR (FIG. 5A) and FPR (FIG. 5B) of HREM compared with RMH, GRIM, and LIPI prognostic scores. HREM has a better prediction of patients with high risk of early mortality (TPR): OS≤4 wks (88.4%);

OS≤8 wks (81.7%); and OS≤12 wks (74.7%). HREM also has a well-controlled FPR. p-value: *<0.001, <0.01, *<0.05.

FIG. 6 shows OS in patients with high risk of early mortality versus patients without high risk of early mortality as identified by HREM. Predicted HREM survival rates drop markedly compared to non-HREM survival rates. Median survival time in weeks and 95% confidence intervals (CI) are shown.

FIG. 7 shows a comparison of OS of patients with high risk of early mortality predicted by HREM versus RMH, GRIM, and LIPI prognostic scores. Median survival time in weeks and 95% confidence intervals (CI) are shown per score.

FIG. 8 shows the PD-L1 effect on OS of predicted patients with high risk of early mortality. FIG. 8A shows a composite graph of survival probabilities based on HREM, RMH, GRIM, and LIPI prognostic scores for PD-L1 low/neg (solid lines) and PD-L1 high (dashed lines) for tested patients. FIGS. 8B, 8C, 8D, and 8E show prognostic scores for PD-L1 low/neg (solid lines) and PD-L1 high (dashed lines) for each of HREM, RMH, GRIM, and LIPI prognostic scores, respectively. A PD-L1 effect was observed in patients with high risk of early mortality predicted by HREM but not the other 3 scores. HREM predicted patients with high risk of early mortality with LOW/NEG PD-L1 progress even faster than the other scores. Median survival time in weeks and 95% confidence intervals (CI) are shown. PD-L1 status was determined in both tumor cells (TC) and immune cells (IC). *For NSCLC, High: TC≥25% and Low/Neg: TC<25%; for UC, High: TC≥25% or IC≥25%, Low/Neg: TC<25% and IC<25%.

FIG. 9 shows the effect of the presence of liver metastases (mets) on OS of predicted patients with high risk of early mortality. FIG. 9A shows a composite graph of survival probabilities based on HREM, RMH, GRIM, and LIPI prognostic scores for liver mets present (solid lines) and liver mets absent (dashed lines) for tested patients. FIGS. 9B and 9C show prognostic scores for liver mets present (solid lines) and liver mets absent (dashed lines) for each of HREM, RMH, GRIM, and LIPI prognostic scores, respectively. Predicted patients with high risk of early mortality from the 4 scores have similar survival profiles in Liver Mets POS population. HREM can better capture faster progressing patients in Liver Mets NEG population compared to the other 3 scores.

FIG. 10 shows PD-L1 and HREM patient stratification by treatment (FIGS. 10A and 10C=durvalumab; FIGS. 10B and 10D=durvalumab+tremelimumab) and by cancer type (FIGS. 10A and 10B=non-small cell lung cancer (NSCLC); FIGS. 10C and 10D=bladder cancer (UBC)).

FIG. 11 shows the FastProgIO prognostic scores are correlated with a high inflammatory proteomic signature.

FIG. 12A shows the F1 model prognostic scores. FIG. 12B highlights a comparison of HREM rates (boxes) with the same tumor types from different trials. Such comparisons may help understanding of unexpected efficacy results. Boxes indicate same tumor types.

FIG. 13 shows the variability in fast progressor rates across study sites used in Example 4. Wide variability in HREM rates across study sites was apparent. About 44% of the study sites had HREM rates ≥20%. Only study sites with enrollment of ≥7 patients were included (n=79 sites).

FIG. 14 illustrates a schematic for developing the F1 model.

FIG. 15 illustrates the predictive performance of the F1 model with training and testing data. A similar predictive performance is seen for the training and testing data. FPR was controlled at 10% for 12-week OS cutoff.

FIG. 16 shows overall survival for F1 model predicted groups.

FIG. 17 shows a comparison of OS of patients with a predicted high risk of early mortality using the F1 model and RMH, GRIM, and LIPI prognostic scores. Patients with a predicted high risk of early mortality predicted by the F1 model had worse OS compared to existing predictors. The F1 model was the only model predicting 12-week life expectancy (i.e., 95% CI not overlapping with the 12-week bar).

FIG. 18 shows the PD-L1 effect on OS in F1 model predicted patients with high risk of early mortality. Most predicted patients with high risk of early mortality with PD-L1 Low/Neg had worse OS compared to PD-L1 High. The F1 model predicted patients with a high risk of early mortality had the worst OS compared to the published scores in both PD-L1 low/neg and high populations.

FIG. 19 shows the Liver metastasis effect on OS in F1 model predicted patients with high risk of early mortality. Predicted patients with a high risk of early mortality with liver metastasis had worse OS compared to those w/o liver metastasis. F1-predicted patients with high risk of early mortality showed the worst OS profile compared to the published scores in both liver metastasis negative and positive populations.

FIG. 20A shows the results of Study 1108 where there was promising efficacy with Durvalumab alone, with a median OS=4.9 months (2.6-9.1). Though cross-trial, outcomes appeared worse and could potentially be explained by F1, in Study 21, durvalumab (D) alone showed much worse outcome in than in 1108, and durvalumab+tremelimumab (D+T) in the INFy+ cohort was also associated with a worse outcome. FIG. 20B shows that applying F1 to study 21 reveals a major imbalance in patients with high risk of early mortality rates between cohorts. An imbalance in "poor prognosis" patients predicted by F1 model is observed across cohorts (i.e. not mitigated by randomization). Both D and D+T (IFNy+) cohorts enrolled much higher proportion of high-risk patients, providing a potential explanation for the poor outcome in these cohorts. Other potential explanations such as differences in baseline clinical prognostic parameters, baseline biomarker differences PDL1 or IFNy+ status did not explain the difference in outcome.

FIG. 21 shows results of the ARCTIC study, which examined NSCLC patients. durvalumab+tremelimumab (D+T) showed more benefit in patients with PD-L1 Neg (<1%). For patients with low concentration of PD-L1 (≥1%, <25%), durvalumab monotherapy and chemotherapy showed similar benefit which was better than D+T and tremelimumab alone.

FIG. 22 shows an evaluation of imbalance in F1 model predicted patients with high risk of early mortality across groups and OS excluding predicted patients with high risk of early mortality. Similar fast progressor rates were predicted across cohorts→OS differences NOT due to imbalance between "poor prognosis" patients. After removing predicted patients with high risk of early mortality, D+T remains associated with better OS than chemo in PD-L1 neg patients.

Figure 27:
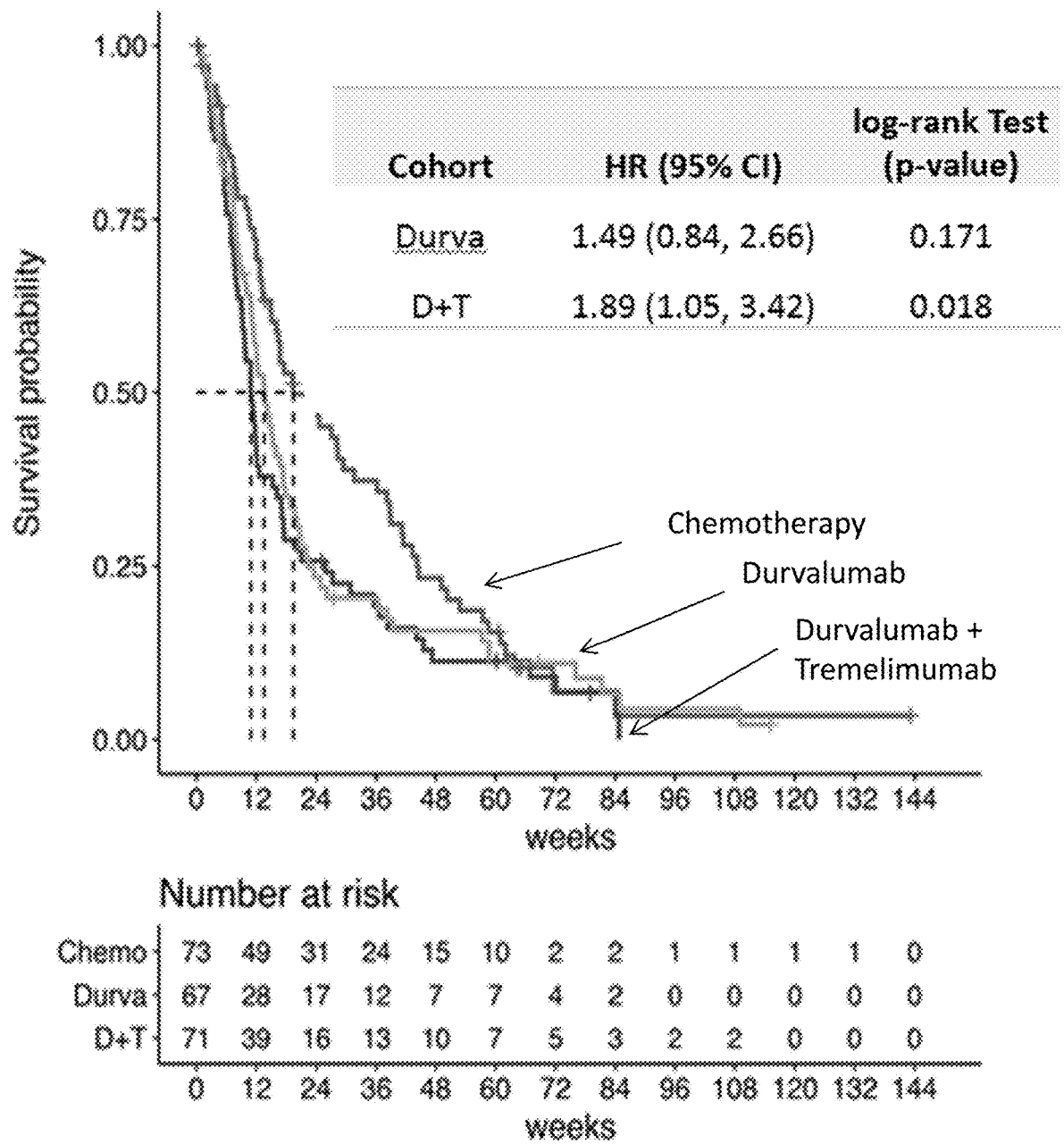

FIG. 27 shows the survival probability analysis for all patients over a period of 144 weeks (top) and a table of patients at risk over the same period (bottom) for three treatment schemes in the EAGLE study: chemotherapy, durvalumab, and durvalumab+tremelimumab. HR, hazard ratio. CI, confidence interval. The hazard ratio (HR) and the p-value for the durvalumab and durvalumab+tremelimumab arms of the EAGLE study for squamous cell cancer of the head and neck are also shown.

Figure 28:
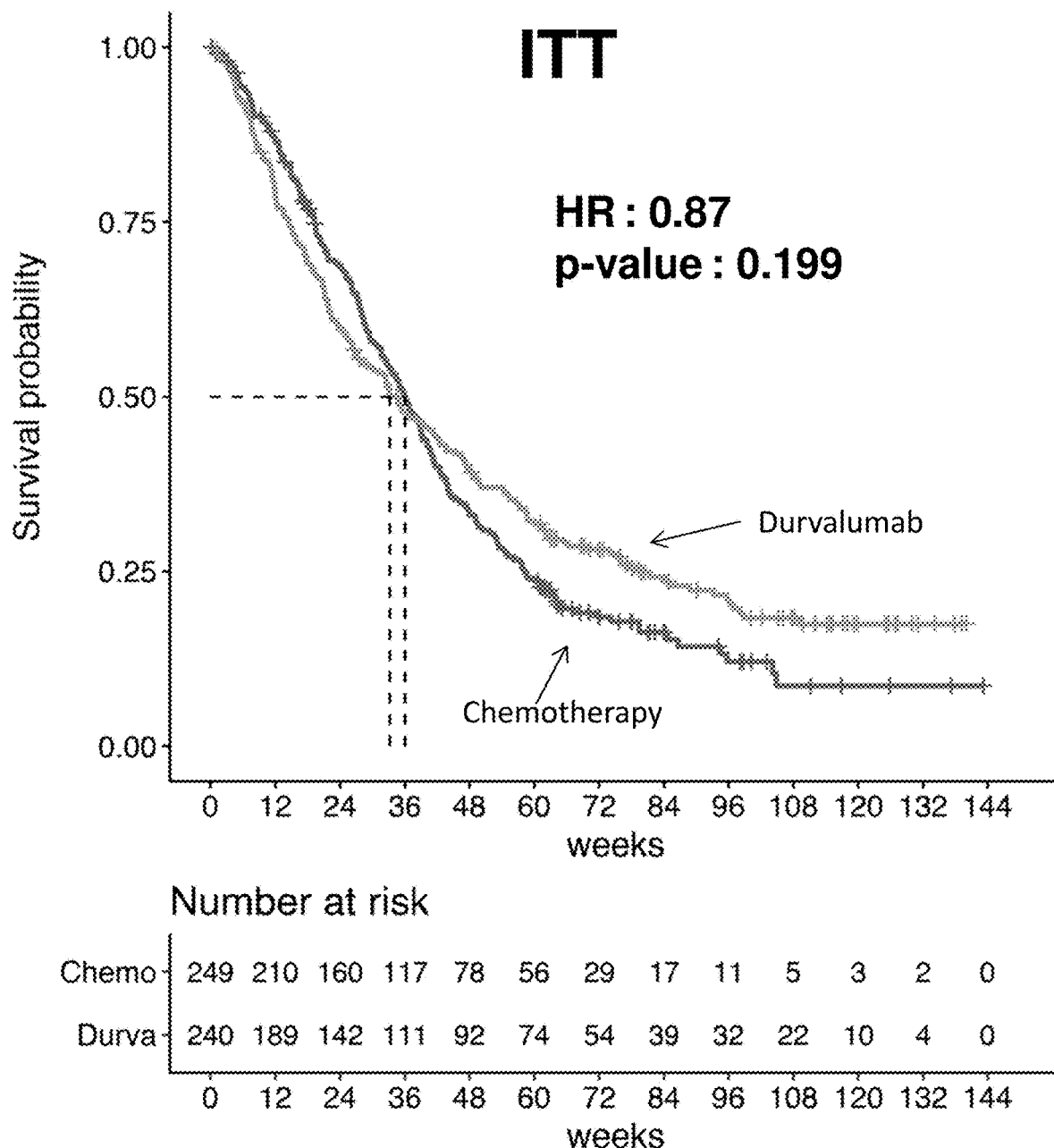

FIG. 28 shows an Intention-to-Treat (ITT) survival probability analysis over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 29:
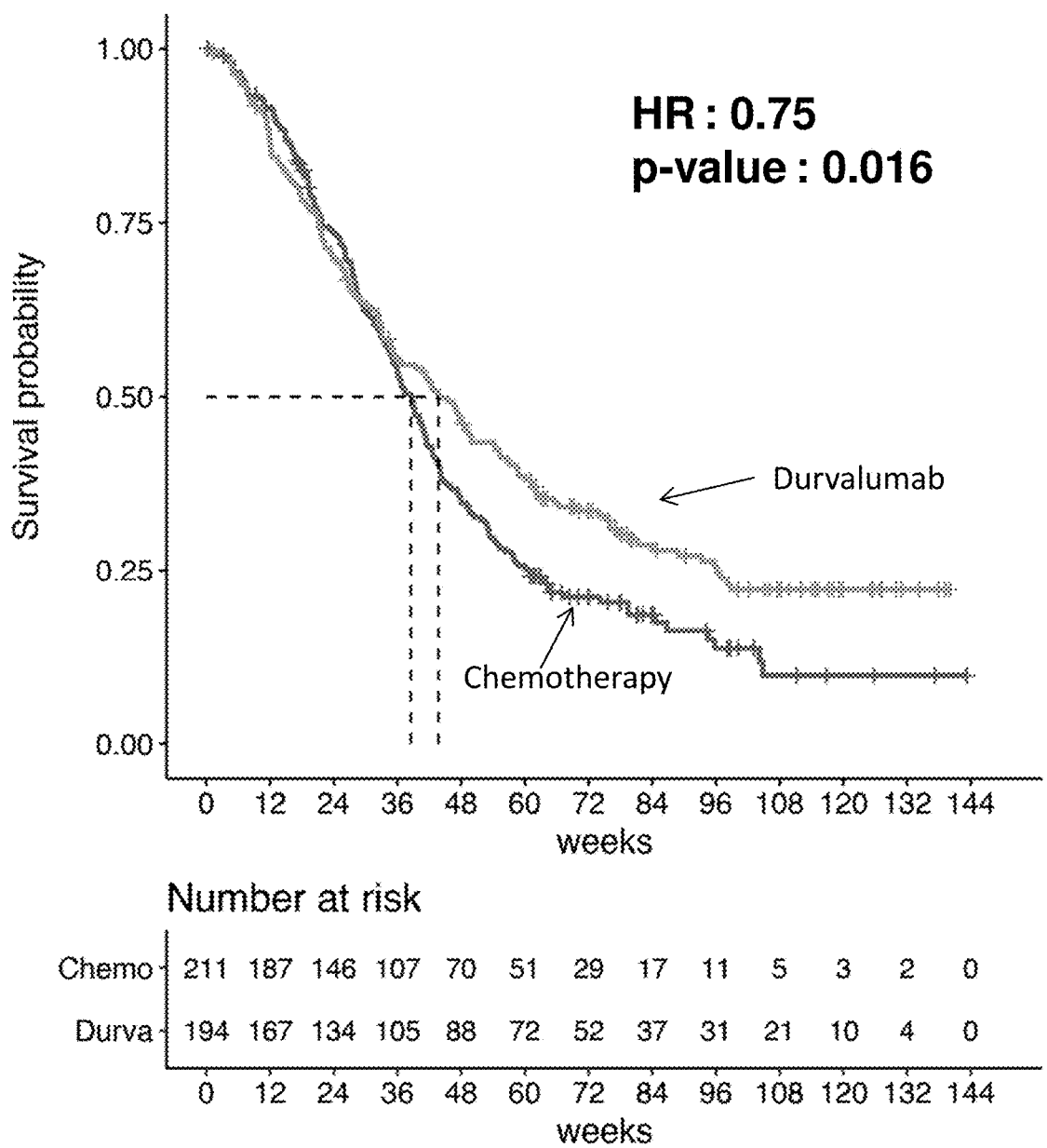

FIG. 29 shows an Intention-to-Treat (ITT) survival probability analysis with patients with high risk of early mortality excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 30:
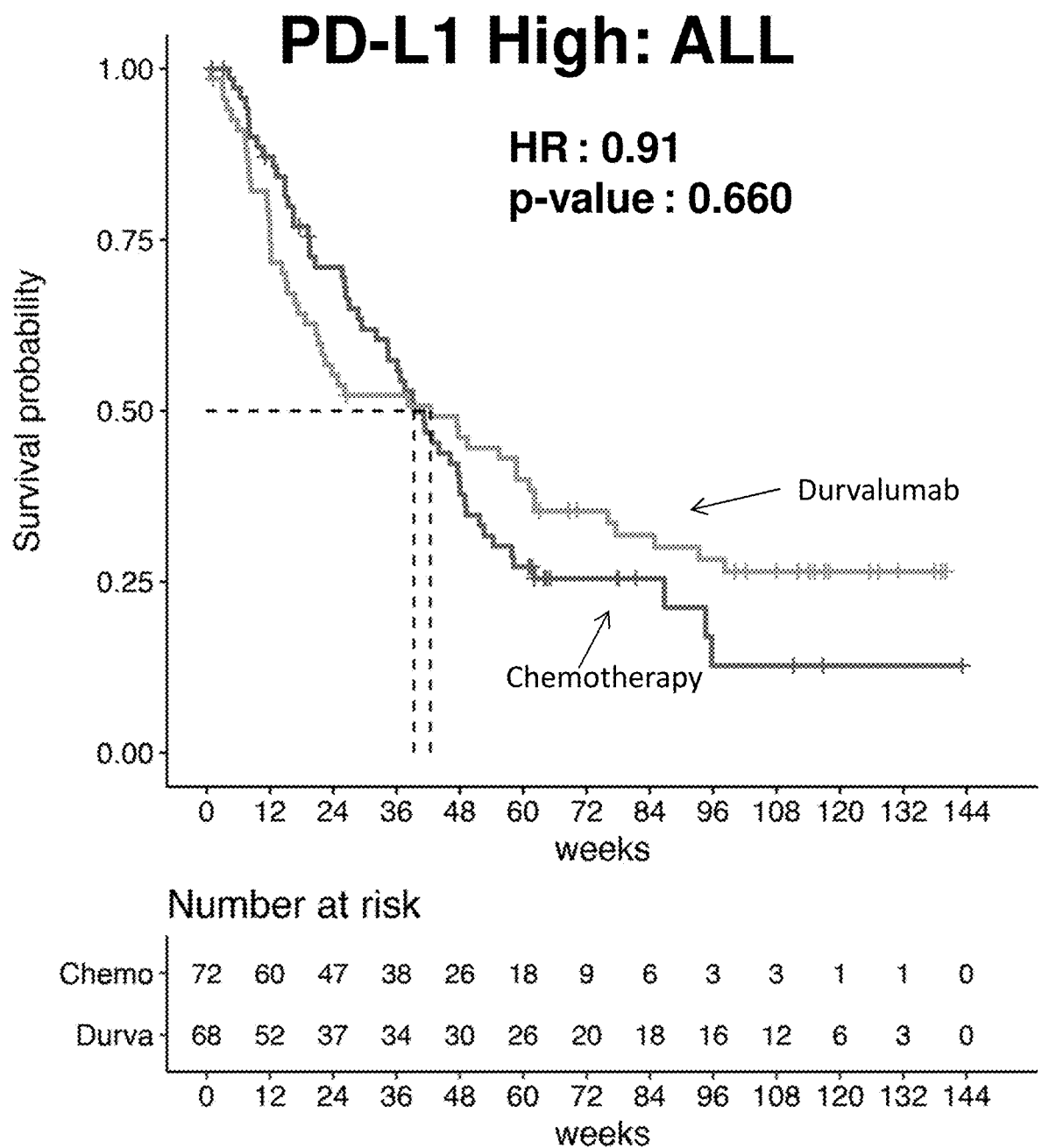

FIG. 30 shows survival probability analysis for PD-L1 high patients (≥25%) over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 31:
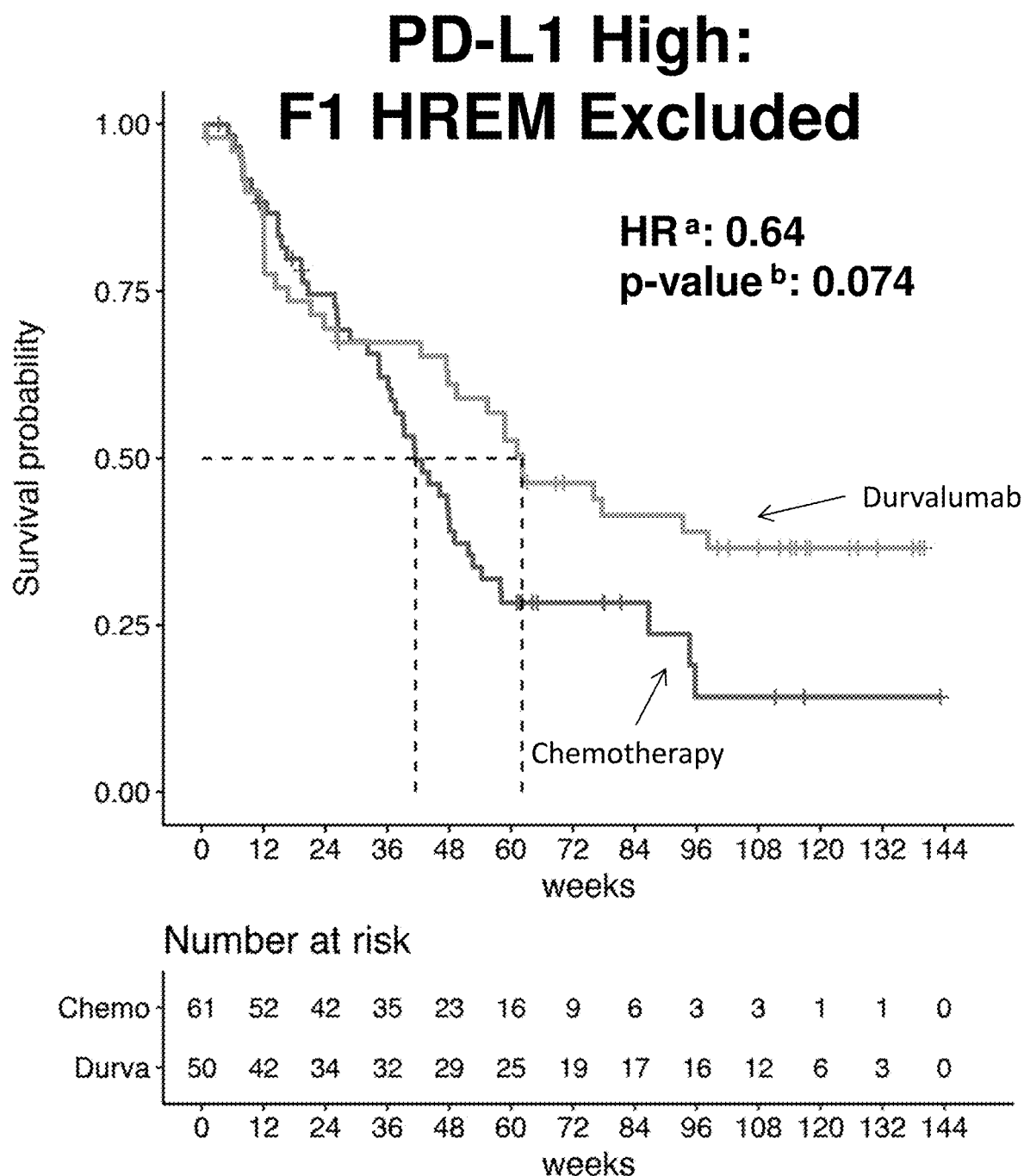

FIG. 31 shows survival probability analysis for PD-L1 high patients (≥25%) with high risk of early mortality excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 32:
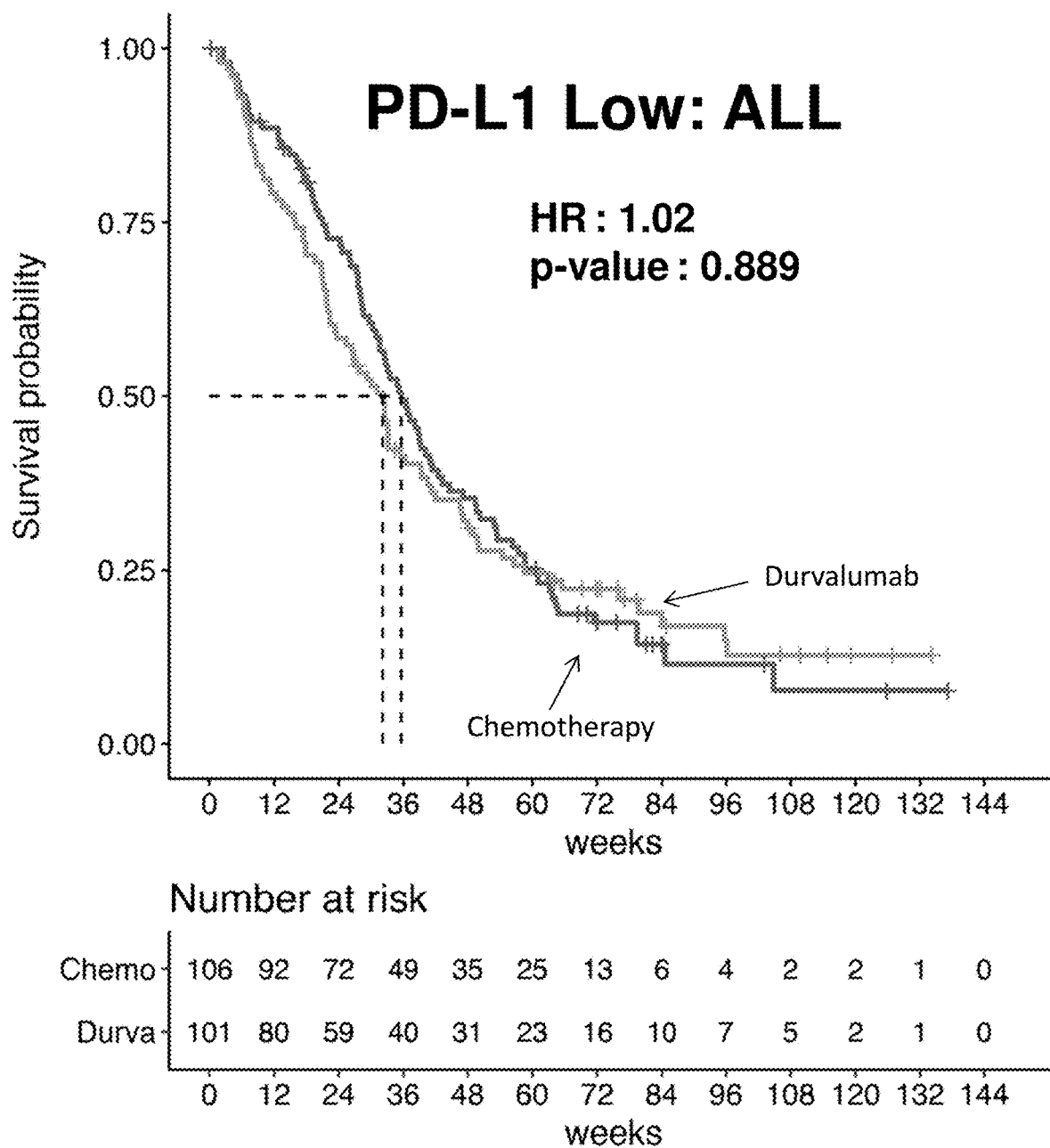

FIG. 32 shows survival probability analysis for PD-L1 low patients (≥1, <25%) over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 33:
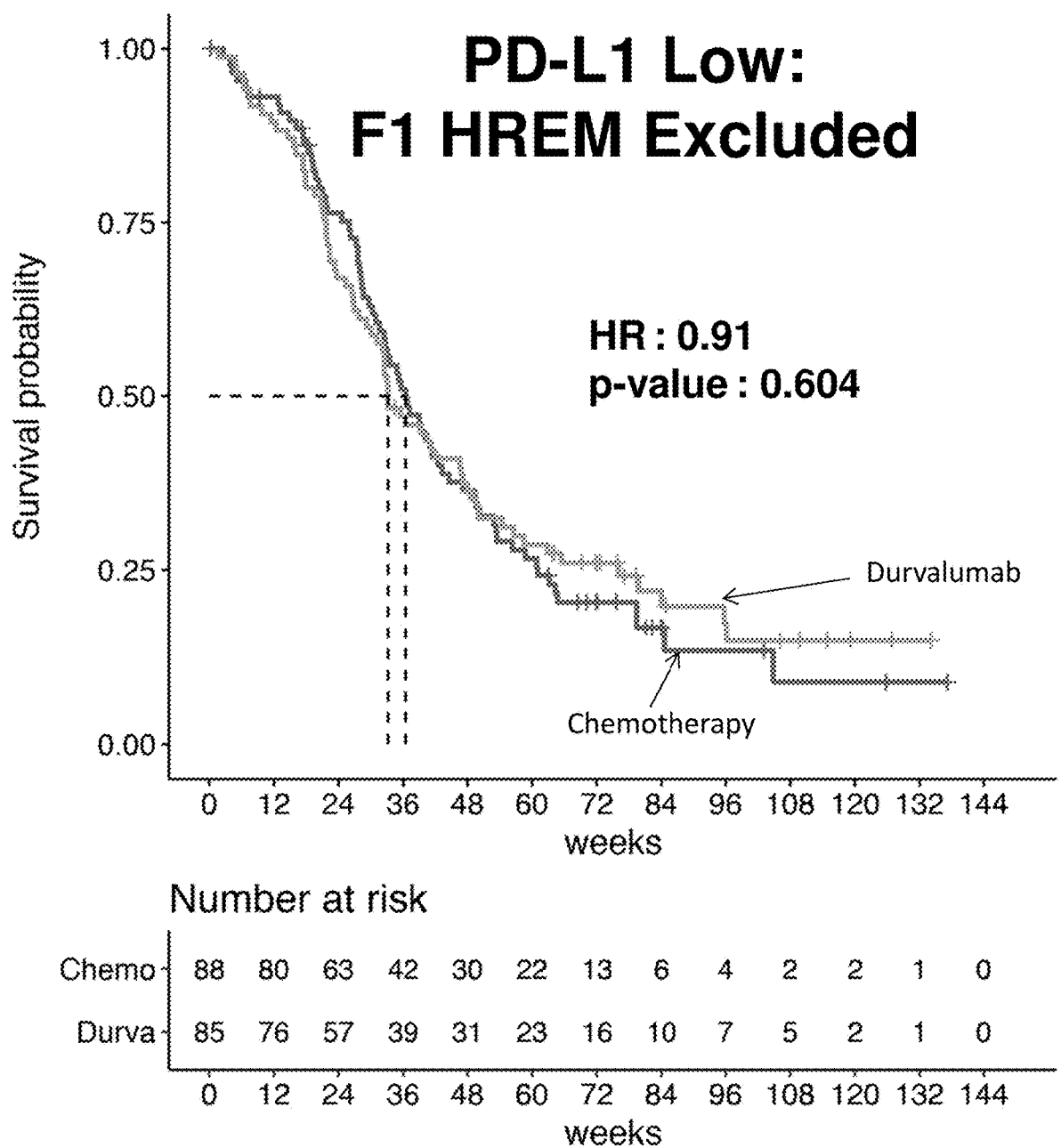

FIG. 33 shows survival probability analysis for PD-L1 low patients (≥1, <25%) with high risk of early mortality excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 34:
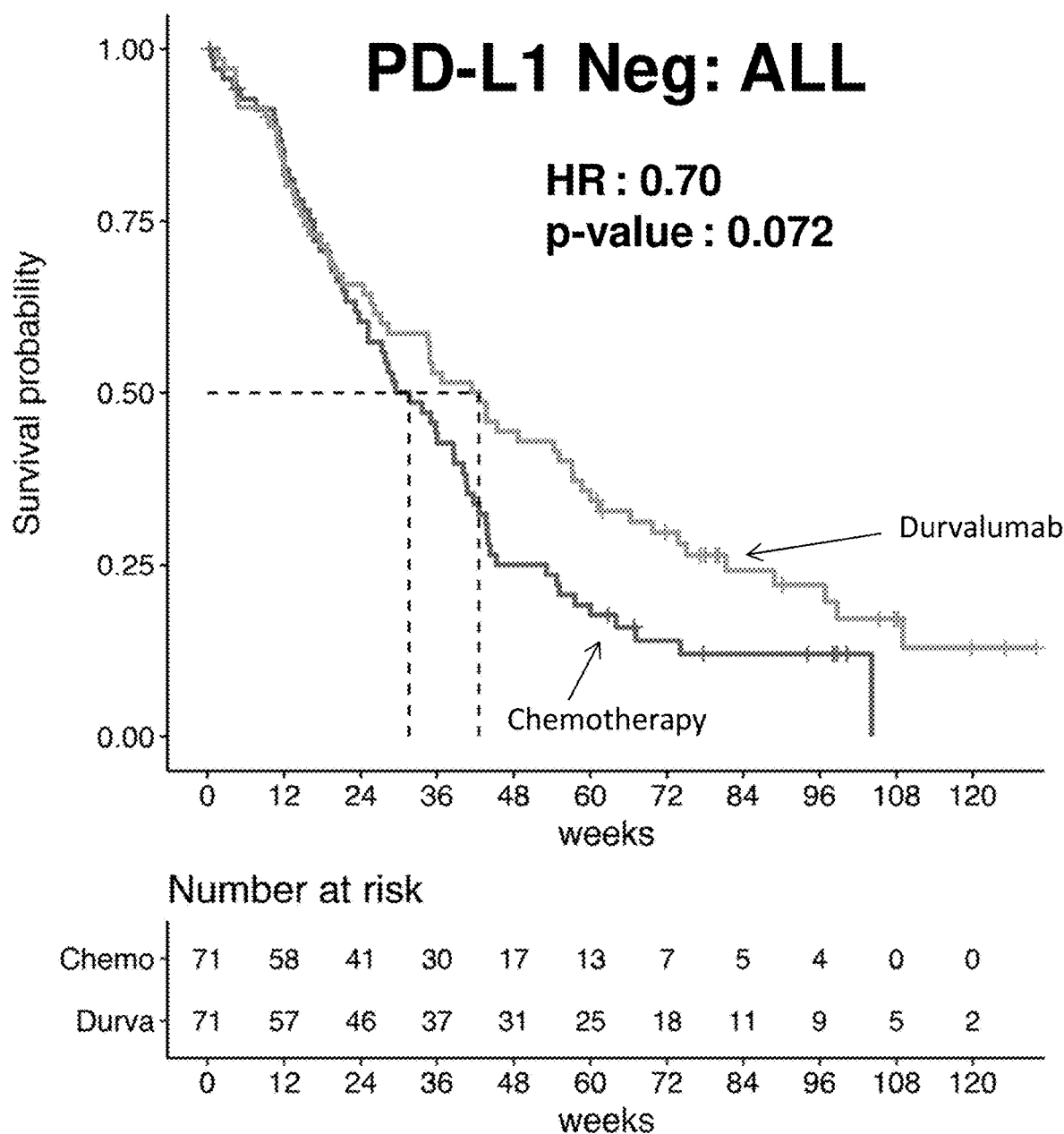

FIG. 34 shows survival probability analysis for PD-L1 negative patients (<1%) over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 35:
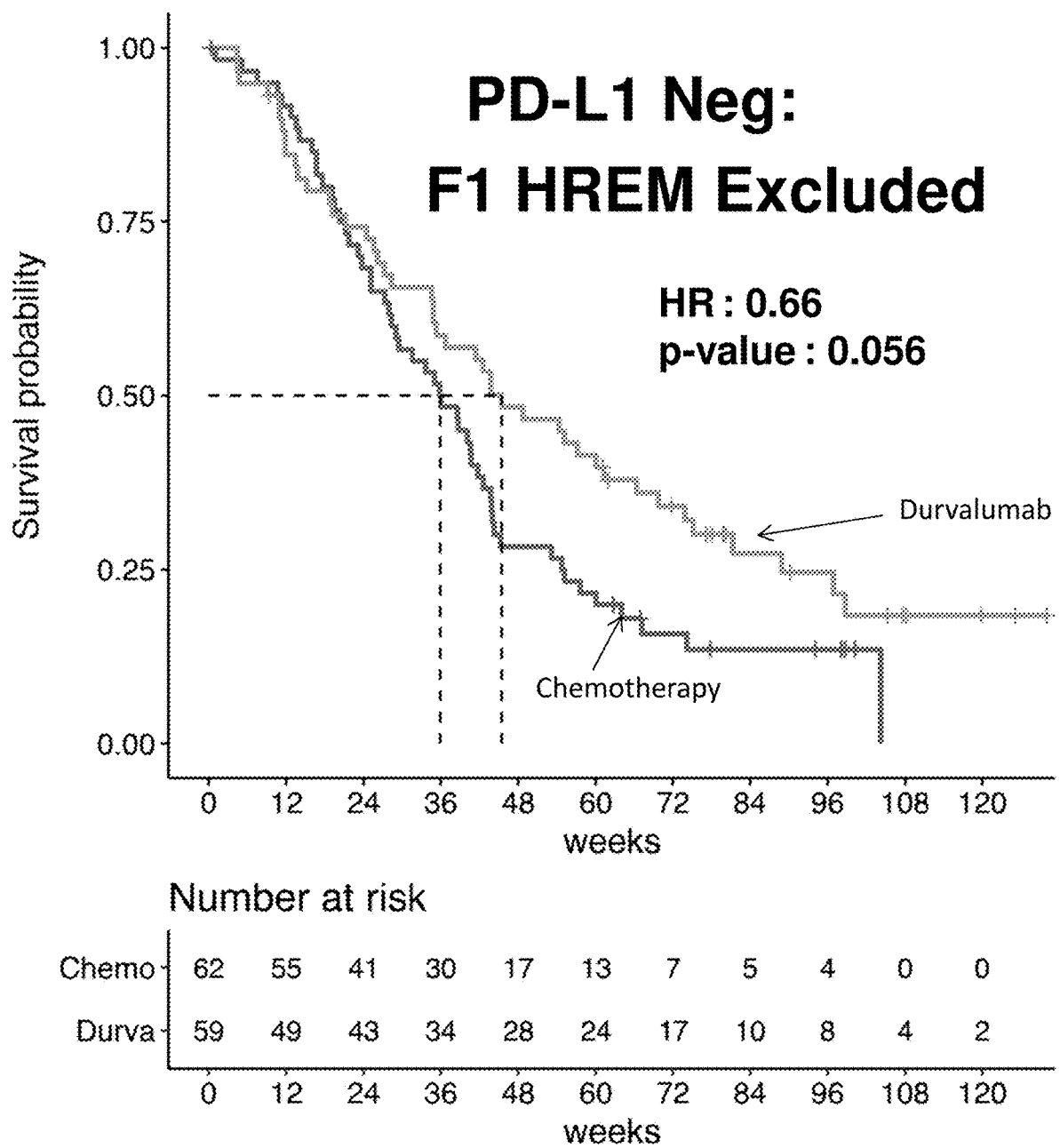

FIG. 35 shows survival probability analysis for PD-L1 negative patients (<1%) with high risk of early mortality excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 36:
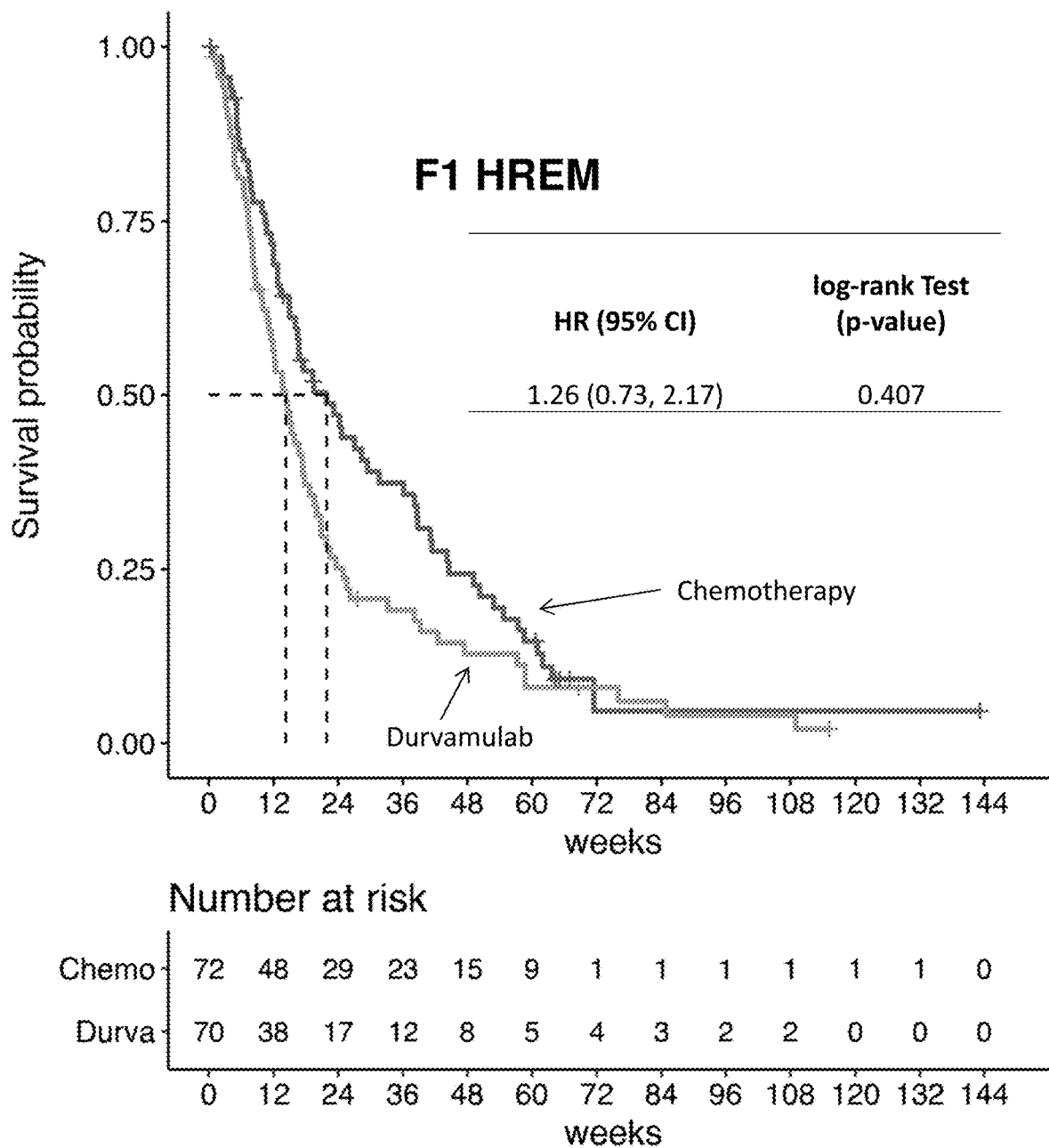

FIG. 36 shows survival probability analysis for patients with high risk of early mortality over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 37:
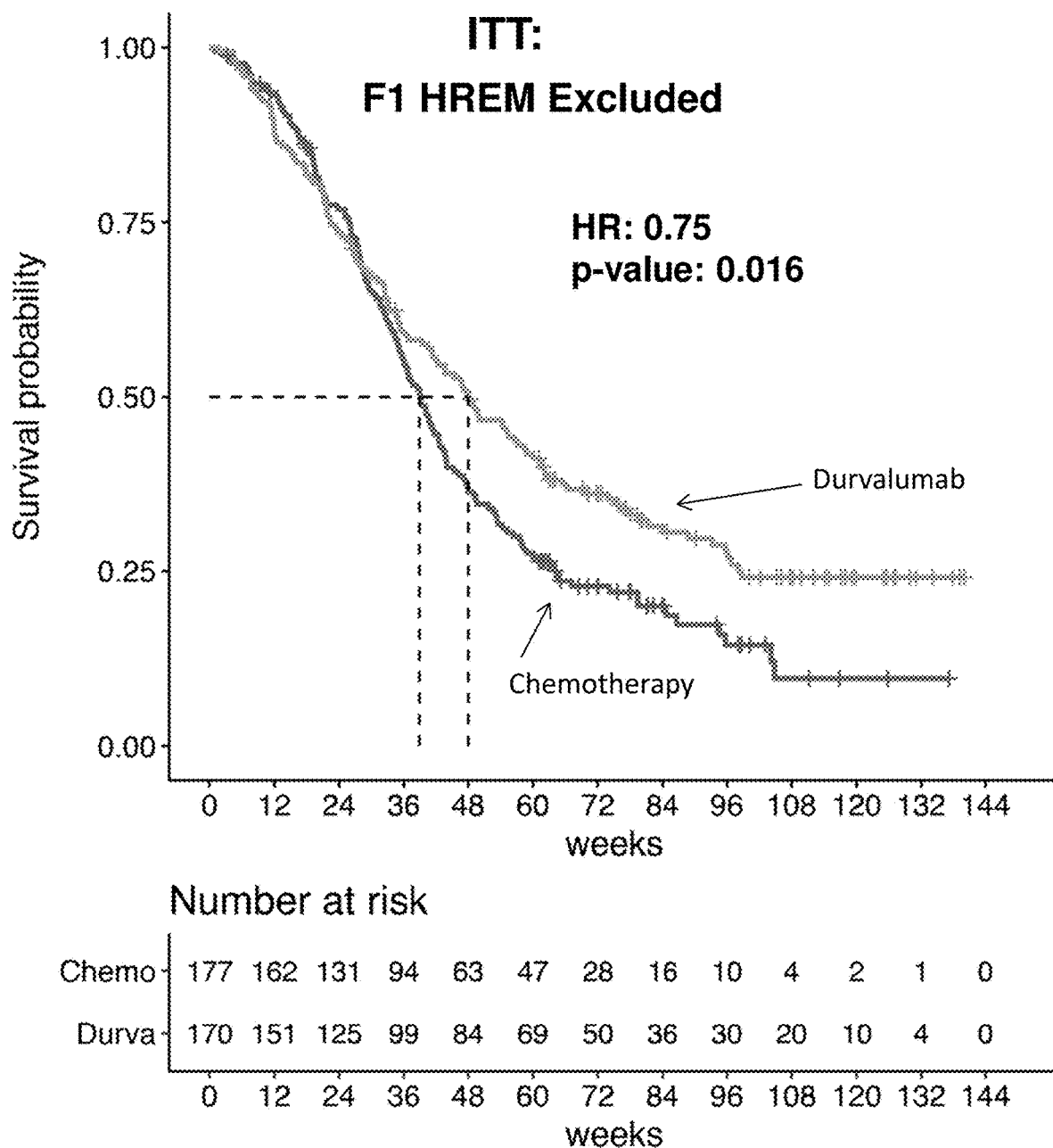

FIG. 37 shows an Intention-to-Treat (ITT) survival probability analysis with patients with high risk of early mortality excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 38:
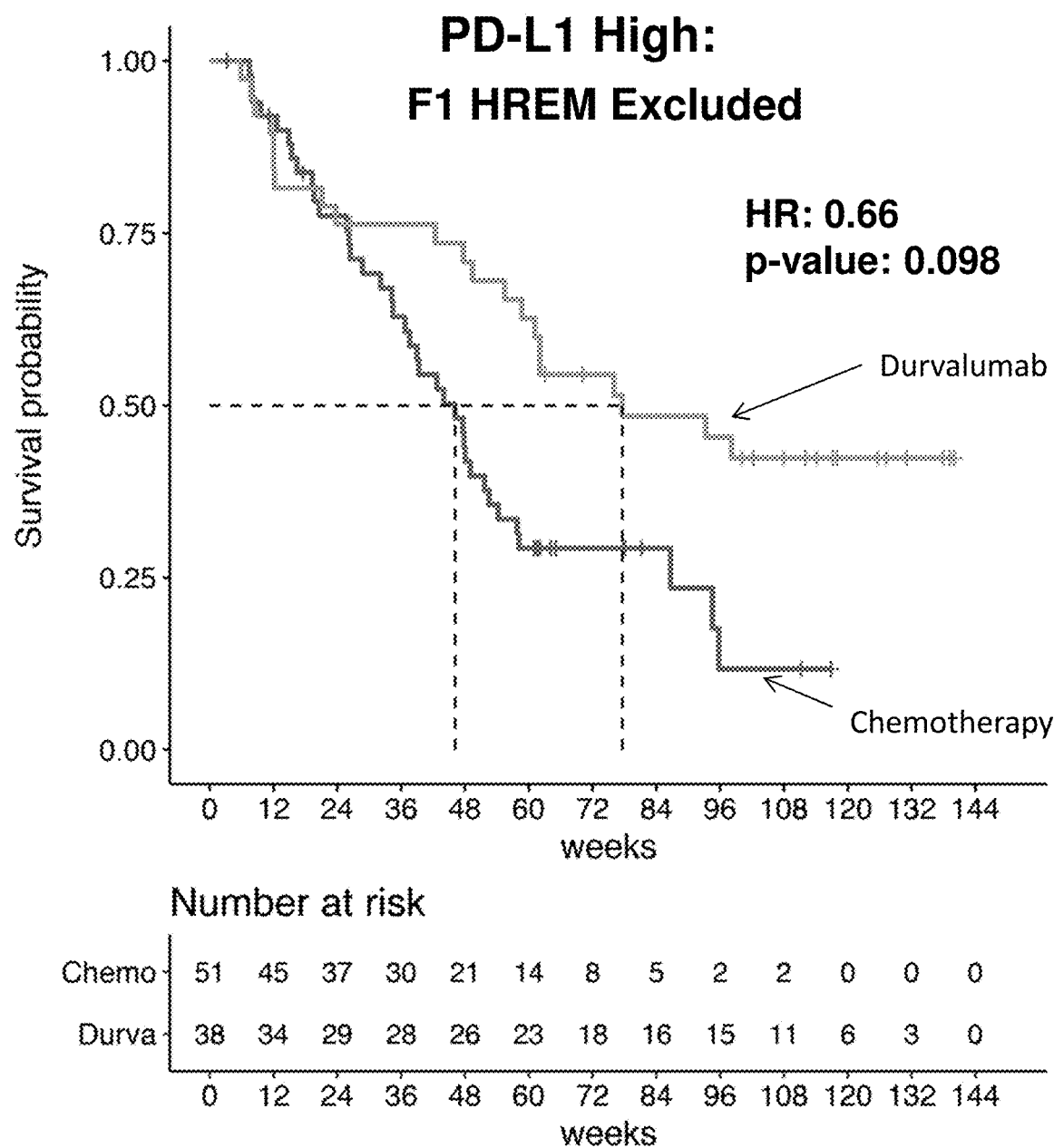

FIG. 38 shows survival probability analysis for PD-L1 high patients (≥25%) with patients with high risk of early mortality excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 39:
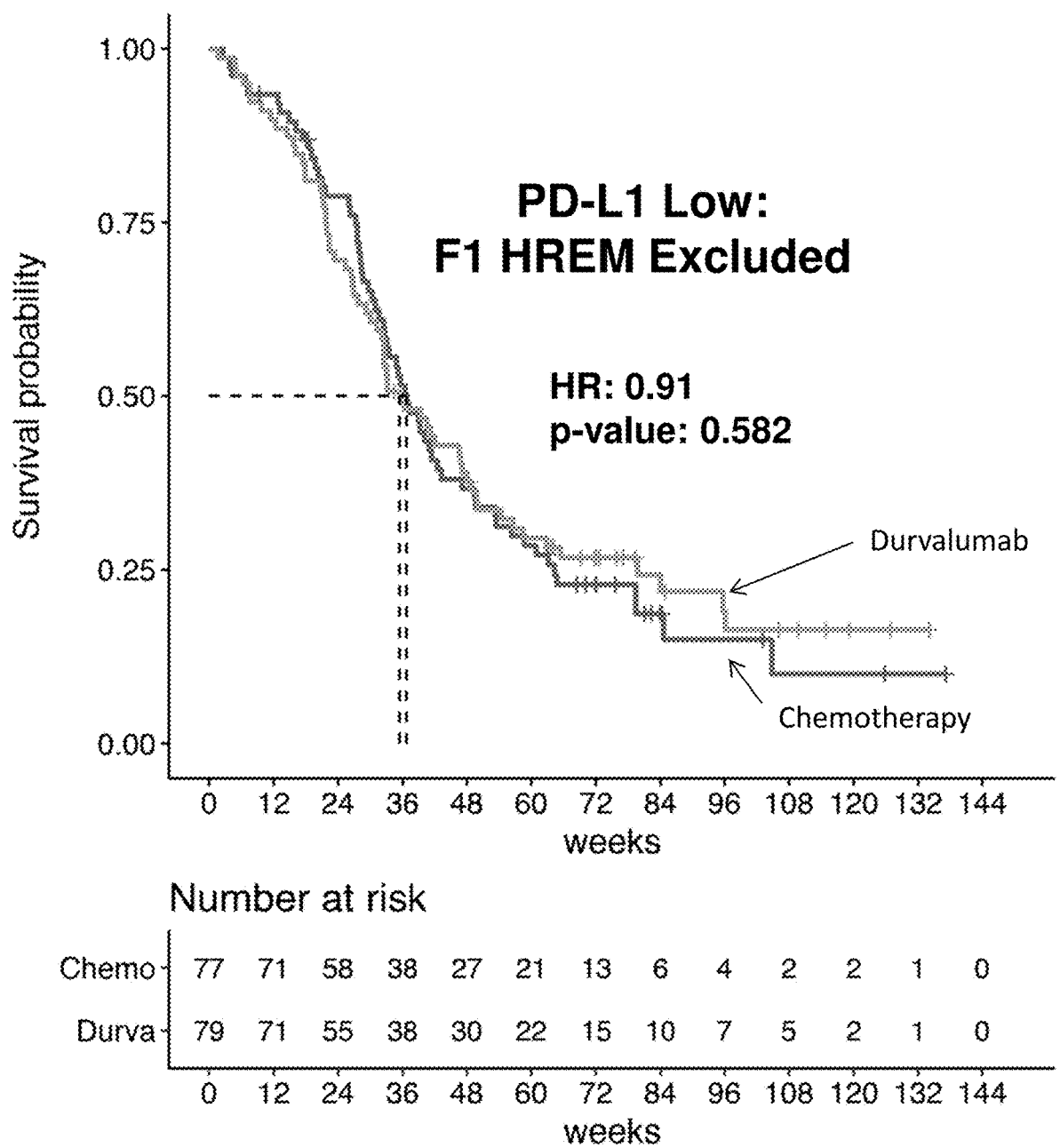

FIG. 39 shows survival probability analysis for PD-L1 low patients (≥1, <25%) with high risk of early mortality excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 40:
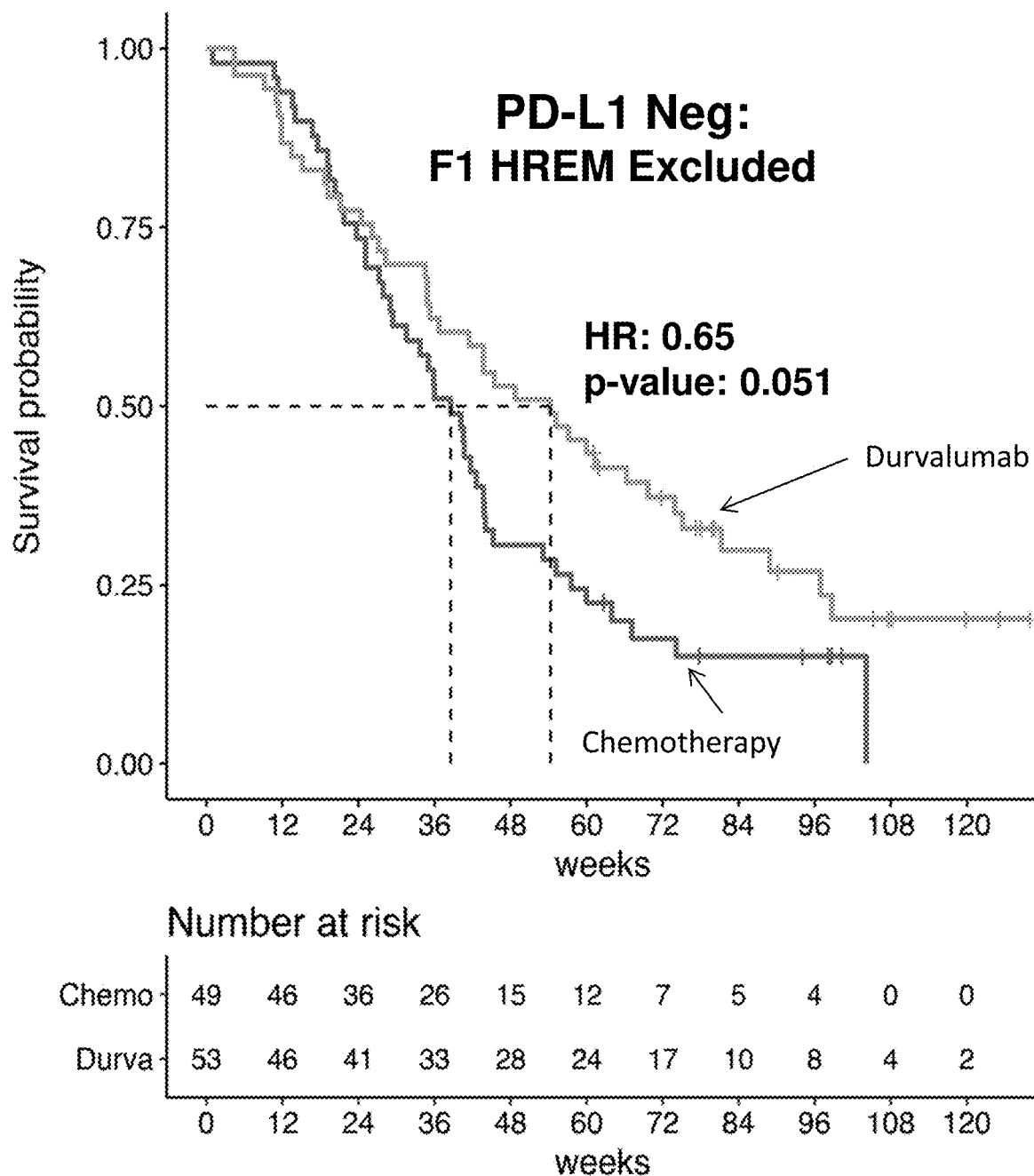

FIG. 40 shows survival probability analysis for PD-L1 negative patients (<1%) with patients with high risk of early mortality excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 41:
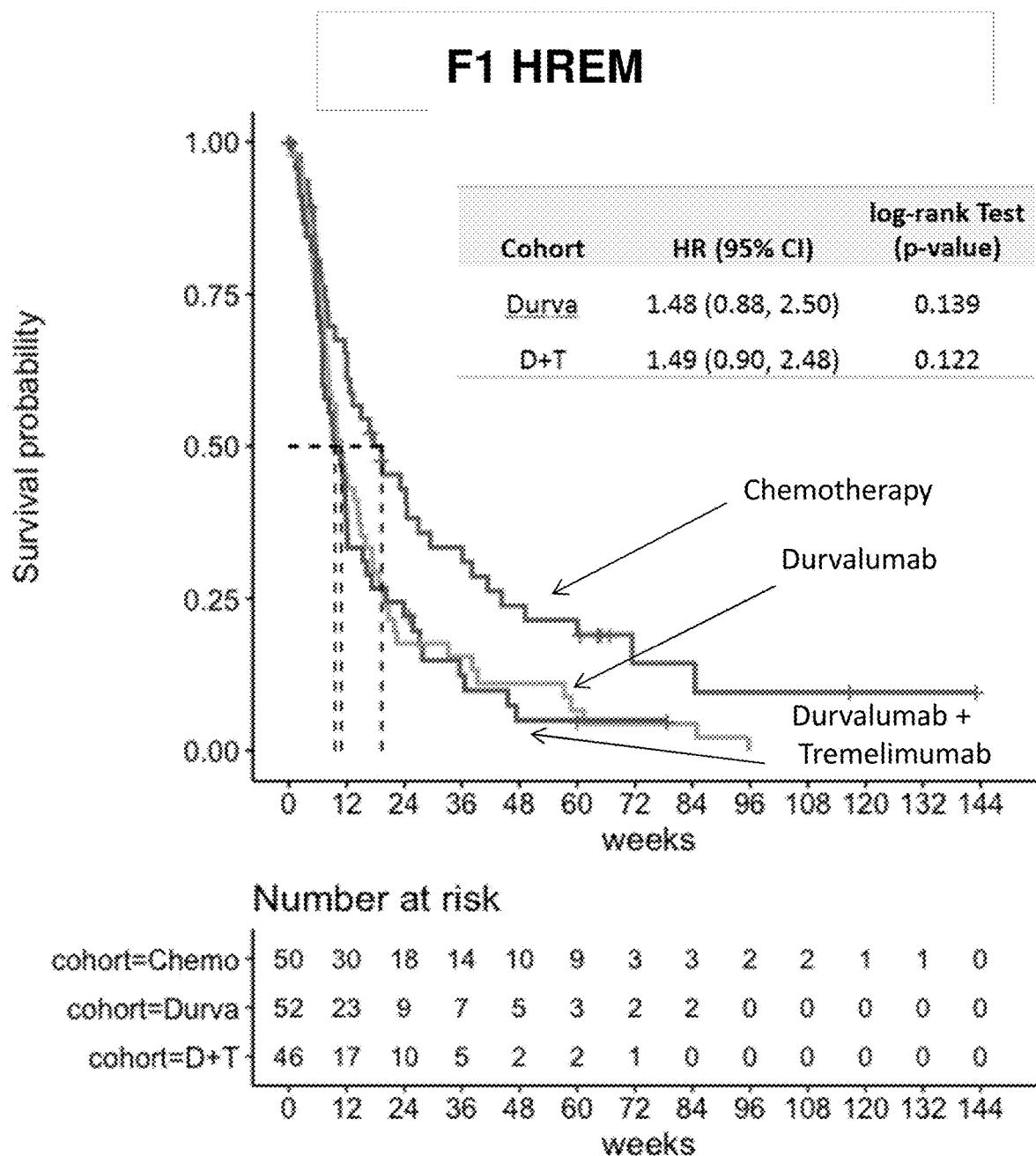

FIG. 41 shows survival probability analysis for patients with high risk of early mortality determined using NLR, NEUT, ALB, LDH, GGT, and AST over a period of 144 weeks (top) and a table of patients at risk over the same period (bottom) for three treatment schemes in the EAGLE study: chemotherapy, durvalumab, and durvalumab+tremelimumab. The hazard ratio (HR) and the p-value for the F1 analysis are also shown.

Figure 42:
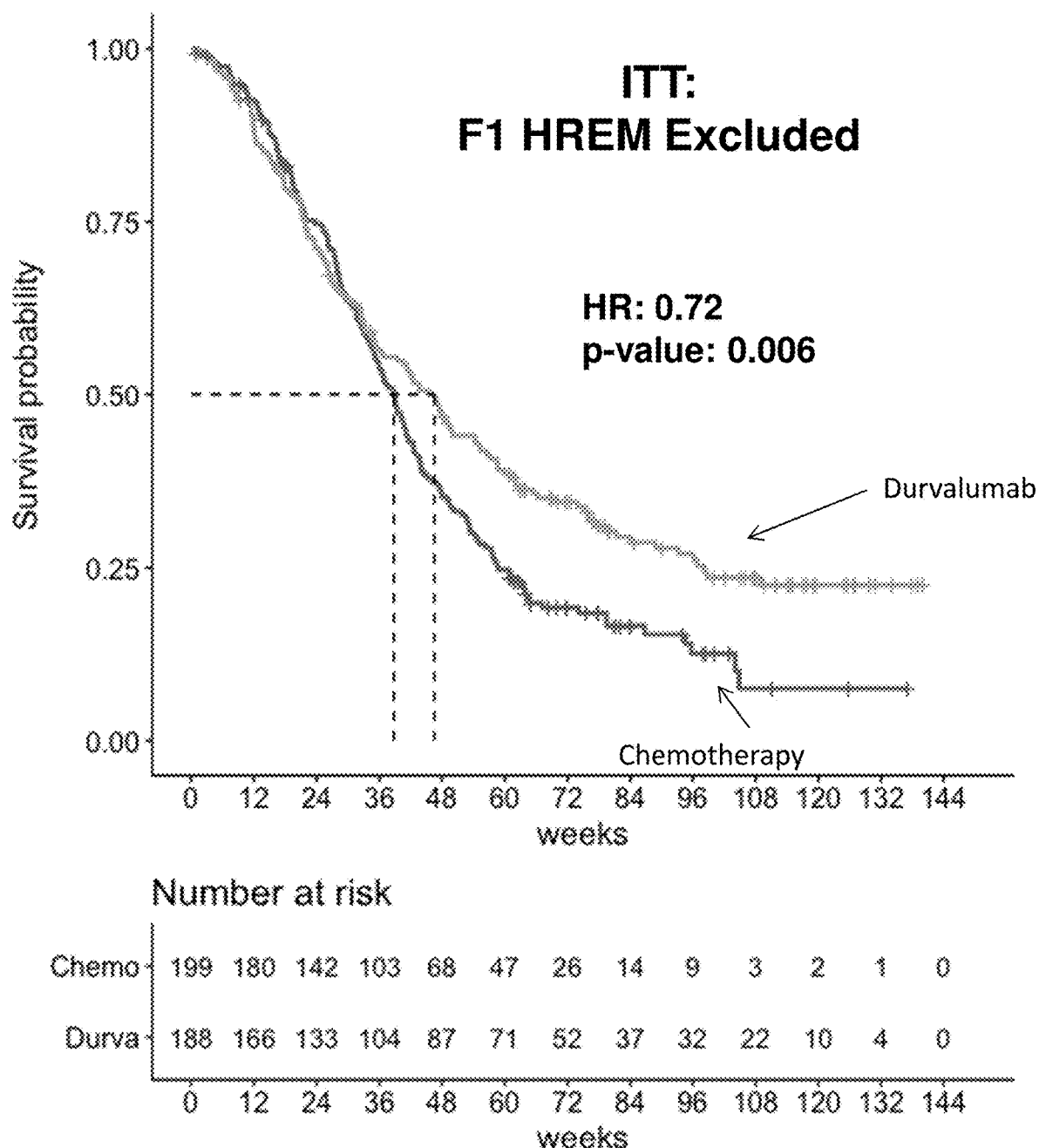

FIG. 42 shows Intention-to-Treat (ITT) survival probability analysis with patients with high risk of early mortality (as determined using NLR, NEUT. ALB, LDH, GGT, and AST) excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 43:
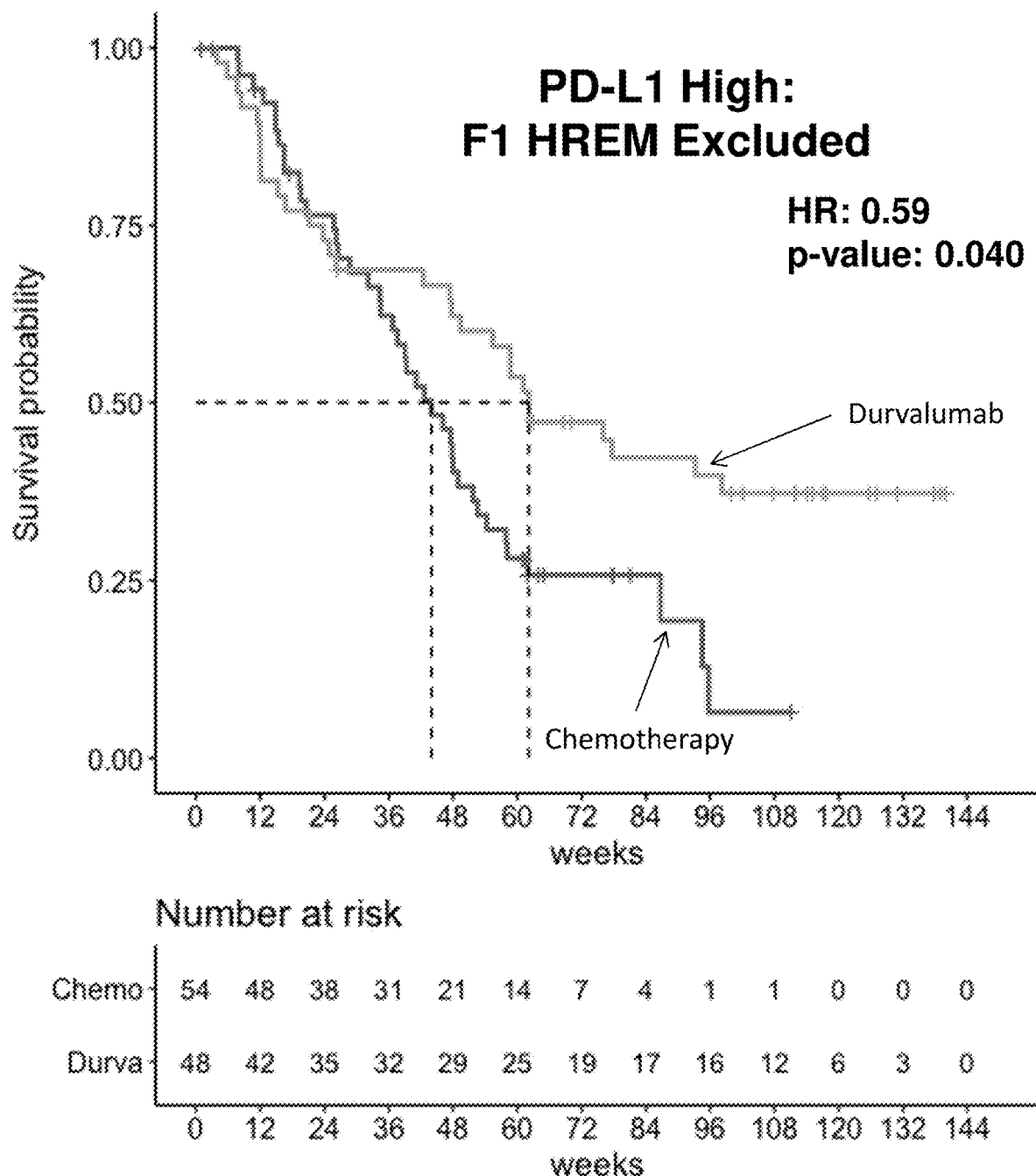

FIG. 43 shows survival probability analysis for PD-L1 high patients (≥25%) with patients with high risk of early mortality (as determined using NLR, NEUT, ALB, LDH, GGT, and AST) excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 44:
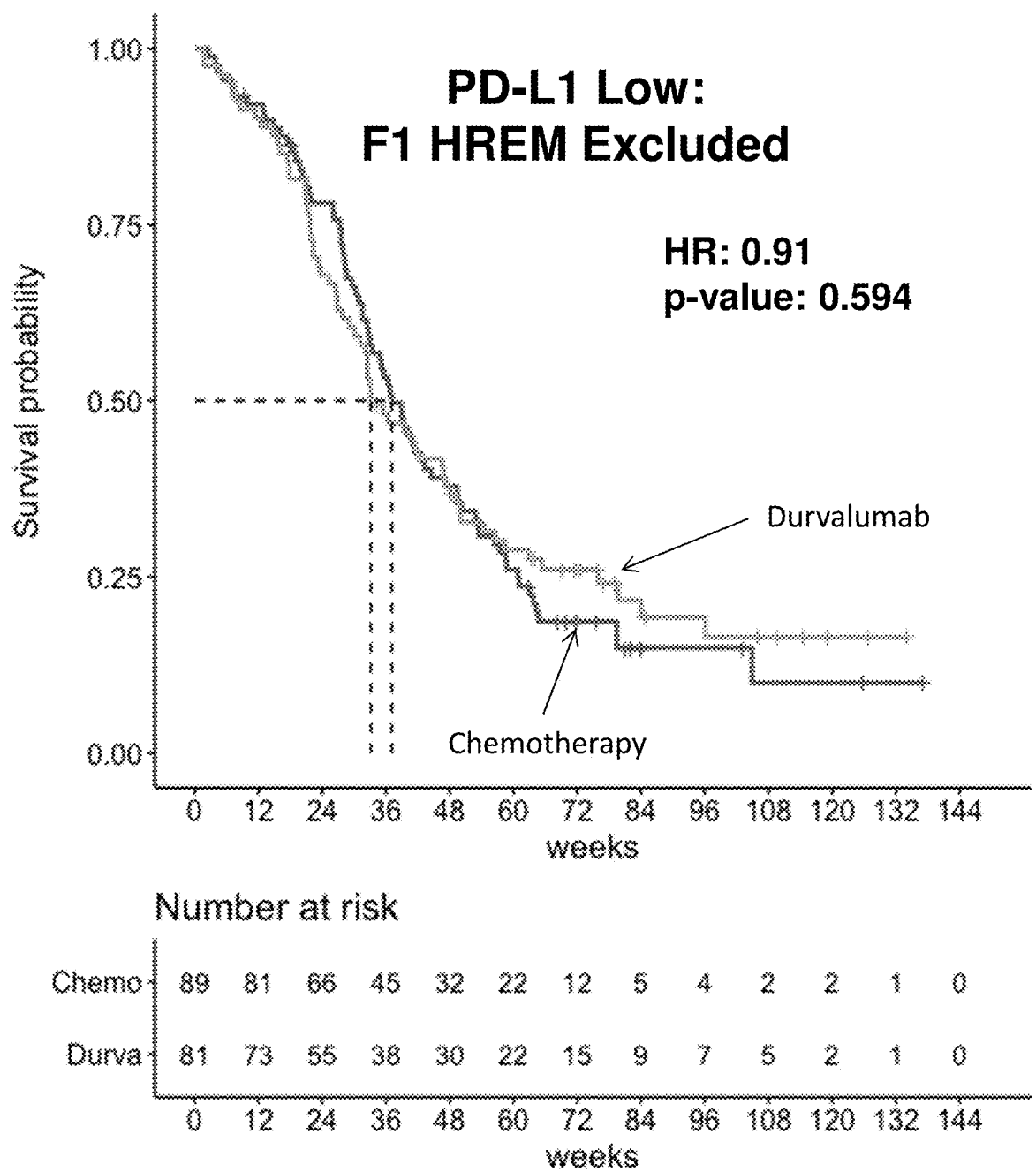

FIG. 44 shows survival probability analysis for PD-L1 low patients (≥1, <25%) with patients with high risk of early mortality (as determined using NLR, NEUT, ALB, LDH, GGT, and AST) excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 45:
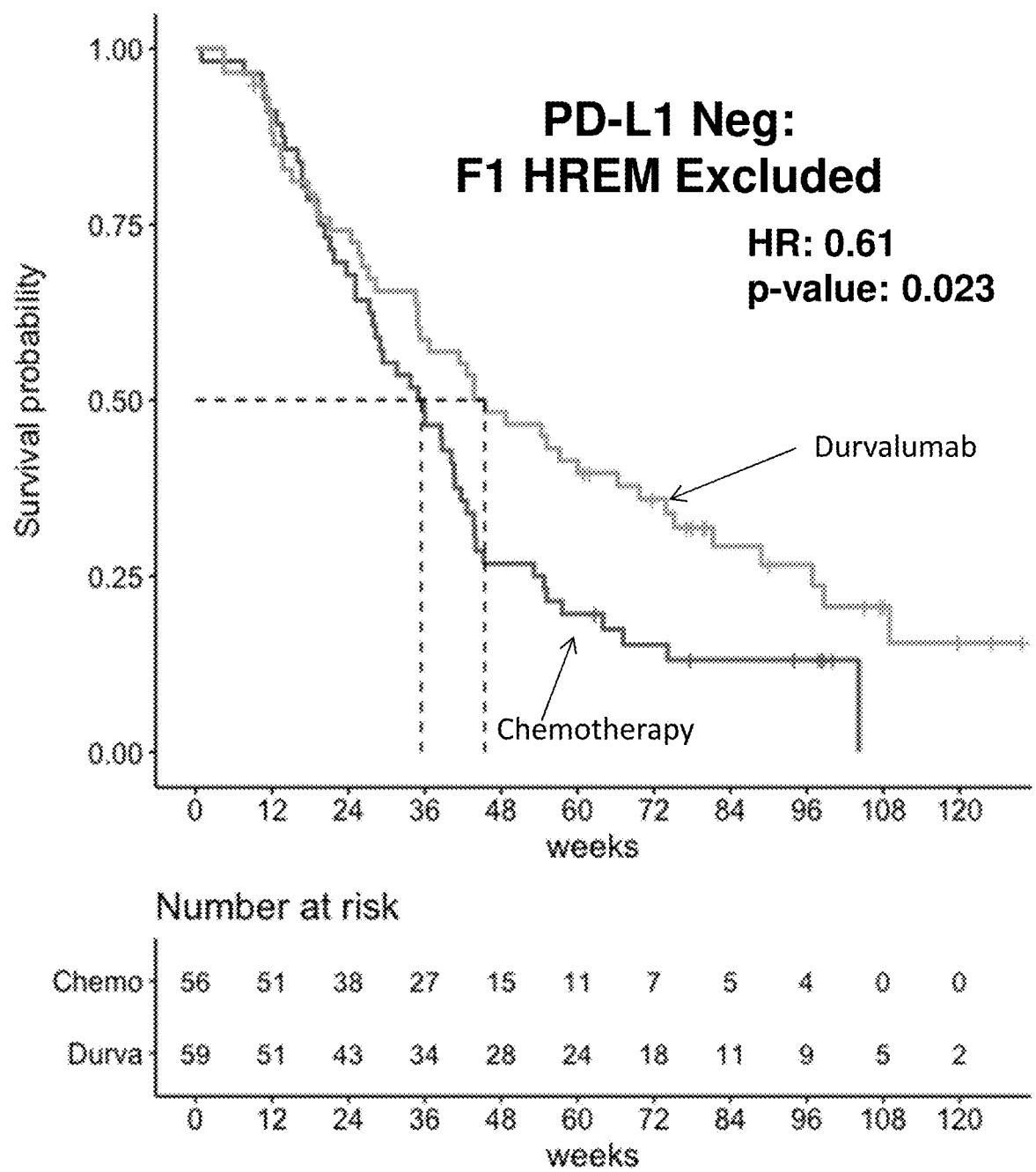

FIG. 45 shows survival probability analysis for PD-L1 negative patients (<1%) with patients with high risk of early mortality (as determined using NLR, NEUT, ALB, LDH, GGT, and AST) excluded over a period of 144 weeks (top) and a table of patients at risk over the same period (bottom) for two treatment schemes in the EAGLE study: chemotherapy and durvalumab. The hazard ratio (HR) and the p-value for the F1 analysis are also shown.

Figure 46:
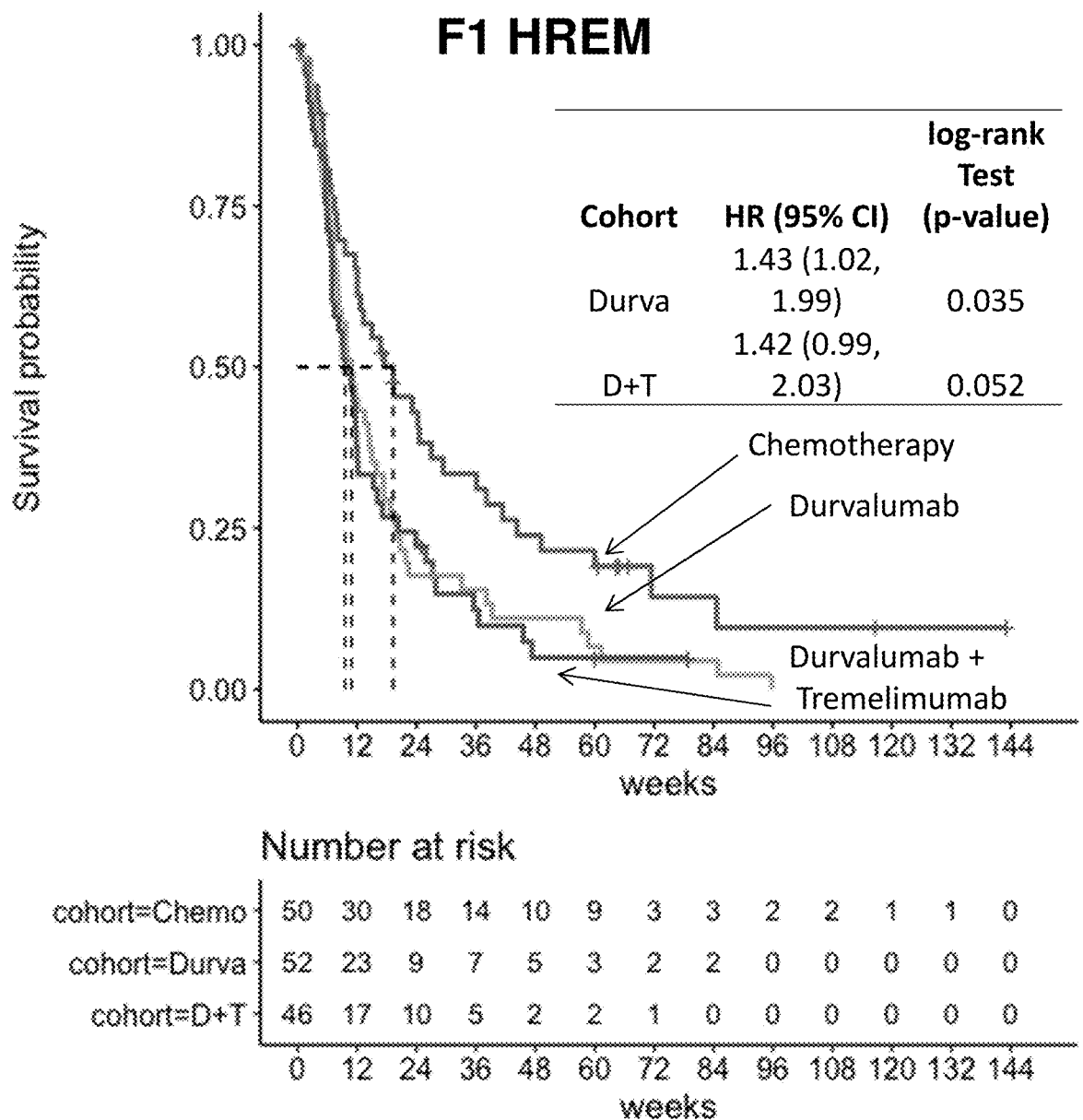

FIG. 46 shows survival probability analysis for patients with high risk of early mortality determined using NLR, NEUT, ALB, LDH, GGT, and AST over a period of 144 weeks (top) and a table of patients at risk over the same period (bottom) for three treatment schemes in the MYSTIC study: chemotherapy, durvalumab, and durvalumab+tremelimumab. The hazard ratio (HR) and the p-value for the F1 analysis are also shown.

Figure 47:
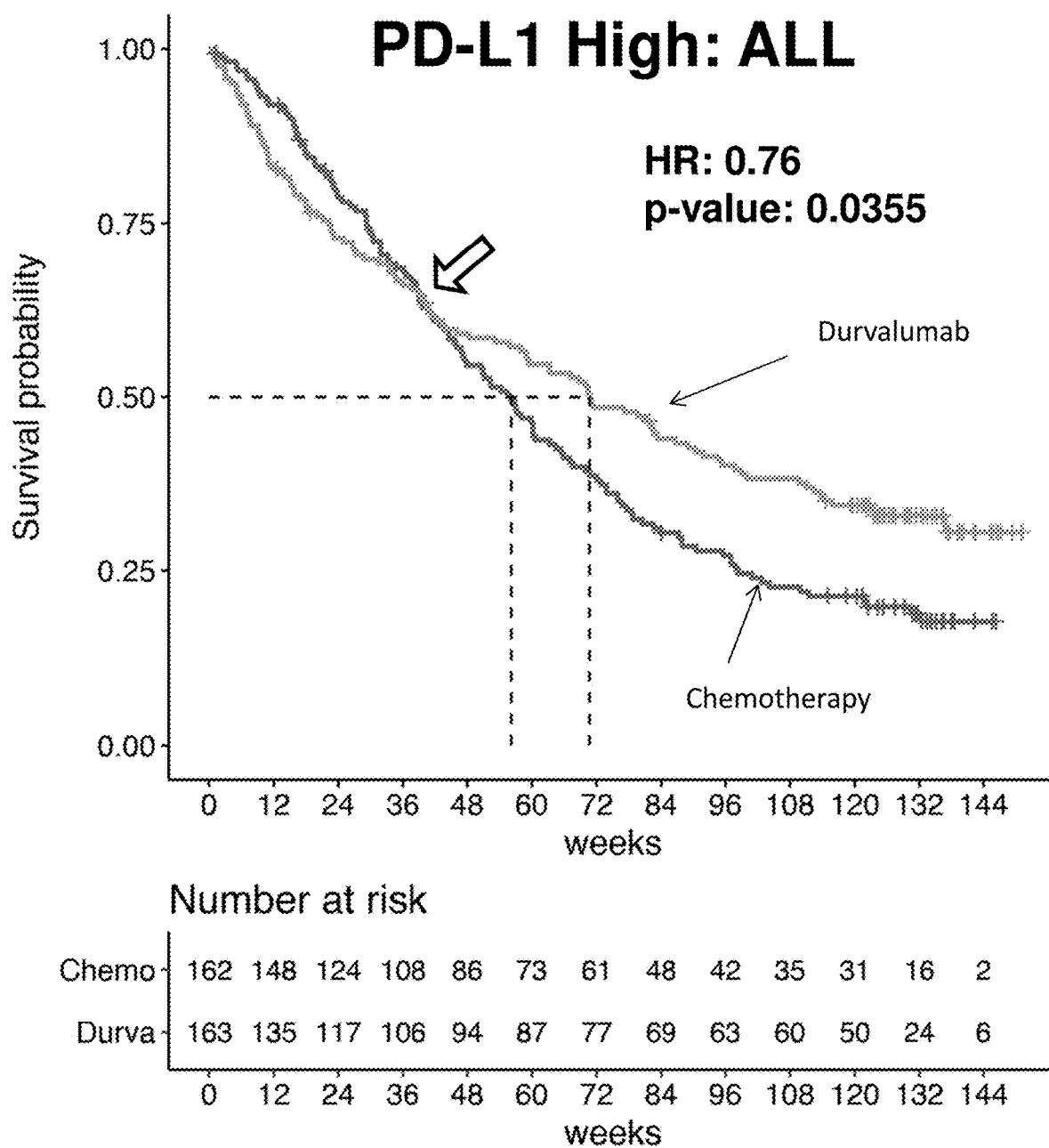

FIG. 47 shows survival probability analysis for PD-L1 high patients (≥25%) over a period of 144 weeks (top) and a table of patients at risk over the same period (bottom) for two treatment schemes in the MYSTIC study: chemotherapy and durvalumab. The hazard ratio (HR) and the p-value for the F1 analysis are also shown. Arrow indicates crossing of Kaplan-Meier (KM) curves.

Figure 48:
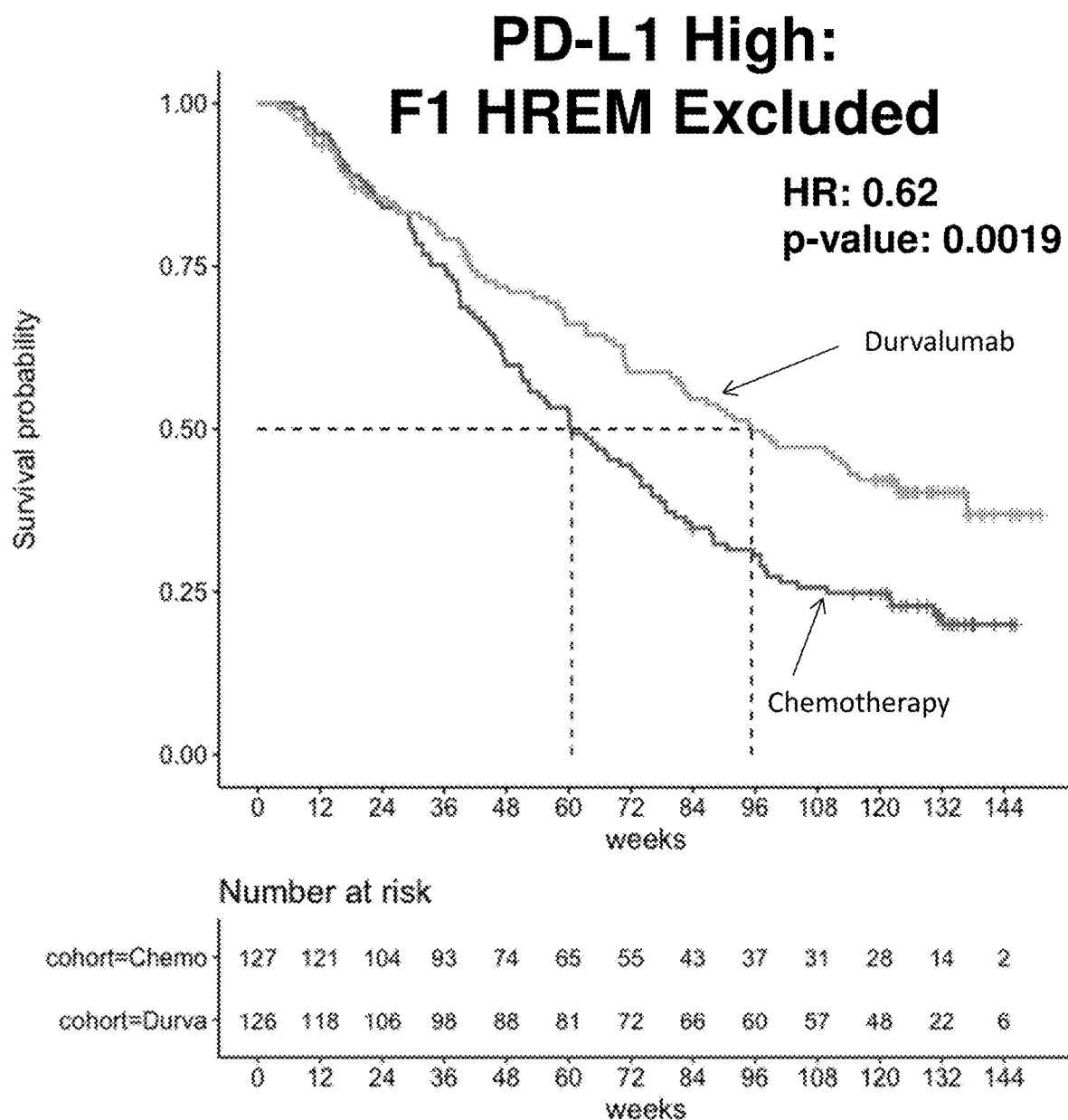

FIG. 48 shows survival probability analysis for PD-L1 high patients (≥25%) with high risk of early mortality (as determined using NLR, NEUT, ALB, LDH, GGT, and AST) excluded over a period of 144 weeks (top) and a table of patients at risk over the same period (bottom) for two treatment schemes in the MYSTIC study: chemotherapy and durvalumab. The hazard ratio (HR) and the p-value for the F1 analysis are also shown.

Figure 49:
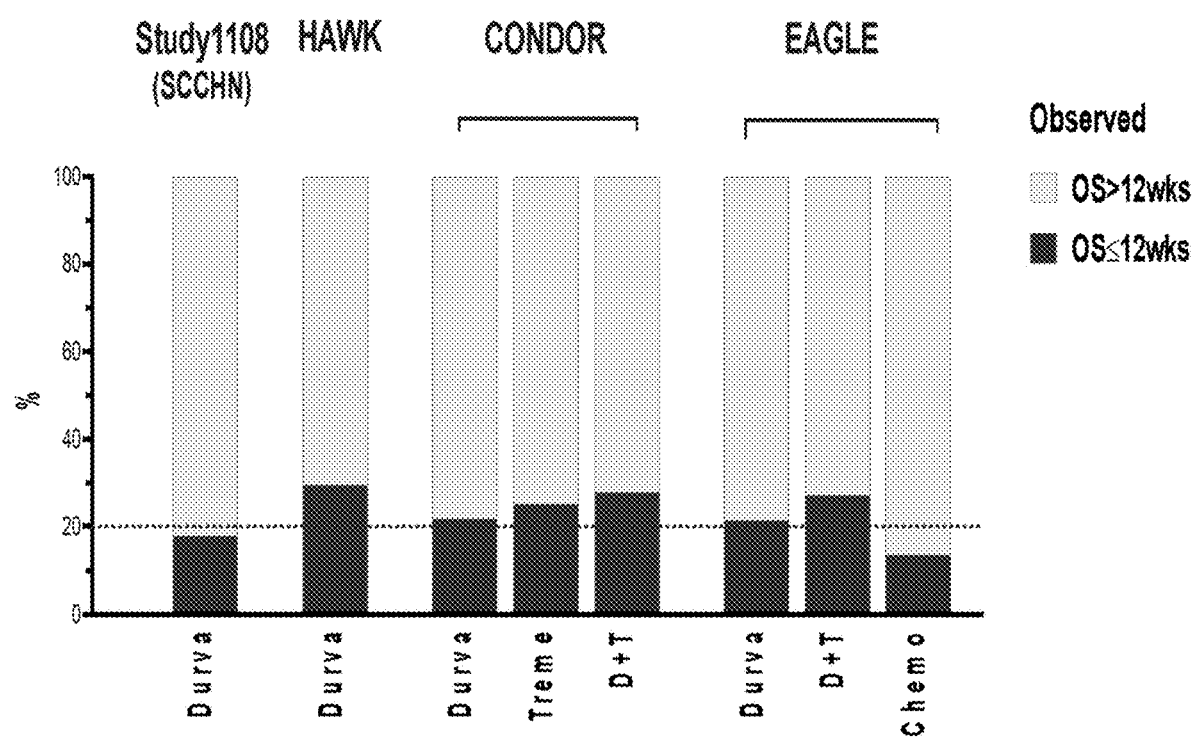

FIG. 49 shows overall survival (OS) in the treatment groups of Study 1108, HAWK, CONDOR, and EAGLE.

Figure 50:
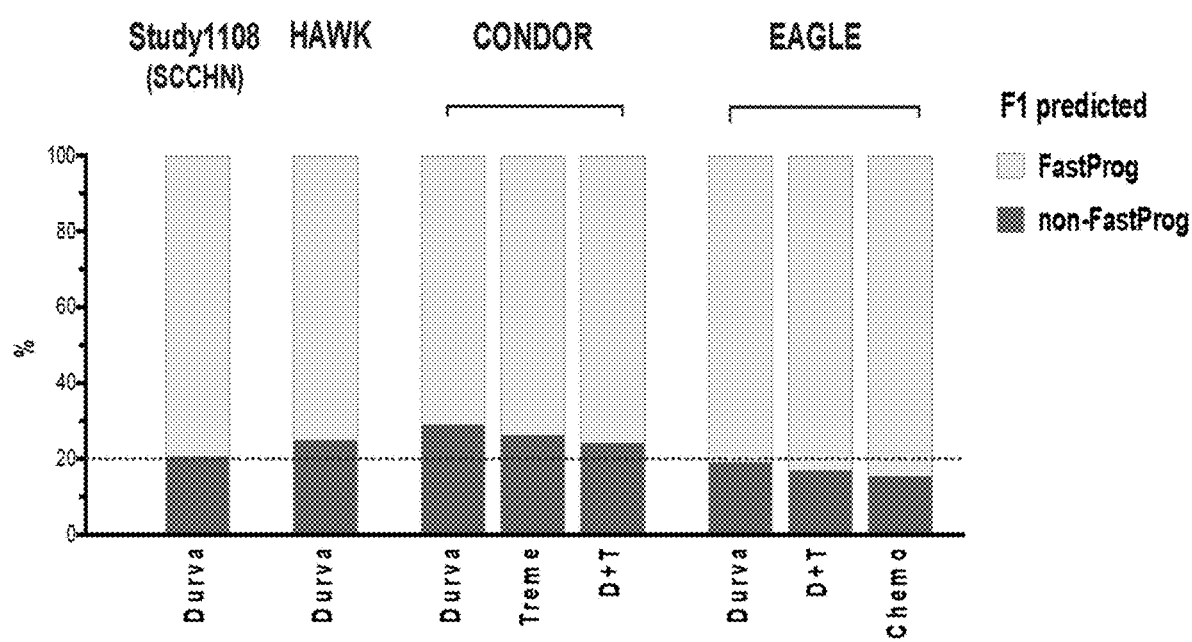

FIG. 50 shows F1-predicted patients with high risk of early mortality (FastProg) and patients without high risk of early mortality (non-FastProg) in the treatment groups of Study 1108, HAWK, CONDOR, and EAGLE.

Figure 51:
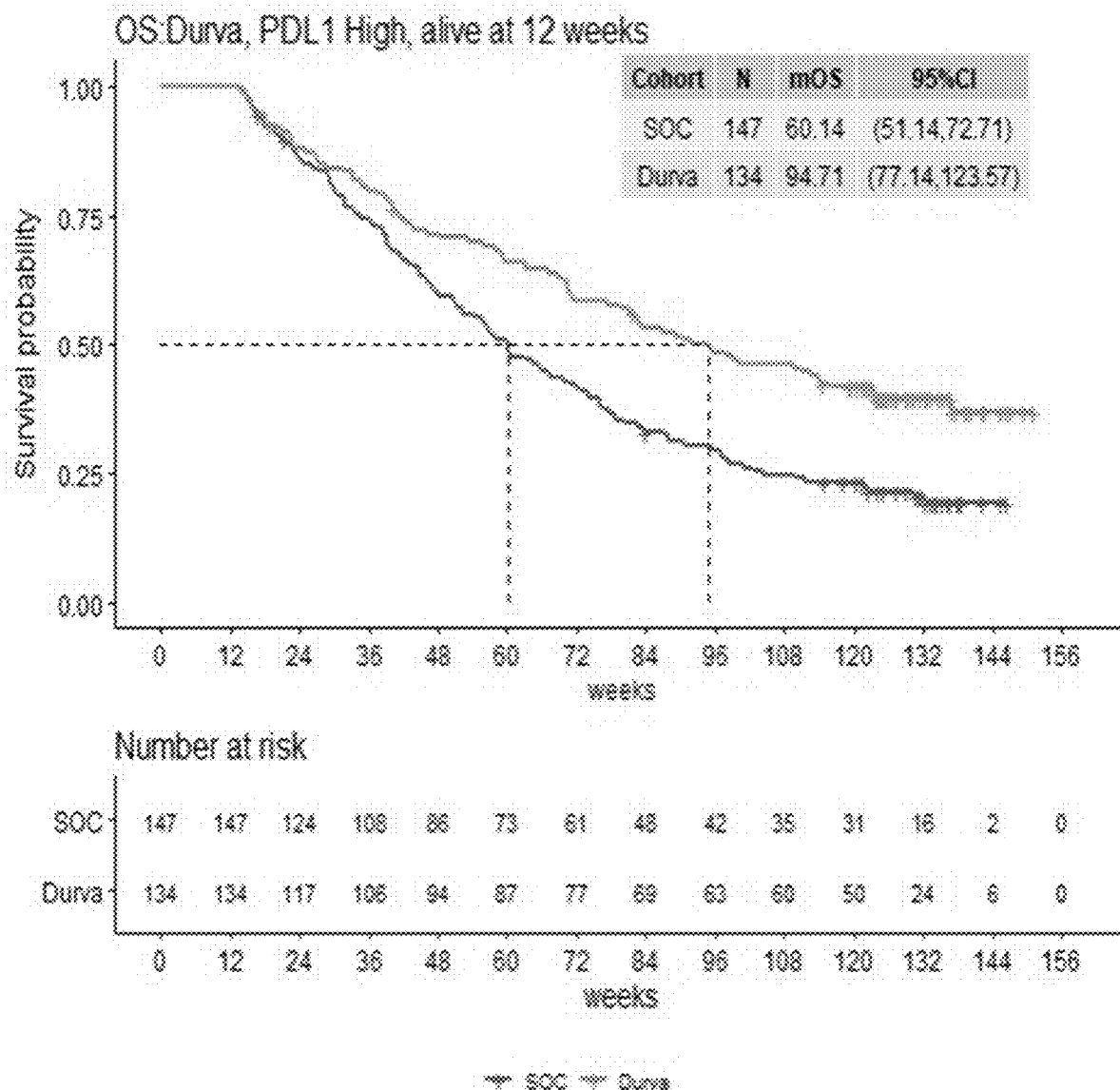

FIG. 51 shows Kaplan-Meier estimate of overall for PD-L1 positive patients alive at 12 weeks.

Figure 52:
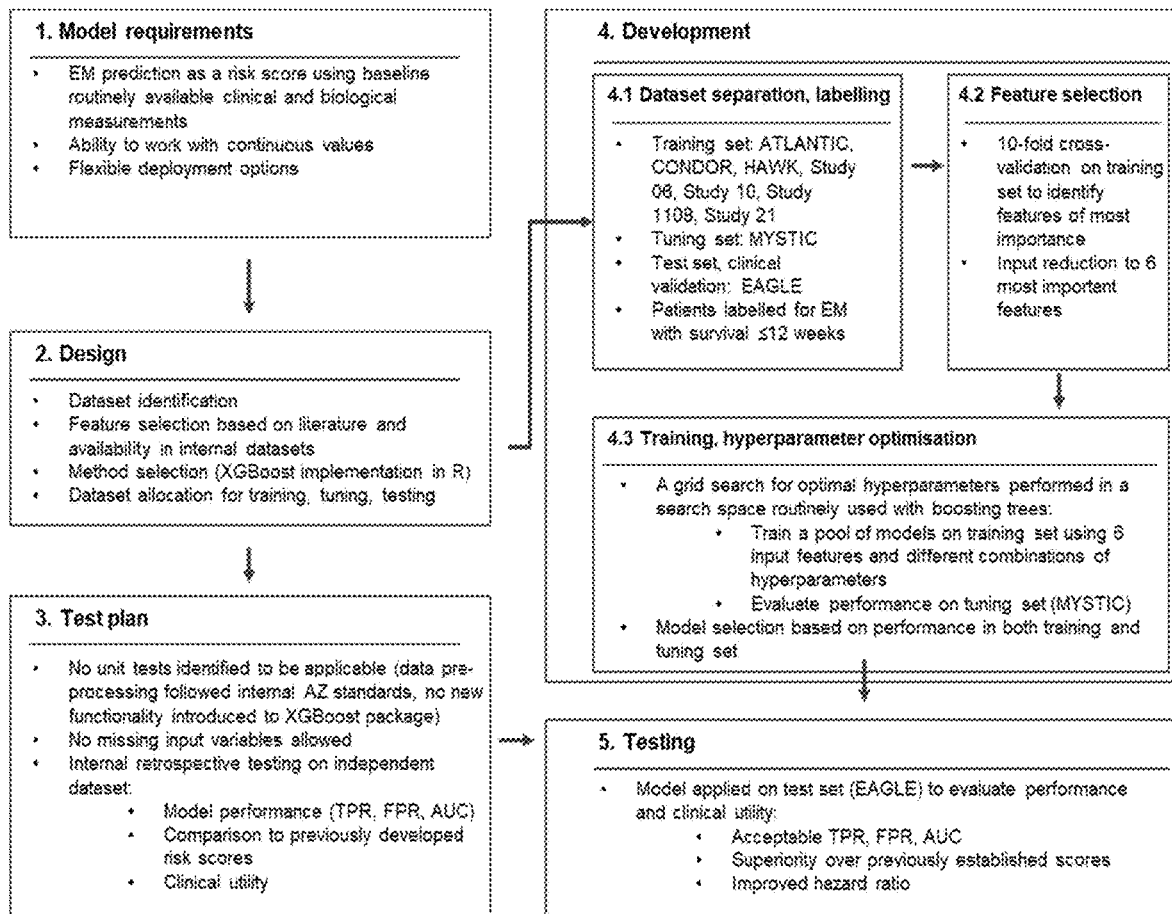
Figure 53:
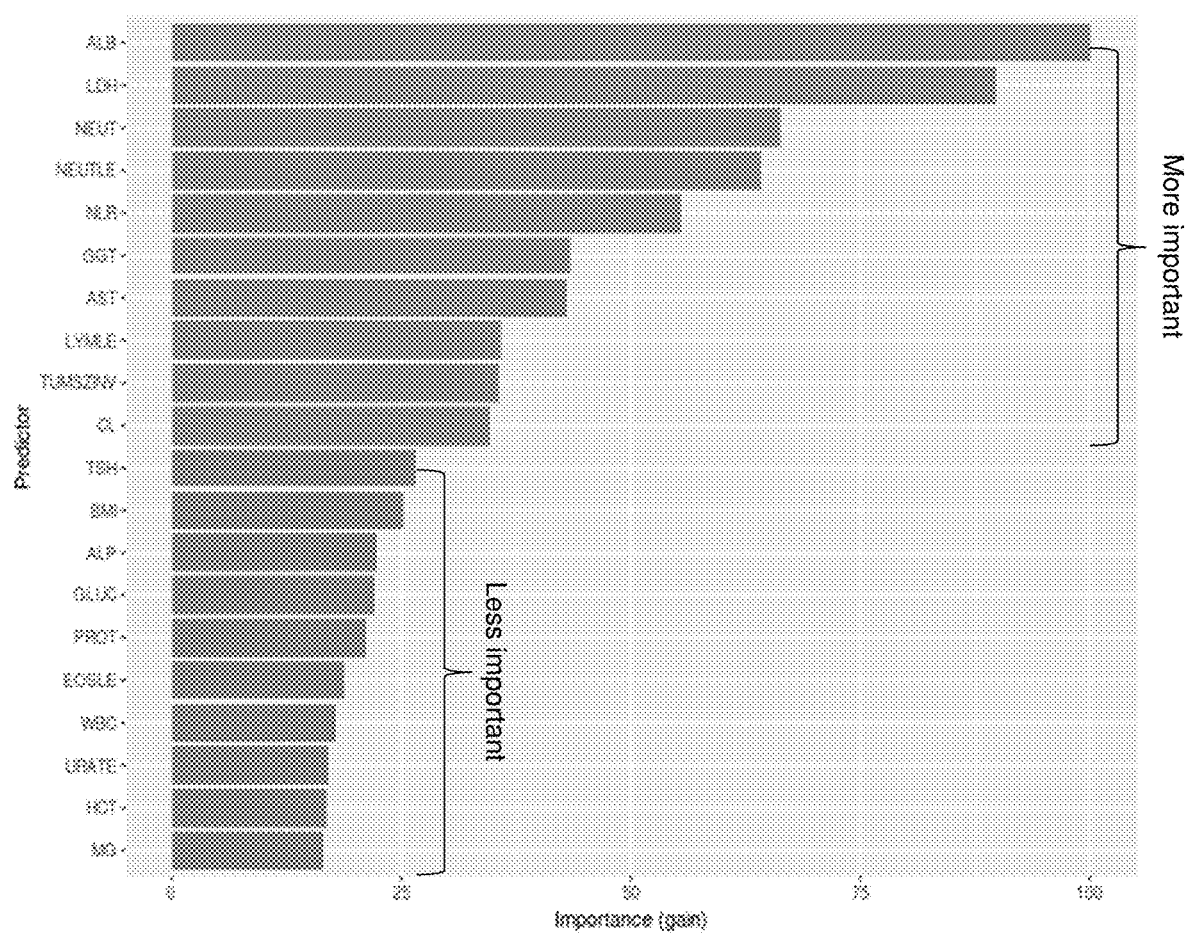

FIG. 52 shows the Immune Immediacy Index (3i) score development workflow. Model Requirements (1) were defined to address current challenges in predicting early mortality. Design (2) choices were made to conform with model requirements in dataset, feature and method selection. Test plan (3) was prepared to evaluate model performance according to globally accepted machine learning practices and to mitigate any risks associated with open source packages in use. Development (4) followed globally accepted principles of dataset separation, k-fold cross-validation during model training, hyperparameter optimization and testing (5) on an independent dataset FIG. 53 shows the quantification of variable importance in feature selection. A gradient boosting model was fitted using a set of variables to predict the 12-week life expectancy. The first 20 variables with the highest importance values are plotted. K-means clustering method was used to cluster variables to more important and less important groups. Abbreviations: ALB=albumin; ALP=alkaline phosphatases; AST=aspartate amino transferase; BMI=body mass index; CL=chloride; EOSLE=eosinophil/leukocyte ratio; GGT=gamma-glutamyl transferase; GLUC=glucose; HCT=haematocrit; LDH=lactate dehydrogenase; LYMLE=lymphocyte/leukocyte ratio; MG=magnesium; NEUT=neutrophils; NEUTLE=neutrophil/leukocyte ratio; NLR=neutrophil/lymphocyte ratio; PROT=protein; TSH=thyrotropin; TUMSZINV=tumor size; URATE=uric acid; WBC=leukocytes.

Figure 54:
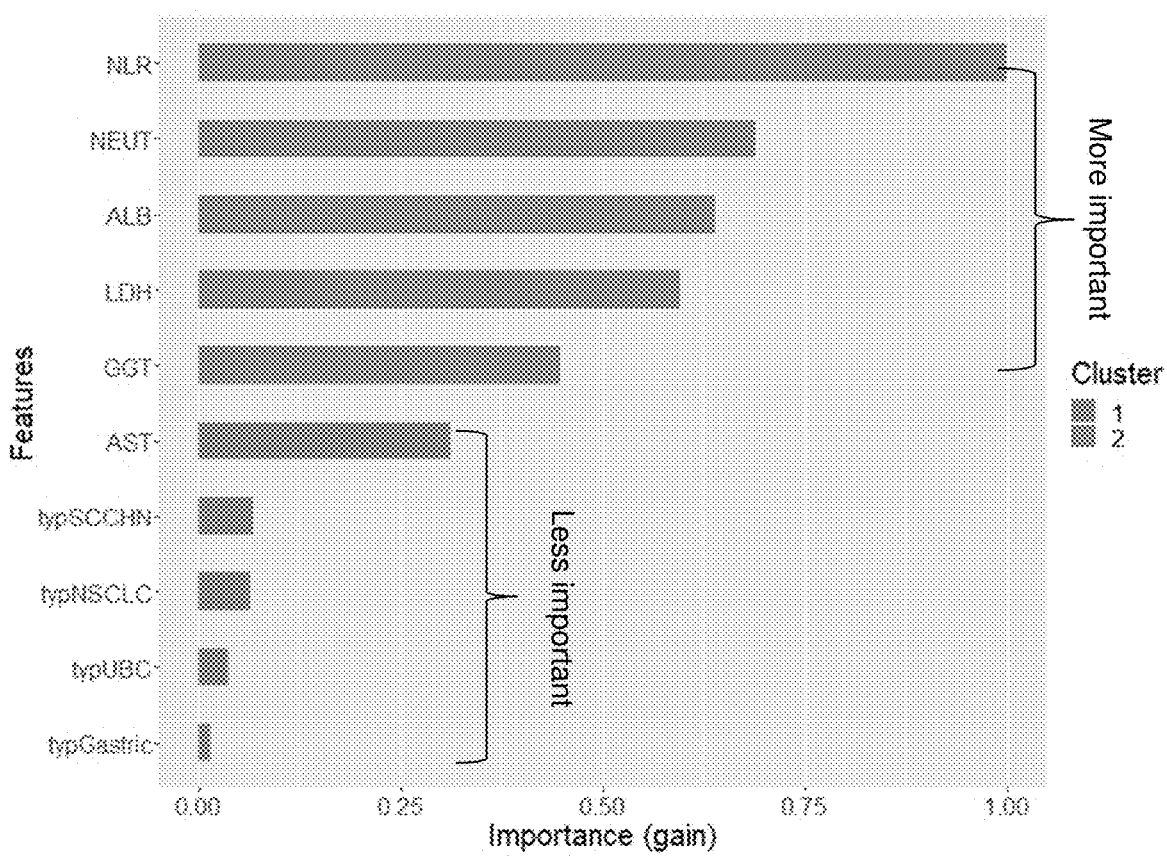

FIG. 54 shows quantification of Immune Immediacy Index (3i) score variable importance in the final 3i score model. K-means clustering method was used to cluster variables to more important and less important groups. Abbreviations: ALB=albumin; AST=aspartate amino transferase; GGT=gamma glutamyl transferase; LDH=lactate dehydrogenase; NEUT=neutrophils; NLR=neutrophil/lymphocyte ratio; NSCLC=non-small cell lung cancer; SCCHN=squamous cell cancer of the head and neck; UBC=urothelial bladder cancer.

Figure 55:
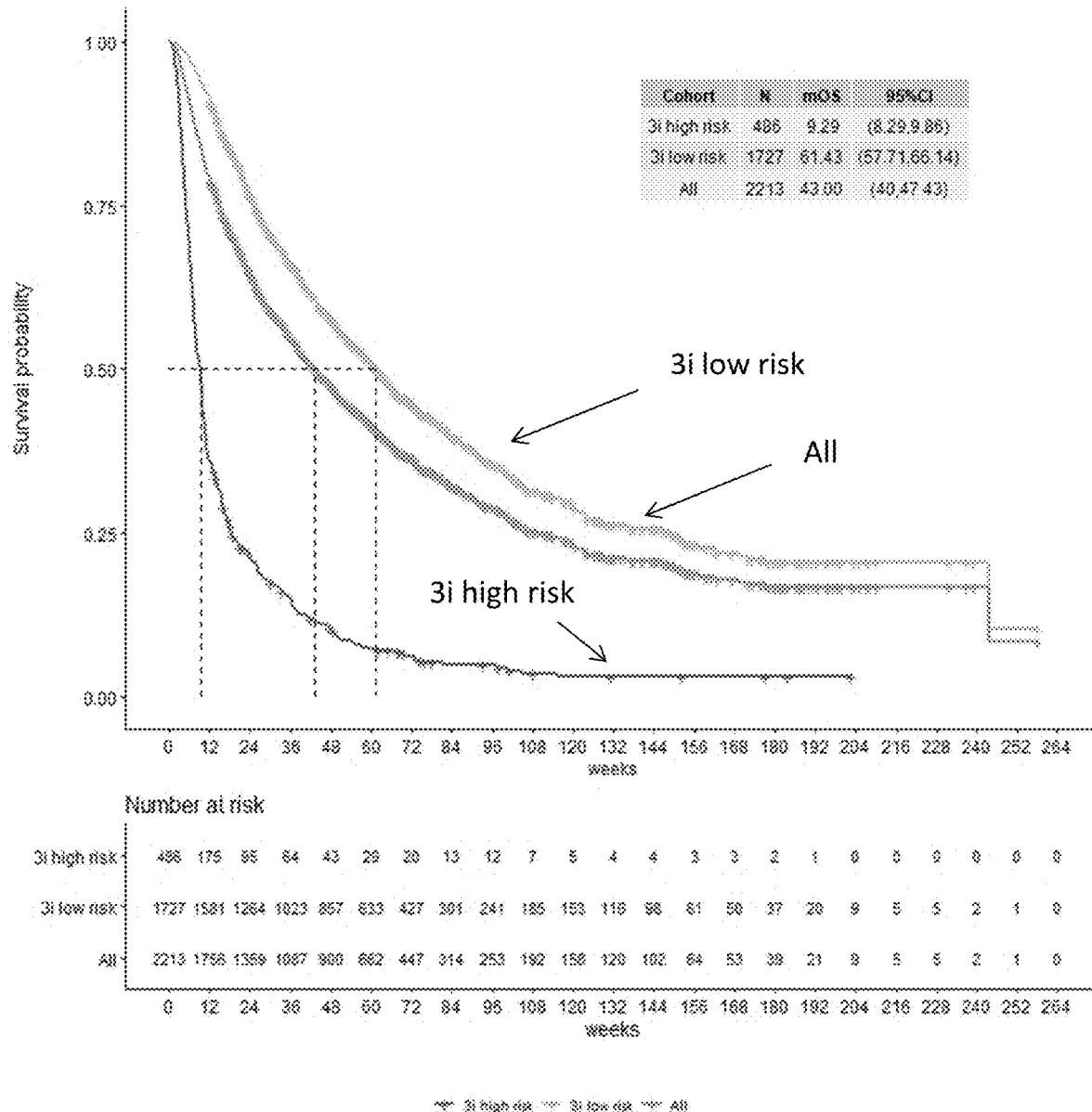

FIG. 55 shows the overall survival according to the 3i score in the training set. Total n=2213; comprising Study 1108 (all solid tumors, n=923), Study 06 (non-small cell lung cancer, n=353), Study 10 (urothelial bladder cancer, n=164), Study 21 (gastric, n=98), ATLANTIC (non-small cell lung cancer, n=371), CONDOR (squamous cell carcinoma of the head and neck, n=193), and HAWK (squamous cell carcinoma of the head and neck, n=111).

Figure 56:
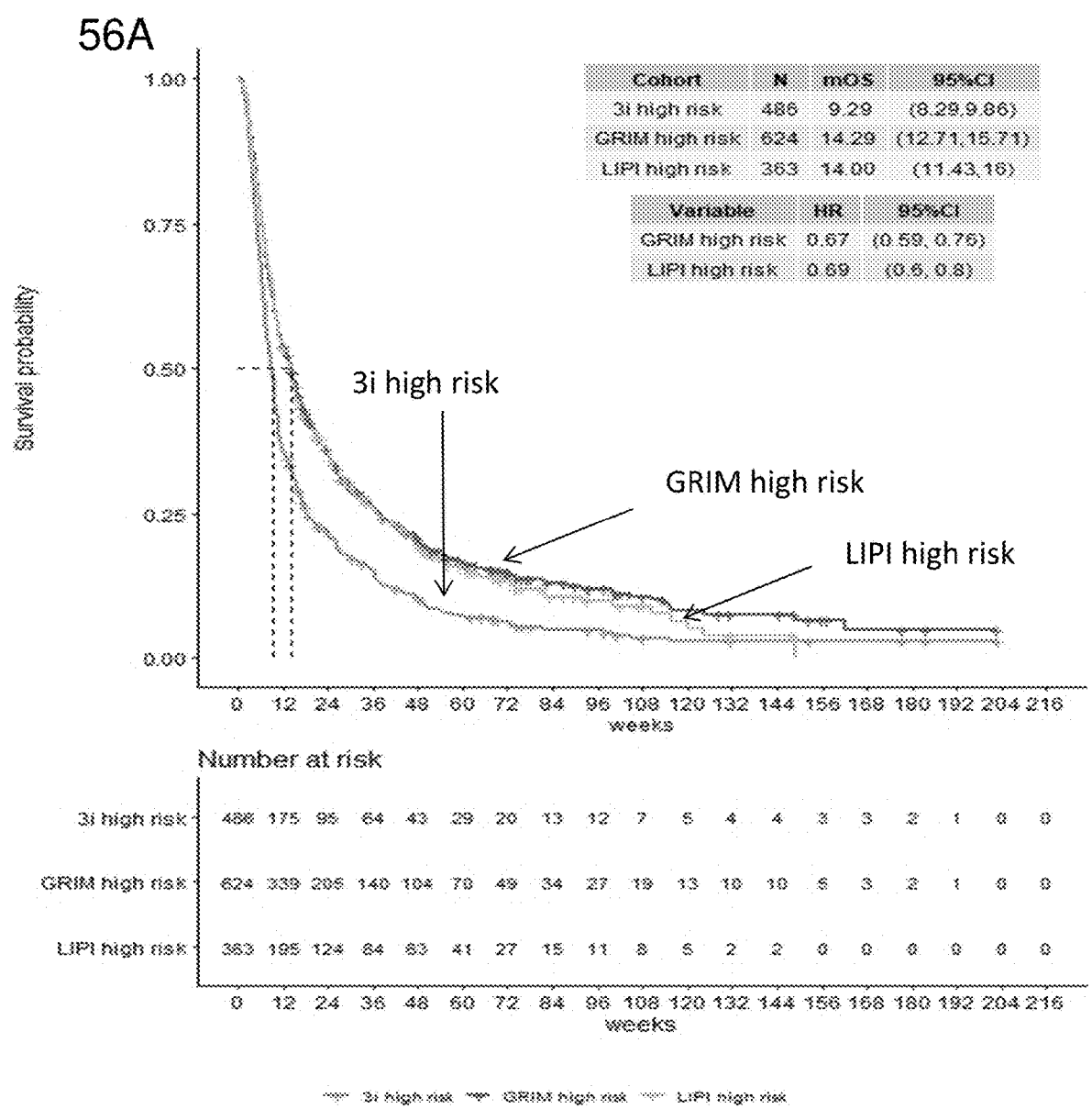
Figure 56:
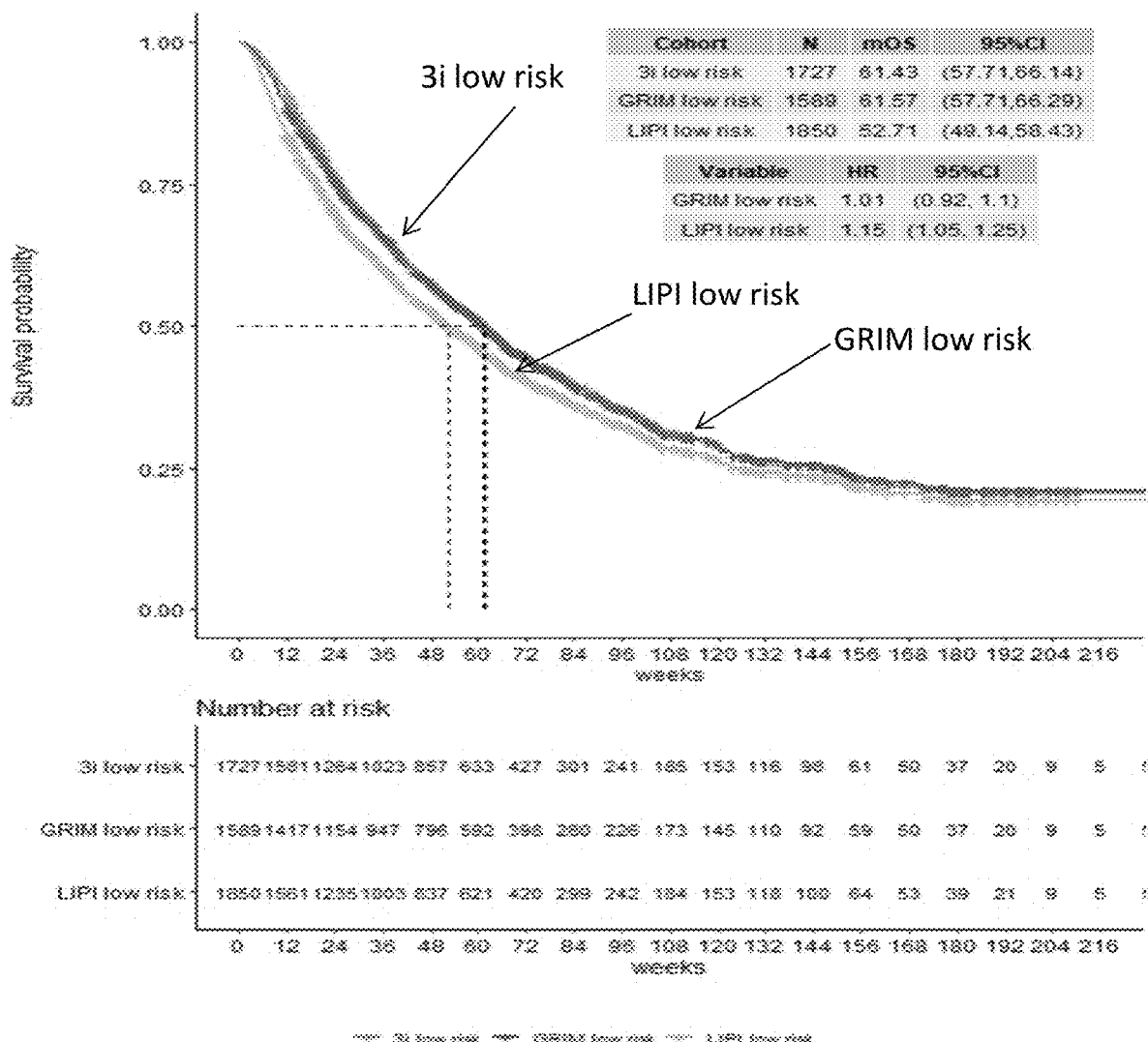

FIGS. 56A and 56B show overall survival by 3i score, GRIM, and LIPI models in the entire training set. Total n=2213; comprising Study 1108 (all solid tumors, n=923), Study 06 (non-small cell lung cancer, n=353), Study 10 (urothelial bladder cancer, n=164), Study 21 (gastric, n=98), ATLANTIC (non-small cell lung cancer, n=371), CONDOR (squamous cell carcinoma of the head and neck, n=193), and HAWK (squamous cell carcinoma of the head and neck, n=111). Left panel: Kaplan-Meier curve of patients identified as high risk using 3i score, GRIM, or LIPI. Right panel: Kaplan-Meier curve of patients identified as low risk using 3i score, GRIM, or LIPI.

Figure 57:
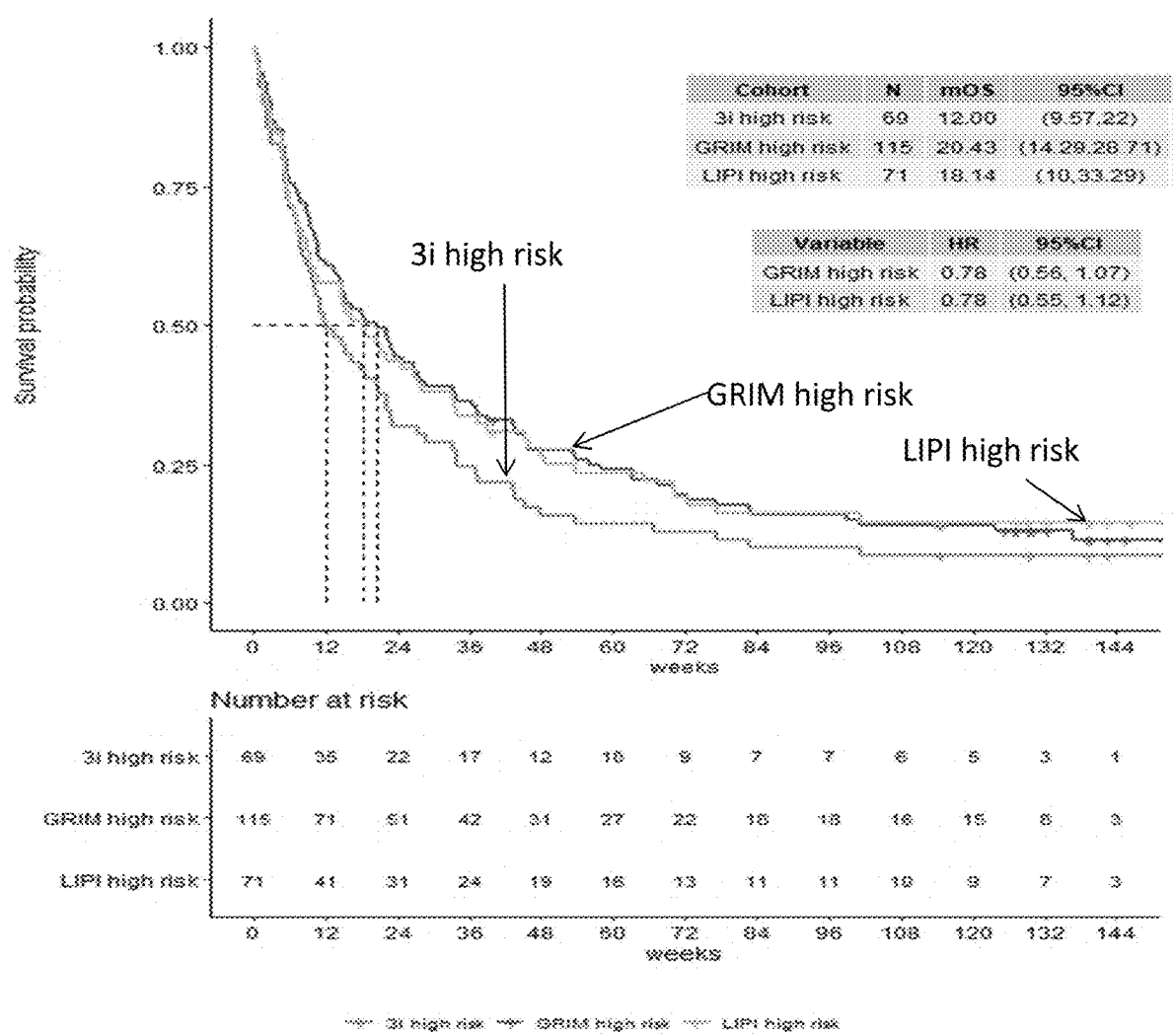
Figure 57:
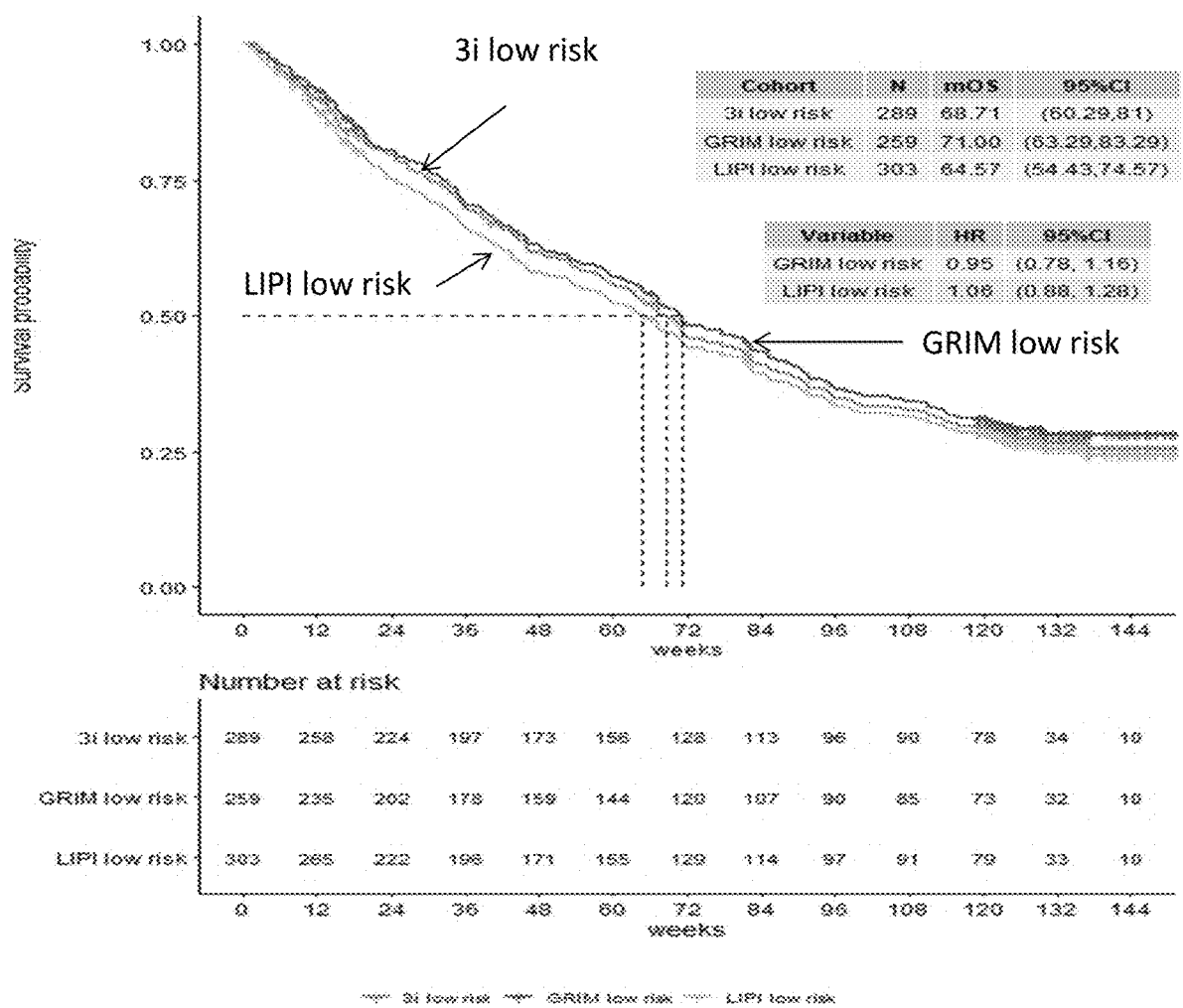

FIGS. 57A and 57B show overall survival by 3i score, GRIM, and LIPI models in MYSTIC ITT patients randomized to durvalumab. N=374, patients with non-small cell lung cancer. Kaplan-Meier curves of patients identified as high risk (left panel) or high risk (right panel) by 3i, GRIM, or LIPI scores.

Figure 58:
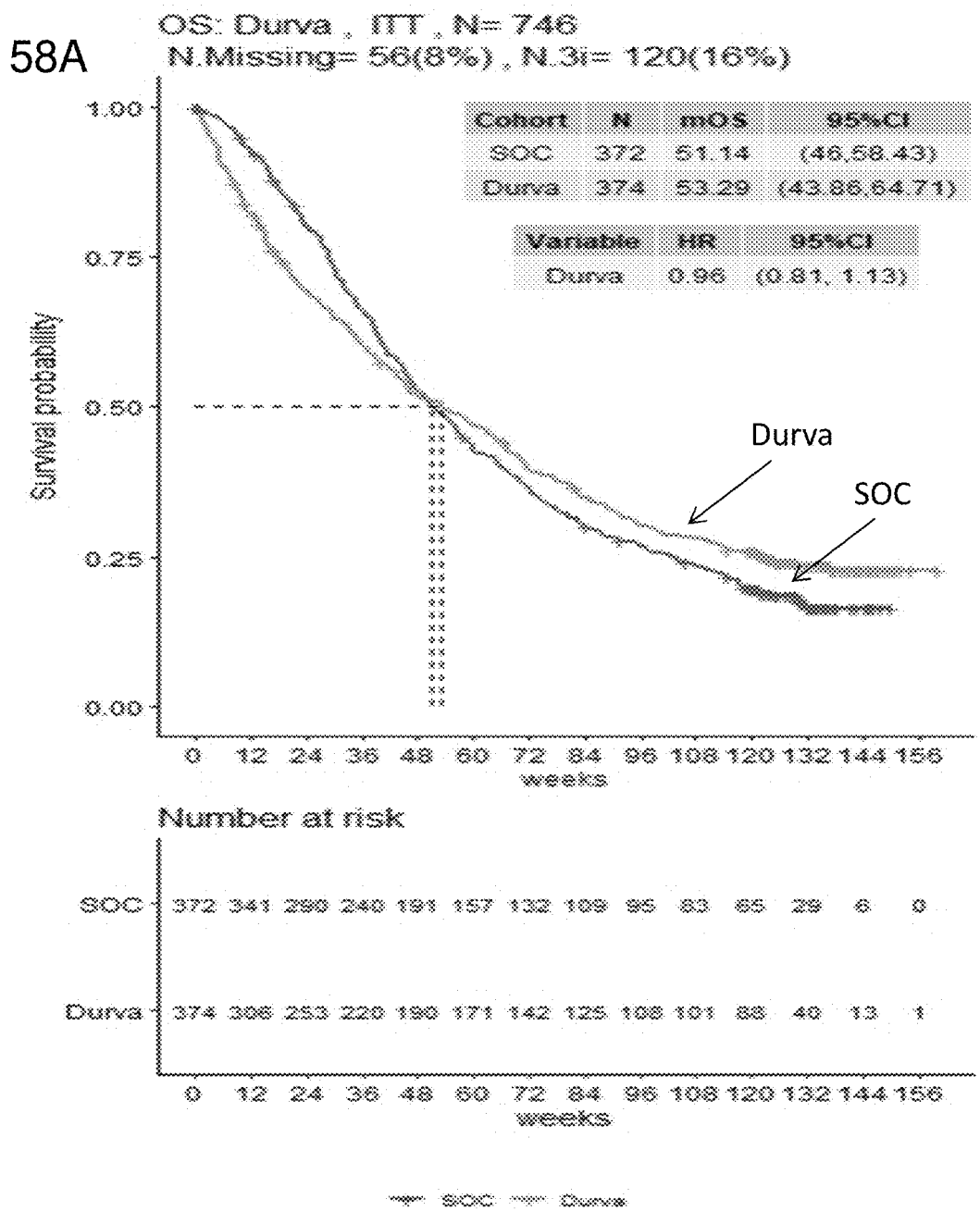
Figure 58:
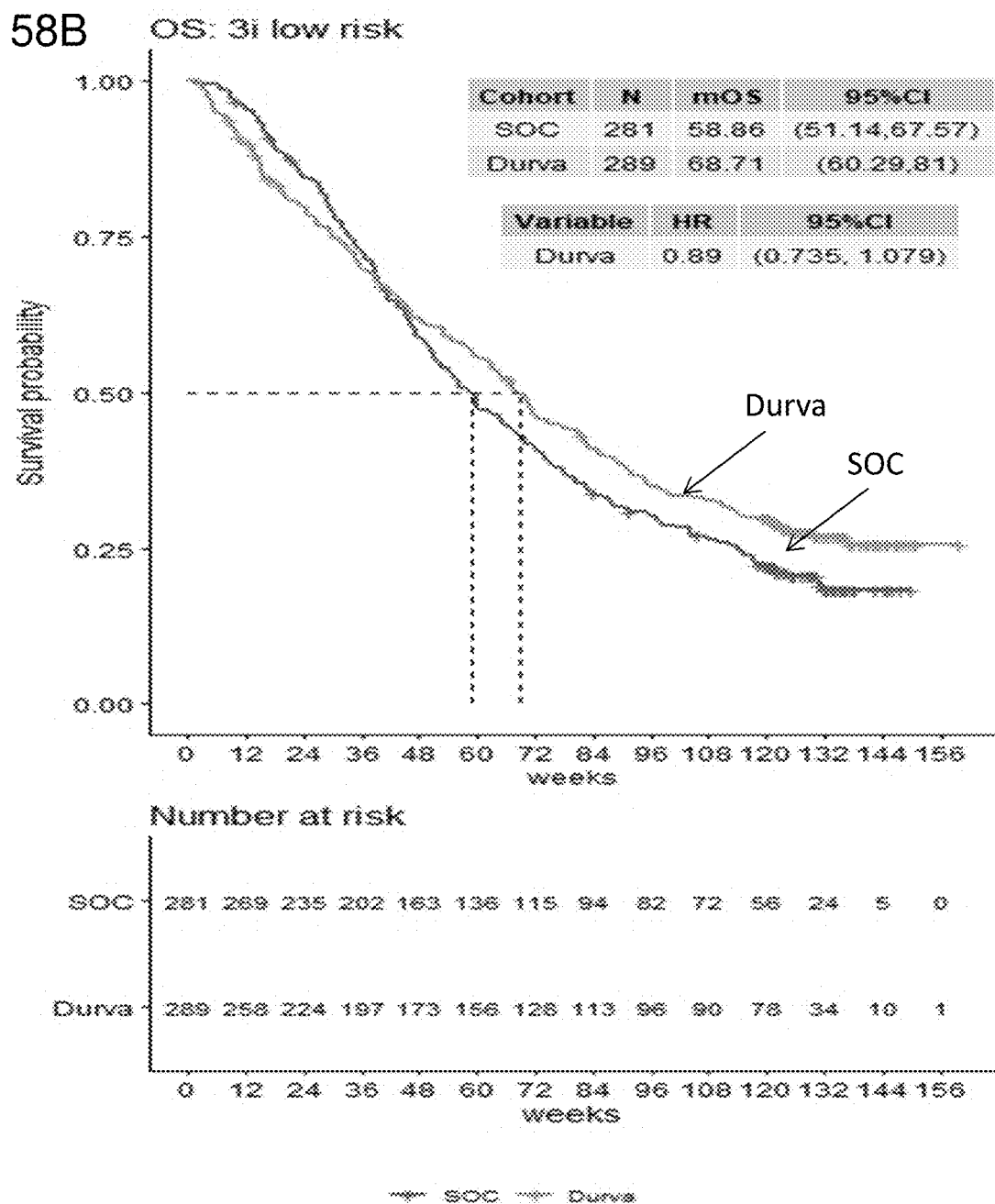
Figure 58:
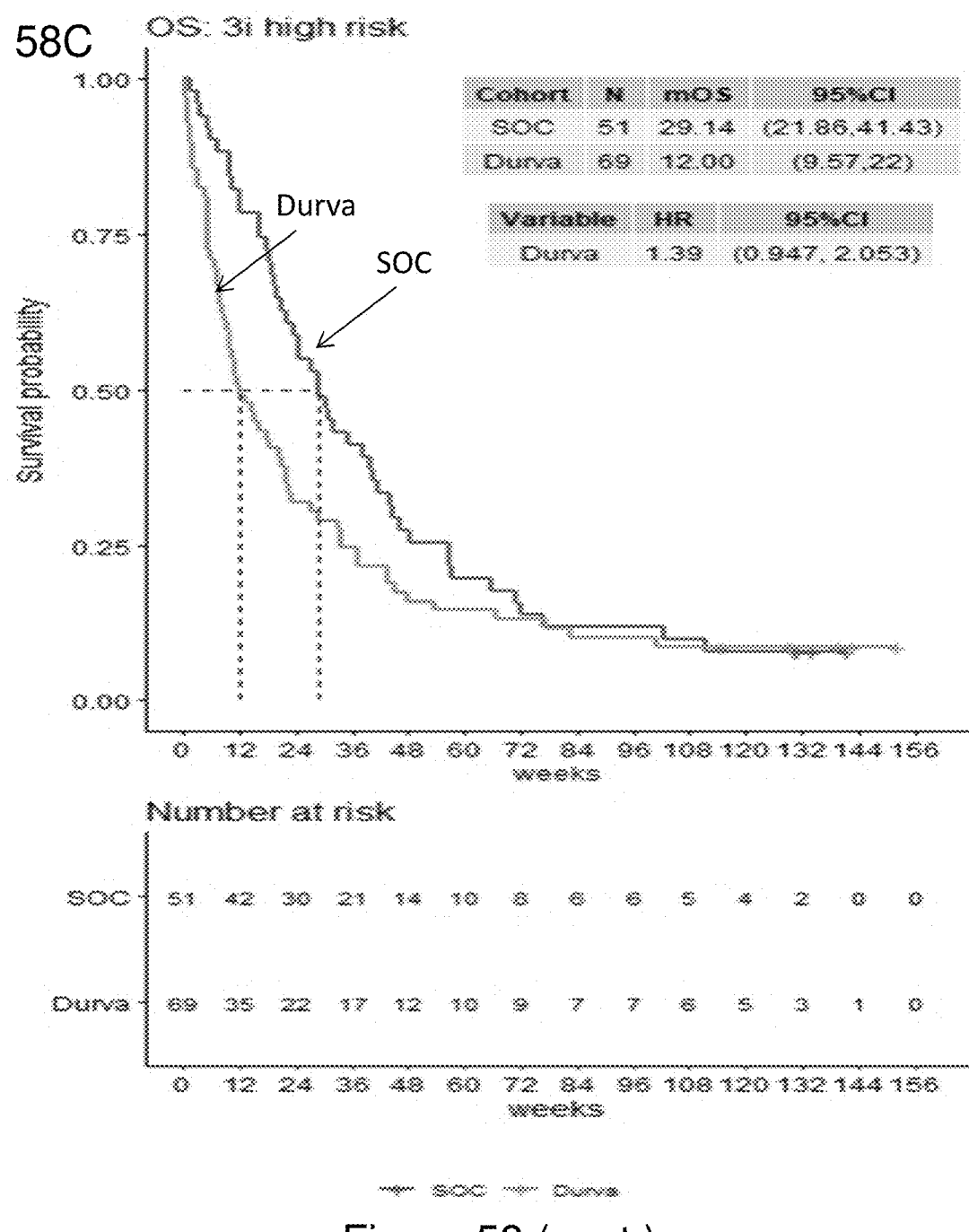

FIGS. 58A-58C show Kaplan-Meier estimates of overall survival in MYSTIC ITT population. FIG. 58A shows all patients, FIG. 58B shows 3i score low risk, and FIG. 58C shows 3i score high risk populations.

Figure 59:
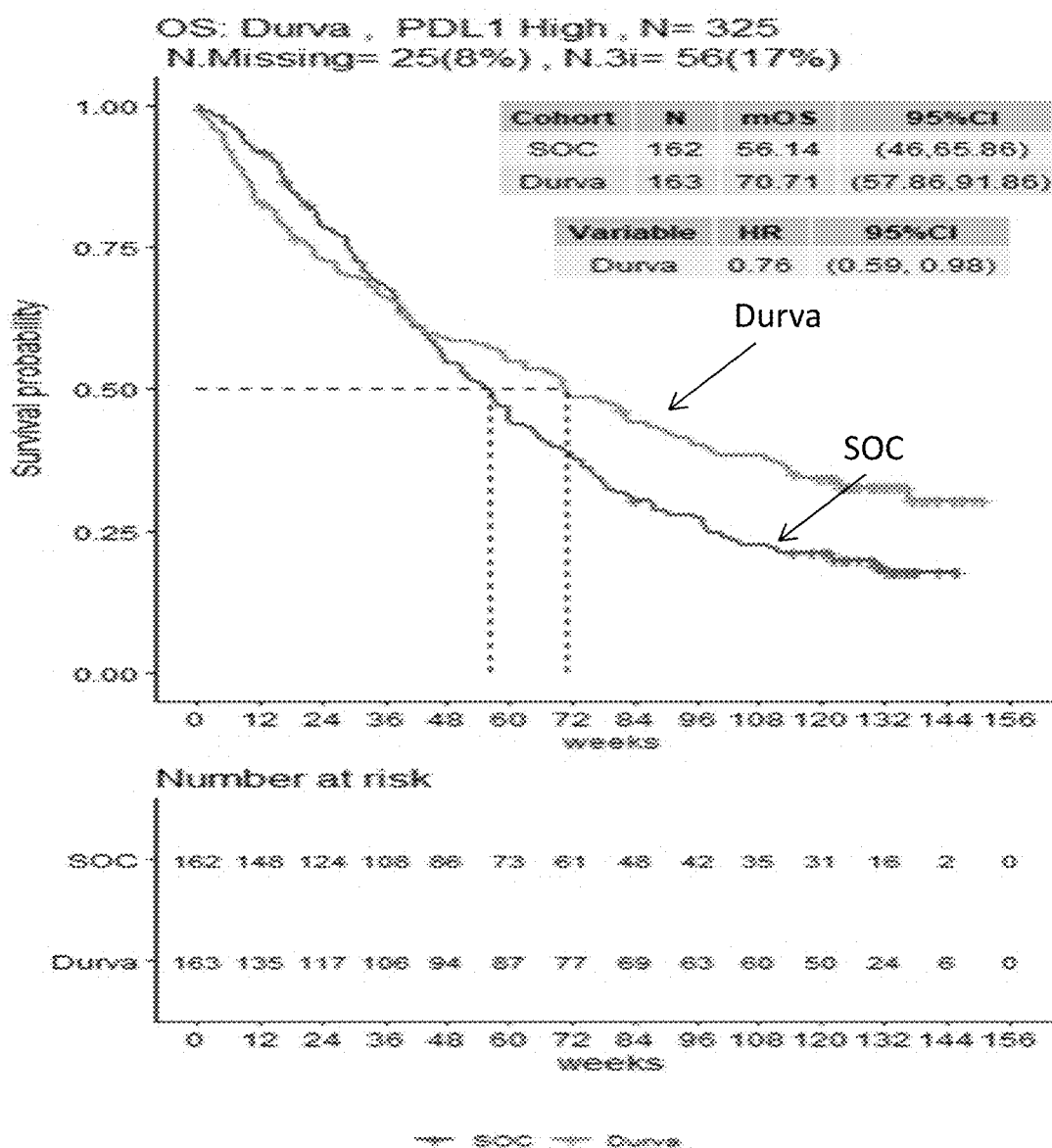
Figure 59:
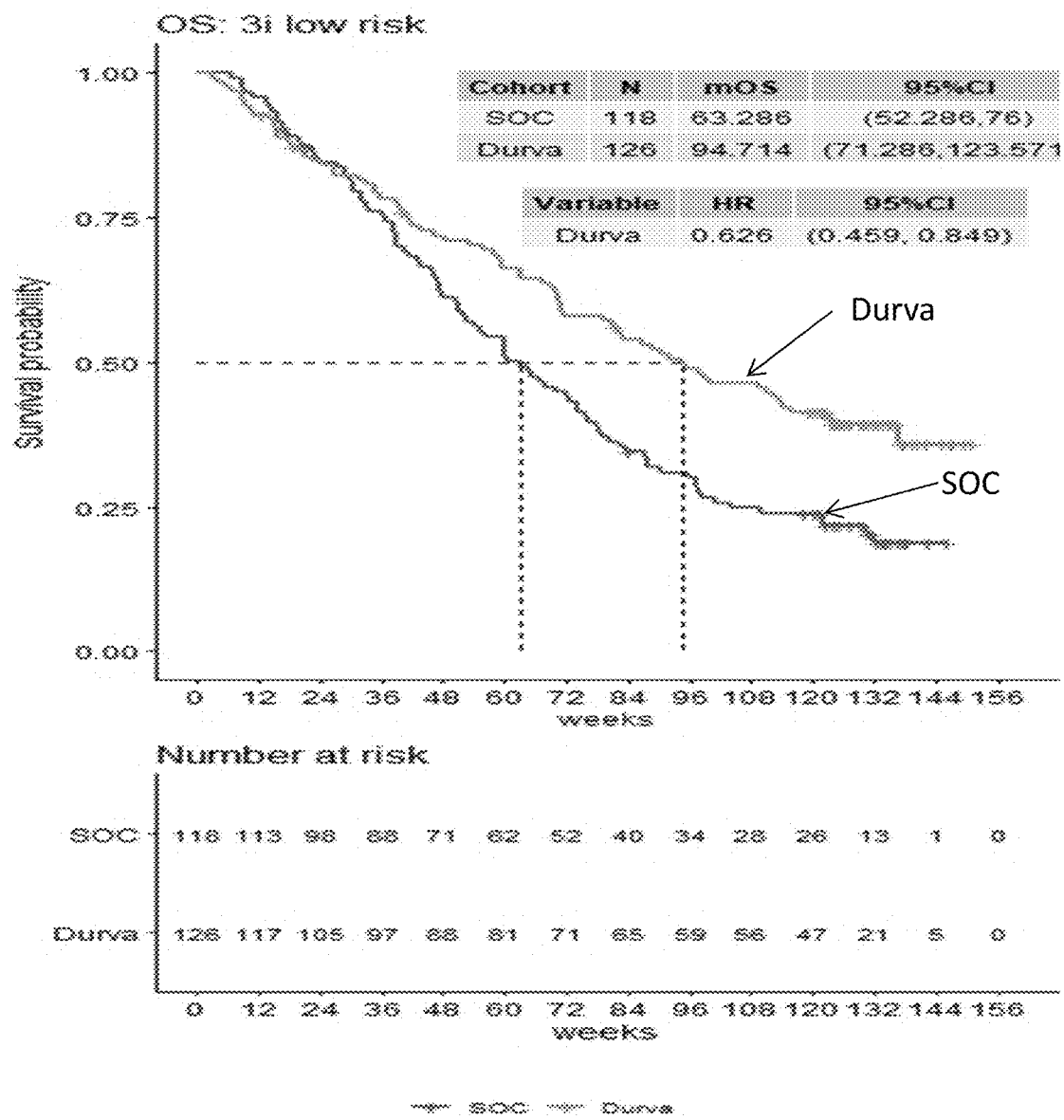
Figure 59:
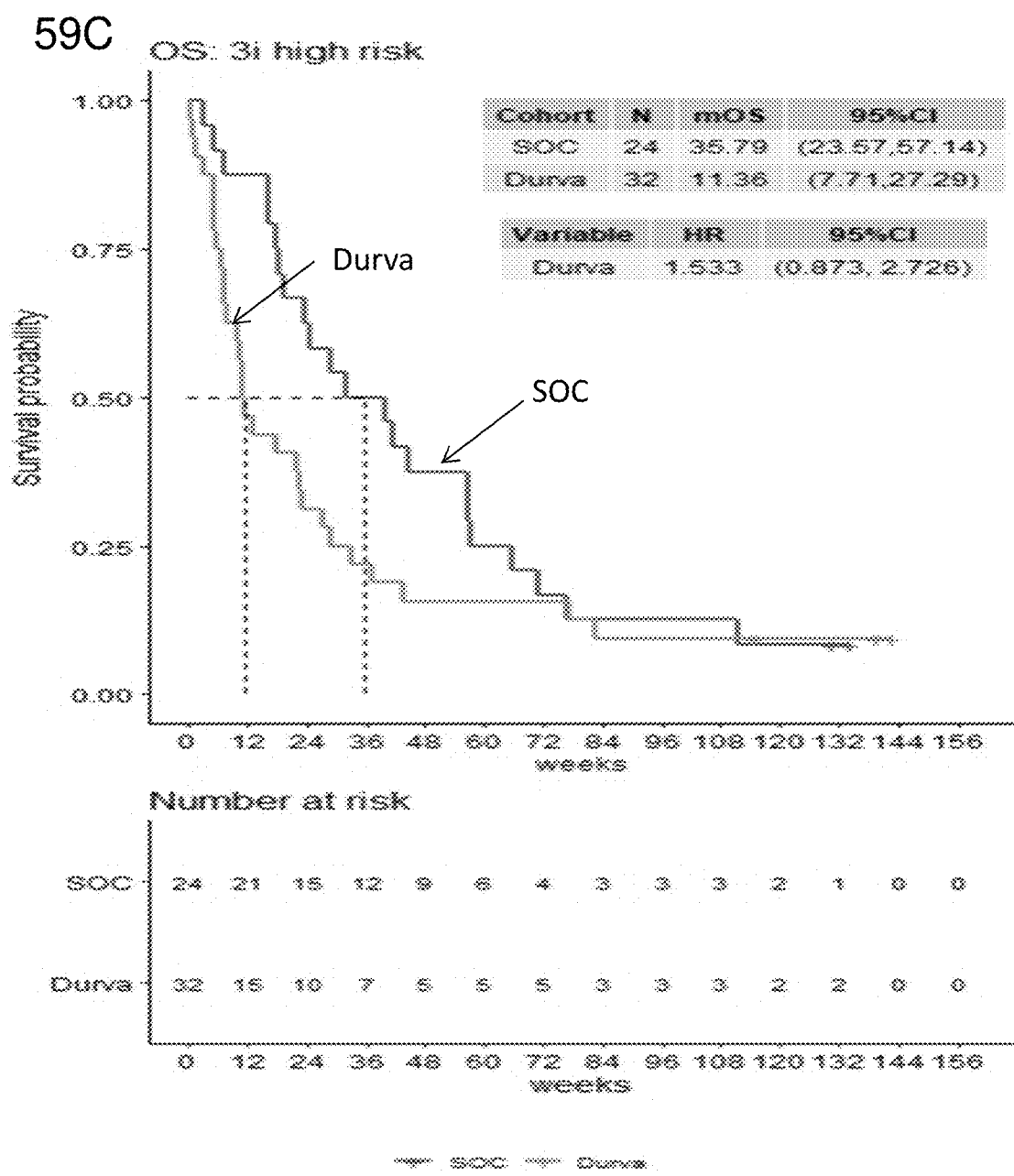

FIGS. 59A-59C show Kaplan Meier estimates of overall survival in MYSTIC PD-L1 ≥25% subgroup. FIG. 59A shows all patients, FIG. 59B shows 3i score low risk, and FIG. 59C shows 3i score high risk populations. N. missing refers to the number of patients who have at least one missing lab values and for which the 3i score cannot be produced. N.3i refers to the number of patients with 3i high risk score.

Figure 60:
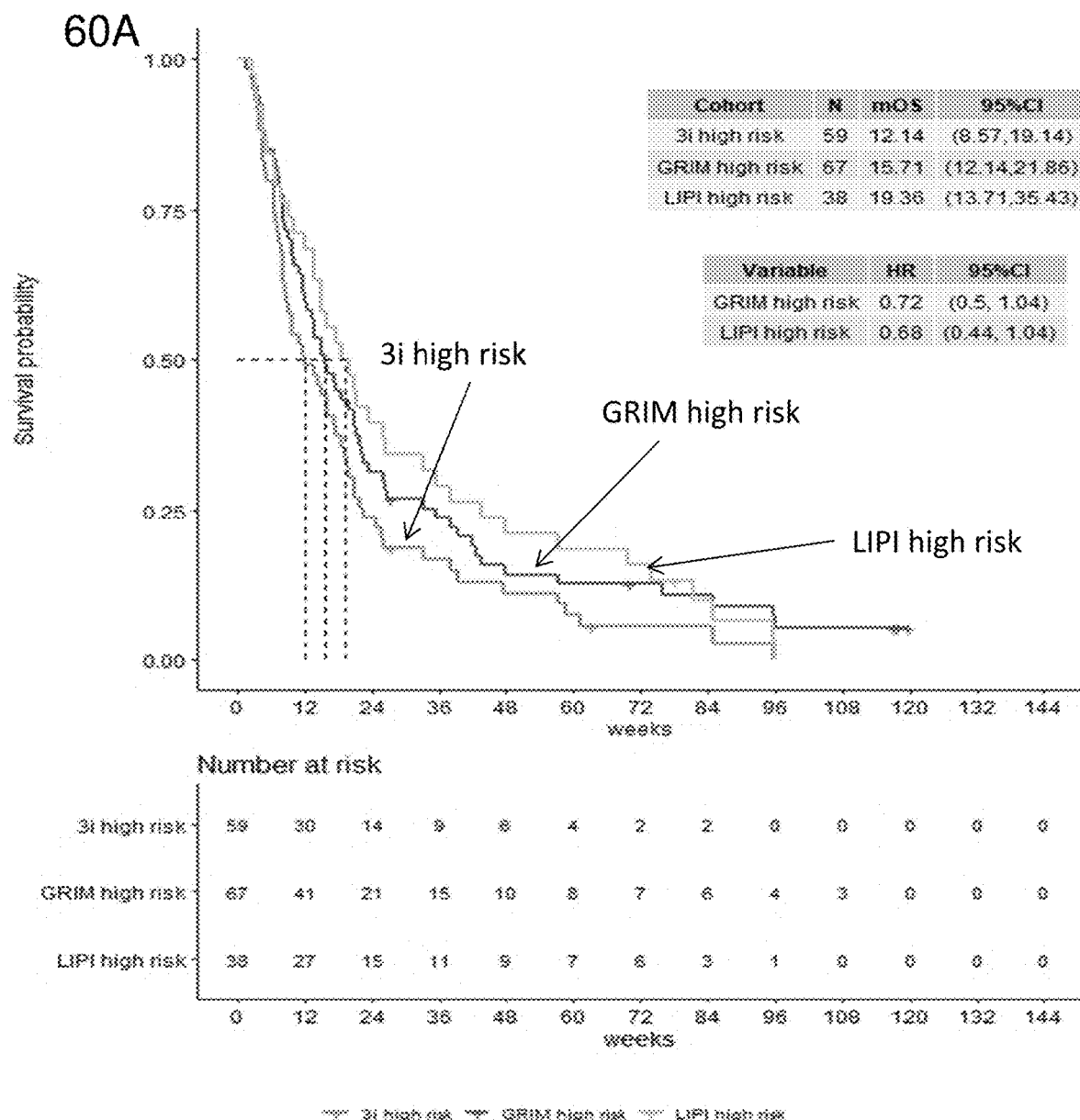
Figure 60:
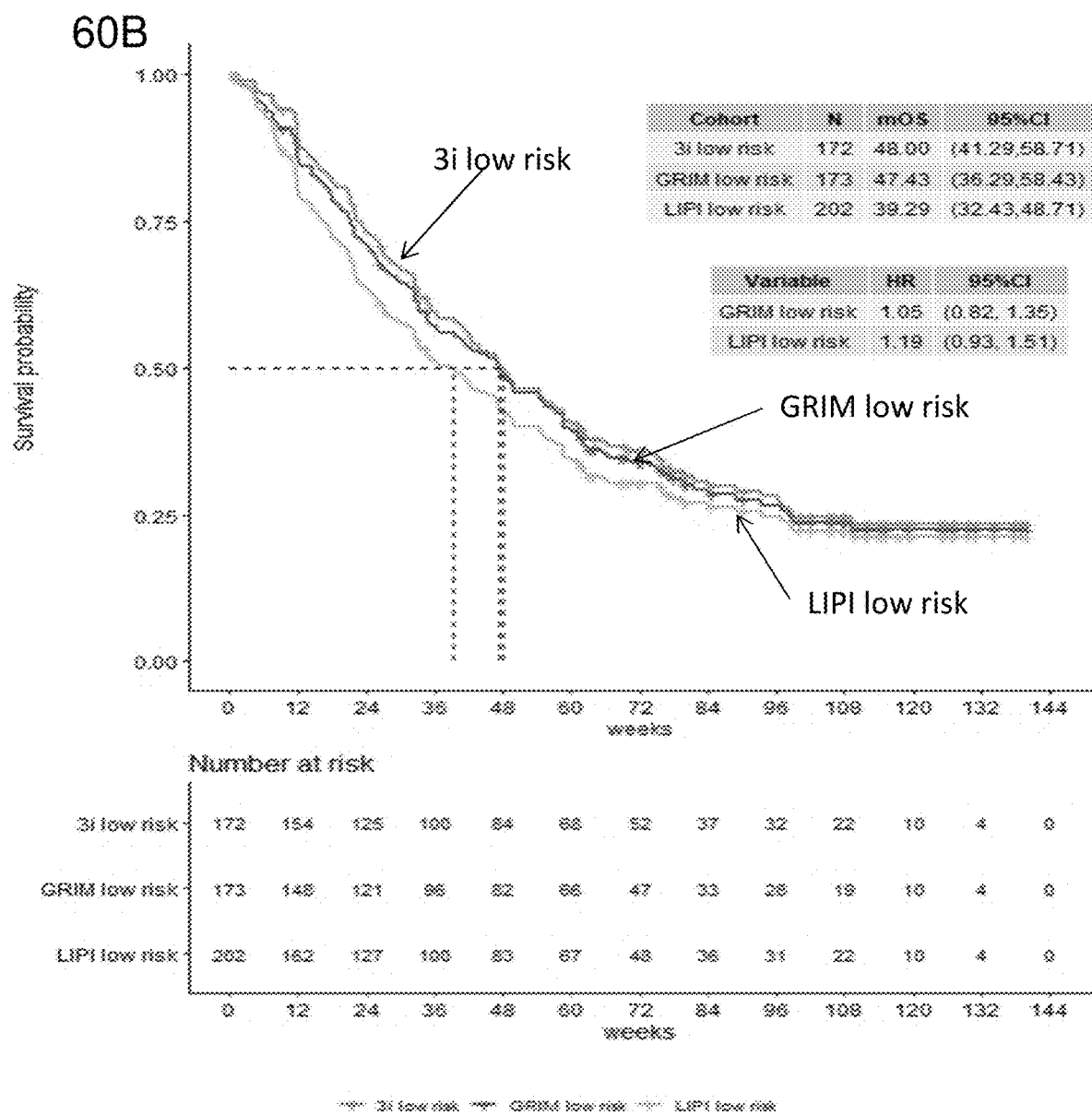
Figure 61:
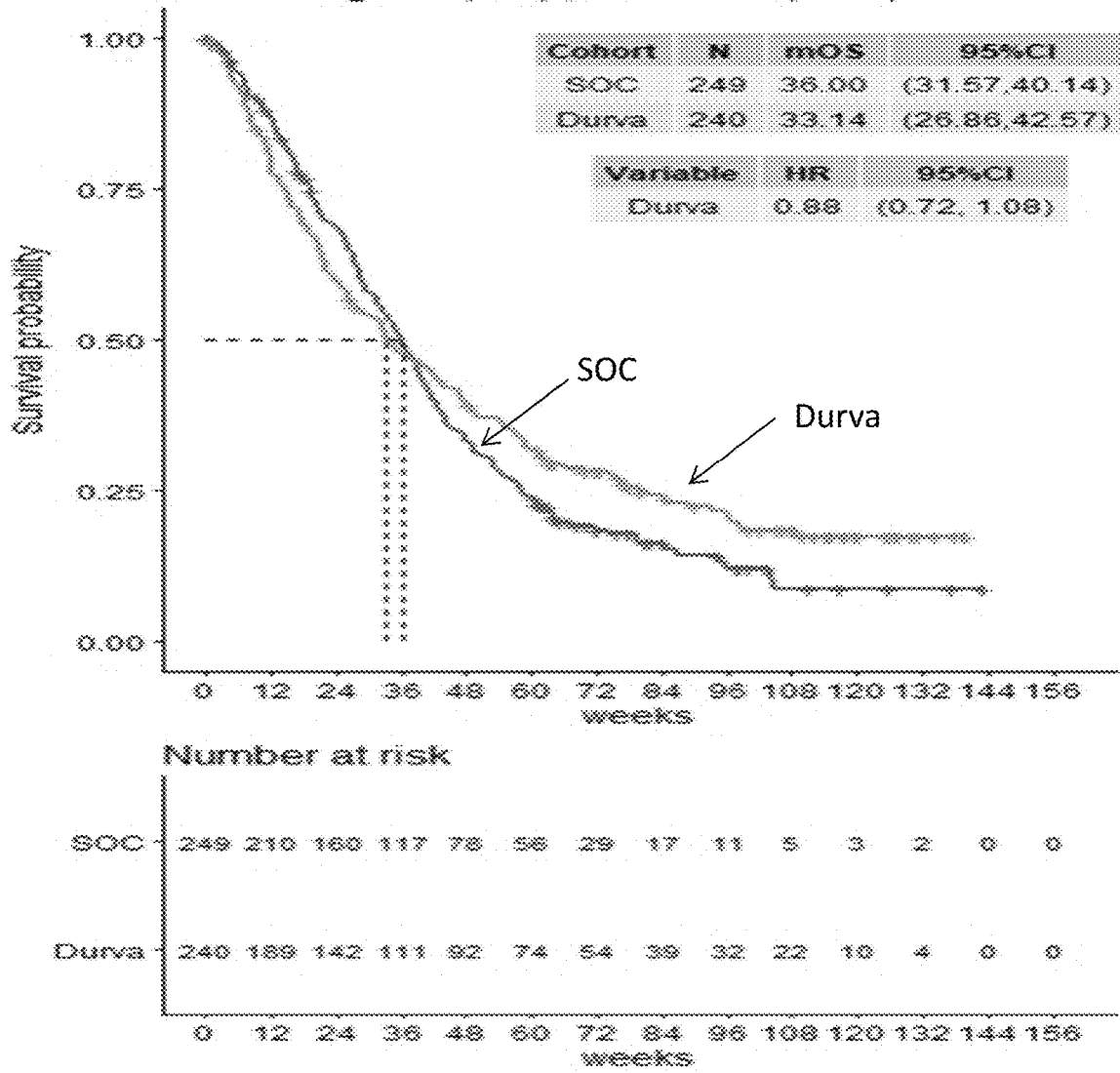
Figure 61:
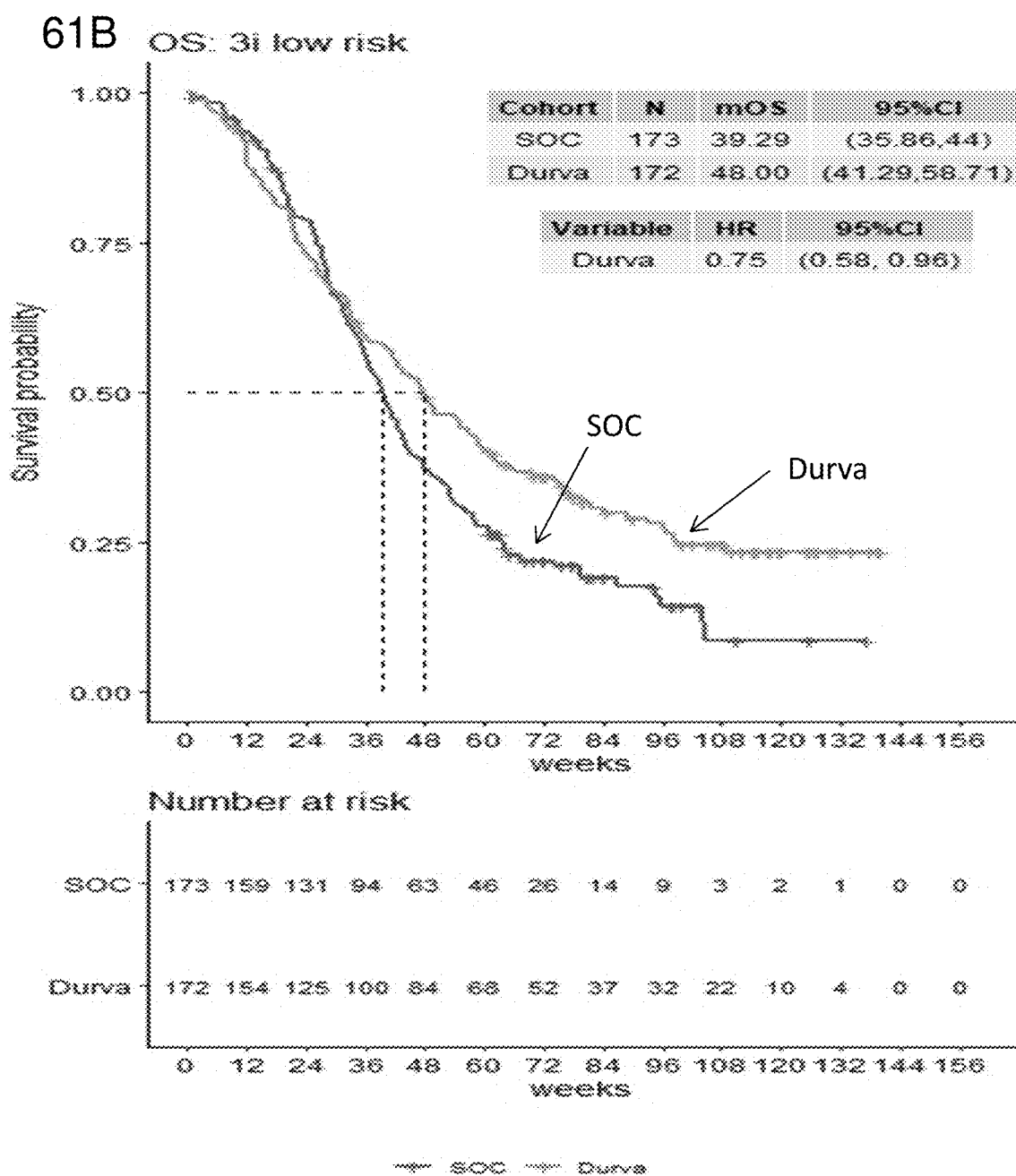
Figure 61:
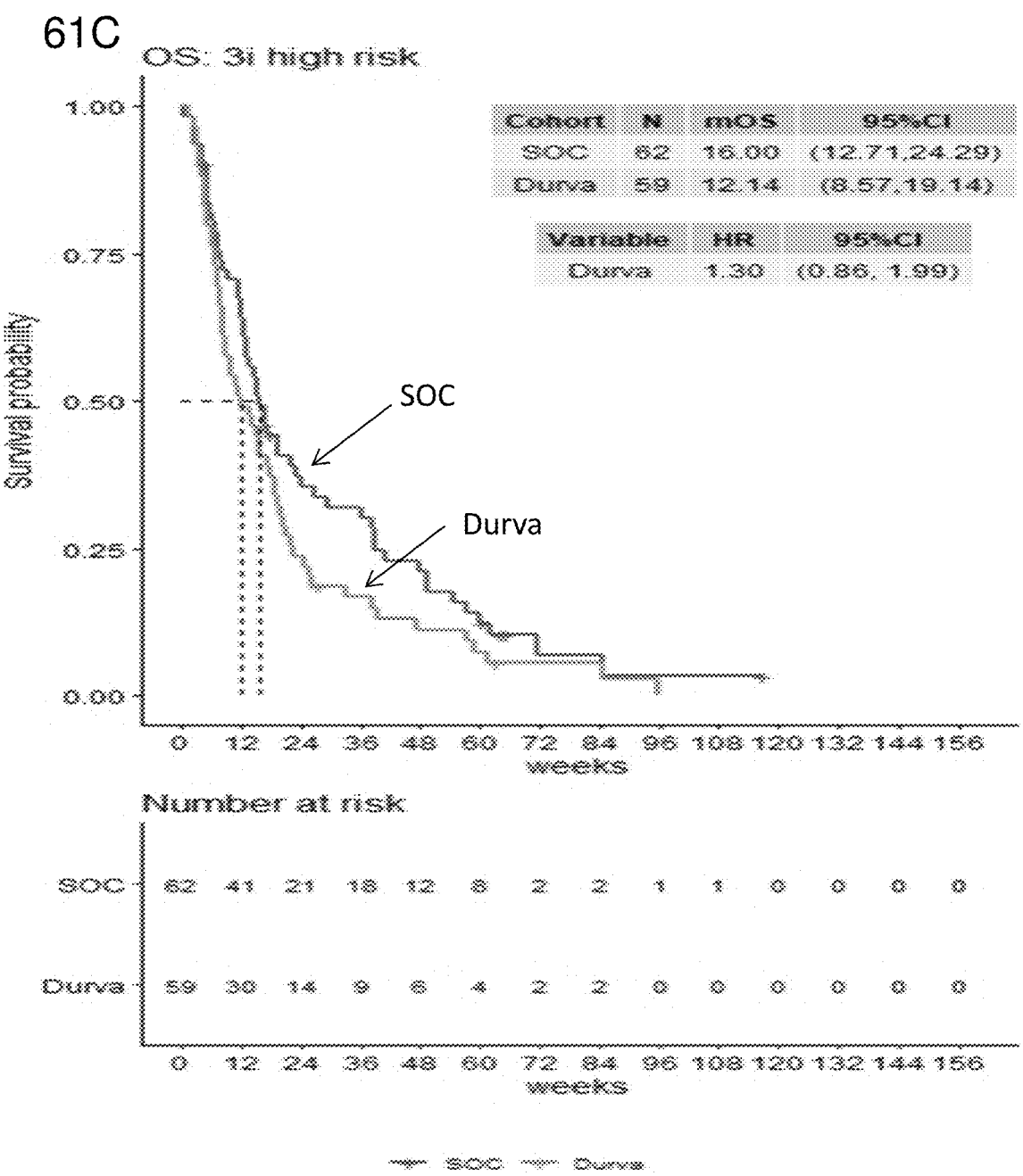

FIGS. 60A and 60B show overall survival by 3i score, GRIM, and LIPI models in EAGLE ITT patients randomized to Durvalumab. N=240, patients with squamous cell carcinoma of the head and neck. Kaplan-Meier curves of patients identified as high risk (60A) or low risk (60B) by 3i, GRIM, or LIPI scores FIGS. 61A-61C show Kaplan Meier estimates of overall survival in EAGLE ITT population. FIG. 61A shows all patients, FIG. 61B shows 3i score low risk, and FIG. 61C shows 3i score high-risk patient populations.

Figure 62:
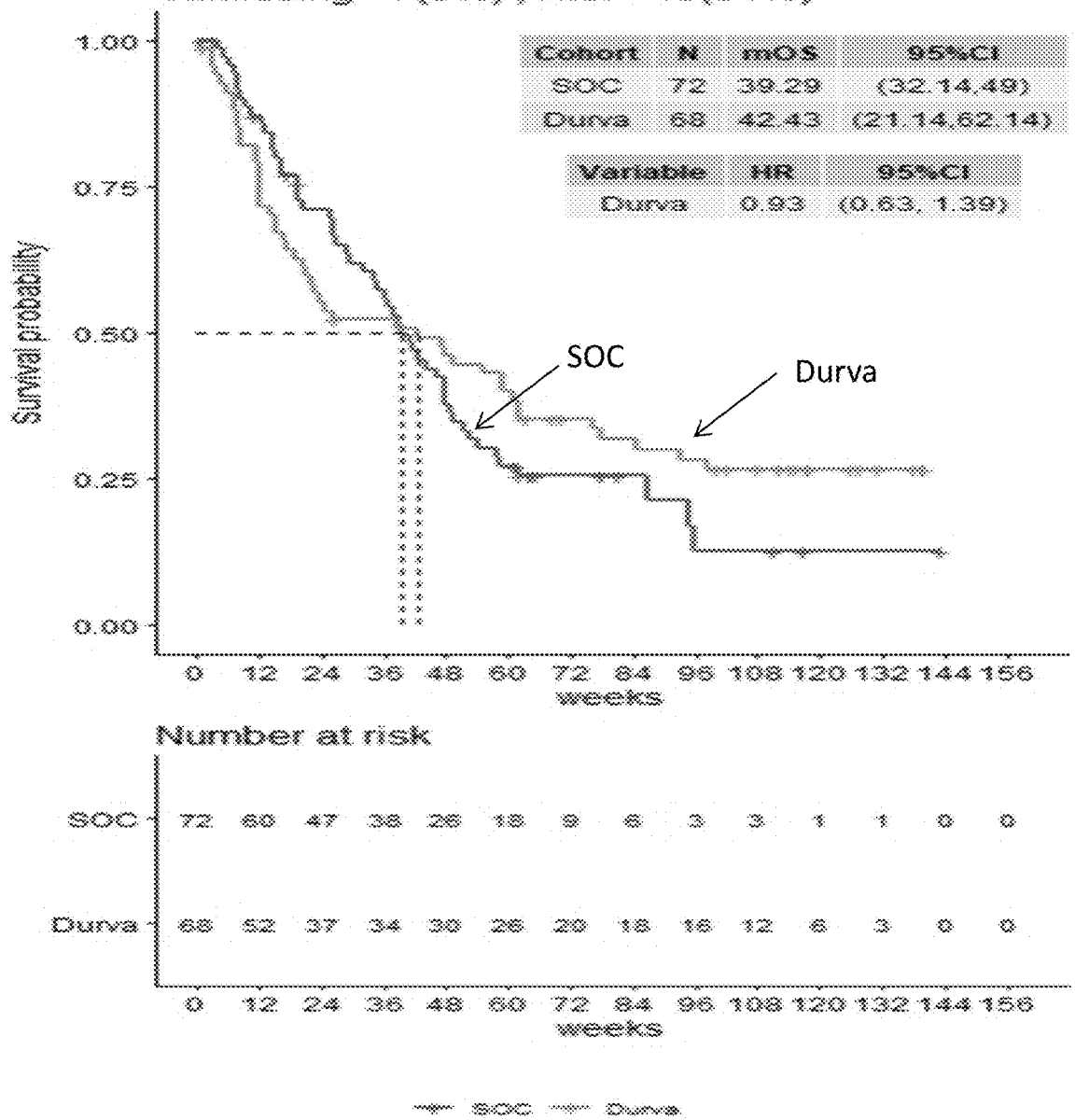
Figure 62:
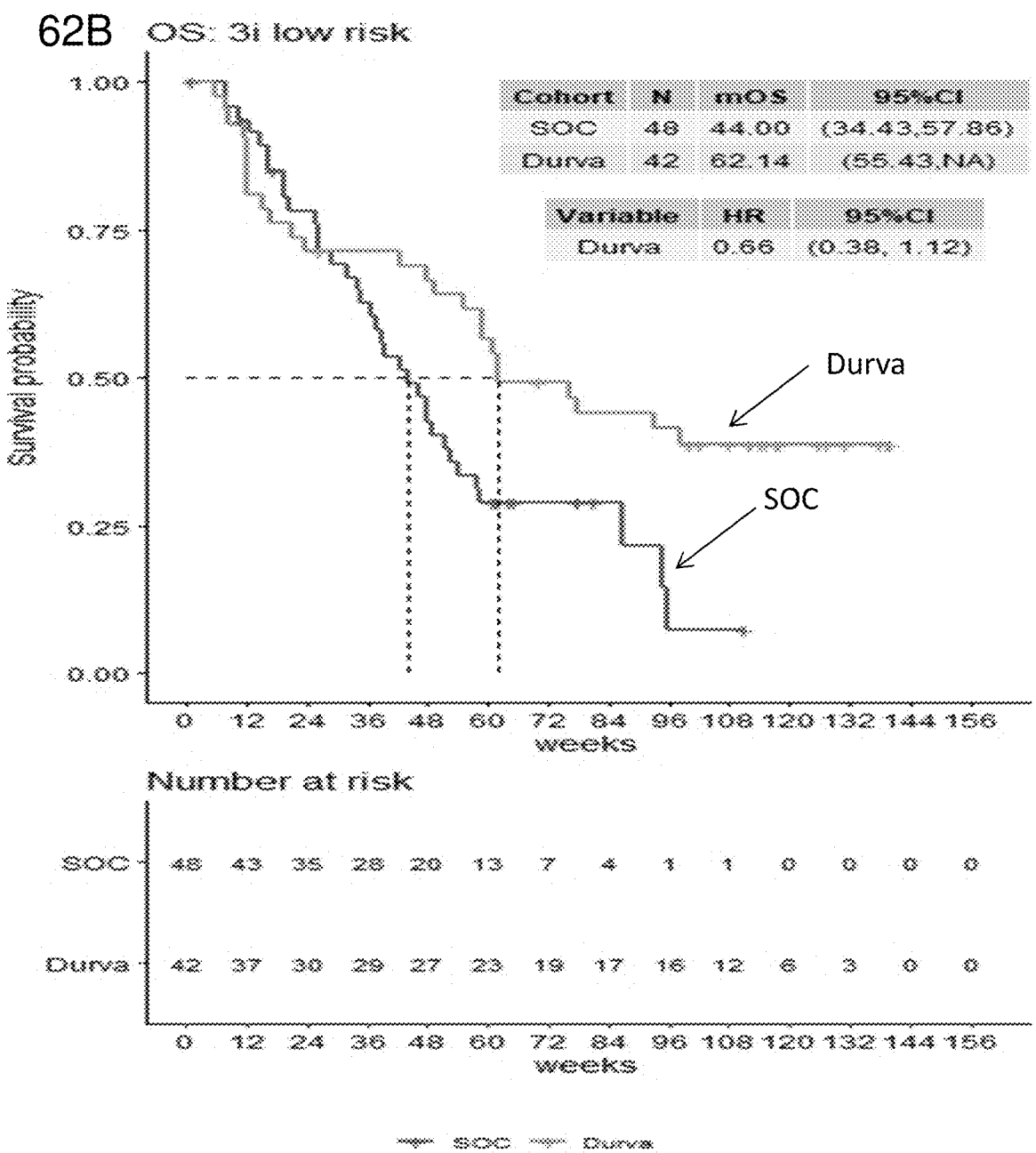
Figure 62:
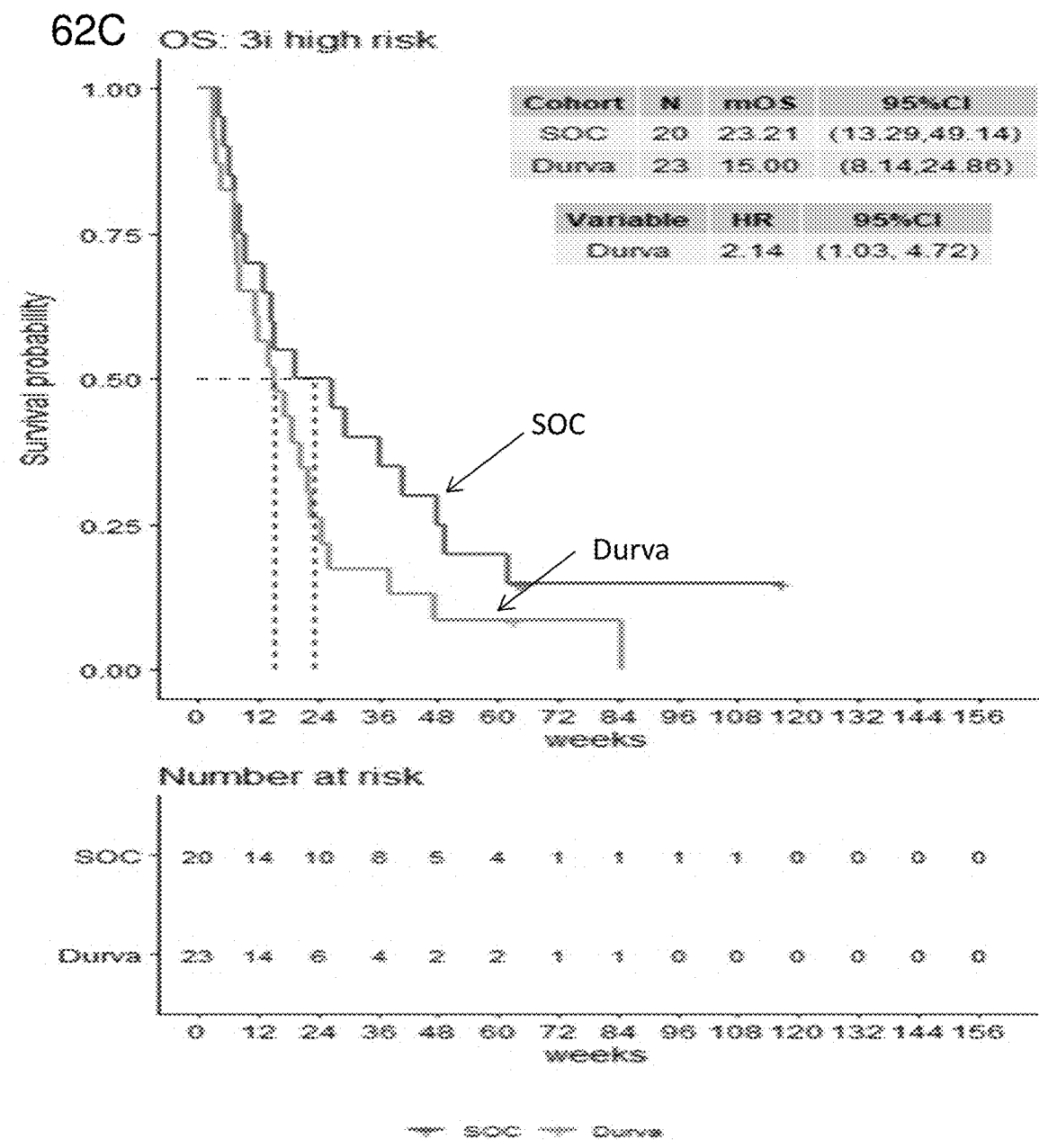

FIGS. 62A-62C show Kaplan Meier estimates of overall survival in EAGLE PD-L1≥25% subgroup. FIG. 62A shows all patients, FIG. 62B shows 3i score low risk, and FIG. 62C shows 3i score high-risk patient populations.

Figure 63:
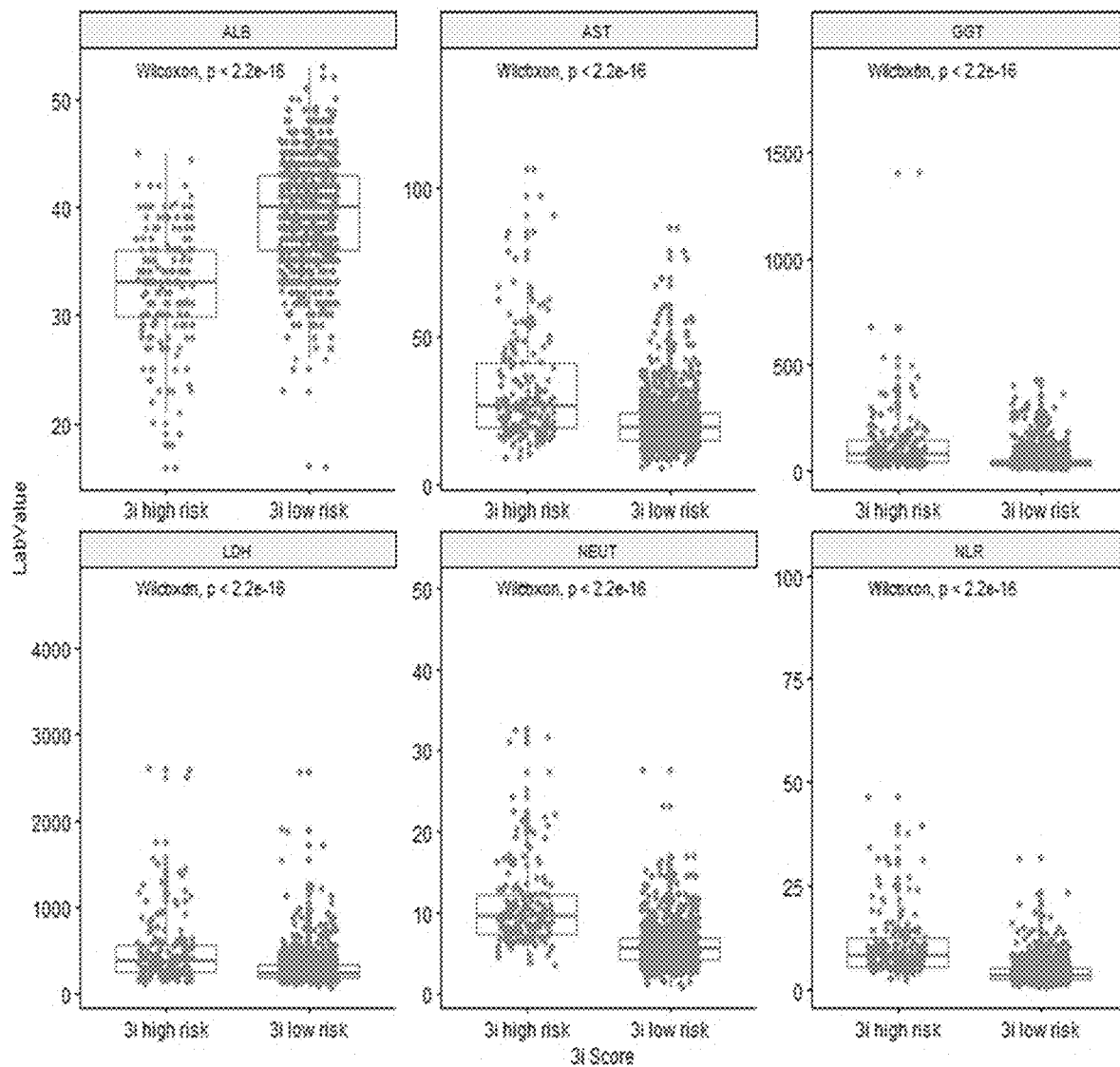

FIG. 63 shows box plots for input variable difference between 3i score high and low risk patients in MYSTIC. Abbreviations: ALB=albumin; AST=aspartate amino transferase; GGT=gamma-glutamyl transferase; LDH=lactate dehydrogenase; NEUT=neutrophils; NLR=neutrophil/lymphocyte ratio.

Figure 64:
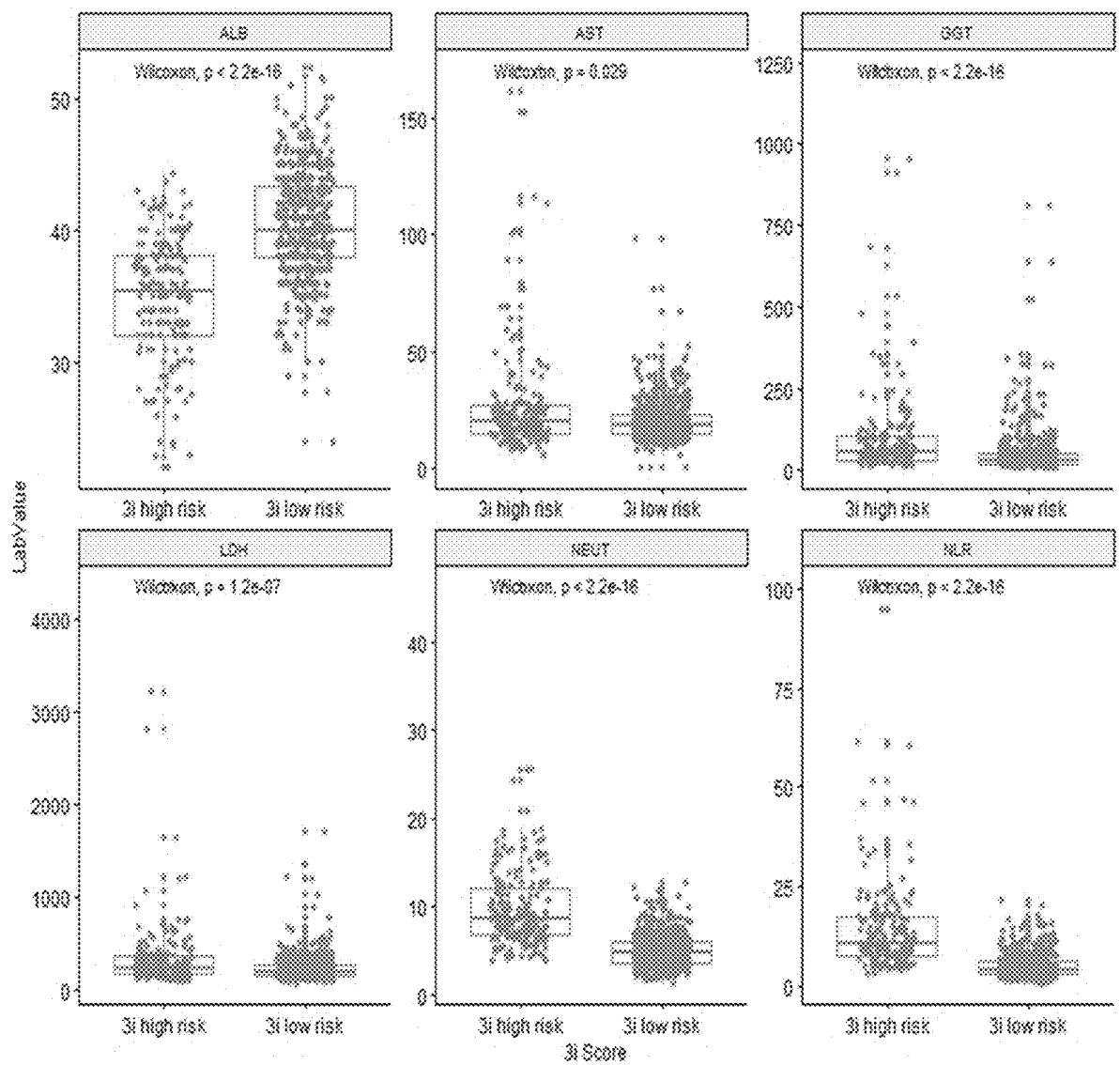

FIG. 64 shows box plots for input variable difference between 3i score high and low risk patients in EAGLE. Abbreviations: ALB=albumin; AST=aspartate amino transferase; GGT=gamma-glutamyl transferase; LDH=lactate dehydrogenase; NEUT=neutrophils; NLR=neutrophil/lymphocyte ratio.

Figure 65:
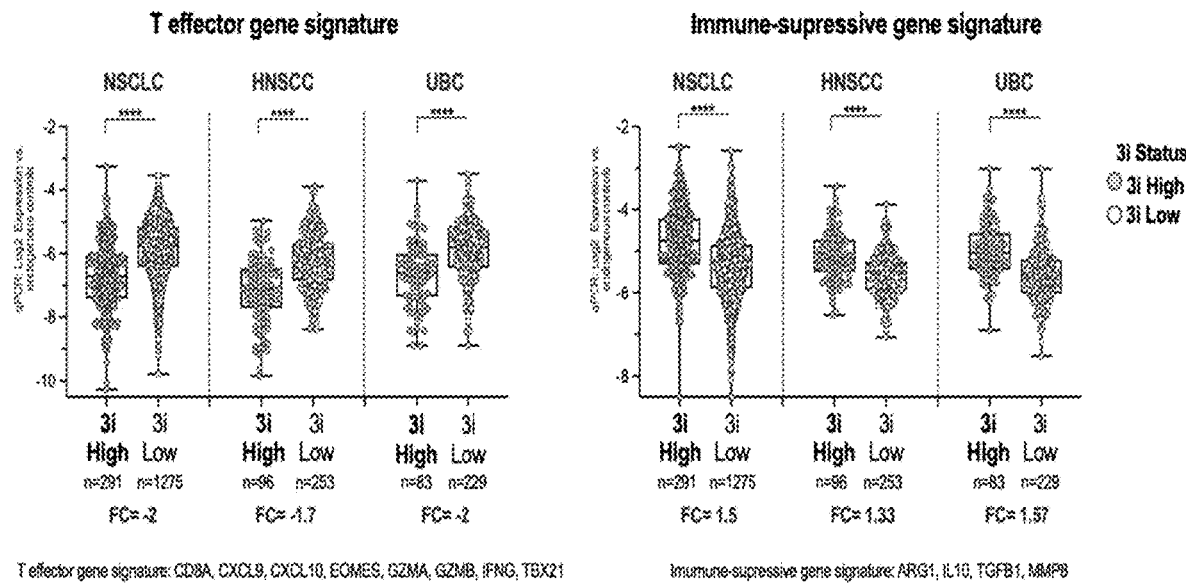

FIG. 65 shows lower expression of T effector and higher immune-suppressive gene signatures in 3i high compared to 3i low NSCLC, HNSCC, and UBC patients. Across solid tumors and studies 3i high patients show 1.9-fold (FC) lower expression in T effector and 1.5-fold higher expression in immune-suppressive gene signatures. Number (n) of patients in each 3i high and low groups and Wilcox test p value is shown (****$P<0.0001$). NSCLC data derived from MYSTIC, ATLANTIC, CP1108, and 006 studies. HNSCC data derived from HAWK, CONDOR, and CP1108. UBC data derived from Study 10 and CP1108.

Figure 66:
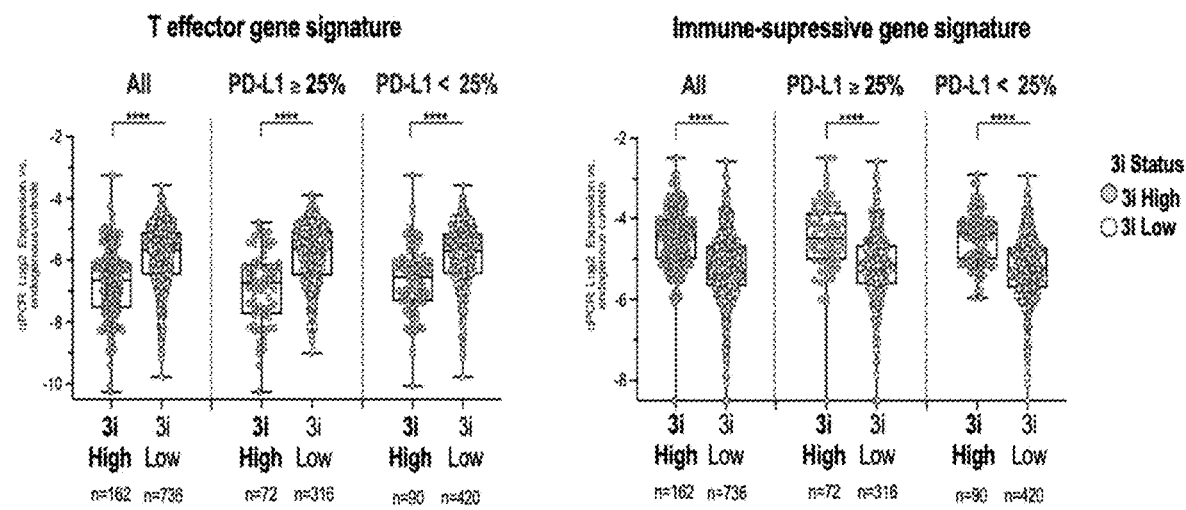

FIG. 66 shows lower expression of T effector and higher immune-suppressive gene signatures in 3i high compared to 3i low NSCLC patients regardless of their PD-L1 status. Number (n) of patients in each 3i high and low groups and Wilcox test p value is shown (****$P<0.0001$).

Figure 67:
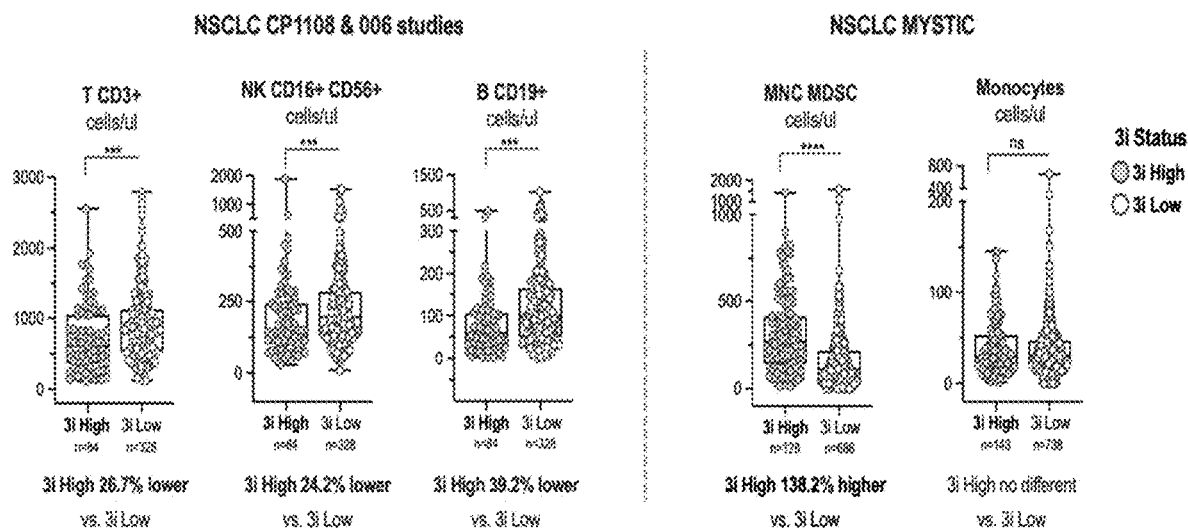

FIG. 67 shows lower T, NK, and B cells and higher MNC MDSC absolute counts in 3i high compared to 3i low NSCLC patients. T, NK and B cells absolute counts are lower by at least 24% in 3i high compared to 3i low NSCLC patients (data derived from CP1108 and 006 studies). MNC MDSC (CD14+ HLA-DRlo/−) and Monocytes (CD14+ HLA-DR+) absolute counts are higher significantly by 138.2% in 3i high vs. 3i low in NSCLC patients (Mystic) while no difference was found in monocyte absolute counts. Number (n) of patients in each 3i high and low groups and Wilcox test p value is shown ((*$P<0.001$; **$P<0.0001$).

Figure 68:
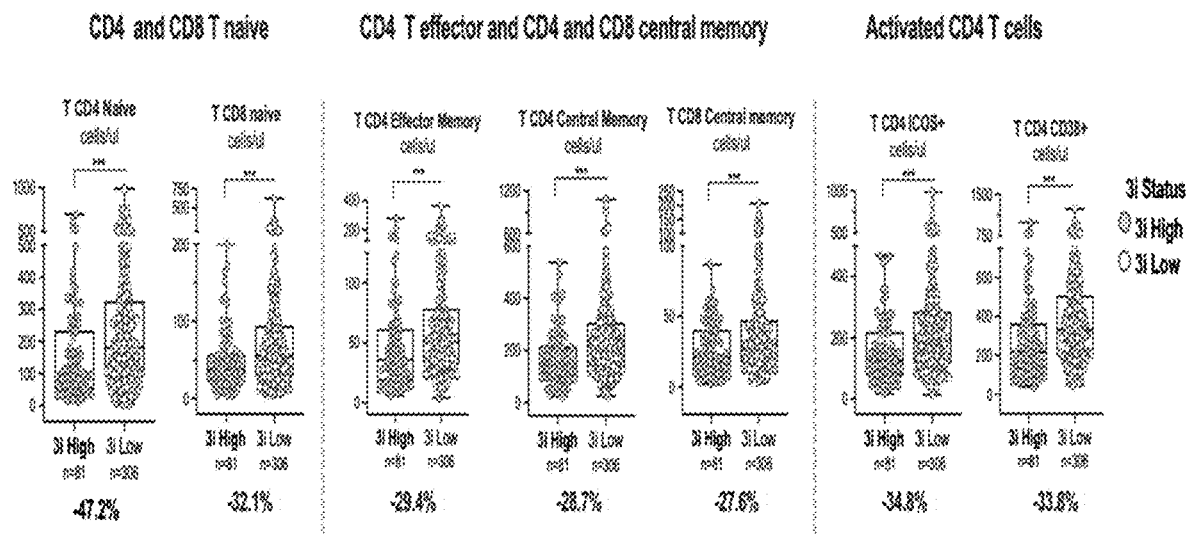

FIG. 68 shows lower naïve, activated and effector and central memory T cell absolute counts in 3i high compared to 3i low NSCLC patients. Data was CP1108 and 006 studies. Number (n) of patients in each 3i high and low groups and Wilcox test p value is shown (*$P<0.001$; **$P<0.0001$).

Figure 69:
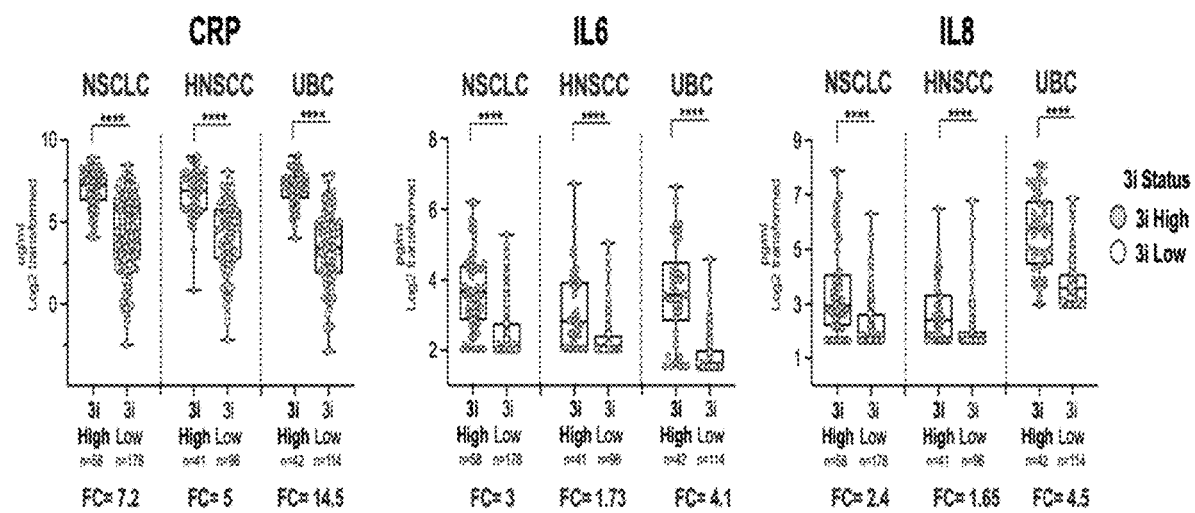

FIG. 69 shows lower serum expression concentrations of CRP, IL6 and IL8 in 3i high compared to 3i low NSCLC, HNSCC and UBC patients. Number (n) of patients in each 3i high and low groups and Wilcox test p value is shown (****$P<0.0001$). NSCLC data derived from CP1108 study. HNSCC data derived from HAWK and CONDOR and CP1108. UBC data derived from CP1108.

Figure 70:
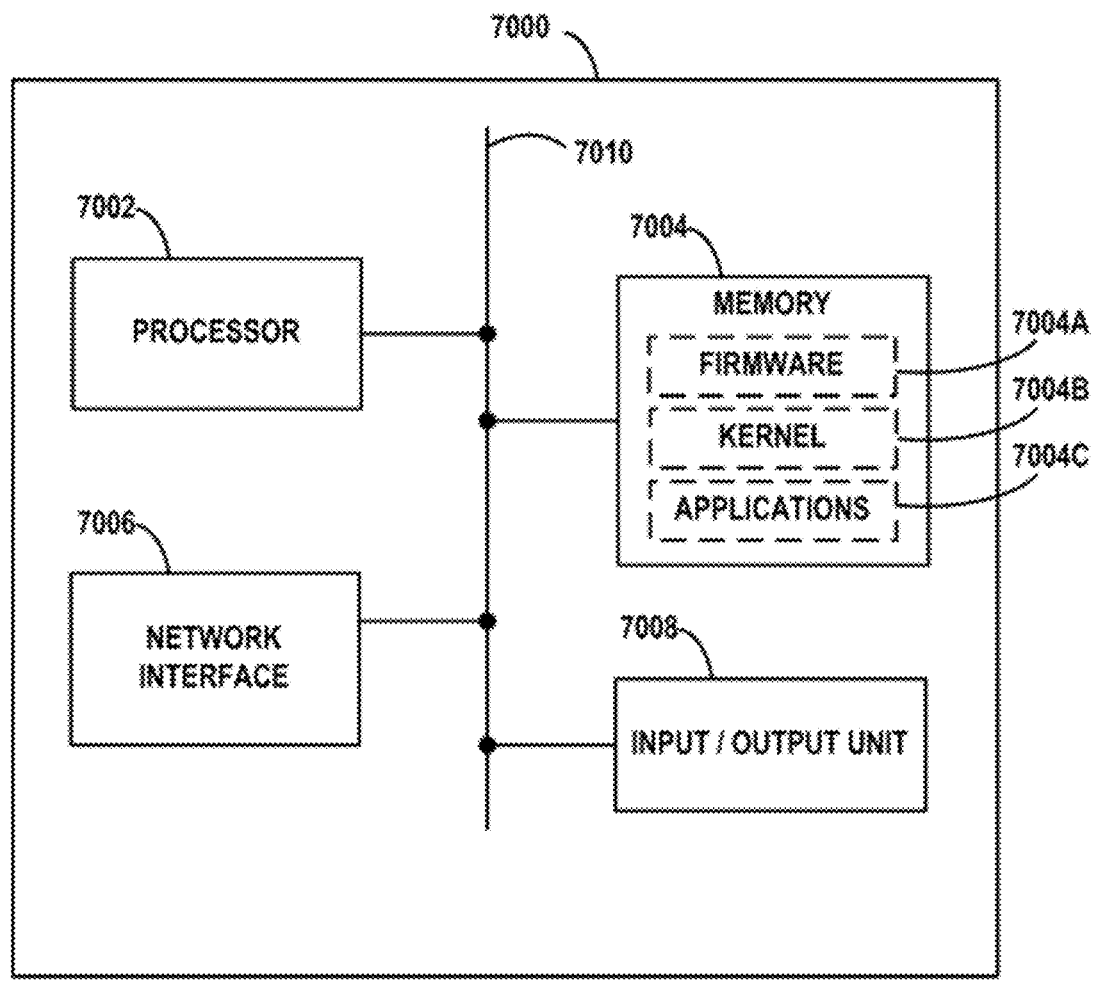

FIG. 70 depicts an example computing device that can be configured to carry out training and/or execution of a gradient boosting machine learning model.

Figure 71:
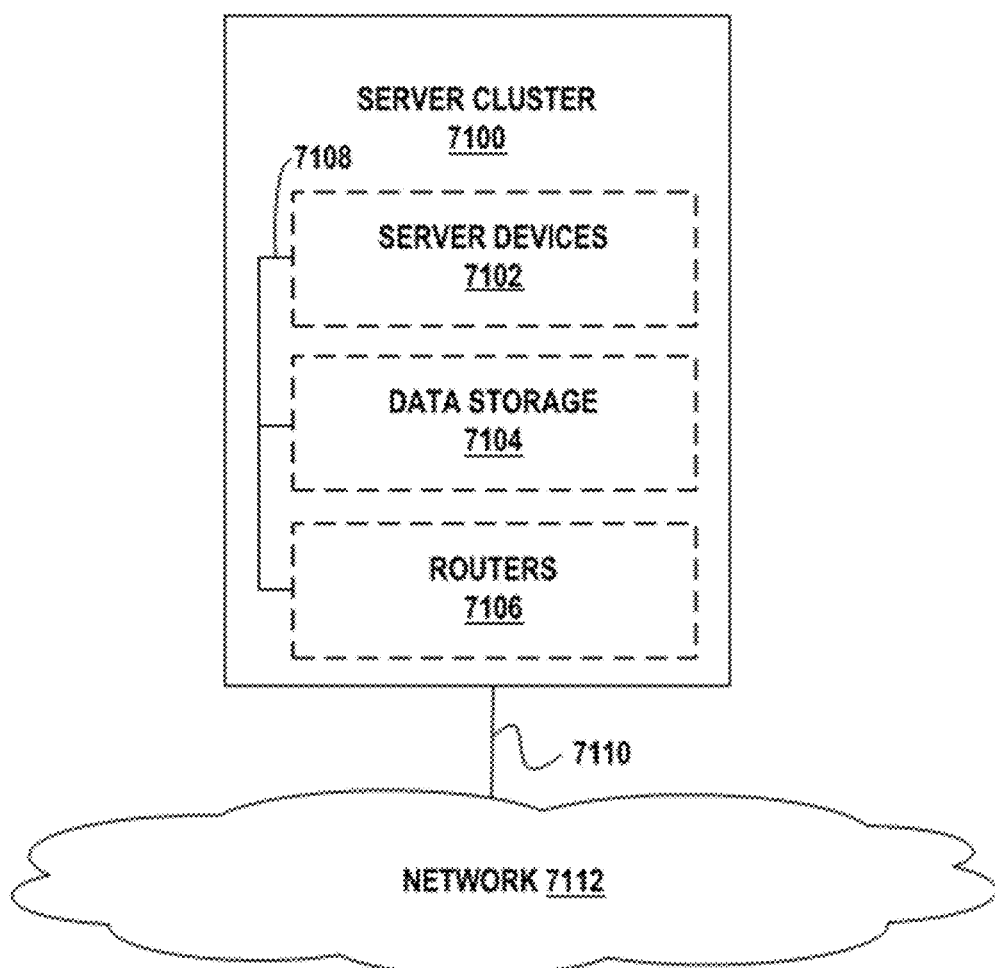

FIG. 71 depicts an example computing cluster that can be configured to carry out training and/or execution of a gradient boosting machine learning model.

Figure 72:
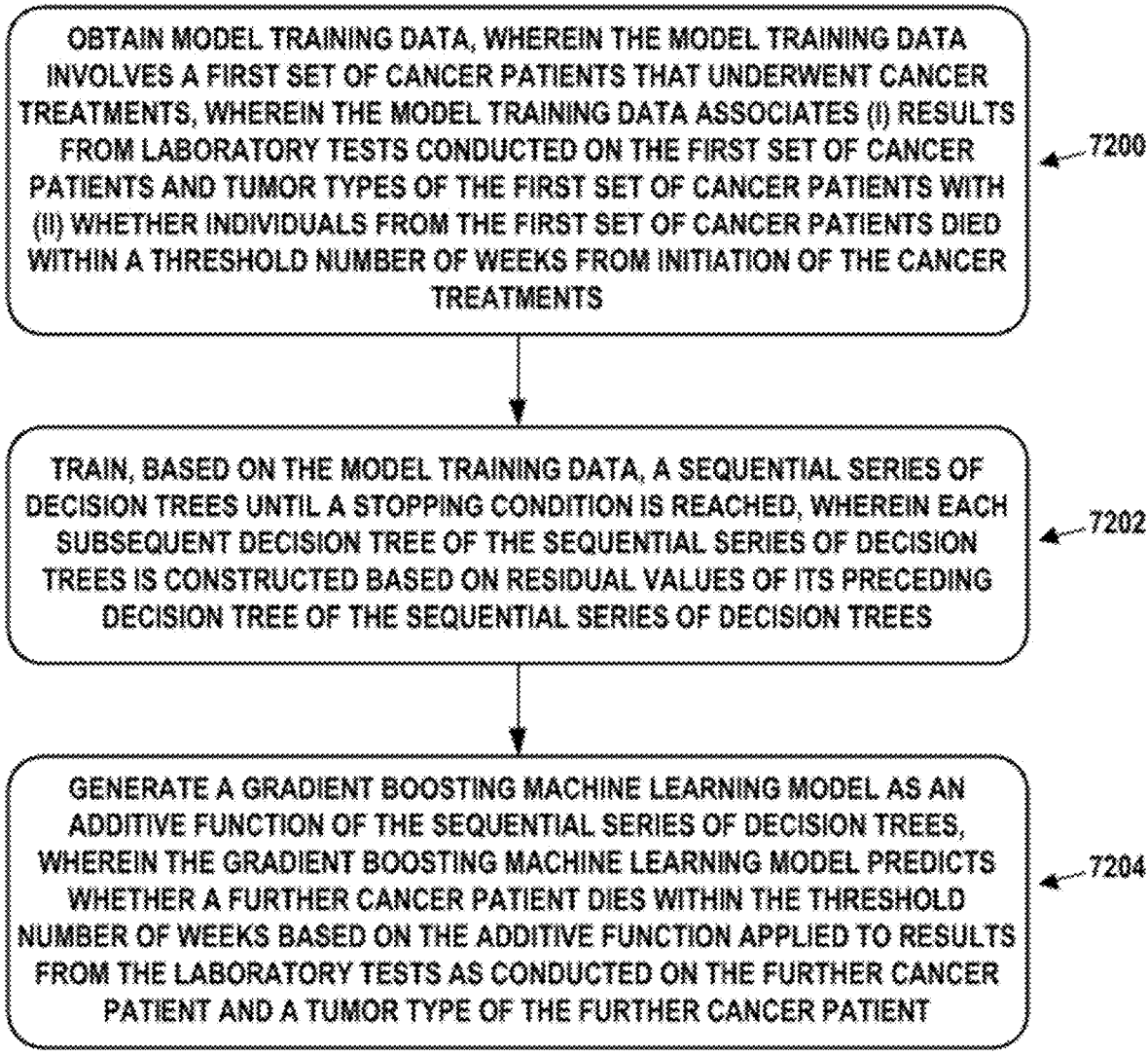

FIG. 72 depicts a flow chart representation of example training of a gradient boosting machine learning model.

FIG. 73 depicts a flow chart representation of example execution of a gradient boosting machine learning model.

DETAILED DESCRIPTION OF THE INVENTION

Unless defined otherwise, all technical and scientific terms used herein have the meaning commonly understood by a person skilled in the art to which this invention belongs. The following references provide one of skill with a general definition of many of the terms used in this invention: Singleton, et al., Dictionary of Microbiology and Molecular Biology (2nd ed. 1994); The Cambridge Dictionary of Science and Technology (Walker ed., 1988); The Glossary of Genetics, 5th Ed., R. Rieger, et al. (eds.), Springer Verlag (1991); and Hale & Marham, The Harper Collins Dictionary of Biology (1991). As used herein, the following terms have the meanings ascribed to them below, unless specified otherwise.

By "anti-PD-L1 antibody" is meant an antibody that selectively binds a PD-L1 polypeptide. Exemplary anti-PD-L1 antibodies are described for example at U.S. Pat. Nos. 8,779,108; 9,493,565; and 10,400,039 which are herein incorporated by reference, which is herein incorporated by reference. Durvalumab (MEDI4736), or "Durva," is an exemplary anti-PD-L1 antibody that is suitable for the methods described herein.

By "an anti-CTLA4 antibody" is meant an antibody that selectively binds a CTLA4 polypeptide. Exemplary anti-CTLA4 antibodies are described for example at U.S. Pat. Nos. 6,682,736; 7,109,003; 7,123,281; 7,411,057; 7,824,679; 8,143,379; 7,807,797; and 8,491,895 (Tremelimumab is 11.2.1, therein), which are herein incorporated by reference. Tremelimumab, or "Treme," is an exemplary anti-CTLA4 antibody.

The term "biomarker," "marker," or "clinicopathological marker" (which can be used interchangeably) as used herein generally refers to a protein, nucleic acid molecule, clinical indicator, or other analyte that is associated with a disease. In one embodiment, a clinicopathological marker can be differentially expressed (or present) in a biological sample obtained from a subject having a disease (e.g., bladder cancer) relative to the concentration present in a control sample or reference.

In another embodiment, a clinicopathological marker is an indicator of extent of a disease. For example, when a concentration of a clinicopathological marker in a patient having a disease (e.g., cancer) is elevated compared to control (for example, a subject without cancer), then the elevated concentration can be indicative of disease progression in the patient. Similarly, when a concentration of a clinicopathological marker in a patient having a disease (e.g., cancer) is elevated compared to an earlier measurement of the marker in the patient herself, then the elevated concentration can be indicative of disease progression in the patient. Further, in some embodiments, a concentration of a clinicopathological marker can be indicative of a patient's relative health (e.g., body mass index) and/or the patient's general physiological resilience (e.g., age).

In some embodiments, concentrations of one or more clinicopathological markers can be indicative of a patient's immune fitness, for example, the relative ability of the patient's immune system to combat a particular disease by itself or the relative ability of the patient's immune system to be augmented or modified to combat a particular disease, such as cancer, by treatment with an therapeutic agent such as an immune checkpoint inhibitor (ICI).

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

As used herein, the terms "determining", "assessing", "assaying", "measuring" and "detecting", and "identifying" refer to both quantitative and qualitative determinations, and as such, the term "determining" is used interchangeably herein with "assaying," "measuring," and the like. Where a quantitative determination is intended, the phrase "determining an amount" of an analyte, substance, protein, and the like is used. Where a qualitative and/or quantitative determination is intended, the phrase "determining a concentration" of an analyte or "detecting" an analyte is used.

By "disease" is meant any condition or disorder that damages, interferes with or dysregulates the normal function of a cell, tissue, or organ. In a disease such as cancer (e.g., bladder cancer) the normal function of a cell tissue or organ is subverted to enable immune evasion and/or escape.

By "responsive" in the context of therapy is meant susceptible to treatment. By "subject" is meant a mammal, including, but not limited to, a human, such as a human patient, a non-human primate, or a non-human mammal, such as a bovine, equine, canine, ovine, or feline animal.

As used herein, the terms "treat," "treating," "treatment," and the like refer to reducing, diminishing, lessening, alleviating, abrogating, or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from its context, the term "or" as used herein is understood to be inclusive. Unless specifically stated or obvious from context, the terms "a", "an", and "the" as used herein are understood to be singular or plural. Similarly, a particular term when expressed in the singular form also contemplates the same term expressed in plural, and vice versa. For example, the term "drug" also contemplates "drugs" and vice versa.

Unless specifically stated or obvious from context, as used herein, the term "about" is understood as within a range of normal tolerance in the art, for example within 2 standard deviations of the mean. The term "about" is understood to refer to within 5%, 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Early Mortality

As described herein, the present invention features, in one embodiment, a method of predicting whether a cancer patient is a fast progressor or is at risk for early mortality (EM; a patient whose overall survival (OS) is 24 weeks or less) by taking a blood sample or other samples and physiological measurements as described herein elsewhere, measuring concentrations of clinicopathological markers, and generating a composite score of the marker concentrations, wherein the clinicopathological markers can be, for example, neutrophils, hemoglobin, aspartate aminotransferase, and alkaline phosphatase.

In certain embodiments EM is defined as a patient whose overall survival (OS) is 12 weeks or less.

In one embodiment, any number of clinicopathological markers can be considered such as those typically measured to determine the relative disease state of a cancer patient and those typically measured to determine the relative health of an individual whether healthy or diseased.

In some embodiments, commercially available tests can be used to measure concentrations of clinicopathological markers, such as antibody-based assays where antibodies specific for a marker of interest are used to target such markers. Binding of the antibodies to the specific markers can be detected and concentrations and/or concentrations of the marker of interest can be determined by the relative amount of antibody binding. Additional tests can be employed, such as those that measure the relative abundance of specific cell type, for example, flow cytometers. Further tests that can be used herein include quantitative PCR, and similar technologies that provide information regarding relative gene expression concentrations. Additional tests are also contemplated herein as would be recognized by a skilled person for measuring various clinicopathological markers for a person's relative health or a specific disease state.

In some embodiments, samples used can include tissue biopsies, cerebrospinal fluid, lymph, whole blood, blood fractions, such as serum or specific blood cell populations, urine, sweat, tears, saliva, and/or feces.

In one embodiment, a patient can be assessed upon arrival at a clinic for enrollment in a clinical trial. In this case, a blood draw can be performed using standard techniques, and the patient's clinicopathological markers (e.g., neutrophils, hemoglobin, aspartate aminotransferase, alkaline phosphatase, etc.) can be assessed and the patient's overall survival predicted over a given period of time, such as 4, 8, 12 or 24 weeks, 4, 6, 8, or 10 months, 1, 2, 3, 4, or 5 years.

In another embodiment, a patient can be preapproved, remotely recruited, or flagged for accelerated therapy by having a lab report reviewed remotely where a centralized software platform can assess the patient's clinicopathological markers (e.g., neutrophils, hemoglobin, aspartate aminotransferase, alkaline phosphatase, etc.) and the overall survival determined.

In some embodiments, the present invention provides a method of conducting a clinical trial for an anticancer therapeutic. The method includes the steps of identifying candidate participants for a clinical trial, wherein the candidate participants have cancer, determining blood concentrations of i) neutrophils, ii) hemoglobin, iii) aspartate dehydrogenase, and iv) alkaline phosphatase of the candidate participants, calculating a predicted overall survival of the candidate participants, administering a first anticancer therapeutic to candidate participants with a predicted overall survival of 12 weeks or greater and administering a second anticancer therapeutic to candidate participants with a predicted overall survival of 12 weeks or less, and reducing at least one of a rate of cancer cell division, tumor growth, tumor size, tumor density, or rate of metastasis of the candidate participants.

In other embodiments, the invention provides a method of treating cancer in a subject in need thereof. The method includes the steps of taking a sample from the subject, determining concentrations of i) neutrophils, ii) hemoglobin, iii) aspartate dehydrogenase, and iv) alkaline phosphatase in the sample, calculating a predicted overall survival score of the subject, administering a first anticancer therapeutic to the subject if the subject's predicted overall survival is 12 weeks or greater or administering a second anticancer therapeutic to the subject if the subject's a predicted overall survival is less than 12 weeks, and reducing at least one of a rate of cancer cell division, tumor growth, tumor size, tumor density, or rate of metastasis in the subject.

In some embodiments, the present invention provides a method of conducting a clinical trial for an anticancer therapeutic. The method includes the steps of identifying candidate participants for a clinical trial, wherein the candidate participants have cancer, determining blood concentrations of i) neutrophil/lymphocyte ratio, ii) neutrophils, iii) albumin, iv) lactate dehydrogenase, v) gamma-glutamyltransferase, and vi) aspartate dehydrogenase of the candidate participants, calculating a predicted overall survival score of the candidate participants, administering a first anticancer therapeutic to candidate participants with a predicted overall survival of 12 weeks or greater and administering a second anticancer therapeutic to candidate participants with a predicted overall survival score 12 weeks or less, and reducing at least one of a rate of cancer cell division, tumor growth, tumor size, tumor density, or rate of metastasis of the candidate participants.

In other embodiments, the invention provides a method of treating cancer in a subject in need thereof. The method includes the steps of taking a sample from the subject, determining concentrations of i) neutrophil/lymphocyte ratio (NLR) proteins, ii) neutrophils, iii) albumin; iv) lactate dehydrogenase, v) gamma-glutamyltransferase, and vi) aspartate dehydrogenase in the sample, calculating a predicted overall survival of the subject, administering a first anticancer therapeutic to the subject if the subject's a predicted overall survival is 12 weeks or greater or administering a second anticancer therapeutic to the subject if the subject's predicted overall survival is less than 12 weeks, and reducing at least one of a rate of cancer cell division, tumor growth, tumor size, tumor density, or rate of metastasis in the subject.

In some embodiments where a patient is predicted to have an overall survival of less than 12 weeks from the date of assessment, a different, accelerated, and/or more aggressive treatment regimen can be prescribed than may have been intended for a particular clinical trial for which the patient was applying when assessed for overall survival.

Immune Checkpoint Inhibitors and Early Mortality

At the forefront of the ICI class are antibodies that target programmed cell death ligand-1 (PD-L1) exhibit therapeutic activity by restoring an antitumor T-cell response. An example of the profound impact demonstrated by ICIs is the 23% 5-year overall survival observed in PD-L1 high advanced or metastatic NSCLC patients treated by pembrolizumab (Garon, et al. 2019). However, during the development of these agents the EM phenomenon has been observed frequently when ICI were delivered as monotherapy in the metastatic disease setting, occurring in the early months of treatment in clinical trials across multiple tumor types including NSCLC (Borghaei, et al. 2015, Rizvi, et al. 2018, Socinski, et al. 2018, Mok, et al. 2019), UC (Bellmunt, et al. 2017, Powles, et al. 2018), HNSCC (Ferris, et al. 2016) and gastric cancer (Shitara, et al. 2018). Early mortality has been observed regardless of any specific antibody targeting PD-1 or PD-L1 (Winquist, et al. 2018, Mulkey, et al. 2019), suggesting a class effect. Though the phenomenon has been widely described, there remains a critical need for an objective measure or tool to better predict a patient's risk for EM and help direct treatment to patients most likely to have a favorable benefit:risk profile when being treated with ICI therapy.

Prevalence of Early Mortality Expectancy Across Clinical Trials Investigating ICI To ensure a comprehensive analysis across tumor types, the prevalence of the death within 4, 8 and 12 weeks of first study treatment was first evaluated in recent Phase I-III studies. These studies included:

Study 1108 (CD-ON-MEDI4736-1108), A Phase 1 Study to Evaluate the Safety, Tolerability, and Pharmacokinetics of MEDI4736 in Subjects with Advanced Solid Tumors (n=1002)

Study 06 (D419000006), A Phase 1b Open-label Study to Evaluate the Safety and Tolerability of MEDI4736 in Combination with Tremelimumab in Subjects with Advanced Non-small Cell Lung Cancer (n=379 pts)

Study 10 (D4190000010), A Phase 1b/2 Multicenter, Open-label Study to Evaluate the Safety, Tolerability, and Efficacy of MEDI4736 in Combination with Tremelimumab in Subjects with Advanced Malignancies (n=168 pts)

Study 21 (D4190000021), A Phase 1b/2 Study of MEDI4736 in Combination with Tremelimumab, MEDI4736 Monotherapy, and Tremelimumab Monotherapy in Subjects with Metastatic or Recurrent Gastric or Gastroesophageal Junction Adenocarcinoma (n=113 pts).

CONDOR (D4193C00003), A Phase II, Multi-Center, Single-Arm, Global Study of MEDI4736 Monotherapy, Tremelimumab monotherapy, and MEDI4736 in combination with Tremelimumab in Patients with Recurrent or Metastatic Squamous Cell Carcinoma of the Head and Neck (N=263).

HAWK (D4193C00001), A Phase II, Multi-Center, Single-Arm, Global Study of MEDI4736 Monotherapy in Patients with Recurrent or Metastatic Squamous Cell Carcinoma of the Head and Neck (N=112).

ATLANTIC (D4191C00003), A Phase II, Non-comparative, Open Label, Multi-centre, International Study of MEDI4736, in Patients with Locally Advanced or Metastatic Non-Small Cell Lung Cancer (Stage IIIB-IV) Who Have Received at Least 2 Prior Systemic Treatment Regimens Including 1 Platinum-based Chemotherapy Regimen (N=371).

MYSTIC (D419AC00001), A Phase III Randomized, Open-Label, Multi-Center, Global Study of MEDI4736 in Combination with Tremelimumab Therapy or MEDI4736 Monotherapy Versus Standard of Care Platinum-Based Chemotherapy in First Line Treatment of Patients with Advanced or Metastatic Non Small-Cell Lung Cancer (N=1118)

EAGLE (D4193C00002), A Phase III Randomized, Open-label, Multi-center, Global Study of MEDI4736 Monotherapy and MEDI4736 in Combination with Tremelimumab Versus Standard of Care Therapy in Patients with Recurrent or Metastatic Squamous Cell Carcinoma of the Head and Neck (N=736)

By pooling these studies together, a range of 17.84% to 30.36% of patients treated by ICI were observed to have died ≤12 weeks after the first day of study treatment (Table 9).

TABLE 9

Prevalence of EM in Clinical Trials

| Varible | | ATLANTIC (N = 371) | CONDOR (N = 263) | HAWK (N = 112) | study06 (N = 379) | study10 (N = 168) | study1108 (N = 1002) | study21 (N = 113) | MYSTIC(N = 1118) MYSTIC_ICI (N = 740) |
|---|---|---|---|---|---|---|---|---|---|
| Data Type | | | | | Training set | | | | Tuning set |
| Tumor Type | | NSCLC | SCCHN | SCCHN | NSCLC | UBC | Solid Tumors | Gastric | NSCLC |
| Overall | ≤4 wks | 4.85% | 3.42% | 11.61% | 4.49% | 7.74% | 5.99% | 7.08% | 5.41% |
| survival | ≤8 wks | 11.59% | 14.83% | 21.43% | 12.66% | 18.45% | 18.06% | 18.58% | 11.62% |
| (OS) | ≤12 wks | 18.60% | 28.52% | 30.36% | 20.58% | 24.40% | 27.15% | 30.09% | 17.84% |

| | | MYSTIC(N = 1118) | | EAGLE(N = 736) | | | |
|---|---|---|---|---|---|---|---|
| Varible | | MYSTIC_SOC (N = 352) | MYSTIC_NT (N = 26) | EAGLE_ICI (N = 483) | EAGLE_SOC (N = 240) | EAGLE_NT (N = 13) | ALL (n = 4262) |
| Data Type | | Tuning set | | | Test set | | |
| Tumor Type | | NSCLC | NSCLC | SCCHN | SCCHN | SCCHN | |
| Overall | ≤4 wks | 1.14% | 38.46% | 4.76% | 3.75% | 38.46% | 5.37% |
| survival | ≤8 wks | 3.12% | 38.46% | 15.11% | 10.83% | 38.46% | 14.03% |
| (OS) | ≤12 wks | 6.82% | 42.31% | 24.64% | 15.83% | 46.15% | 21.89% | all solid tumors including NSCLC, SCCHN, UBC, Gastric cancer, HPV positive cancer, advanced malignant melanoma, uveal melanoma, pancreatic adenocarcinoma, advanced cutaneous melanoma, Hepatocellular carcinoma, Nasopharyngeal carcinoma, Ovarian cancer, SCLC, Soft tissue sarcoma, MSI-High cancer, Triple negative breast cancer, colorectal cancer, Renal cell carcinoma. ICI represents patients treated by immune checkpoint inhibitor treatments; SOC represents patients treated by chemo therapy; NT represents patients not being treated.

Overall, the potential of higher EM in patients treated with ICI relative to active comparator signifies the need for improved prognostic methodologies to better identify those patients who are unlikely to survive beyond 12 weeks and thus benefit from ICI treatment.

Existing Prognostic Scores for Predicting Early Mortality

A number of studies have been conducted to improve physicians' prognostic accuracy for patients with advanced or metastatic cancer (Ploquin, et al., Crit Rev Oncol Hematol. 2012) and have contributed to the development of prognostic scores for use in the clinic. Most of these studies identified specific clinical characteristics and laboratory values that are associated with poor outcomes in clinical studies. Several issues have limited the utility of these studies in addressing the early mortality phenomenon. First, several studies relied upon subjective and investigator-dependent parameters such as performance status (i.e., Eastern Cooperative Oncology Group ("ECOG"), Karnfosky index) (Krishnan M; J Support Oncol 2013). Another limitation of these clinical scores is the lack of validation in large independent studies. Finally, very few of these scores have been developed in the ICI era, so their relevance in this context remains unknown. A summary of these scores follows.

Royal Marsden Hospital (RMH) Score

The RMH score was amongst the first scores to predict early life expectancy in oncology. It was originally developed in the context of phase 1 trials investigating cytotoxic and targeted therapies. The RMH score is based on the following variables: lactate dehydrogenase (LDH, >upper limit of normal [ULN]), albumin (<35 g/L), and number of metastatic sites (>2) (Arkenau, et al., 2009). Each variable gives 1 point. A patient is classified poor prognostic by RMH if the sum of these variables exceeds 1. The application of the RMH score in large retrospective cohorts (N>1000 pts) of patients across tumor types (Wheler, et al. 2012) confirmed the poor prognosis associated with RMH score>1. High risk RMH was associated with poor prognosis in the ICI context in a retrospective series of patients (Bigot, et al., 2017; Minami et al, 2019).

Gustave Roussy Immune (GRIm) Score

The GRIm-Score is a more recent attempt to improve the life expectancy estimation of patients in the context of oncology phase 1 trials investigating ICI. It is based on albumin (<35 g/l), LDH (>ULN), and neutrophil to lymphocyte ratio (NLR; >6) (Bigot, et al. 2017). Similar to the RMH score, each variable gives 1 point. Patients treated with ICI whose sum of variables >1 are associated with poor overall survival in retrospective series of patients (Bigot, et al., 2017; Minami, et al., 2019).

Lung Immune Prognostic Index (LIPI) Score

The LIPI score was developed to predict the outcome in NSCLC patients treated with ICI in a variety of settings including routine clinical care, expanded access, compassionate-use programs, and clinical trials. It is based on the following variables: derived neutrophils/(leukocytes minus neutrophils) ratio (dNLR) >3 and LDH >ULN. Each variable gives 1 point. NSCLC patients whose sum of variables >1 are associated with poor prognosis per LIPI. In the original publication, the LIPI score was applied retrospectively in two independent cohorts of NSCLC patients treated with ICI (N=305 pts) or chemotherapy (N=162 pts) (Mezquita et al., 2018). The authors found that LIPI score >1 was associated with poor overall survival in ICI treated patients but not in chemotherapy treated patients. However, a subsequent analysis of LIPI performed by the FDA on pooled clinical trial data from studies evaluating 1368 second line metastatic NSCLC patients who received ICI and 1072 patients who received chemotherapy did not confirm these results (Kazandjian, et al. 2018). This study indicated that LIPI may exert a prognostic impact irrespective of therapeutic modalities (ICI or chemotherapy) for 2nd line metastatic NSCLC. Finally, another study investigated the LIPI score in the context of metastatic patients with various solid tumors enrolled in phase 1 trials. While this analysis was performed on a very heterogeneous cohort, a LIPI score >1 was also associated with poor overall survival, suggesting its prognostic role is not limited to NSCLC patients (Varga, et al. 2019).

Immune Fitness

All six 3i blood test variables (NLR, Neutrophils, Albumin, LDH, GGT, AST) assessed through standard laboratory measures and identified by feature selection, have previously been reported to be prognostic in various tumor types. For example, high NLR has been associated with poor prognosis in multiple tumor types including gastrointestinal (Bowen, et al. 2017), melanoma (Ding, et al. 2018), NSCLC (Fukui, et al. 2019), UC (Sacdalan, et al. 2018) and HNSCC (Yu, et al. 2018, Tham, et al. 2018). The ratio likely reflects a measure of immune fitness which may impact tumor immune responses, and the association with poor prognosis is judged to be independent of type of ICI. Fukui, et al. observed a significant association between high NLR and poor prognosis in NSCLC patients treated with nivolumab. In a meta-analysis of ICI studies in melanoma, NSCLC, and UC, Sacdalan, et al. observed an association of high NLR with poorer outcomes, suggesting it has potential as a prognostic marker. It has also been speculated that tumor burden and chronic inflammation lead to high NLR followed by poor prognosis (Bigot, et al. 2017). Absolute neutrophil count (ANC) is a surrogate marker of physiological stress including inflammation, and in NSCLC patients, high ANC after nivolumab treatment has been observed to be independently associated with inferior overall survival (Khunger, et al. 2018). Albumin (ALB) is a well-known marker of malnutrition and cachexia in cancer patients, and low ALB has been observed to be associated with poor overall survival in many malignancies such as SCCHN, breast, lung, and gastrointestinal cancers (Gupta, et al. 2010). The production of ALB is also reduced in the context of chronic inflammation.

LDH is an established marker that reflects increased cell turnover mainly in malignant disease, but also in non-malignant disease (e.g. hemolytic anemia). In a recent FDA analysis of early mortality in ICI studies, elevated LDH was reported as an important risk factor mainly in melanoma patients (Mulkey, et al. 2019). In a systematic review of 76 studies, high LDH was associated with poor prognosis in renal, melanoma, gastric, prostate, nasopharyngeal and lung cancers (Petrelli, et al. 2015). In advanced cancers, the increased concentrations of LDH in the blood reflect increased metabolic activity and rapid cell proliferation that result in increased leakage of the intracellular enzyme LDH into the blood circulation.

Abnormalities in liver function tests such as AST and GGT are carefully monitored in cancer patients. Abnormal liver function tests not only reflect pre-existing disease, but also cancer progression/liver metastasis and drug toxicity, which are all known causes of death among cancer patients. Hence, AST and GGT have been reported as prognostic markers in cancer (Freis, et al. 2017, Luo, et al. 2017), and GGT has also been suggested to play a role in tumor initiation, invasion and drug resistance.

Method of Identifying Immunocompromised Patients

The 3i score can be used to identify patients with a high likelihood of EM, and who may therefore lack immune fitness. Lack of immune fitness suggests that ICI treatment should be postponed until such patients are effectively treated to improve their immune fitness. Therefore, therapeutic interventions in 3i high risk patients that bolster immune system fitness may enable these patients to receive to ICI treatment with a decreased risk of EM and moreover an increased chance for therapeutic benefit from an ICI treatment.

Similarly, methods of predicting the effectiveness of ICI treatment are contemplated herein. For example, a patient who is determined to be a 3i high risk patient would be predicted to not be effectively treated with an ICI, such as durvalumab.

Types of Cancer

Types of cancer that are contemplated for treatment herein include, for example, NSCLC, advanced solid malignancies, biliary tract neoplasms, bladder cancer, colorectal cancer, diffuse large b-cell lymphoma, esophageal neoplasms, esophageal squamous cell carcinoma, extensive stage small cell lung cancer, gastric adenocarcinoma, gastric cancer, gastroesophageal junction cancer, head and neck cancer, head and neck squamous cell carcinoma, hepatocellular carcinoma, Hodgkin lymphoma, lung cancer, melanoma, mesothelioma, metastatic clear cell renal carcinoma, metastatic melanoma, metastatic non-cutaneous melanoma, multiple myeloma, nasopharyngeal neoplasms, non-Hodgkin lymphoma, ovarian cancer, fallopian tube cancer, peritoneal neoplasms, pleural mesothelioma, prostatic neoplasms, recurrent or metastatic PD-L1 positive or negative SCCHN, recurrent squamous cell lung cancer, renal cell cancer, renal cell carcinoma, SCCHN, hypo pharyngeal squamous cell carcinoma, laryngeal squamous cell carcinoma, small cell lung cancer, squamous cell carcinoma of the head and neck, squamous cell lung carcinoma, TNBC, transitional cell carcinoma, unresectable or metastatic melanoma, urothelial cancer, and urothelial carcinoma. In a particular embodiment, a treatment regimen contemplated can include a biological component, such as an antibody and a chemotherapeutic component. Contemplated antibodies include an anti-PD-L1 antibody such as durvalumab (MEDI4736), nivolumab, pembrolimumab, avelumab, atezolizumab, KNO35, an anti-PD-1 antibody such as REGN2810, SHR1210, IBI308, PDR001, Anti-PD-1, BGB-A317, BCD-100, and JS001, and an anti-CTLA4 antibody, such as tremelimumab or ipilimumab. Additional antibodies are also contemplated herein. Any therapeutically effective antibody subparts are also contemplated herein.

Methods of Treatment

In one embodiment, the present disclosure is directed to effectively treating cancer patients with novel anticancer therapeutics and providing cancer patients with greater access to existing therapeutics. For example, the present disclosure contemplates treating cancer patients with immune checkpoint inhibitors (ICIs), such as those that target the PD-1/PD-L1 axis (PDX) and other IO treatments, such as immune system agonists.

Anticancer Therapeutics

Information regarding durvalumab (or fragments thereof) for use in the methods provided herein can be found in U.S. Pat. Nos. 8,779,108; 9,493,565; and 10,400,039 the disclosures of which are incorporated herein by reference in its entirety. In a specific aspect, durvalumab or an antigen-binding fragment thereof for use in the methods provided herein comprises the variable heavy chain and variable light chain CDR sequences of the 2.14H9OPT antibody as disclosed in the aforementioned U.S. patents.

Information regarding tremelimumab (or antigen-binding fragments thereof) for use in the methods provided herein can be found in U.S. Pat. No. 6,682,736 (in which tremelimumab is referred to as 11.2.1), the disclosure of which is incorporated herein by reference in its entirety.

The amount of anticancer therapeutics, such as antibodies or antigen-binding fragments thereof to be administered to a patient will depend on various parameters such as the patient's age, weight, clinical assessment, tumor burden and/or other factors, including the judgment of the attending physician. Any acceptable route of administration is contemplated, such as, without limitation, administration intravenous (e.g., intravenous infusion), parenteral, or subcutaneous routes of administration.

Additional therapeutics (chemotherapies or biologics) contemplated herein include without limitation cisplatin/gemcitabine or methotrexate, vinblastine, ADRIAMYCIN™ (doxorubicin), cisplatin (MVAC), carboplatin-based regimen, or single-agent taxane or gemcitabine, temozolomide, or dacarbazine, vinflunine, docetaxel, paclitaxel, nab-paclitaxel, Vemurafenib, Erlotinib, Afatinib, Cetuximab, Bevacizumab, Erlotinib, Gefitinib, and/or Pemetrexed. Further examples include drugs targeting DNA damage repair systems, such as poly (ADP-ribose) polymerase 1 (PARP1) inhibitors and therapeutics inhibiting WEE1 protein kinase activity, ATR protein kinase activity, ATM protein kinase activity, Aurora B protein kinase activity, and DNA-PK activity.

Any therapeutic compositions or methods contemplated herein can be combined with one or more of any of the other therapeutic compositions and methods provided herein.

Companion Diagnostics

In one embodiment, the present disclosure contemplates a device that includes one or more laboratory tests, as described elsewhere herein, for measuring concentrations of clinicopathological markers of a patient sample applied to the device. The device can further include a computing system comprising a gradient boosting machine learning model to predict whether the patient is likely to die within a given period of time based on the measured concentrations of clinicopathological markers from the one or more laboratory tests.

In another embodiment, a system is contemplated that includes one or more testing devices that is directly or indirectly linked to one or more computing devices such that upon determination of concentrations of one or more clinicopathological markers, the data be sent to a computing device to be provided to a gradient boosting machine learning model within the computing device. In turn, the gradient boosting machine learning model can output a prediction regarding patient EM and/or immune fitness or a prediction of effectiveness of an ICI therapeutic, such as durvalumab, to another component of the system.

In some embodiments, commercially available tests can be used to measure concentrations of clinicopathological markers, such antibody-based assays where antibodies specific for a marker of interest are used to target such markers. Binding of the antibodies to the specific markers can be detected and concentrations and/or concentrations of the marker of interest can be determined by the relative amount of antibody binding.

In some embodiments, samples used include tissue biopsies, cerebrospinal fluid, lymph, whole blood, blood fractions, such as serum or specific blood cell populations, urine, sweat, tears, saliva, and/or feces.

In one embodiment, a patient can be assessed upon arrival at a clinic for enrollment in a clinical trial. In this case, a blood draw can be performed using standard techniques and the patient's clinicopathological markers (e.g., neutrophils, hemoglobin, aspartate aminotransferase, alkaline phosphatase, etc.) can be assessed and the patient's overall survival predicted over a given period of time, such as 4, 8, 12 or 24 weeks, 4, 6, 8, or 10 months, 1, 2, 3, 4, or 5 years.

In another embodiment, a patient can be preapproved, remotely recruited, or flagged for accelerated therapy by having a lab report reviewed remotely where a centralized software platform can assess the patient's clinicopathological markers (e.g., neutrophils, hemoglobin, aspartate aminotransferase, alkaline phosphatase, etc.) and the overall score determined.

The following examples are set forth to provide those of ordinary skill in the art with a complete disclosure and description of how to practice the invention and are not intended to limit the scope of what the inventors regard as their invention.

Example 1—Validation of a Prognostic Score to Improve Patient Selection for Immuno-Oncology Trials (High Risk of Early Mortality; HREM)

This example provides an overview of a new prognostic scoring methodology for use in immuno-oncology clinical trials. As used herein, "High Risk of Early Mortality", "HREM" and "FastProgIO" are interchangeable.

Background

Figures 1A, 1B:
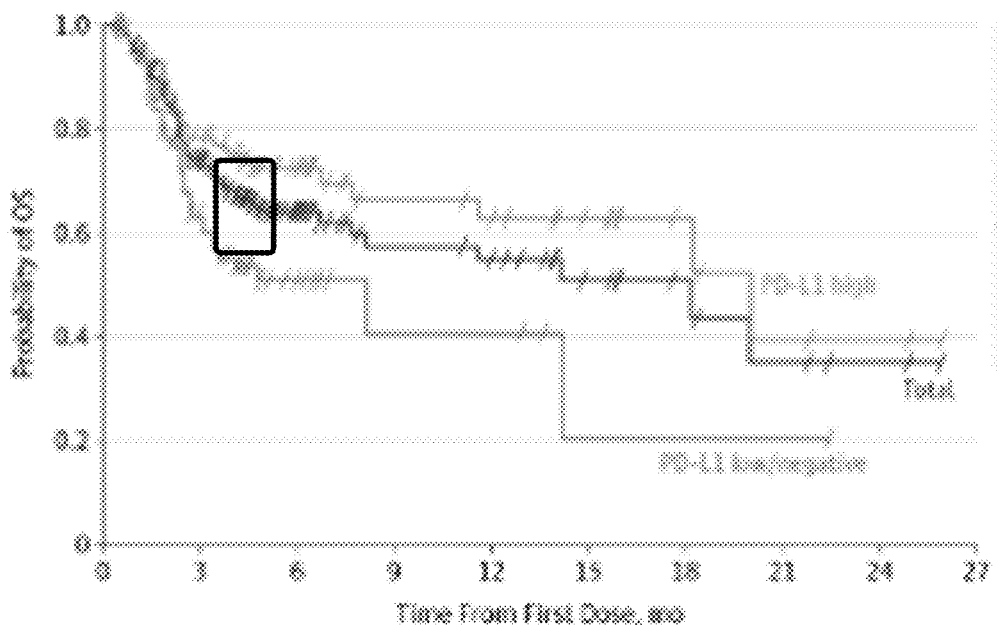

Life expectancy estimation is critical to selecting patients for oncology clinical trials, notably in the Phase 1 setting. However, most study protocols use subjective eligibility criteria to meet this goal (e.g., 12-week life expectancy). While eligibility criteria can help determine which patients could be included, they do not provide a reliable metric for determining overall survival (see FIG. 1A). Several prognostic scores have been developed from retrospective studies to help predict EM and OS of patients (FIG. 1B) but their utility in the immuno-oncology (IO) context remains unknown. The observation of a high percentage of patients with EM (overall survival [OS]≤12 weeks) in IO trials further underscores the need for more objective prediction criteria.

Objectives

The purpose of this study was to develop a new prognostic score using basic laboratory tests at baseline to identify patients with high risk of early mortality (OS≤12 weeks) using data from three Phase I IO trials that included patients with non-small cell lung cancer (NSCLC) and urothelial carcinoma (UC). Further, this study also sought to compare the prevalence of patients with high risk of early mortality across clinical sites in these studies. The new prognostic score (HREM) was benchmarked against three published prognostic scores (RMH, GRIM and LIPI). Finally, the effects of tumour/immune cell programmed cell death ligand-1 (PD-L1) expression and liver metastasis on the prediction of patients with high risk of early mortality were assessed.

Methods

NSCLC and UC patients (N=972) prospectively enrolled in three Phase 1 trials (NCT01693562, NCT02000947, and NCT02261220) investigating durvalumab (anti-PD-L1) ±tremelimumab (anti-cytotoxic T lymphocyte antigen [CTLA]-4) across 160 centers were analyzed. The variability in 12-week life expectancy rate across centers was also assessed.

Figure 2:
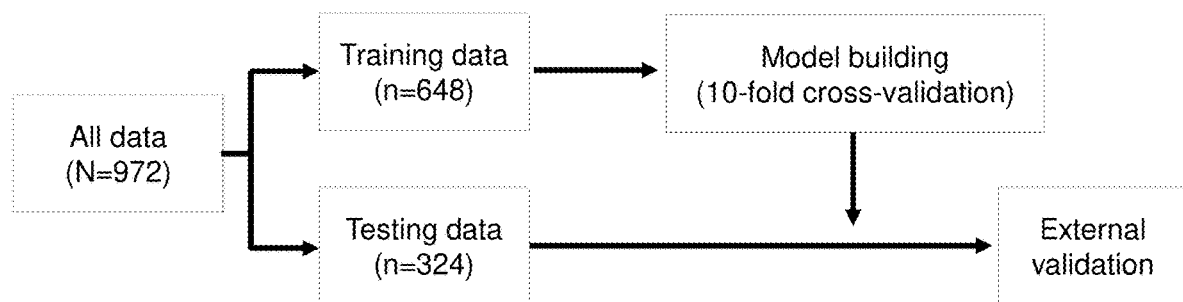

A composite score (HREM) of clinicopathological variables predicting 12-week life expectancy was developed in 648 patients and validated in 324 patients using a multivariate regression method (FIG. 2). Blood samples taken from the patients were measured for neutrophils, haemoglobin aspartate aminotransferase, and alkaline phosphate concentrations using commercially available assays.

HREM performance (prediction of patients with high risk of early mortality with an overall survival of less than or equal to 12 weeks) was compared to that of existing published scores (see FIG. 1) in terms of time-dependent true positive rate (TPR) and false positive rate (FPR).

Results

Figure 3A:
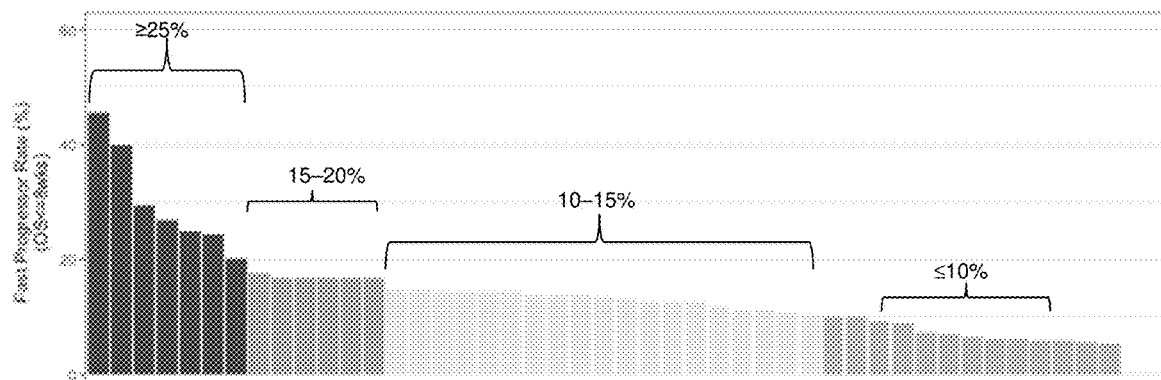
Figure 3B:
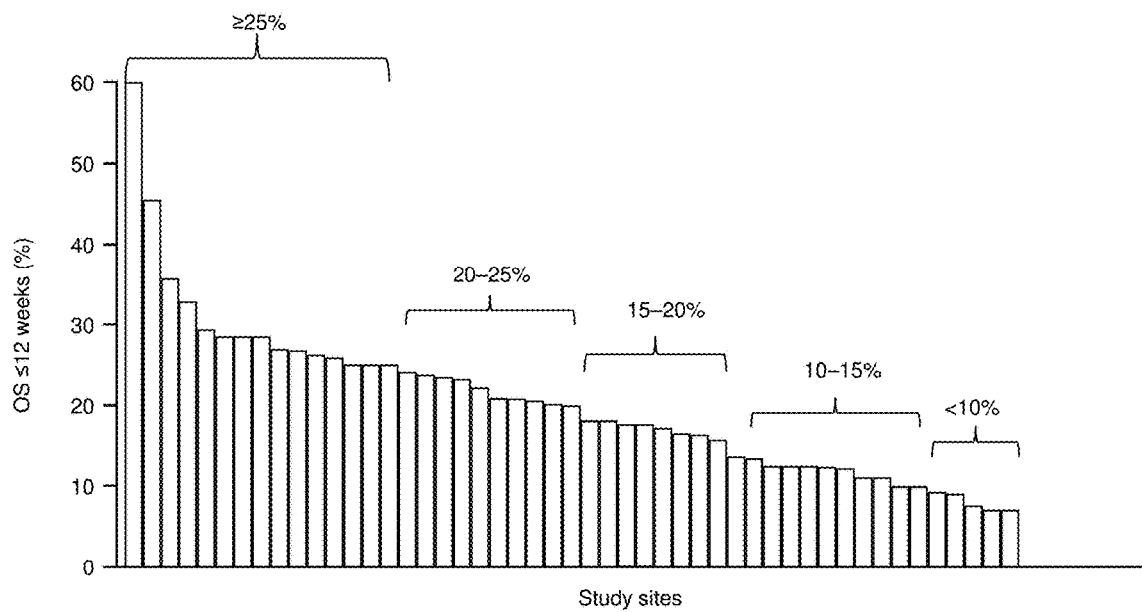

Fast progressor rates of patients analyzed per trial are indicated in Table 1 (see also, FIGS. 3A and 3B).

TABLE 1

Fast progressor rates in phase I immune-oncology trials

| Tumor Type | I/O Treatment | Study, Cohort | N | Fast Progressor Rate OS ≤ 4 wks | OS ≤ 8 wks | OS ≤ 12 wks |
|---|---|---|---|---|---|---|
| NSCLC | Durva + Treme | Study06, A* | 45 | 0.0% | 0.0% | 2.6% |
|  |  | Study06, B co-administration | 19 | 5.3% | 15.8% | 15.8% |
|  |  | Study06, B sequential | 213 | 3.8% | 8.6% | 15.4% |
|  |  | Study06, Dose escalation | 102 | 1.0% | 10.0% | 16.3% |
|  | Durva | Study1108, NSCLC NON-SQUAMOUS | 144 | 7.7% | 12.7% | 23.1% |
|  |  | Study1108, NSCLC SQUAMOUS | 160 | 6.3% | 12.3% | 17.1% |
| UBC | Durva + Treme | Study10, UBC Expansion | 98 | 7.2% | 15.6% | 20.9% |
|  | Durva | Study1108, BLADDER CANCER | 191 | 3.7% | 13.7% | 25.9% |
|  |  | Total | 972 | 4.7% | 11.4% | 19.0% |

Baseline characteristics for NSCLC and UC patients (shown in Table 2) were similar.

TABLE 2

Patient Characteristics

|  | NSCLC (N = 683) | UC (N = 289) |
|---|---|---|
| Age, mean ± SD | 63.45 ± 10.56 | 65.31 ± 9.64 |
| Gender, n (%) |  |  |
| Female | 293 (43) | 72 (25) |
| Male | 390 (57) | 217 (75) |
| Body mass index, mean ± SD | 25.47 ± 5.11 | 26.52 ± 4.75 |
| ECOG performance score, n (%) |  |  |
| 0 | 186 (27) | 100 (35) |
| 1 | 495 (73) | 188 (65) |
| ≥2 | 1 (0) | 1 (0) |
| PD-L1 expression, n (%)* |  |  |
| High | 269 (44) | 134 (50) |
| Low/Neg | 348 (56) | 132 (50) |
| Liver metastasis, n (%) |  |  |
| Yes | 156 (23) | 113 (39) |
| No | 527 (77) | 176 (61) |
| No. of metastasic sites, median (min, max) | 2 (1, 9) | 2 (1, 6) |
| Albumin (g/L), mean ± SD | 37.85 ± 4.98 | 38.11 ± 5.11 |
| Lactate dehydrogenase (U/L), mean ± SD | 329.84 ± 377.68 | 324.22 ± 385.25 |
| Neutrophils ($10^9$/L), mean ± SD | 6.09 ± 3.69 | 6.05 ± 4.2 |
| Lymphocytes ($10^9$/L), mean ± SD | 1.28 ± 0.66 | 1.25 ± 0.56 |
| Neutrophil/lymphocyte ratio, mean ± SD | 6.26 ± 5.73 | 6.25 ± 7.18 |
| Haemoglobin (g/L), mean ± SD |  |  |
| All | 119.68 ± 17.1 | 114.33 ± 15.86 |
| Female | 117.53 ± 15.28 | 109.41 ± 14.03 |
| Male | 121.3 ± 18.2 | 116.01 ± 16.12 |
| Aspartate aminotransferase (U/L), mean ± SD | 24.05 ± 16.8 | 24.52 ± 14.64 |
| Alkaline phosphatase (U/L), mean ± SD | 109.34 ± 91.55 | 116.63 ± 93.15 |

*For NSCLC, High: TC ≥ 25% and Low/Neg: TC < 25%; for UC, High: TC ≥ 25% or IC ≥ 25%, Low/Neg: TC < 25% and IC < 25%.

HREM Score

Figure 6:
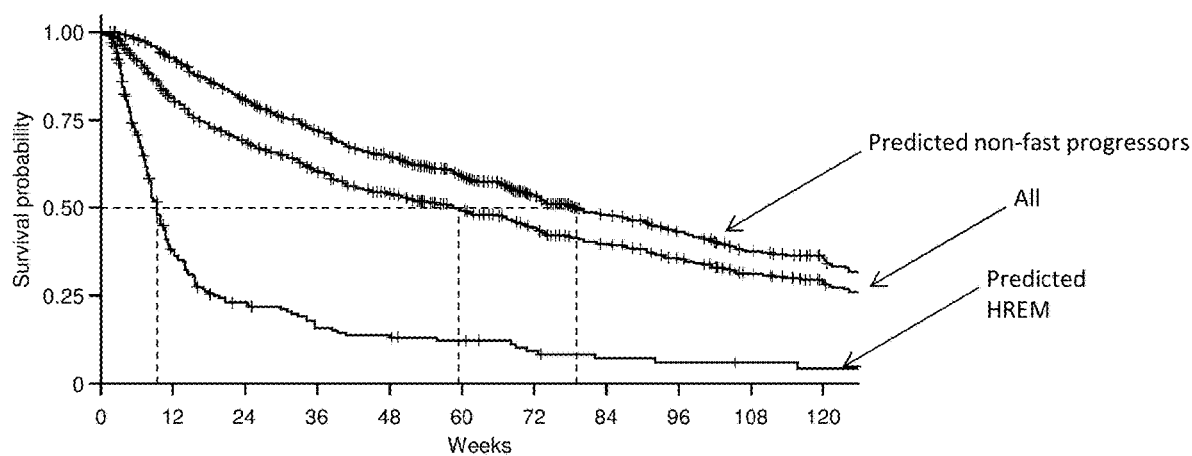
Figure 7:
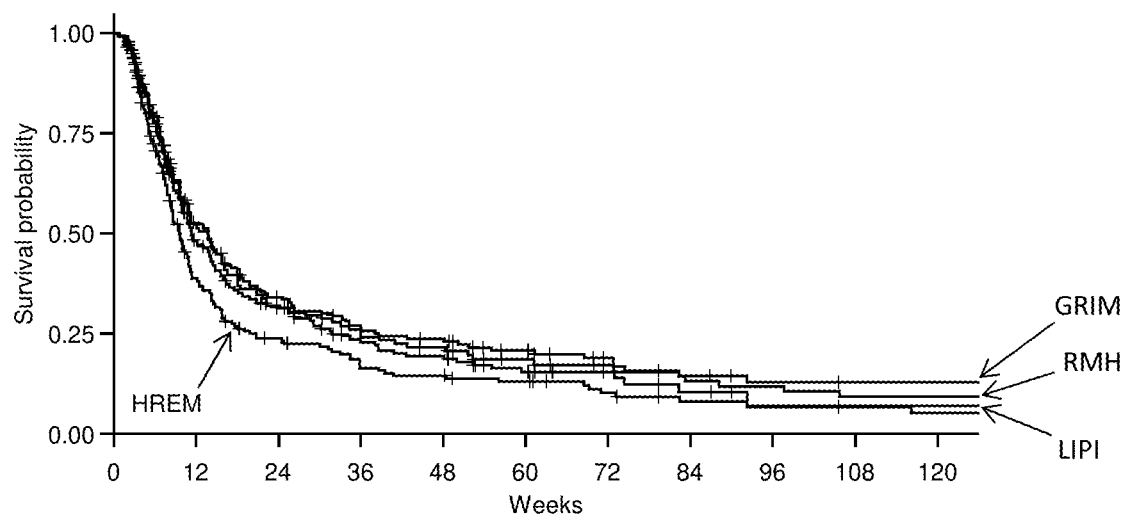

The HREM score included neutrophil counts, aspartate aminotransferase, alkaline phosphatase, and haemoglobin as the predictive markers. The true positive rate (TPR) of identifying patients with OS≤12 weeks was 74.7% (74.1% in the training data set and 75.9% in the testing data set), while the false positive rate (FPR) was controlled at around 10% (FIG. 4). The time-dependent TPR of HREM was superior or similar to that of RMH, GRIM, and LIPI across the OS range of 4-12 weeks (FIG. 5). The time-dependent FPR of HREM was superior to that of GRIM, slightly lower than that of RMH and higher than that of LIPI (FIG. 5B). Patients with high risk of early mortality and non-patients with high risk of early mortality identified by HREM showed distinct survival profiles (FIG. 6). Patients with high risk of early mortality identified by HREM had shorter OS than those identified by the three published scores (FIG. 7).

Figure 8:
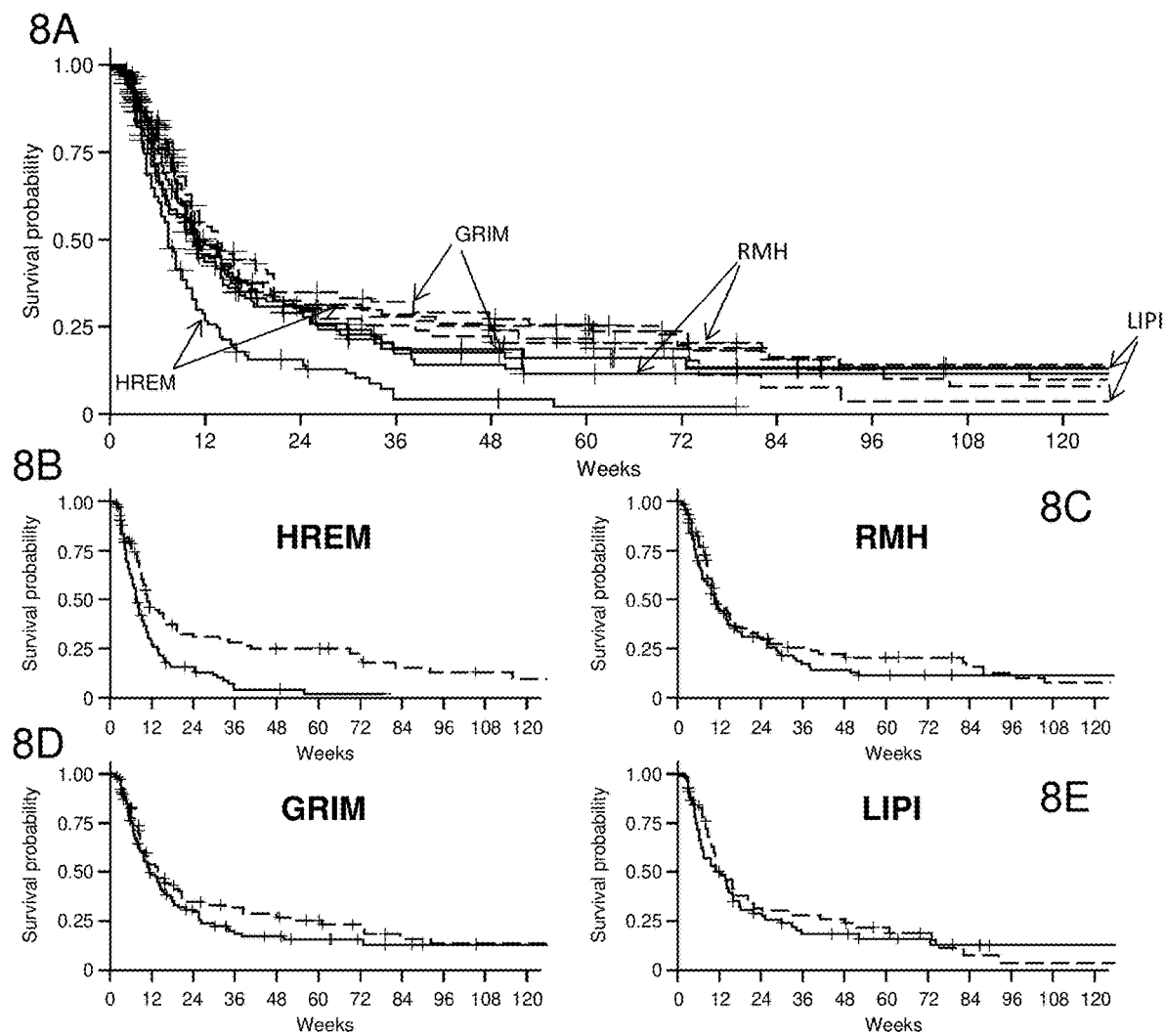

Effect of PD-L1 Expression and Liver Metastasis in Predicted Patients with High Risk of Early Mortality A PD-L1 effect was observed in patients with high risk of early mortality predicted by HREM but not in those predicted by the other scores: HREM predicted that patients with high risk of early mortality with PD-L1 Low/Neg expression progressed faster than those with PD-L1 High expression (FIG. 8).

An effect of liver metastasis was observed in patients with high risk of early mortality predicted by all four scores: patients with liver metastasis (mets) progressed faster than those without (FIG. 9). In patients without liver mets, patients with high risk of early mortality predicted by HREM had poorer survival than those predicted by the other three scores.

Conclusions

Substantial variability across sites in the prevalence of patients with high risk of early mortality suggests that the use of subjective criteria to estimate 12-week life expectancy for study enrollment is clearly suboptimal. In this large cohort of NSCLC and UC patients, HREM significantly outperformed RMH, GRIM, and LIPI prognostic scores in the prediction of patients with high risk of early mortality. A PD-L1 effect was observed in patients with high risk of early mortality as predicted by HREM but not by the three published scores, which demonstrates the greater sensitivity of the HREM approach to assessing patients.

An effect of liver metastasis was observed in predicted patients with high risk of early mortality by all four scores. However, in patients without liver metastasis, patients with high risk of early mortality as predicted by HREM had a shorter OS than those predicted by the published scores. The success of the HREM prognostic assessment for NSCLC and UC patients suggests that this approach could be effective in additional cancer types.

Example 2—Evaluation of HREM in Various Tumour Types

This example demonstrates the applicability of the HREM prognostic scoring methodology for use in scoring other cancer types.

Methods

Patients with various cancer types from a Phase I study (Study 1108) centers were analyzed for prevalence of predicted patients with high risk of early mortality.

Results

Figure 10:
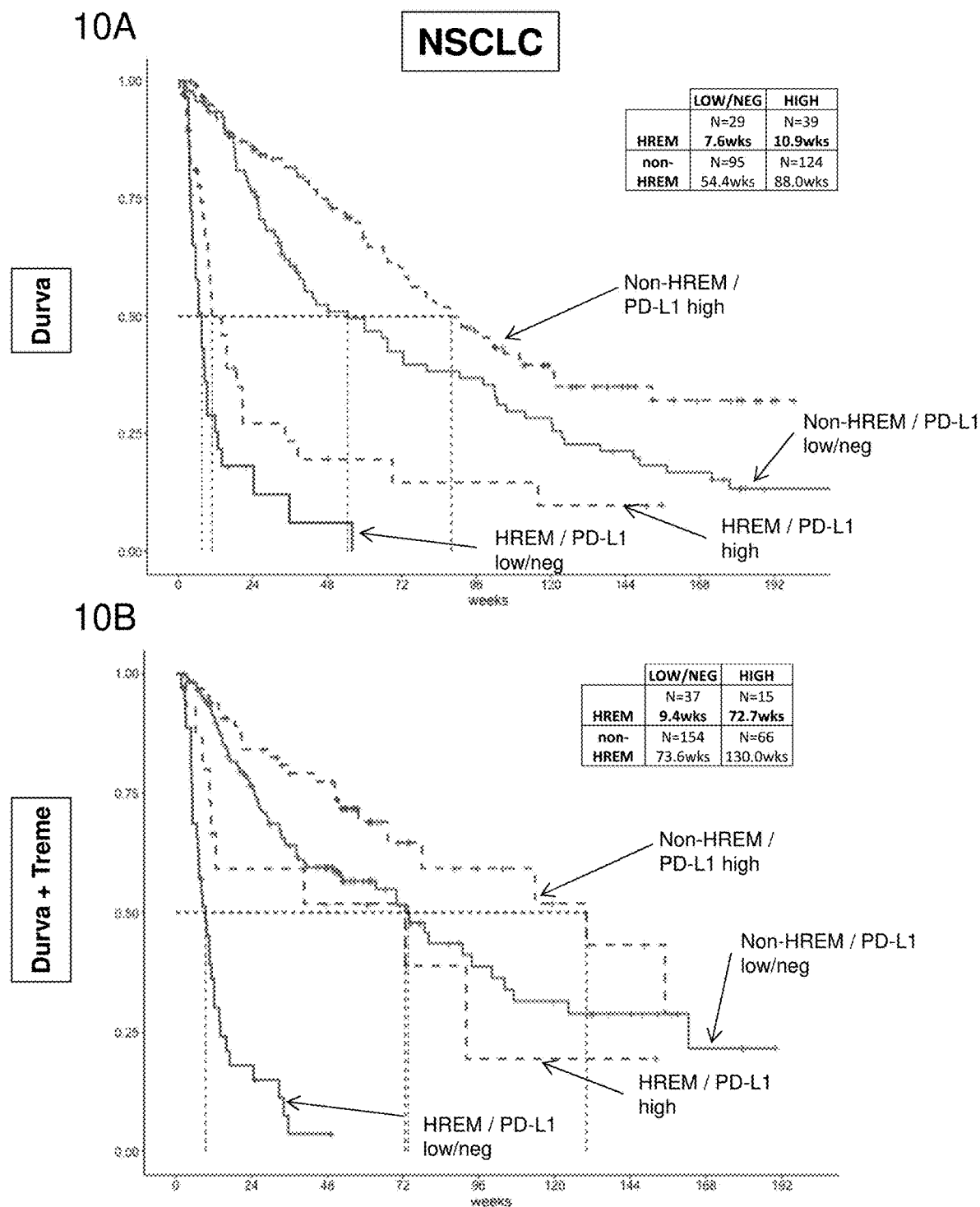
Figure 10:
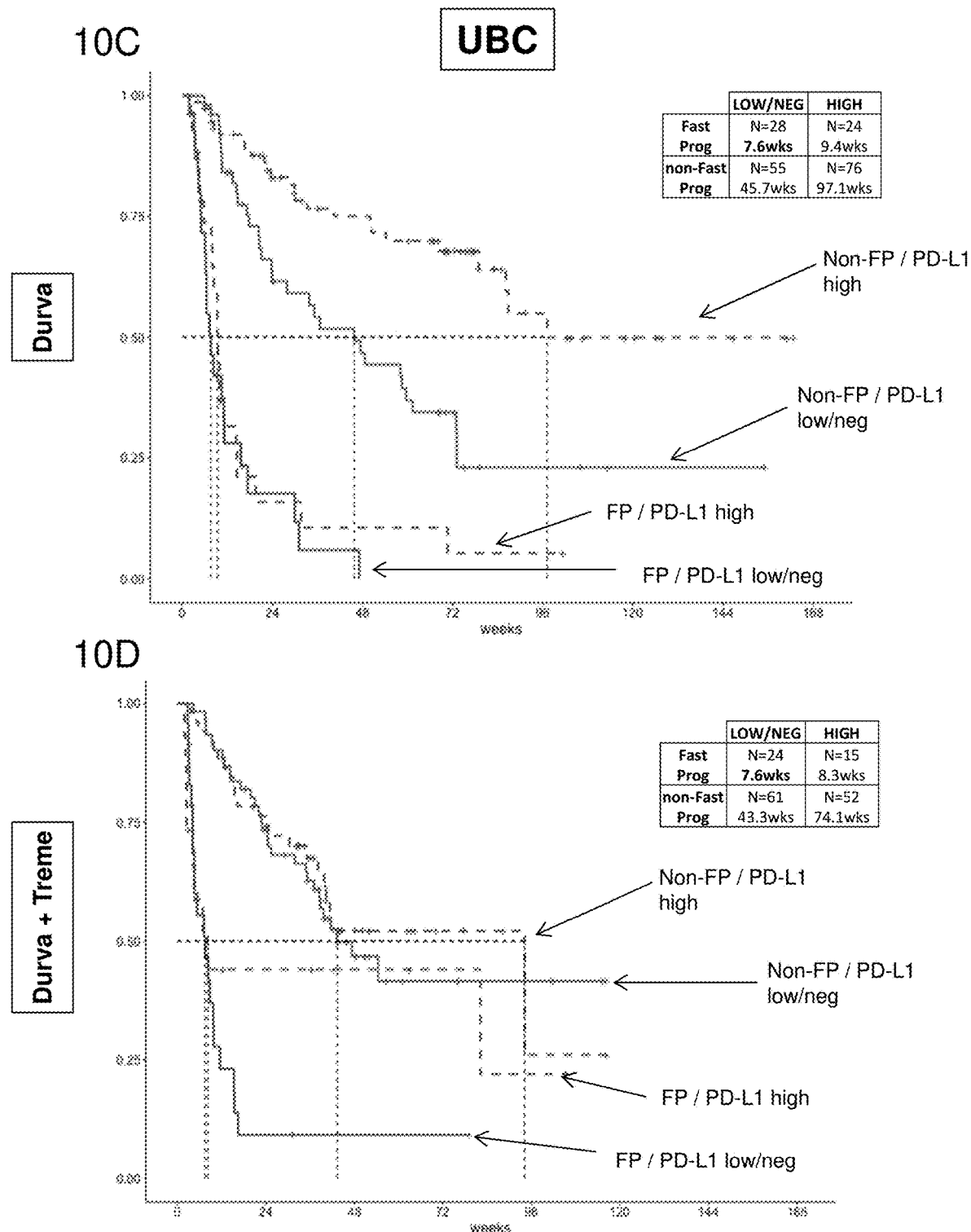

Fast progressor rates of patients analyzed are indicated in Table 3 (see also, FIG. 10).

TABLE 3

Fast progressor rates in multiple cancer types

| Study 1108, Cohort | N | Fast Progressor Rate (OS ≤ 12 wks) |
|---|---|---|
| SCCHN | 63 | 18% |
| MSI-HIGHCANCER | 62 | 5% |
| GASTROESOPHAGEAL CANCER | 54 | 34% |
| OVARIAN CANCER | 47 | 9% |
| TNBC | 41 | 19% |
| HCC | 40 | 8% |
| PANCREATICADENO CARCINOMA | 37 | 29% |
| UVEAL MELANOMA | 24 | 21% |
| ADVANCED CUTANEOUS MELANOMA | 22 | 19% |
| HPV POSITIVE CANCER | 22 | 23% |
| SCLC | 21 | 39% |
| GBM | 20 | 11% |
| SOFT TISSUE SARCOMA | 20 | 12% |
| NASOPHARYNGEAL CARCINOMA | 10 | 20% |
| ADVANCED MALIGNANT MELANOMA | 8 | 0% |
| CRC | 2 | 0% |
| RCC | 2 | 0% |

Table 4 illustrates a comparison of HREM versus other published scores.

Conclusions

HREM can be used to predict patients with high risk of early mortality in multiple cancer types. Therefore, this prognostic score can be used to improve patient intervention and phase I results in multiple cancer types. The strength of the prediction can be increased by increasing sample sizes.

Example 3—Correlation of HREM with Inflammatory Proteins

This example investigated potential correlation between HREM results and inflammatory proteins.

Methods

Using the UC cohort, patient serum samples were tested for concentrations of inflammatory proteins which were correlated with HREM scores using a Spearman correlation.

Results

Figure 11:
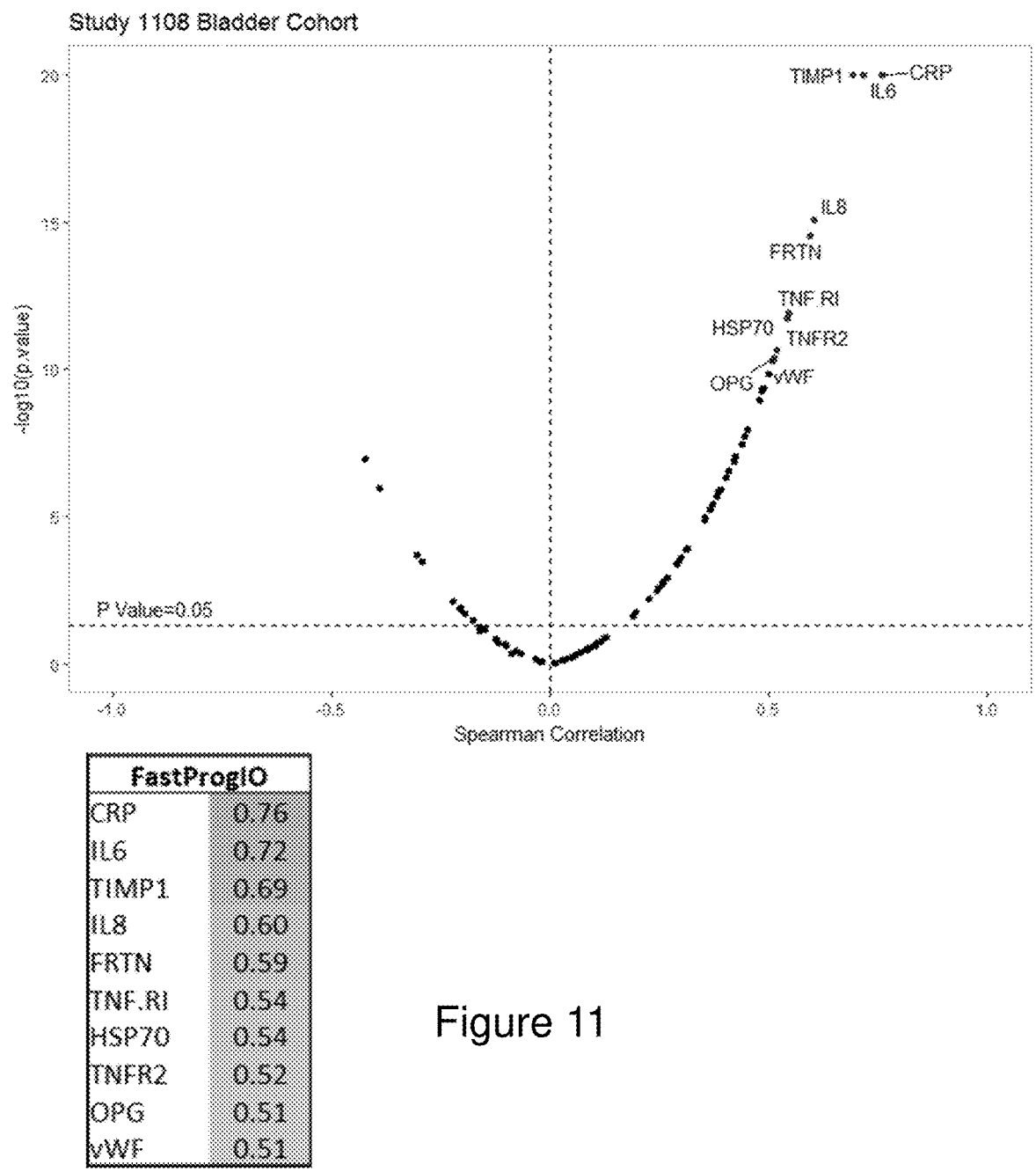

HREM scores were significantly correlated with 10 different inflammatory proteins (see FIG. 11).

Conclusions

HREM could be useful for making therapeutically relevant biological inferences for that could help inform patient care and/or Phase I study selection.

Example 4—Development of a Pan-Tumor Prognostic Model (F1 Model)

This example sought to develop an improved prognostic model (F1 model) building upon the success of the HREM model.

Methods

Figure 12:
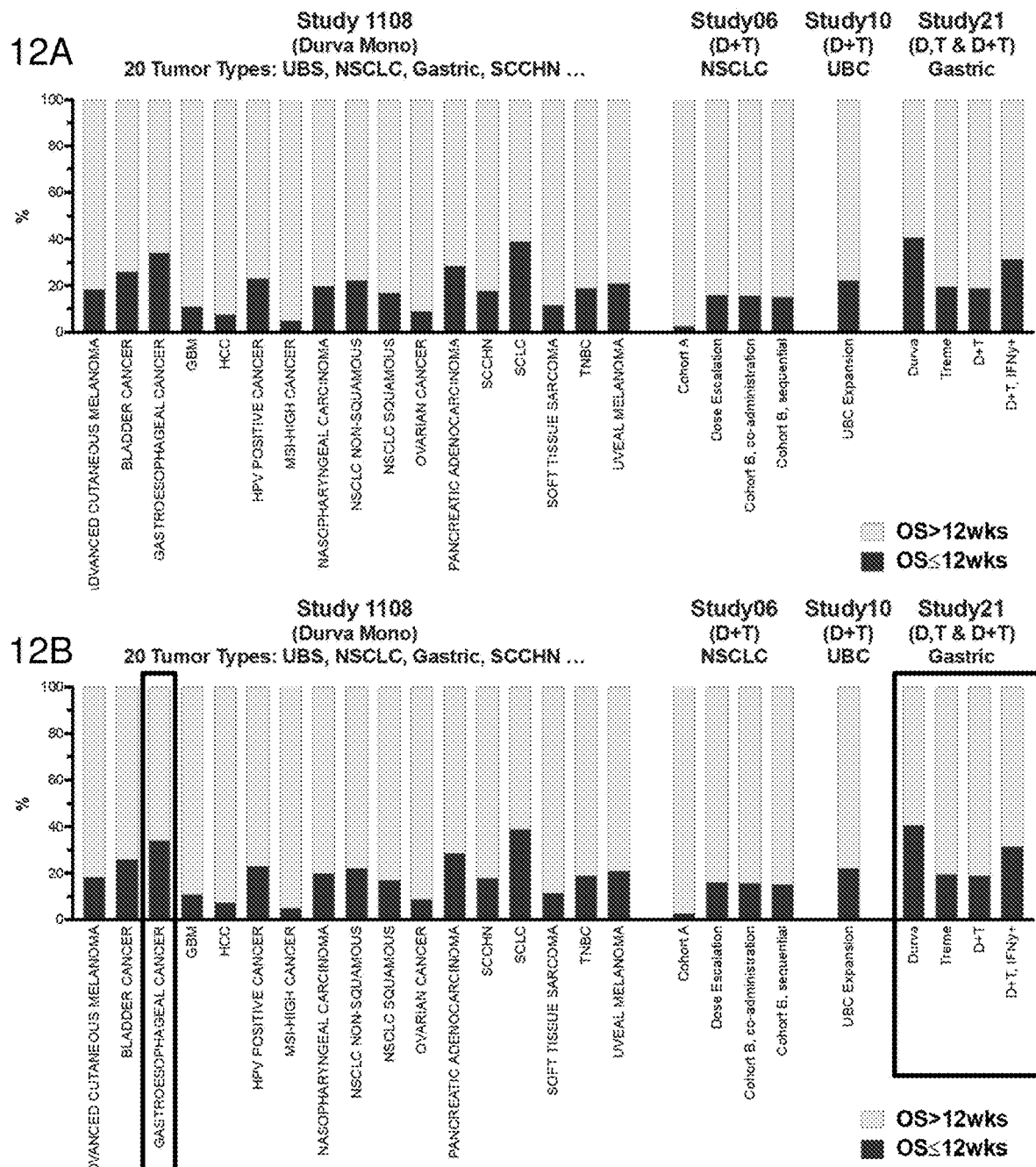
Figure 13:
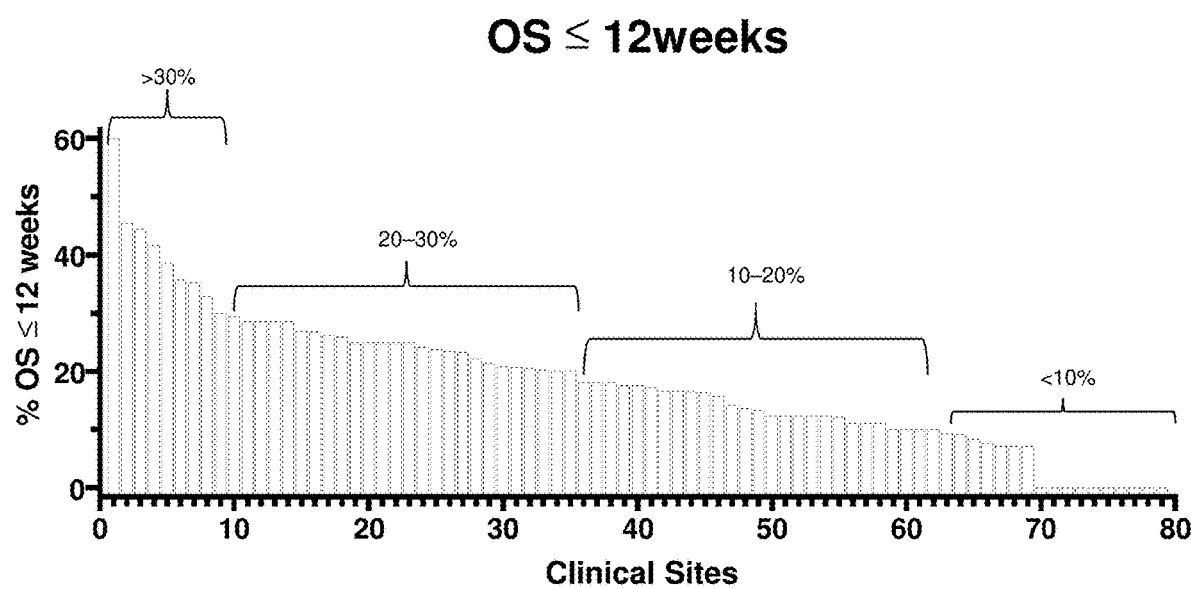

Patients from a combination of 4 studies with several cancer types were used to develop a new prognostic model with improved true positive and false positive rates (Table 5) (see also, FIGS. 12 and 13).

TABLE 4

Comparison of predictive scores in other cancer types

| Study1108, Cohort | N | HREM Rate (OS ≤ 12 wks) | HREM TPR | HREM FPR | RMH TPR | RMH FPR | GRIM TPR | GRIM FPR | LIPI TPR | LIPI FPR | Selected Score |
|---|---|---|---|---|---|---|---|---|---|---|---|
| Advanced Cutaneous Melanoma | 22 | 19% | 85% | 11% | 100% | 16% | 100% | 16% | 85% | 16% | HREM |
| Hpv Positive Cancer | 22 | 23% | 82% | 17% | 86% | 24% | 79% | 29% | 49% | 11% | HREM |
| Msi-High Cancer | 62 | 5% | 100% | 15% | 33% | 29% | 100% | 17% | 0% | 5% | HREM |
| Ovarian Cancer | 47 | 9% | 60% | 7% | 52% | 26% | 86% | 7% | 64% | 5% | GRIM, LIPI, HREM |
| Scchn | 63 | 18% | 65% | 10% | 39% | 11% | 76% | 18% | 43% | 8% | HREM |
| Sclc | 21 | 39% | 61% | 0% | 65% | 32% | 79% | 16% | 55% | 16% | HREM |
| Uveal Melanoma | 24 | 21% | 79% | 11% | 40% | 26% | 40% | 17% | 40% | 22% | HREM |
| Pancreatic Adeno Carcinoma | 37 | 29% | 56% | 34% | 56% | 11% | 46% | 8% | 9% | 9% | None |
| Gastroesophageal Cancer | 54 | 34% | 91% | 25% | 85% | 22% | 68% | 23% | 45% | 0% | None |
| Gbm | 20 | 11% | 0% | 0% | ND | ND | 0% | 11% | 0% | 11% | None |
| Hcc | 40 | 8% | 99% | 58% | 66% | 42% | 66% | 23% | 33% | 6% | None |
| Nasopharyngeal Carcinoma | 10 | 20% | 50% | 29% | 0% | 29% | 50% | 43% | 50% | 14% | None |
| Soft Tissue Sarcoma | 20 | 12% | 0% | 27% | 64% | 27% | 100% | 21% | 71% | 21% | None |
| Tnbc | 41 | 19% | 61% | 21% | 79% | 36% | 87% | 24% | 79% | 24% | None |

TABLE 5

Studies used for F1 patient pools

| Study | Tumor Type | Treatment | Fast progressor rate | | |
|---|---|---|---|---|---|
| | | | OS ≤ 4 wks | OS ≤ 8 wks | OS ≤ 12 wks |
| Study 1108 (N = 1022) | Advanced Cutaneous Melanoma, Advanced Malignant Melanoma, Bladder Cancer, Colorectal cancer, Gastroesophageal Cancer, Glioblastoma, Hepatocellular carcinoma HPV Positive Cancer, MSI-High Cancernasopharyngeal Carcinoma, Non-small cell lung cancer Non-Squamous, Non-small cell lung cancer Squamous, Ovarian Cancer, Pancreatic Adenocarcinoma, Renal cell carcinoma Squamous cell head and neck cancer Small cell lung cancer Soft Tissue Sarcoma, Triple Negative Breast Cancer, Uveal Melanoma | Durva Mono | 4.2% | 13.2% | 19.9% |
| Study 06 (N = 379) | Non-small cell lung cancer | Durva + Treme | 2.7% | 8.4% | 14.2% |
| Study 10 (N = 168) | Urinary bladder cancer | Durva + Treme | 6.0% | 16.3% | 22.4% |
| Study 21 (N = 113) | Gastric cancer | Durva Mono Treme Mono Durva + Treme | 4.5% | 14.6% | 25.9% |
| All (N = 1682) | | | 4.0% | 12.5% | 19.3% |

Figure 14:
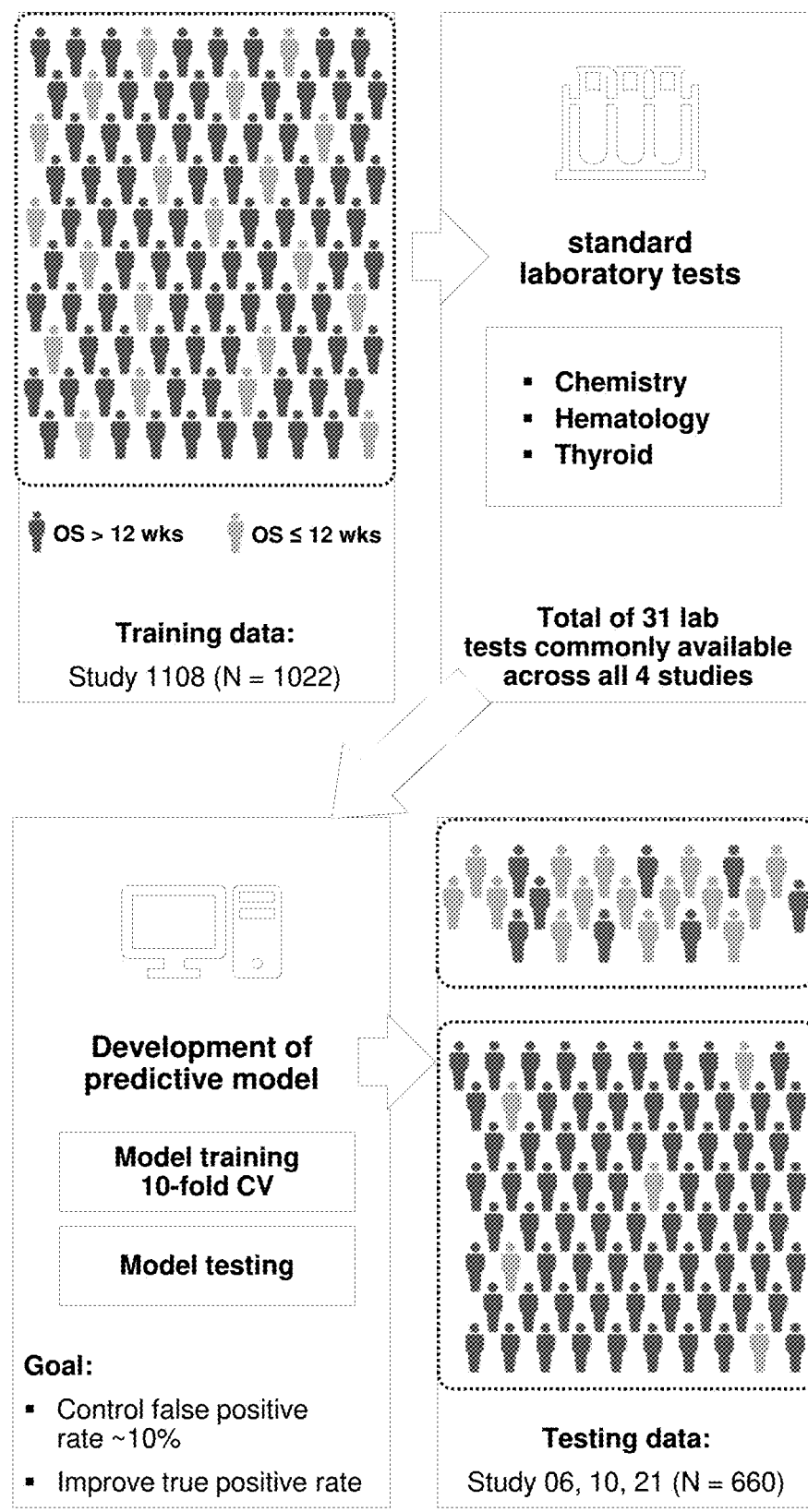

Development of the F1 model is illustrated in FIG. 14. Several standard lab tests were included in the model, such as ALB, LAP, AST, LDH, NEUT, and WBC. Predictive modelling approaches, such as Ensemble trees-based models and Random Forest models were used to develop the model.

Results

Figure 16:
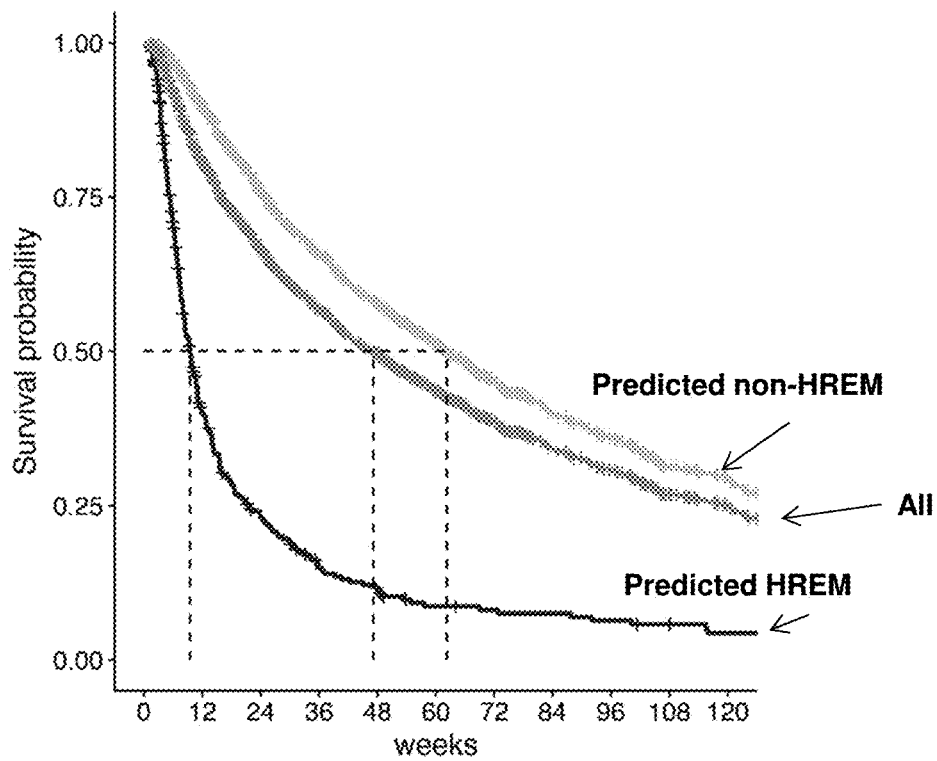
Figure 17:
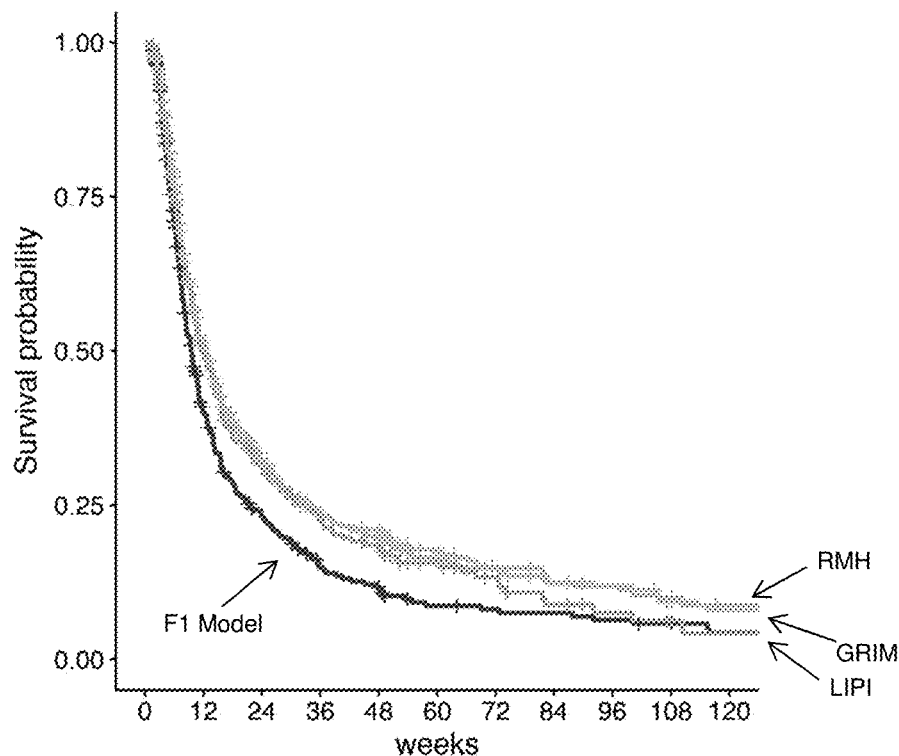
Figure 18:
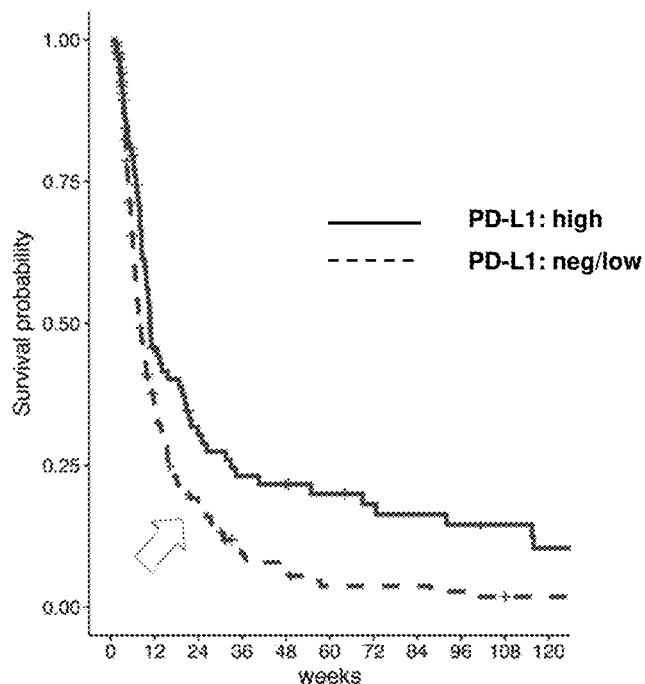
Figure 19:
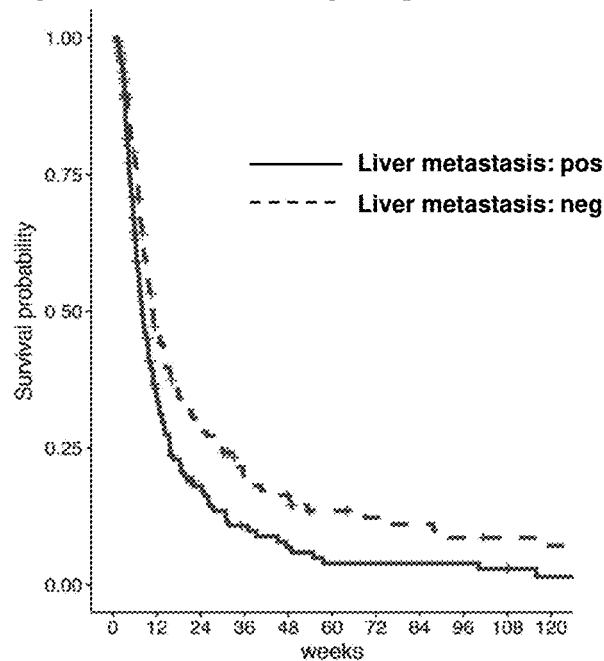

Predictive performance of the F1 model in the training and testing data is shown in FIG. 15. Overall survival of the F1 model is shown in FIG. 16. A comparison of the F1 model to published prognostic scores is shown in FIG. 17. PD-L1 liver metastases effects are seen in FIGS. 18 and 19, respectively. Collectively, these results show that the F1 model is a much better predictor of OS than previously available prognostic scores, such as RMH, GRIM, and LIPI.

Example 5—Retrospective Application of F1 Model to Study 21 (Gastroesophageal Cancer) and ARCTIC (NSCLC)

Figure 20:
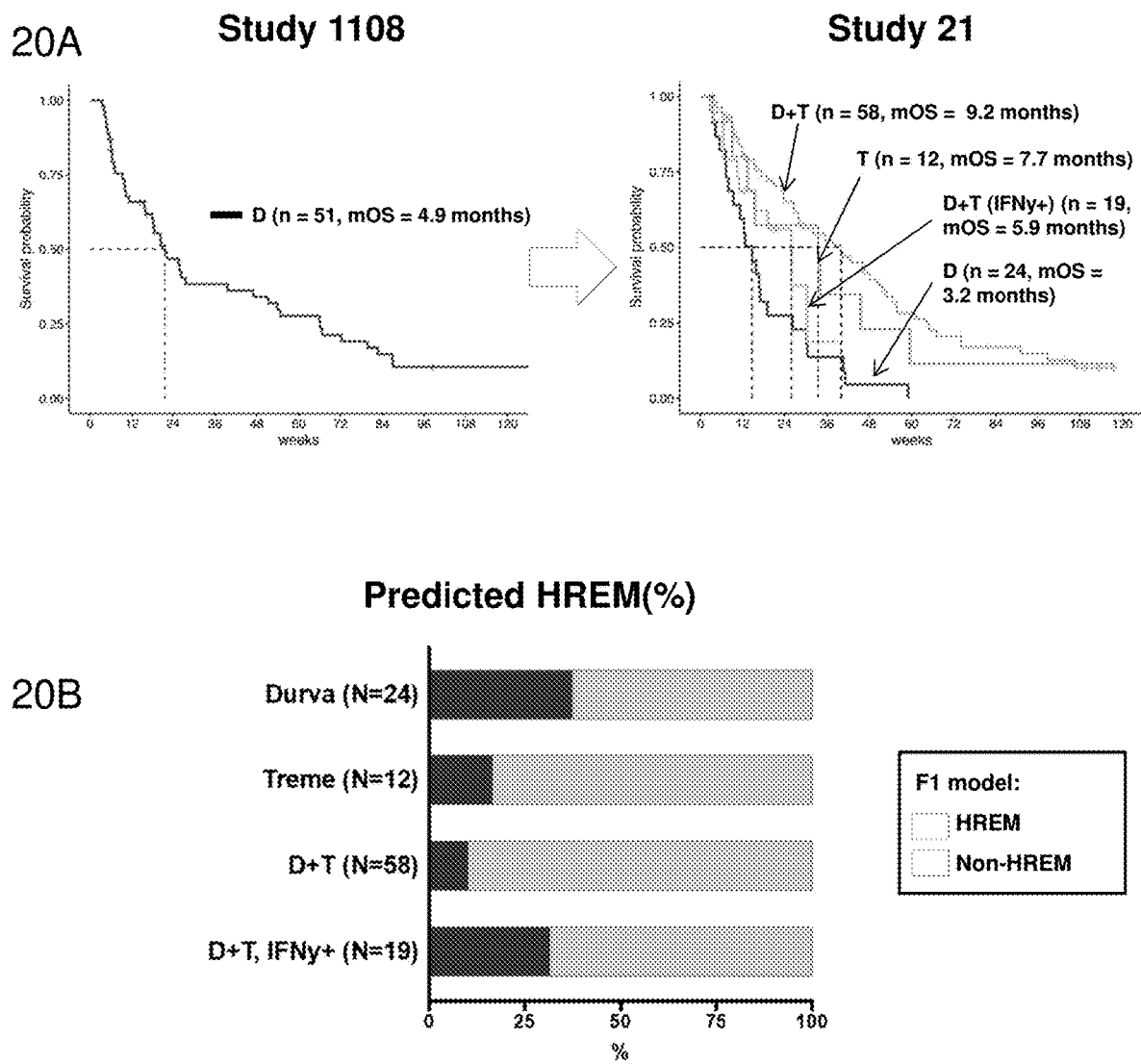

To demonstrate its usefulness in retrospective analysis of previous trials, the F1 model was used to review 2 phase I trials for gastroesophageal cancer using Durvalumab alone (Study 1108) or Durvalumab (D) alone, Tremelimumab (T) alone, Durvalumab+Tremelimumab (D+T), and Durvalumab+Tremelimumab in IFNy+ cohorts (Study 21). Results are seen in comparing FIGS. 20A and 20B.

Figure 21:
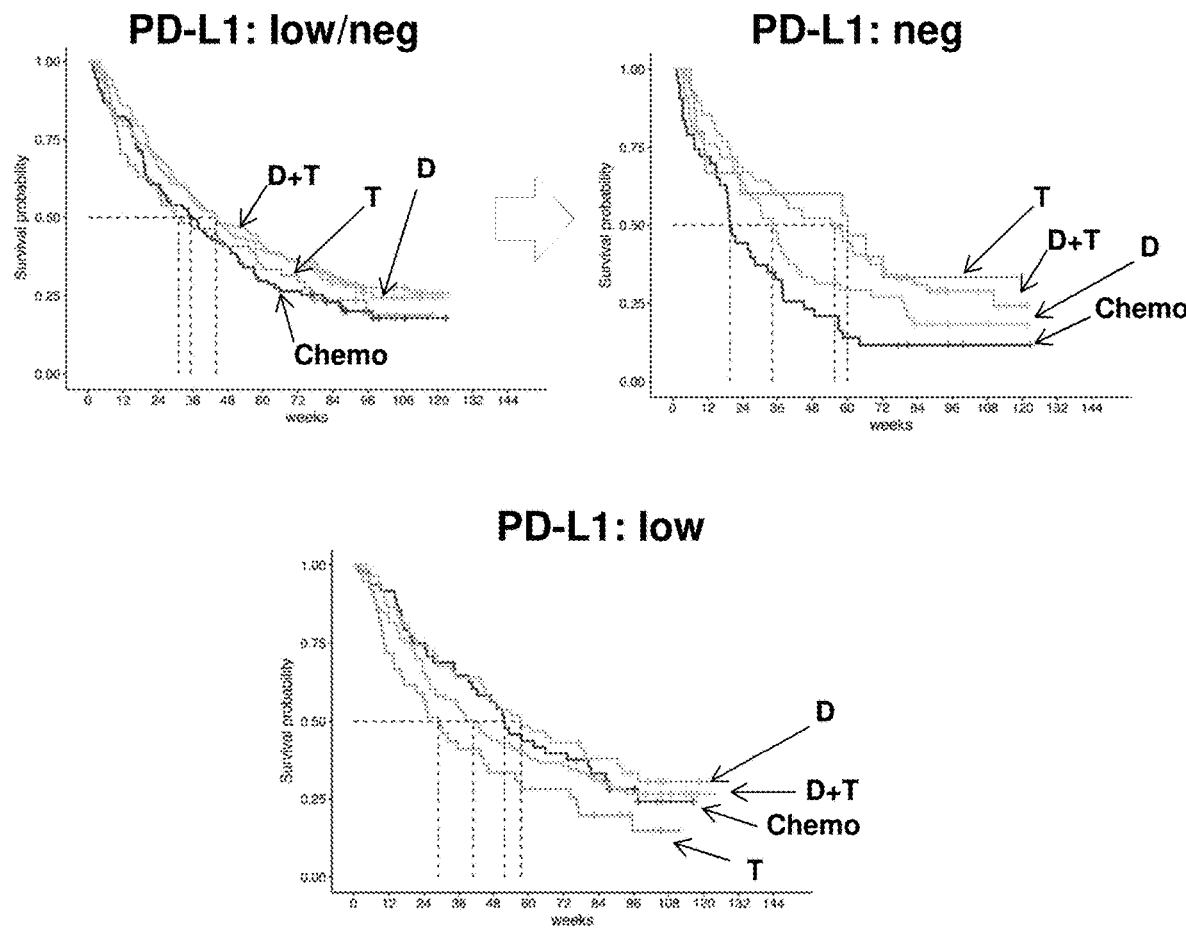

ARCTIC study results (FIG. 21) were also considered. The results of applying the F1 model to the ARCTIC study are shown in FIG. 22.

Conclusions

The F1 model is an even more powerful predictor of OS that the HREM model. It outperforms published scores (poor OS, generalizable to all tumor types, PD-L1 effect).

The F1 model can be used to appraise ongoing or previously conducted clinical trials in order to assess for any imbalance in the fast progressor rates between arms that may have potential impact on the outcome. Further, it is believed that the F1 model can be incorporated into inclusion/exclusion criteria in future phase I trials (escalation phase, randomized expansion) as a more objective way to exclude poor risk patients. Further, it can be used to improve the selection of study sites by excluding sites with history of enrolling high rate of patients with high risk of early mortality. Excluding patients with high risk of early mortality in phase 1 studies (escalation and randomized expansion parts) will likely increase the ability to detect efficacy signals of phase I trials.

Example 6—Correlation of F1 Model with Inflammatory Proteins

This example investigated potential correlation between F1 model results and inflammatory proteins.

Methods

Using the Study 1108, UC cohort, patient serum samples were tested for concentrations of inflammatory proteins (C-reactive protein, IL-6, TIMP-1, and IL-8) which were correlated with F1 model scores.

Results

Figure 23:
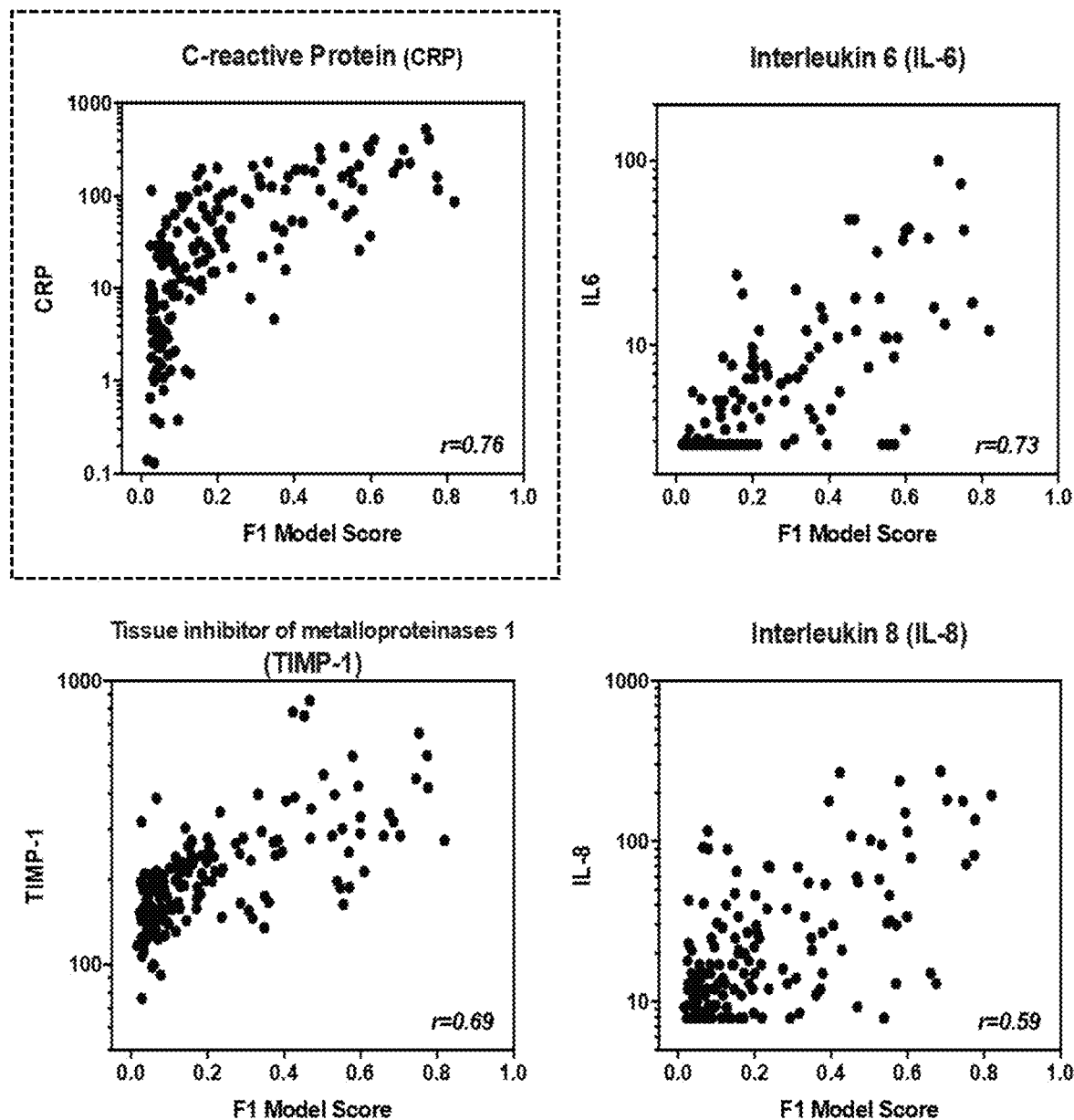
FIG. 23 shows a correlation of the F1 model results with an inflammatory proteomic signature (Study 1108, UBC).

HREM scores were significantly correlated with 10 different inflammatory proteins (see FIG. 23). Other correlated biomarkers (r>0.5) include Ferritin (FRTN), Tenascin-C (TN-C), 70 kiloDalton Heat Shock Proteins (HSP70), necrosis factor receptor 1 (TNFR1), Interleukin-2 Receptor alpha (IL-2Ra), Tumor Necrosis Factor Receptor 2 (TNFR2), Insulin like Growth Factor Binding Protein 2 (IGFBP2), and Myeloid Progenitor Inhibitory Factor 1 (MPIF1).

Conclusions

F1 model could be useful for making therapeutically relevant biological inferences for that could help inform patient care and/or Phase I study selection.

Example 7—Training and Testing of an Updated F1 Model Using the EAGLE Trial and Neutrophils (NEUT), Lymphocyte Percentage (LYM %), Albumin (ALB), Lactate Dehydrogenase (LDH), and URATE as Clinicopathological Markers This example sought to test an improved prognostic model (F1 model) building upon the success of the first F1 model.

Methods

Patients from a combination of 3 studies with several cancer types were used to develop a new prognostic model with improved true positive and false positive rates (Table 6).

TABLE 6

Studies used for training F1 model

| Study | Tumor Type | Treatment |
|---|---|---|
| Study 1108 (N = 1022) | Squamous Cell Carcinoma of the Head and Neck | Durva Mono |
| CONDOR (N = 267) | Head and Neck Squamous Cell Carcinoma | Durva Mono Durva + Treme |
| HAWK (N = 111) | Head and Neck Squamous Cell Carcinoma | Durva Mono |

Development of the model was performed as depicted in FIG. 14.

Figure 24:
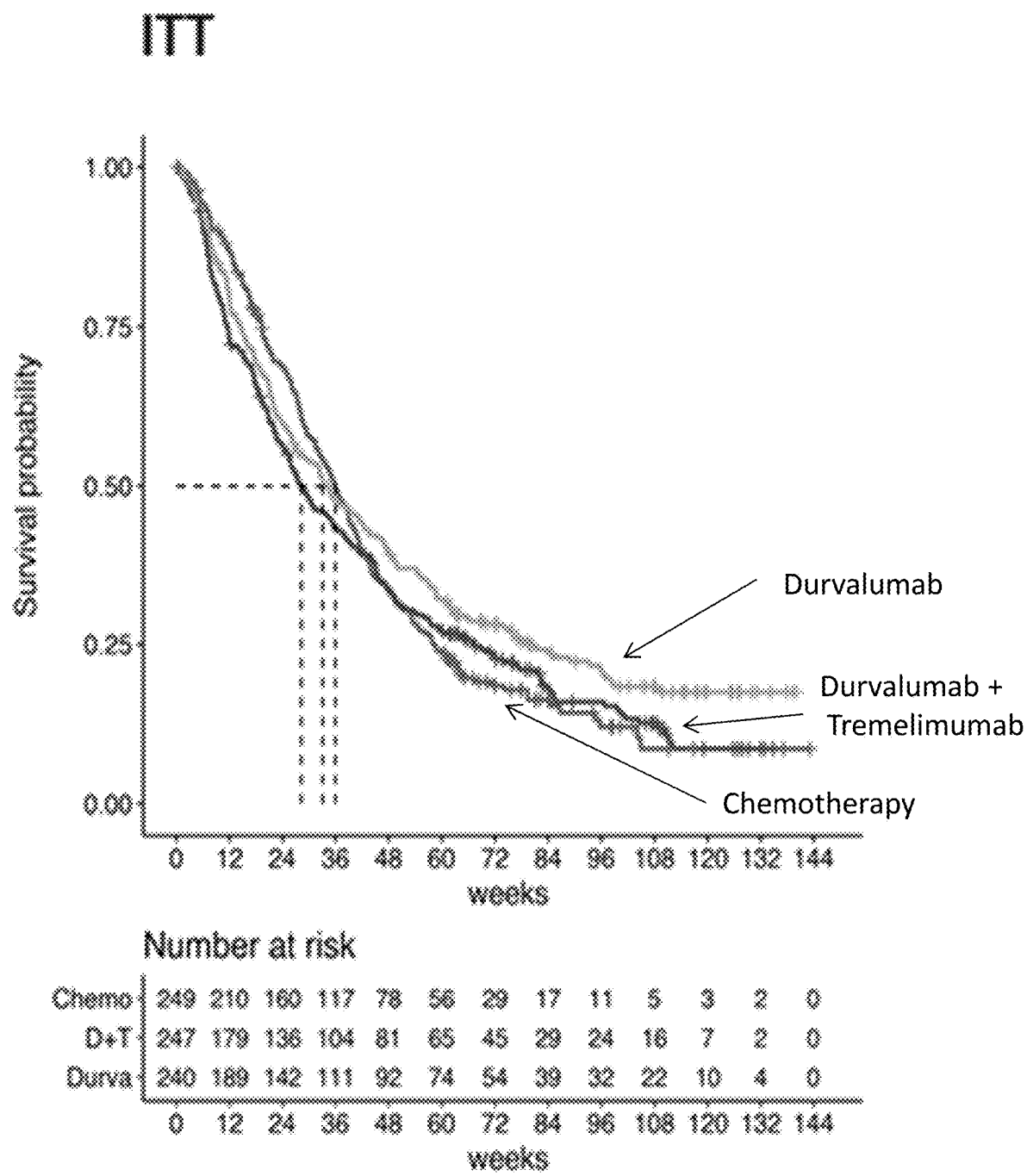
FIG. 24 shows an Intention-to-Treat (ITT) survival probability analysis over a period of 144 weeks (top) and a table of patients at risk over the same period (bottom) for three treatment schemes in the EAGLE study: chemotherapy, durvalumab, and durvalumab+tremelimumab.
Figure 25:
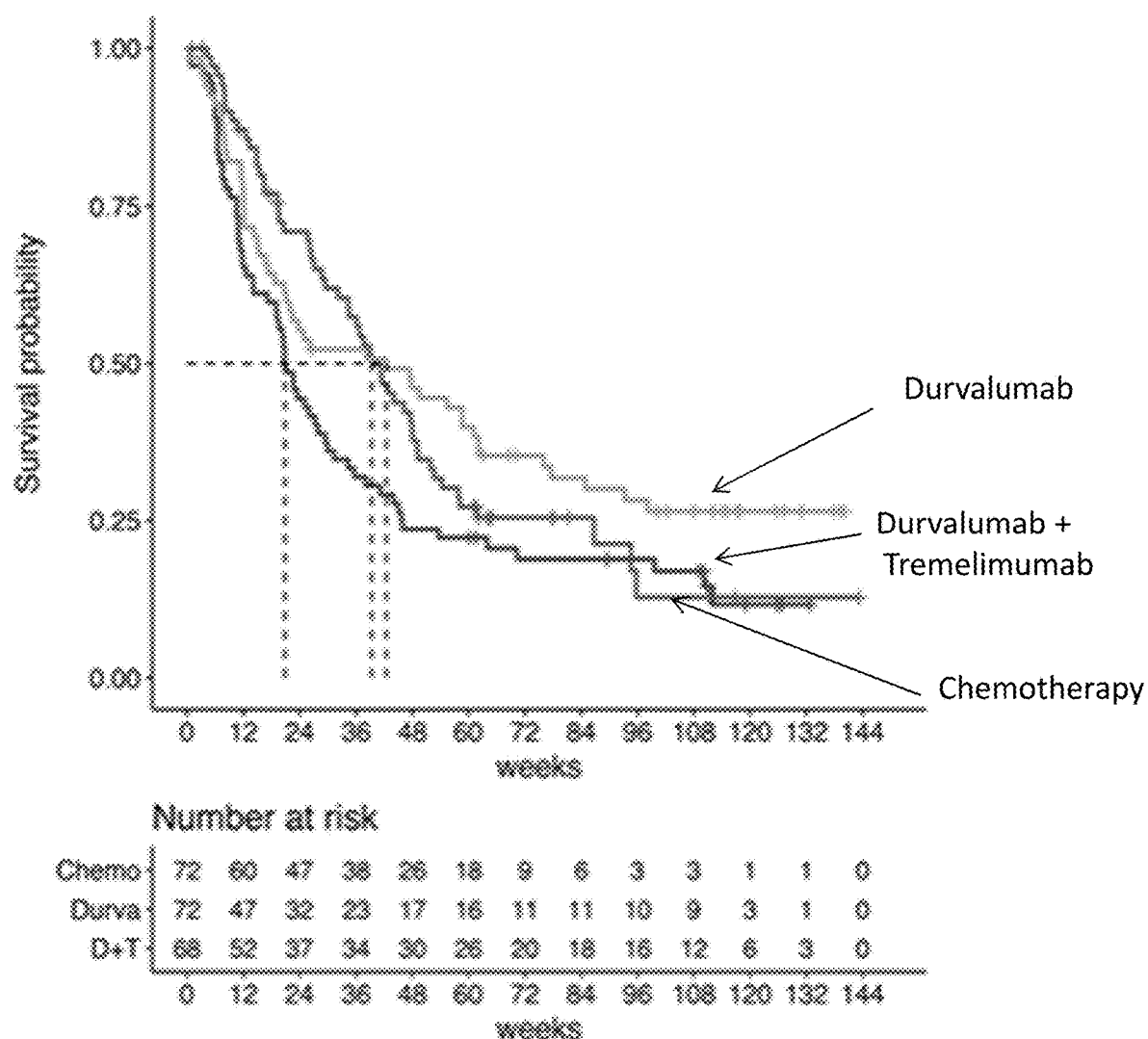
FIG. 25 shows a PD-L1 High (≥25%) survival probability analysis over a period of 144 weeks (top) and a table of patients at risk over the same period (bottom) for three treatment schemes in the EAGLE study: chemotherapy, durvalumab, and durvalumab+tremelimumab.
Figure 26:
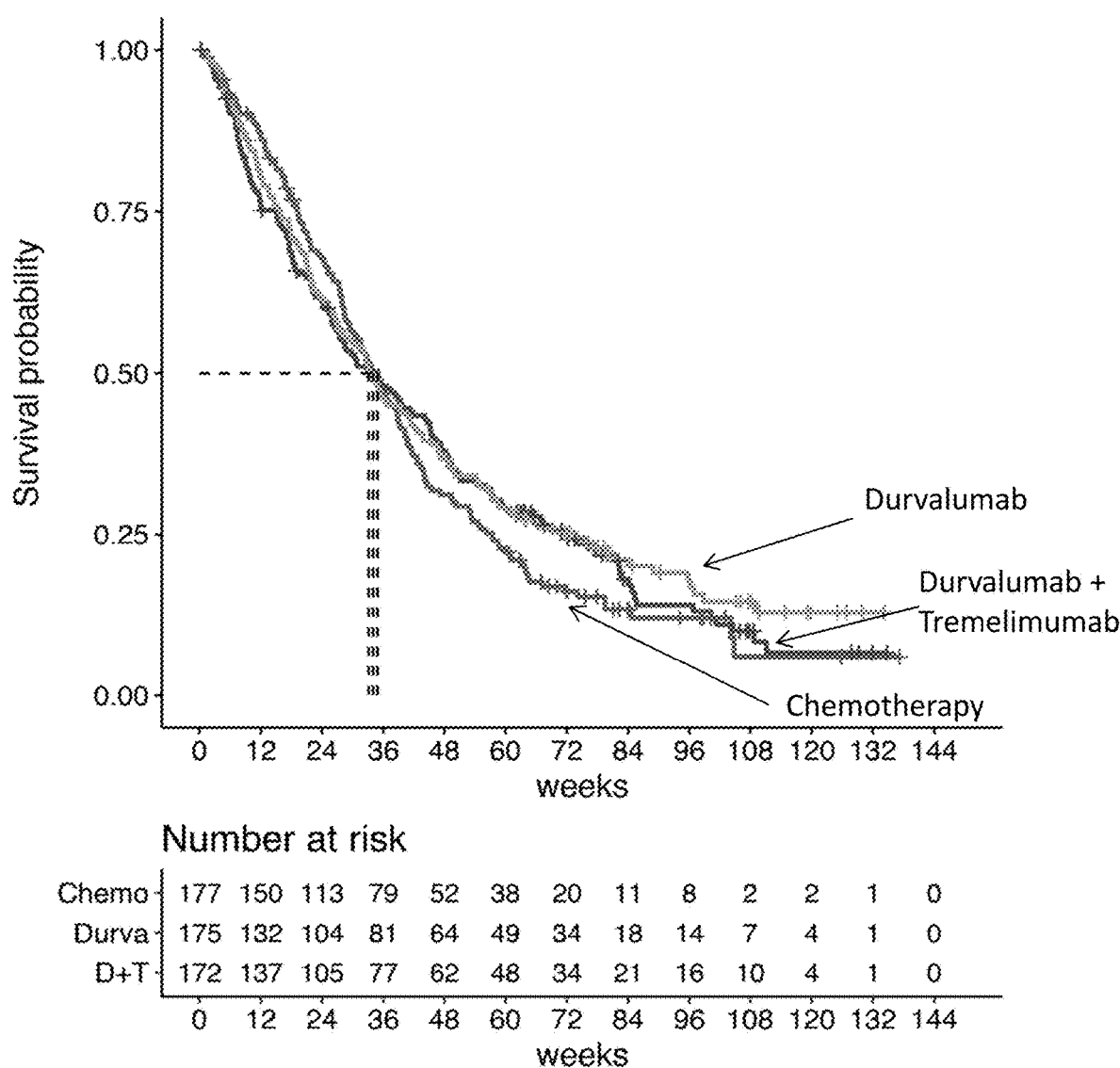
FIG. 26 shows an PD-L1 Low/negative (≤25%) survival probability analysis over a period of 144 weeks (top) and a table of patients at risk over the same period (bottom) for three treatment schemes in the EAGLE study: chemotherapy, durvalumab, and Durvalumab+Tremelimumab.

To test the model, the EAGLE study was used. (736 participants with Squamous Cell Carcinoma of the Head and Neck, with three treatment schemes: chemotherapy, Durva Mono, and Durva+Treme). Overall survival for each scheme for intention-to-treat, PD-L1 high, and PD-L1 low in the trial is shown in FIGS. 24-26. The hazard ratio (HR) is calculated from proportional cox regression including PD-L1 (≥25% vs <25%), tumor location/HPV status and smoking status as strata. The p-value is calculated from a stratified log-rank test stratified by PD-L1 (≥25% vs <25%), tumor location/HPV status and smoking status.

Results

The updated F1 model predicted patients with high risk of early mortality (FIG. 27). Overall survival of the patients in the chemotherapy and durva schemes tested with the updated F1 model is shown in FIG. 28. Overall survival of patients in the chemotherapy and Durva schemes with a predicted high risk of early mortality excluded is shown in FIG. 29. Overall survival of all PD-L1 high patients is shown in FIG. 30, and the data without the patients predicted to have a high risk of early mortality is shown in FIG. 31. Overall survival of all PD-L1 low patients is shown in FIG. 32, and the data without the patients predicted to have a high risk of early mortality is shown in FIG. 33. Overall survival of all PD-L1 negative patients is shown in FIG. 34, and the data without the predicted patients with high risk of early mortality is shown in FIG. 35.

Example 8—Training and Testing of an Updated F1 Model Using the EAGLE Trial and Neutrophils (NEUT), Lymphocyte Percentage (LYM %), Albumin (ALB), and Lactate Dehydrogenase (LDH) as Clinicopathological Markers This example sought to improve the F1 model by eliminating URATE from the clinicopathological markers used.

Methods

Patients from a combination of 3 studies with several cancer types were used to develop a new prognostic model with improved true positive and false positive rates (Table 7). The hazard ratio (HR) is calculated from proportional cox regression including PD-L1 (≥25% vs <25%), tumor location/HPV status and smoking status as strata. The p-value is calculated from a stratified log-rank test stratified by PD-L1 (≥25% vs <25%), tumor location/HPV status and smoking status.

TABLE 7

Studies used for training F1 model

| Study | Tumor Type | Treatment |
|---|---|---|
| Study 1108 (N = 1022) | Squamous Cell Carcinoma of the Head and Neck | Durva Mono |
| CONDOR (N = 267) | Head and Neck Squamous Cell Carcinoma | Durva Mono Durva + Treme |
| HAWK (N = 111) | Head and Neck Squamous Cell Carcinoma | Durva Mono |

Development of the model was performed as depicted in FIG. 14.

To test the model, the EAGLE study was used. (736 participants with Squamous Cell Carcinoma of the Head and Neck, with three treatment schemes: chemotherapy, Durva Mono, and Durva+Treme).

Results

The F1 model using neutrophils (NEUT), lymphocyte percentage (LYM %), albumin (ALB), and lactate dehydrogenase (LDH) predicted patients with high risk of early mortality (FIG. 36). Overall survival of the patients in the chemotherapy and Durva schemes tested with the updated F1 model, excluding those identified as having a high risk of early mortality, is shown in FIG. 37. Overall survival of all PD-L1 high patients with the patients with predicted to have a high risk of early mortality excluded is shown in FIG. 38, overall survival for PD-L1 low patients without the patients predicted to have a high risk of early mortality is shown in FIG. 39, and overall survival for PD-L1 negative patients without the patients predicted to have a high risk of early mortality is shown in FIG. 40.

Example 9—Training and Testing of an Updated F1 Model for Both Non-Small Cell Lung Cancer and Squamous Cell Carcinoma Head and Neck Cancer Using the EAGLE and MYSTIC Trials and Neutrophil/Lymphocyte Ratio (NLR); Neutrophils; Albumin; Lactate Dehydrogenase; Gamma-Glutamyltransferase; and Aspartate Aminotransferase as Clinicopathological Markers This example sought to use the findings from non-small cell lung cancer and squamous cell carcinoma head and neck cancer predictors of patients with high risk of early mortality to develop a single model for predicting both cancers. The non-small cell lung cancer markers evaluated are neutrophil/lymphocyte ratio (NLR); albumin (ALB), lactate dehydrogenase (LDH), gamma-glutamyltransferase (GGT), and aspartate aminotransferase (AST). The squamous cell carcinoma head and neck cancer predictors of patients with high risk of early mortality evaluated are neutrophils (NEUT), lymphocyte percentage (LYM %), albumin (ALB), lactate dehydrogenase (LDH), and URATE. Six markers were selected: neutrophil/lymphocyte ratio (NLR); neutrophils (NEUT), albumin (ALB), lactate dehydrogenase (LDH), gamma-glutamyltransferase (GGT), and aspartate aminotransferase (AST).

Methods

Patients from a combination of 7 studies with several cancer types were used to develop a new prognostic model with improved true positive and false positive rates (Table 8). The hazard ratio (HR) is calculated from proportional cox regression including PD-L1 (≥25% vs <25%), tumor location/HPV status and smoking status as strata. The p-value is calculated from a stratified log-rank test stratified by PD-L1 (≥25% vs <25%), tumor location/HPV status and smoking status.

TABLE 8

Studies used for training F1 model

| Study | Tumor Type | Treatment |
|---|---|---|
| Study 1108 (N = 1022) | Advanced Cutaneous Melanoma Advanced Malignant Melanoma Bladder Cancer, Colorectal cancer, Gastroesophageal Cancer, Glioblastoma, Hepatocellular carcinoma HPV Positive Cancer, MSI-High Cancernasopharyngeal Carcinoma, Non-small cell lung cancer Non-Squamous, Non-small cell lung cancer Squamous, Ovarian Cancer, Pancreatic Adenocarcinoma, Renal cell carcinoma Squamous cell head and neck cancer Small cell lung cancer Soft Tissue Sarcoma, Triple Negative Breast Cancer, Uveal Melanoma | Durva Mono |
| Study 06 (N = 379) | Non-Small Cell Lung Cancer | Durva + Treme |
| Study 10 (N = 168) | Urinary Bladder Cancer | Durva + Treme |
| Study 21 (N = 113) | Gastric Cancer | Durva Mono Treme Mono Durva + Treme |
| ATLANTIC (n = 444) | Non-Small Cell Lung Cancer | |
| CONDOR (N = 267) | Head and Neck Squamous Cell Carcinoma | Durva Mono Durva + Treme |
| HAWK (N = 111) | Head and Neck Squamous Cell Carcinoma | Durva Mono |

Development of the model was performed as depicted in FIG. 14.

To test the model, the ARCTIC, EAGLE (736 participants with Squamous Cell Carcinoma of the Head and Neck, with three treatment schemes: chemotherapy, Durva Mono, and Durva+Treme), and MYSTIC studies were used (1118 participants with PD-L1 high non-small cell lung cancer, with multiple treatment schemes: chemotherapy, Durva Mono, and Durva+Treme).

Results

The F1 model using neutrophil/lymphocyte ratio (NLR); neutrophils; albumin; lactate dehydrogenase; gamma-glutamyltransferase; and aspartate aminotransferase predicted patients with high risk of early mortality in the EAGLE trial (FIG. 41). Overall survival of the patients in the chemotherapy and Durva schemes of the EAGLE trial tested with this F1 model, excluding those identified as having a high risk of early mortality, is shown in FIG. 42. Overall survival of all PD-L1 high patients in the EAGLE trial with the patients predicted to have a high risk of early mortality excluded is shown in FIG. 43, overall survival for PD-L1 low patients without the patients predicted to have a high risk of early mortality is shown in FIG. 44, and overall survival for PD-L1 negative patients without the patients predicted to have a high risk of early mortality is shown in FIG. 45. This F1 model predicted patients with high risk of early mortality in the MYSTIC trial (FIG. 46). Overall survival of all PD-L1 high patients in the MYSTIC trial is shown in FIG. 47, with PD-L1 high patients in the MYSTIC trial predicted to have a high risk of early mortality excluded shown in FIG. 48. Percentage of observed overall survival for longer than 12 weeks or equal to or less than 12 weeks is shown for several cohorts in FIG. 49, with F1-predicted patients with high risk of early mortality and patients without high risk of early mortality in those cohorts shown in FIG. 50.

Conclusions

The F1 model using neutrophil/lymphocyte ratio (NLR); neutrophils; albumin; lactate dehydrogenase; gamma-glutamyltransferase; and aspartate aminotransferase as clinicopathological markers is a powerful predictor of OS. The F1 model can be used to appraise ongoing or previously conducted clinical trials in order to assess for any imbalance in the fast progressor rates between arms that may have potential impact on the outcome. Further, it is believed that the F1 model can be incorporated into inclusion/exclusion criteria in future phase 1 trials (escalation phase, randomized expansion) as a more objective way to exclude poor risk patients. Further, it can be used to improve the selection of study sites by excluding sites with history of enrolling high rate of patients with high risk of early mortality. Excluding patients with high risk of early mortality in phase 1 studies (escalation and randomized expansion parts) will likely increase the ability to detect efficacy signals of phase I trials.

Example 10—Development of Immune Immediacy Index (3i Score) for Identifying Patients at Risk of Early Mortality Summary New Approach: Identify Patients with High Risk of Early Mortality in the ICI Context While RMH, GRIM, and LIPI scores demonstrated prognostic impact, the recent availability of large set of patients treated with ICI in prospective trials at AstraZeneca represents an opportunity to improve the identification of patients with high risk of early mortality relative to an active chemotherapy comparator in the ICI context.

In randomized trials of ICI versus an active comparator in an advanced disease setting, where the crossing of the Kaplan-Meier (KM) curves for OS has been predominantly observed the higher rate of mortality in the ICI arm has been generally seen within the first 12 weeks after randomization. This is illustrated in the MYSTIC study of durvalumab versus chemotherapy in first line NSCLC. FIG. 47 shows the OS curves (the crossing of the curves is indicated by the arrow) in the primary analysis population of PD-L1 positive patients (defined as patients whose tumours express PD-L1 in ≥25% of cells). The percentage of deaths in the first 12 weeks was 17.2% in the experimental arm vs. 8.0% in the control arm. In the 12 weeks to 24-weeks period, these rates were 12.7% vs. 15.0% respectively. Over time, the rate of deaths continued to improve in favor of durvalumab. FIG. 51 shows the KM curve for OS after excluding patients who died within the first 12 weeks. In this subset of patients who were alive at 12 weeks or beyond, crossing of the OS curves is no longer observed. A similar observation has been seen in other studies of ICI vs. chemotherapy (Borghaei, et al. 2015, Mok, et al. 2019). Therefore, based on this empirical observation across multiple trials, to predict the risk of EM with ICI, EM has been defined as any death occurring within the first 12 weeks after randomization (in randomized trials) or start of study therapy (in single arm trials).

Development of the 3i Score

Given the data collected across studies investigating ICI, the challenges in objectively predicting EM, and the limitations of previously established scores, we set out to use machine learning to develop a prognostic model (hereafter referred to as Immune Immediacy Index [3i score]) for identifying patients at risk of EM. Development workflow, including the definition of model requirements, design, development, and testing is described below.

Model Requirements

As illustrated in FIG. 52, the key requirements for the 3i score were to predict for EM (deaths within 12 weeks of randomization or start of treatment) using machine learning, ideally leveraging continuous input values acquired from some or all routinely performed baseline laboratory tests. Machine learning models are increasingly used in healthcare and the clinic to identify subtle, yet predictive, patterns in raw data, which may be lost by discretizing lab parameters. Deploying machine learning models in a real-world setting is complex due to the need for robust performance and interface software. Consequently, acceptable performance metrics throughout training, tuning and testing, as well as flexible deployment options, influenced the final 3i score.

The design choices in dataset identification for development, dataset separation for training, tuning and testing, as well as feature and method selection were driven by model requirements and cross-functional expertise in machine learning and clinical research.

Machine Learning Model Development Through Training, Tuning and Testing

The core activities in developing supervised machine learning models are most commonly sub-divided into three critical steps: training, tuning and testing.

During training, the model's parameters, such as tree depth, are optimized to encode relationships between input and output. In an iterative manner the model accepts an input from the training data set and produces an output which is compared against ground truth, and the error guides update of model parameters. Over time the model learns the representations of input that lead to desired target output using the training dataset.

The same machine learning technique can yield a different model in terms of architecture, weights and performance depending on what training constraints have been chosen. The optimal training constraints, called hyperparameters, are different in each machine learning situation and are set before training, as opposed to other model parameters that are developed during training.

Hyperparameter optimization, also called tuning, is a step in machine learning development that is often found to have a profound effect on a model's ability to generalize successfully. A choice of hyperparameters can lead to a model that will overfit or underfit on the same training set. One common approach to exploring a space of hyperparameter ranges is a grid search where each time a set of hyperparameters is sampled, the model is trained on a training data set and then evaluated on an independent dataset (tuning data set). Performance evaluation on a tuning set guides the selection of optimal training constraints that produce a model robust enough to function beyond the training set.

Model testing is performed to evaluate the final model fit on the training dataset using hyperparameters of choice. Testing is performed on an independent dataset, which was neither used in training nor in tuning, to evaluate how well the model generalises and derives patterns beyond the data it has encountered before.

Dataset Identification

A comprehensive set of ICI trials was utilized with individual patient concentration data (Table 9) for developing the 3i score model. The trials were selected so that the training and tuning sets would include data for patients with a diverse range of tumor types and across different lines of therapy.

Dataset Separation for Training, Tuning and Testing

Data separation for training, tuning, testing was as follows:

Training set (used in final input feature selection, model training and hyperparameter optimization):
Study 1108 (N=923), Study 06 (N=353), Study 10 (N=164), Study 21 (N=98)
ATLANTIC (D4191C00003), A Phase II, Non-comparative, Open Label, Multi-centre, International Study of MEDI4736, in Patients with Locally Advanced or Metastatic Non-Small Cell Lung Cancer (Stage IIIB-IV) Who Have Received at Least 2 Prior Systemic Treatment Regimens Including 1 Platinum-based Chemotherapy Regimen (N=371)
CONDOR (D4193C00003), A Phase II, Multi-Center, Single-Arm, Global Study of MEDI4736 Monotherapy, Tremelimumab monotherapy, and MEDI4736 in combination with Tremelimumab in Patients with Recurrent or Metastatic Squamous Cell Carcinoma of the Head and Neck (N=193)
HAWK (D4193C00001), A Phase II, Multi-Center, Single-Arm, Global Study of MEDI4736 Monotherapy in Patients with Recurrent or Metastatic Squamous Cell Carcinoma of the Head and Neck (N=111)
Note: Patients censored before 12 weeks were not included in the training set.

Tuning set (used in model hyperparameter optimization):
MYSTIC (D419AC00001), A Phase III Randomized, Open-Label, Multi-Center, Global Study of MEDI4736 in Combination with Tremelimumab Therapy or MEDI4736 Monotherapy Versus Standard of Care Platinum-Based Chemotherapy in First Line Treatment of Patients with Advanced or Metastatic Non Small-Cell Lung Cancer (N=1118)

Test set (used in model testing):
EAGLE (D4193C00002), A Phase III Randomized, Open-label, Multi-center, Global Study of MEDI4736 Monotherapy and MEDI4736 in Combination with Tremelimumab Versus Standard of Care Therapy in Patients with Recurrent or Metastatic Squamous Cell Carcinoma of the Head and Neck (N=736)

The total training data set includes 2213 patients, including mostly patients diagnosed with NSCLC, SCCHN, UBC, and Gastric cancer, summarized in Table 10.

TABLE 10

Number of patients in different tumor types in the training set

| Study | NSCLC | SCCHN | UBC | Gastric | Other |
|---|---|---|---|---|---|
| ATLANTIC | 371 | 0 | 0 | 0 | 0 |
| CONDOR | 0 | 193 | 0 | 0 | 0 |

TABLE 10-continued

Number of patients in different tumor types in the training set

| Study | NSCLC | SCCHN | UBC | Gastric | Other |
|---|---|---|---|---|---|
| HAWK | 0 | 111 | 0 | 0 | 0 |
| Study 06 | 353 | 0 | 0 | 0 | 0 |
| Study 10 | 0 | 0 | 164 | 0 | 0 |
| Study 1108 | 303 | 57 | 183 | 52 | 328 |
| Study 21 | 0 | 0 | 0 | 98 | 0 |
| Total | 1027 | 361 | 347 | 150 | 328 |

Abbreviations:
NSCLC = non-small cell lung cancer;
SCCHN = squamous cell carcinoma of the head and neck;
UBC = urothelial bladder cancer;
Other = HPV positive cancer, advanced malignant melanoma, uveal melanoma, pancreatic adenocarcinoma, advanced cutaneous melanoma, hepatocellular carcinoma, nasopharyngeal carcinoma, ovarian cancer,
SCLC, soft tissue sarcoma,
MSI-High cancer, triple negative breast cancer, colorectal cancer, renal cell carcinoma.

Feature Selection

One strength of using certain machine learning algorithms is their ability to determine feature importance and weigh predictive features over non-predictive ones. Given that model complexity increases with a growing number of features or dimensions, and that one of the requirements was to use routinely available laboratory measurements (i.e. laboratory measurements covering hematology, chemistry and thyroid hormones available in the clinical trials selected here), a comprehensive starting list of 37 candidate predictors were collated and summarized in Table 11. Removal of non-important or highly-correlated features was planned to occur during the development stage.

TABLE 11

List of candidate predictors considered for building a prognostic early mortality model

| Name | Description |
|---|---|
| Typ | Tumor type: NSCLC, SCCHN, UBC, gastric, Other |
| AGE | Age |
| ALB | Albumin (g/L) |
| ALP | Alkanine phosphatases (U/L) |
| ALT | Alanine amino transferase (U/L) |
| AST | Aspartate amino transferase (U/L) |
| BASO | Basophils ($10^3/\mu L$) |
| BASOLE | Basophils/Leukocytes (%) |
| BILI | Bilirubin (µmol/L) |
| BMI | Body Mass Index |
| CA | Calcium (mmol/L) |
| CL | Chloride (mmol/L) |
| EOS | Eosinophils ($10^3/\mu L$) |
| EOSLE | Eosinophils/Leukocytes (%) |
| GGT | Gamma-glutamyl transferase (U/L) |
| GLUC | Glucose (mmol/L) |
| HCT | Hematocrit (%) |
| HGB | Hemoglobin (g/L) |
| K | Potassium (mmol/L) |
| LDH | Lactate dehydrogenase (U/L) |
| Name | Description |
| LIVERBL | Liver Metastasis (yes/no) |
| LYM | Lymphocytes ($10^3/\mu L$) |
| LYMLE | Lymphocytes/Leukocytes (%) |
| MG | Magnesium (mmol/L) |
| MONO | Monocytes ($10^3/\mu L$) |
| MONOLE | Monocytes/Leukocytes (%) |
| NEUT | Neutrophils ($10^3/\mu L$) |
| NEUTLE | Neutrophils/Leukocytes (%) |
| NLR | Neutrophils/Lymphocytes (%) |
| PLAT | Platelets ($10^3/\mu L$) |
| PROT | Protein (g/L) |
| SEX | gender |
| SODIUM | Sodium (mmol/L) |

TABLE 11-continued

List of candidate predictors considered for building a prognostic early mortality model

| Name | Description |
|---|---|
| TSH | Thyrotropin (mU/L) |
| TUMSZINV | Tumor size (estimated by RECIST) |
| URATE | Uric acid (mmol/L) |
| WBC | Leukocytes ($10^3/\mu L$) |

Machine Learning Method Selection (Gradient Boosting Trees)

A gradient boosting modelling approach was chosen for predicting 12-week EM. The particular version of gradient boosting method adopted is called XGBoost (Extreme Gradient Boosting). This machine learning approach has increasingly become a preference of the statistical community because of its robust prediction performance, its speed (i.e. scalability on parallel processes), and accommodation of missing values (Friedman, et al. 2000, Friedman, et al. 2001, Chen and Guestrin 2016). Decision trees are used as a weak learner in gradient boosting. One variable is selected at each time to divide a node into two sub-nodes until no split is available to further improve the model fitting. A separate tree is built on the residuals of the previous tree. A variable may be selected multiple times within one tree and in different trees. Decision trees are sequentially built until stop criteria are met. The final gradient boosting model is built by assembling decision trees additively, possibly applying a weighted learning rate to each. Through selecting proper model hyperparameters, XGBoost models can be trained to minimize the prediction error with the controlled model complexity, which leads to a good balance of bias-variance trade-off. XGBoost model treats missing values by learning default directions. Internally, XGBoost learns the direction to go when a value is missing.

Test Plan

The test plan was designed to evaluate the 3i score by retrospective application on an ICI clinical trial test set (EAGLE). EAGLE study was excluded from training and tuning to represent an independent test set where the model would be evaluated in terms of (1) ability to generalize beyond training set as defined by true positive rate (TPR), false positive rate (FPR) and partial area under the curve (AUC) in specificity region between 0.7 and 0.9; (2) comparison to other, previously developed risk scores; (3) clinical utility as defined by increased therapeutic effect after exclusion of the 3i score high-risk group.

Code tests were not applicable in the testing plan as no new functionality was introduced, nor any existing functionality extended in open-source R packages used in development.

Development

Development Environment

All development was performed in R v.3.5.1 on x86_64 pc linux gnu(64-bit) operating system. All open source packages used for development are listed in Table 12.

TABLE 12

Open source packages used for development of the 3i score model

| Package | Purpose |
|---|---|
| bshazard_1.1 | Nonparametric Smoothing of the Hazard Function |

TABLE 12-continued

Open source packages used for development of the 3i score model

| Package | Purpose |
|---|---|
| caret_6.0-76 | Classification and Regression Training |
| DescTools_0.99.24 | Descriptive Statistics |
| dplyr_0.7.4 | Data Manipulation |
| Epi_2.30 | Statistical Analysis |
| forcats_0.2.0 | Categorical Variables |
| ggplot2_3.0.0 | Graphics |
| ggpubr_0.1.7 | Graphics |
| gridExtra_2.2.1 | Graphics |
| lattice_0.20-35 | Graphics |
| parallelMap_1.3 | Process Parallelisation |
| plotly_4.6.0 | Graphics |
| plyr_1.8.4 | Data Manipulation |
| pROC_1.12.1 | Display and Analyse ROC Curves |
| purrr_0.2.4 | Functional Programming |
| readr_1.1.1 | Read Structured Files |
| readxl_1.0.0 | Read Excel Files |
| reshape2_1.4.3 | Data Manipulation |
| RevoUtils_11.0.1 | Utility Functions |
| RevoUtilsMath_11.0.0 | Math Kernel |
| stringr_1.3.1 | String Operations |
| survival_2.42-6 | Survival Analysis, Cox models |
| survminer_0.4.2 | Graphics |
| tibble_1.4.2 | Display Data Frames |
| tidyr_0.8.0 | Data Manipulation |
| tidyverse_1.2.1 | Data Manipulation |
| WriteXLS_4.0.0 | File Writing |
| xgboost_0.71.2 | Gradient Boosting |

Dataset Separation, Labelling

Acquired datasets were pre-processed internally according to internal data management standards. Patients who died within 12 weeks (i.e. time from randomization/first dose to death ≤12 weeks) were labelled as EM. Patients who survived beyond 12 weeks (i.e. time from randomization/first dose to death ≥12 weeks) were not labelled as EM. Patients who were censored within 12 weeks (i.e. patients lost to follow up ≤12 weeks) were not included in the training set during the development of the model. No other data manipulations were performed.

Feature Selection

Feature selection was performed to examine a broad range of candidate predictors for the 3i score model, and to return a subset of predictors from which a performant model could be fitted. First, a full model was fitted using a gradient boosting fitting procedure on the training data (FIG. 52) with 37 predictors (see Table 11). Model fitting was performed using 10-fold cross-validation. A grid search of hyperparameters was conducted, and the model which gave the highest partial AUC was used to guide feature selection.

A gradient boosting model was fitted to the training data to calculate variable importance. Variable importance is quantified by how much improvement in accuracy was brought by including the variable. All available pre-treatment blood test variables (n=31) covering haematology, clinical chemistry, and thyroid hormones were initially included in this first step (i.e., all laboratory variables). Clinical variables well-recognized to be associated with prognosis in oncology such as age ("AGE"), gender ("SEX"), baseline tumor size (estimated by RECIST, "TUMSZINV"), Body Mass Index ("BMI"), tumor type ("typ"), and the presence of liver metastasis ("LIVERBL") were also introduced in this model. As shown in FIG. 53, albumin, LDH, neutrophils, neutrophil/leukocyte ratio (NEUTLE), NLR, gamma-glutamyl transferase (GGT), and aspartate amino transferase (AST) were found to be the most important variables. NEUTLE was not selected in building the final model because neutrophils and NEUTLE are highly correlated (r=0.98, p<0.001). Based on this feature importance analysis and subject matter expert input, the final set of input features for training and tuning the 3i score model were albumin, LDH, neutrophils, NLR, GGT, and AST.

Biological Relevance of Blood Test Variables Selected for the 3i Score Model

All six blood test variables assessed through standard laboratory measures and identified by feature selection, have previously been reported to be prognostic in various tumor types.

High NLR has been associated with poor prognosis in multiple tumor types including gastrointestinal (Bowen, et al. 2017), melanoma (Ding, et al. 2018), NSCLC (Fukui, et al. 2019), UC (Sacdalan, et al. 2018) and HNSCC (Yu, et al. 2018, Tham, et al. 2018). The ratio likely reflects a measure of immune fitness which may impact tumor immune responses, and the association with poor prognosis is judged to be independent of type of ICI. Fukui, et al. observed a significant association between high NLR and poor prognosis in NSCLC patients treated with nivolumab. In a meta-analysis of ICI studies in melanoma, NSCLC and UC, Sacdalan, et al. observed an association of high NLR with poorer outcomes, suggesting it has potential as a prognostic marker. It has also been speculated that tumor burden and chronic inflammation lead to high NLR followed by poor prognosis (Bigot, et al. 2017).

Absolute neutrophil count (ANC) is a surrogate marker of physiological stress including inflammation, and in NSCLC patients, high ANC after nivolumab treatment has been observed to be independently associated with inferior overall survival (Khunger, et al. 2018).

ALB is a well-known marker of malnutrition and cachexia in cancer patients, and low ALB has been observed to be associated with poor overall survival in many malignancies such as SCCHN, breast, lung, and gastrointestinal cancers (Gupta, et al. 2010).

LDH is an established marker that reflects increased cell turnover mainly in malignant disease, but also in non-malignant disease (eg, haemolytic anaemia). In a recent FDA analysis of early mortality in ICI studies, elevated LDH was reported as an important risk factor mainly in melanoma patients (Mulkey, et al. 2019). In a systematic review of 76 studies, high LDH was associated with poor prognosis in renal, melanoma, gastric, prostate, nasopharyngeal and lung cancers (Petrelli, et al. 2015). In advanced cancers, the increased concentrations of LDH in the blood reflect increased metabolic activity and rapid cell proliferation that result in increased leakage of the intracellular enzyme LDH into the blood circulation.

Abnormalities in liver function tests such as AST and GGT are carefully monitored in cancer patients. Abnormal liver function tests not only reflect pre-existing disease, but also cancer progression/liver metastasis and drug toxicity, which are all known causes of death among cancer patients. Hence, AST and GGT have been reported as prognostic markers in cancer (Freis, et al. 2017, Luo, et al. 2017), and GGT has also been suggested to play a role in tumor initiation, invasion and drug resistance.

Training and Hyperparameter Selection for the 3i Score Model

Only the most predictive biological variables (NLR, neutrophils, albumin, LDH, AST, GGT), described in the feature selection step previously (FIG. 53), and tumor type were retained for training the final 3i score model (FIG. 52). There are 12 tree booster hyperparameters in XGBoost that set the training constraints such as the type of base learner, learning rate, maximum tree depth allowed, weight regularization. Since each set of hyperparameters will yield a different XGBoost model during training, we used MYSTIC data as a tuning set to guide the selection of the optimal set of hyperparameters. A grid search of max.depth, gamma, min.child.weight, colsample.bytree, and subsample hyperparameters was conducted. A pool of XGBoost models was generated by fitting a model on the training data set using different sets of hyperparameters. Model performance in the training set was quantified as True Positive Rate and Partial AUC (specificity between 0.7 and 0.9). Hazard ratio and p value (Cox-regression) for interaction between 3i score status and treatment in the PD-L1 population were calculated and used as quantification of model performance in the tuning set (MYSTIC). The model with the smallest interaction p value in the tuning set (MYSTIC) and high partial AUC in the training set was selected as the final model.

The final 3i score model, selected from the pool of 432 models, had pAUC (0.7, 0.9) of 0.83 (ranked No. 8 among all 432 models) in the training dataset and was trained with the following non-default XGBoost hyperparameters:

Maximum depth of a tree (max.depth): 3
Minimum loss reduction required to make a further partition on a leaf node of the tree (gamma): 1
Minimum sum of instance weight (hessian) needed in a child (min.child.weight):
Subsample ratio of columns when constructing each tree (colsample.bytree): 1
Subsample ratio of the training instances (subsample): 0.6
scale_pos_weight: negative_cases/postive_cases
nrounds: 22

To describe the nature of the final model, the importance of each variable selected in the final model was computed. As shown in FIG. 54, NLR, NEUT, ALB, LDH, and GGT are classified more important than AST, and tumor types.

Final 3i Score Model

The following six key predictors: NLR, NEUT, ALB, LDH, GGT, AST, and the tumor type were retained in the final model. The model produces a score (i.e. value between 0 and 1) representing the probability of death occurring in ≤12 weeks for each patient. The 3i score is then converted to a status that assigns patients to prognostic or risk categories of high or low. The cut-off was determined to allow 10% false positive rate at predicting EM in the training data set and calculated as 0.649 on 2 Jul. 2019. Patients with a score above the cut-off of 0.649 are identified as high risk of EM and patients at or below the cut-off (0.649) are identified as low risk of EM. For patients missing any of the 6 lab test values, the 3i score will not be calculated. This decision was supported by the expectation that globally, patients will have data on these variables readily available as they are routinely-collected, standard laboratory measures.

3i Vs GRIm and LIPI in Training and Tuning Data Sets

When applied in the training set (N=2213 patients), the TPR at 12 weeks was 67% and the FPR was 10%. Performance as defined by pAUC (0.7, 0.9) was 0.83. The median OS of patients identified with a high risk 3i score status (486/2213 patients) was 9.29 weeks (95% CI: 8.29 weeks, 9.86 weeks) and the median OS of patients with a low risk 3i score status was 61.43 weeks (95% CI: 57.71, 66.14) (see FIG. 55).

The patients identified as high risk by the 3i score (see FIGS. 56A and 56B) had shorter median OS compared with patients identified as high risk using other prognostic models developed to predict for early death in patients with advanced or metastatic cancers: GRIm (624 patients, median OS 14.29 weeks [95% CI: 12.71, 15.71]); and LIPI score (363 patients, median OS 14.00 weeks [95% CI: 11.43, 16.00]). ULN=240 is used for LDH for calculating GRIm and LIPI scores.

When applied in the tuning set (MYSTIC) (N=1118) (see FIGS. 57A and 57B), the TPR at 12 weeks was 52% and the FPR was 11% for the durvalumab treated patients. Performance as defined by pAUC (0.7, 0.9) was 0.63. The median OS of patients identified with a high risk 3i score status (69/374 patients) was 12.00 weeks (95% CI: 9.57, 22.00) and the median OS of patients with a low risk 3i score status (289/374 patients) was 68.71 weeks (95% CI: 60.29, 81.00). The patients identified as high risk by the 3i score had shorter median OS compared with patients identified as high risk using other prognostic models: GRIm score (115 patients, median OS 20.43 [95% CI: 14.29, 28.71]); and LIPI score (71 patients, median OS 18.14 [95% CI: 10.00, 33.29]).

In the MYSTIC intent-to-treat population (ITT) (see FIGS. 58A-58C), the median OS for the durvalumab and SoC arms was 53.29 and 51.14 weeks, respectively. Applying the 3i score in the MYSTIC ITT population (N=746), 120 patients (16%) were identified as high risk, 51 patients in the SoC arm and 69 patients in the durvalumab arm. The median OS of patients identified with a high risk 3i score status (120/746, 16% of patients) appeared to exhibit a worse outcome in the durvalumab arm (median OS: 12.00 weeks) than in the chemotherapy arm (median OS: 29.14 weeks, HR=1.39 [95% CI: 0.947, 2.053]). In the low risk patients, there was still only a modest improvement in treatment effect (HR=0.89 [95% CI: 0.735, 1.079]) and the crossing of the OS curve was not eliminated. This may be attributable to the potential lack of benefit with monotherapy ICIs in PD-L1 low/negative patients relative to an active chemotherapy comparator in advanced disease settings.

In the MYSTIC PD-L1≥25% subgroup (see FIGS. 59A-59C), a total of 56 patients (17%) were identified as high 3i score risk, 24 in the SoC arm, and 32 in the durvalumab arm. As in the ITT, for high risk 3i score patients in the PD-L1≥25% subgroup, median OS was shorter in the durvalumab arm than the chemotherapy arm (chemotherapy 35.79 weeks vs. durvalumab 11.36 weeks, HR=1.533 [95% CI: 0.873, 2.726], FIG. 59C). Importantly, excluding patients with a high risk status by the 3i score from the MYSTIC PD-L1≥25% subgroup (56/325 pts, 17% patients excluded by the 3i score) reduced the previously observed crossing of the OS curves (FIG. 59B). The treatment effect of durvalumab vs. chemotherapy was larger (HR: 0.626 [95% CI: 0.459, 0.849]) compared to the original primary analysis PD-L1≥25% population (HR: 0.76 [95% CI: 0.59, 0.98]).

Testing of 3i Score

Application of the 3i Score Model in EAGLE (Test Set)

When applied in the test set (EAGLE) (N=736) (see FIGS. 60A and 60B), the TPR at 12 weeks was 57% and the FPR was 16% for the durvalumab treated patients. Performance as defined by pAUC (0.7, 0.9) was 0.64. The median OS of patients identified with a high risk 3i score status (59/240 patients) was 12.14 weeks (95% CI: 8.57, 19.14) and the median OS of patients with a low risk 3i score status (172/240 patients) was 48.00 weeks (95% CI: 41.29, 58.71). The patients identified as high risk by the 3i score had lower OS compared with patients identified as high risk using other prognostic models: GRIm score (67 patients, median OS 15.71 weeks [95% CI: 12.14, 21.86]); and LIPI score (38 patients, median OS 19.36 weeks [95% CI: 13.71, 35.43]).

In the EAGLE ITT (see FIGS. 61A-61C), the median OS for the durvalumab (N=240) and SoC (N=249) arms was 33.14 and 36.00 weeks, respectively. Applying the 3i score in the EAGLE ITT, a total of 121 patients (25%) were identified as high risk, 62 in the SoC arm and 59 in the durvalumab arm. The median OS of patients identified with a high risk status by the 3i score appeared worse in the durvalumab arm (median OS=12.14 weeks) than in the chemotherapy arm (median OS=16.00 weeks, HR 1.30 [95% CI: 0.86, 1.99]). Excluding from the EAGLE ITT those patients identified by the 3i score as high risk (i.e. 25% pts) reduced the crossing of the overall survival curves (FIG. 61B). The magnitude of the therapeutic effect of durvalumab increased (HR: 0.75 [95% CI: 0.58, 0.96]) compared to the original ITT population (HR: 0.88 [95% CI: 0.72, 1.08]).

In the PD-L1≥25% subgroup (N=140) (see FIGS. 62A-62C), a total of 43 patients (31%) were identified as high risk by the 3i score, 20 in the SoC arm and 23 in the durvalumab arm (FIG. 62C). Similar to what is seen in the MYSTIC dataset (tuning set), excluding these patients partially eliminated the crossing of the overall survival curves (FIG. 62B). The magnitude of the therapeutic effect of durvalumab increased (HR: 0.66 [95% CI: 0.38, 1.12]) compared to the original primary analysis PD-L1≥25% population (HR: 0.93 [95% CI: 0.63, 1.39]).

Lab Test Distributions in 3i Score Low Risk Vs. 3i Score High Risk Patients

In the MYSTIC and EAGLE studies, a Wilcoxon test was used to compare the 6 lab values used in the 3i score between patients identified with a high risk (predicted life expectancy ≤12 weeks) or low risk (predicted life expectancy of >12 weeks) by the 3i score. For all 6 parameters, the values from patients with a high risk and low risk 3i score status are significantly different (p<0.05) (see FIGS. 63 and 64).

Example 11—Determination of Patient Immune Fitness

Summary

The variables included in the 3i score are associated with host immune fitness and cancer-related inflammation. Further, the additional translational analyses conducted from samples acquired in clinical trials show that 3i high-risk patients are characterized with higher baseline concentration of blood peripheral immune suppressive cells (MDSC) and higher expression of immune suppressive gene signatures and pro-inflammatory protein concentrations in the serum (CRP, IL6 and IL8). Interestingly, unlike immune checkpoint blockade, chemotherapy is well recognized to reduce the IL6, IL8, and CRP concentrations. This finding could explain the early mortality phenomenon observed with ICB vs. chemotherapy in patients with advanced/metastatic cancer.

To investigate whether the 3i score can be used as an indicator of patient immune fitness, the baseline molecular profiles of 3i high-risk patients were assessed by blood gene expression, peripheral blood immunoprofiling by flow cytometry, and serum protein expression.

Results

Peripheral Blood Gene Expression 3i high (poor prognosis) is associated with lower baseline T effector and higher immune-suppressive cell gene expression signatures compared to 3i low in NSCLC, HNSCC, and UBC patients irrespective of patient PD-L1 status (see FIGS. 65 and 66). 51/80 genes measured by qPCR across MYSTIC, ATLANTIC, CP1108, HAWK, CONDOR, 006, and 10 studies were found differentially expressed between 3i high and 3i low with a cutoff of 1.5-fold difference and p-value <0.01% (Wilcox test).

Peripheral Immunoprofiling by Flow Cytometry 3i high is associated with lower baseline T, NK, and B cells and higher monocytic myeloid-derived suppressive cells (MNC MDSC) absolute counts compared to 3i low in NSCLC patients (see FIGS. 67 and 68). 11/22 immunophenotypes assessed in CP1108, 006 and Mystic NSCLC patients and derived from 5 flow cytometry panels were found differentially expressed between 3i high and 3i low patient groups (>20% CV with Wilcox test p-value <0.05%).

Serum Protein Expression 3i high (poor prognosis) is highly associated with higher baseline pro-inflammatory protein concentrations in particular C-reactive protein (CRP) and interleukins IL6 and IL8 compared with 3i low NSCLC, HNSCC, and UBC patients (see FIG. 69). 16-22/66 serum protein concentration evaluated by Luminex immune assay (Myriad RBM) across CP1108, HAWK, and CONDOR studies were found differentially expressed in 3i high compared with 3i low NSCLC, HNSCC, and UBC patients (% difference compared with 3i low >20% CV with Wilcox test p-value <0.05%). In addition to CRP, IL6, and IL8, pro-vasculogenic and -angiogenic proteins (e.g. ANGPT2, VEGF, ICAM1, and vWF) were found to be higher in 3i high compared with 3i low patient groups.

Conclusion

The 3i index appears to have clinical utility in identifying patients who may lack immune fitness. Lack of immune fitness suggests that ICI treatment should be postponed until such patients are effectively treated to improve their immune fitness or that patients should be treated with a non-ICI treatment. Therefore, therapeutic interventions in 3i high patients that bolster immune system fitness may enable these patients to receive to ICI treatment with a decreased risk of EM and moreover an increased chance for therapeutic benefit from ICI treatment.

Example Computing Systems

FIG. 70 is a simplified block diagram exemplifying a computing device 7000, illustrating some of the components that could be included in a computing device arranged to operate in accordance with the embodiments herein. Computing device 7000 could be a client device (e.g., a device actively operated by a user), a server device (e.g., a device that provides computational services to client devices), or some other type of computational platform. Some server devices may operate as client devices from time to time in order to perform particular operations, and some client devices may incorporate server features.

In this example, computing device 7000 includes processor 7002, memory 7004, network interface 7006, and input/output unit 7008, all of which may be coupled by system bus 7010 or a similar mechanism. In some embodiments, computing device 7000 may include other components and/or peripheral devices (e.g., detachable storage, printers, and so on).

Processor 7002 may be one or more of any type of computer processing element, such as a central processing unit (CPU), a co-processor (e.g., a mathematics, graphics, or encryption co-processor), a digital signal processor (DSP), a network processor, and/or a form of integrated circuit or controller that performs processor operations. In some cases, processor 7002 may be one or more single-core processors. In other cases, processor 7002 may be one or more multi-core processors with multiple independent processing units. Processor 7002 may also include register memory for temporarily storing instructions being executed and related data, as well as cache memory for temporarily storing recently-used instructions and data.

Memory 7004 may be any form of computer-usable memory, including but not limited to random access memory (RAM), read-only memory (ROM), and non-volatile memory (e.g., flash memory, hard disk drives, solid state drives, compact discs (CDs), digital video discs (DVDs), and/or tape storage). Thus, memory 7004 represents both main memory units, as well as long-term storage. Other types of memory may include biological memory.

Memory 7004 may store program instructions and/or data on which program instructions may operate. By way of example, memory 7004 may store these program instructions on a non-transitory, computer-readable medium, such that the instructions are executable by processor 7002 to carry out any of the methods, processes, or operations disclosed in this specification or the accompanying drawings.

As shown in FIG. 70, memory 7004 may include firmware 7004A, kernel 7004B, and/or applications 7004C. Firmware 7004A may be program code used to boot or otherwise initiate some or all of computing device 7000. Kernel 7004B may be an operating system, including modules for memory management, scheduling and management of processes, input/output, and communication. Kernel 7004B may also include device drivers that allow the operating system to communicate with the hardware modules (e.g., memory units, networking interfaces, ports, and buses) of computing device 7000. Applications 7004C may be one or more user-space software programs, such as web browsers or email clients, as well as any software libraries used by these programs. Memory 7004 may also store data used by these and other programs and applications.

Network interface 7006 may take the form of one or more wireline interfaces, such as Ethernet (e.g., Fast Ethernet, Gigabit Ethernet, and so on). Network interface 7006 may also support communication over one or more non-Ethernet media, such as coaxial cables or power lines, or over wide-area media, such as Synchronous Optical Networking (SONET) or digital subscriber line (DSL) technologies. Network interface 7006 may additionally take the form of one or more wireless interfaces, such as IEEE 802.11 (Wifi), BLUETOOTH®, global positioning system (GPS), or a wide-area wireless interface. However, other forms of physical layer interfaces and other types of standard or proprietary communication protocols may be used over network interface 7006. Furthermore, network interface 7006 may comprise multiple physical interfaces. For instance, some embodiments of computing device 7000 may include Ethernet, BLUETOOTH®, and Wifi interfaces.

Input/output unit 7008 may facilitate user and peripheral device interaction with computing device 7000. Input/output unit 7008 may include one or more types of input devices, such as a keyboard, a mouse, a touch screen, and so on. Similarly, input/output unit 7008 may include one or more types of output devices, such as a screen, monitor, printer, and/or one or more light emitting diodes (LEDs). Additionally or alternatively, computing device 7000 may communicate with other devices using a universal serial bus (USB) or high-definition multimedia interface (HDMI) port interface, for example.

In some embodiments, one or more computing devices like computing device 7000 may be deployed to support a machine leaning architecture. The exact physical location, connectivity, and configuration of these computing devices may be unknown and/or unimportant to client devices. Accordingly, the computing devices may be referred to as "cloud-based" devices that may be housed at various remote data center locations.

FIG. 71 depicts a cloud-based server cluster 7100 in accordance with example embodiments. In FIG. 71, operations of a computing device (e.g., computing device 7000) may be distributed between server devices 7102, data storage 7104, and routers 7106, all of which may be connected by local cluster network 7108. The number of server devices 7102, data storages 7104, and routers 7106 in server cluster 7100 may depend on the computing task(s) and/or applications assigned to server cluster 7100.

For example, server devices 7102 can be configured to perform various computing tasks of computing device 7000. Thus, computing tasks can be distributed among one or more of server devices 7102. To the extent that these computing tasks can be performed in parallel, such a distribution of tasks may reduce the total time to complete these tasks and return a result. For purposes of simplicity, both server cluster 7100 and individual server devices 7102 may be referred to as a "server device." This nomenclature should be understood to imply that one or more distinct server devices, data storage devices, and cluster routers may be involved in server device operations.

Data storage 7104 may be data storage arrays that include drive array controllers configured to manage read and write access to groups of hard disk drives and/or solid state drives. The drive array controllers, alone or in conjunction with server devices 7102, may also be configured to manage backup or redundant copies of the data stored in data storage 7104 to protect against drive failures or other types of failures that prevent one or more of server devices 7102 from accessing units of data storage 7104. Other types of memory aside from drives may be used.

Routers 7106 may include networking equipment configured to provide internal and external communications for server cluster 7100. For example, routers 7106 may include one or more packet-switching and/or routing devices (including switches and/or gateways) configured to provide (i) network communications between server devices 7102 and data storage 7104 via local cluster network 7108, and/or (ii) network communications between server cluster 7100 and other devices via communication link 7110 to network 7112.

Additionally, the configuration of routers 7106 can be based at least in part on the data communication requirements of server devices 7102 and data storage 7104, the latency and throughput of the local cluster network 7108, the latency, throughput, and cost of communication link 7110, and/or other factors that may contribute to the cost, speed, fault-tolerance, resiliency, efficiency, and/or other design goals of the system architecture.

As a possible example, data storage 7104 may include any form of database, such as a structured query language (SQL) database. Various types of data structures may store the information in such a database, including but not limited to tables, arrays, lists, trees, and tuples. Furthermore, any databases in data storage 7104 may be monolithic or distributed across multiple physical devices.

Server devices 7102 may be configured to transmit data to and receive data from data storage 7104. This transmission and retrieval may take the form of SQL queries or other types of database queries, and the output of such queries, respectively. Additional text, images, video, and/or audio may be included as well. Furthermore, server devices 7102 may organize the received data into web page or web application representations. Such a representation may take the form of a markup language, such as the hypertext markup language (HTML), the extensible markup language (XML), or some other standardized or proprietary format. Moreover, server devices 7102 may have the capability of executing various types of computerized scripting languages, such as but not limited to Perl, Python, PHP Hypertext Preprocessor (PHP), Active Server Pages (ASP), JAVASCRIPT®, and so on. Computer program code written in these languages may facilitate the providing of web pages to client devices, as well as client device interaction with the web pages. Alternatively or additionally, JAVA® may be used to facilitate generation of web pages and/or to provide web application functionality.

Example Operations

FIGS. 72 and 73 are flow charts illustrating example embodiments. The processes illustrated by FIGS. 72 and 73 may be carried out by a computing device, such as computing device 7000, and/or a cluster of computing devices, such as server cluster 7100. However, the processes can be carried out by other types of devices or device subsystems. The embodiments of FIGS. 72 and 73 may be simplified by the removal of any one or more of the features shown therein. Further, these embodiments may be combined with features, aspects, and/or implementations of one another and/or any of the previous figures or otherwise described herein.

Block 7200 of FIG. 72 may involve obtaining model training data, wherein the model training data involves a first set of cancer patients that underwent cancer treatments, wherein the model training data associates (i) results from laboratory tests conducted on the first set of cancer patients and tumor types of the first set of cancer patients with (ii) whether individuals from the first set of cancer patients died within a threshold number of weeks from initiation of the cancer treatments. The laboratory tests may include tissue biopsy, cerebrospinal fluid, lymph, whole blood, serum, blood cell, urine, sweat, tears, saliva, and/or feces tests, or any type of test that is indicative of a clinicopathological marker.

Block 7202 may involve training, based on the model training data, a sequential series of decision trees until a stopping condition is reached, wherein each subsequent decision tree of the sequential series of decision trees is constructed based on residual values of its preceding decision tree of the sequential series of decision trees.

Block 7204 may involve generating a gradient boosting machine learning model as an additive function of the sequential series of decision trees, wherein the gradient boosting machine learning model predicts whether a further cancer patient dies within the threshold number of weeks based on the additive function applied to results from the laboratory tests as conducted on the further cancer patient and a tumor type of the further cancer patient.

In some embodiments, the threshold number of weeks is 12 weeks. But other values are possible (e.g., 8, 10, 15, or 20 weeks).

In some embodiments, the results from the laboratory tests provide one or more of: a neutrophil to lymphocyte ratio, a neutrophil concentration, an albumin concentration, a lactate dehydrogenase concentration, an aspartate amino transferase concentration, or a gamma-glutamyl transferase concentration. Some or all of these results may be used.

In some embodiments, the neutrophil to lymphocyte ratio, the neutrophil concentration, the albumin concentration, the lactate dehydrogenase concentration, the aspartate amino transferase concentration, and the gamma-glutamyl transferase concentration were selected from 20 or more laboratory tests conducted on the first set of cancer patients. The selecting may involve (i) training the gradient boosting machine learning model on the 20 or more laboratory tests; (ii) for each respective laboratory test, training a respective variation of the gradient boosting machine learning model on the 20 or more laboratory tests with the respective laboratory test removed; and (iii) determining predictive values of each of the 20 or more laboratory tests by comparing accuracies of the variations of the gradient boosting machine learning model. The 20 or more laboratory tests may be selected from the predictors of Table 11, and may include non-test predictors, such as gender and age.

In some embodiments, the tumor type is one of: non-small cell lung cancer, urothelial carcinoma, squamous cell carcinoma of head and neck, gastric cancer, renal cell carcinoma, or Hodgkin's lymphoma. Other types may be possible.

In some embodiments, the additive function applies a multiplicative learning rate to outcomes from each of the sequential series of decision trees.

In some embodiments, predicting whether the further cancer patient dies within the threshold number of weeks comprises determining, by using the additive function, a probability that the further cancer patient dies within the threshold number of weeks.

In some embodiments, predicting whether the further cancer patient dies within the threshold number of weeks further comprises based on the probability and a cutoff value, placing the further cancer patient into either a high risk of death category or a low risk of death category. In some embodiments, the cutoff value is selected so that there is no more than a false positive rate of 5-20% when predicting whether the first set of cancer patients die within the threshold number of weeks. In some cases, the cutoff value may be selected so that the false positive rate is 10%.

In some embodiments, cancer patients placed in the high risk of death category are excluded from a clinical trial for treatment of cancer, and wherein cancer patients placed in the low risk of death category are included in the clinical trial for treatment of cancer.

In some embodiments, the stopping condition is that the sequential series of decision trees includes a threshold number of decision trees. Alternatively or additionally, the stopping condition is that the residual values of a particular decision tree in the sequential series of decision trees are all below a threshold value.

Some embodiments may further involve obtaining model tuning data, wherein the model tuning data involves a second set of cancer patients that underwent cancer treatments, wherein the model tuning data associates (i) results from the laboratory tests as conducted on the second set of cancer patients and tumor types of the second set of cancer patients with (ii) whether the second set of cancer patients died within the threshold number of weeks from initiation of the cancer treatments; generating two or more variations of the gradient boosting machine learning model by training the sequential series of decision trees for each variation with different sets of hyperparameters; applying the variations to the model training data and the model tuning data; and selecting, as the gradient boosting machine learning model, a particular variation from the variations that provides predictions of whether the first set of cancer patients and the second set of cancer patients die within the threshold number of weeks from initiation of the cancer treatments within a threshold degree of accuracy.

The threshold degree of accuracy can be based on a true positive rate or a true negative rate of predictions of whether the first set of cancer patients die within the threshold number of weeks from initiation of the cancer treatments. Alternatively or additionally, the threshold degree of accuracy can be based on a p-value for interaction between: (i) predictions of whether the second set of cancer patients die within the threshold number of weeks from initiation of the cancer treatments, and (ii) PD-L1 positive patients in the second set of cancer patients.

In some embodiments, the hyperparameters include one or more of: maximum depth of the decision trees set to 2, 3, 4, 5, or 6, minimum loss reduction required to split a node in the decision trees set to 0, 1, 2, 3, or 4, minimum sum of weights of all observations required in a child node in the decision trees set between 3.0 and 7.0, fraction of input parameters to be randomly sampled for each of the decision trees set between 0.7 and 1.0, fraction of observations to be randomly sampled for each of the decision trees set between 0.4 and 0.8, number of decision trees in the sequential series of decision trees set between 10 and 25. Other ranges may be used as well.

Block 7300 of FIG. 73 may involve obtaining a gradient boosting machine learning model, wherein the gradient boosting machine learning model was trained on model training data, wherein the model training data involves a first set of cancer patients that underwent cancer treatments, wherein the model training data associates (i) results from laboratory tests conducted on the first set of cancer patients and tumor types of the first set of cancer patients with (ii) whether individuals from the first set of cancer patients died within a threshold number of weeks from initiation of the cancer treatments, wherein training the gradient boosting machine learning model involved: (i) training a sequential series of decision trees until a stopping condition was reached, wherein each subsequent decision tree of the sequential series of decision trees was constructed based on residual values of its preceding decision tree of the sequential series of decision trees, and (ii) determining an additive function of the sequential series of decision trees. The laboratory tests may include tissue biopsy, cerebrospinal fluid, lymph, whole blood, serum, blood cell, urine, sweat, tears, saliva, and/or feces tests, or any type of test that is indicative of a clinicopathological marker.

Block 7302 may involve obtaining results from the laboratory tests as conducted on a further cancer patient.

Block 7304 may involve obtaining a tumor type of the further cancer patient.

Block 7306 may involve applying the gradient boosting machine learning model to results from the laboratory tests as conducted on a further cancer patient and the tumor type of the further cancer patient.

Block 7308 may involve receiving, from the gradient boosting machine learning model, a prediction of whether the further cancer patient dies within the threshold number of weeks.

In some embodiments, the threshold number of weeks is 12 weeks. But other values are possible (e.g., 8, 10, 15, or 20 weeks).

In some embodiments, the results from the laboratory tests provide one or more of: a neutrophil to lymphocyte ratio, a neutrophil concentration, an albumin concentration, a lactate dehydrogenase concentration, an aspartate amino transferase concentration, or a gamma-glutamyl transferase concentration. Some or all of these results may be used.

In some embodiments, the tumor type is one of: non-small cell lung cancer, urothelial carcinoma, squamous cell carcinoma of head and neck, gastric cancer, renal cell carcinoma, or Hodgkin's lymphoma. Other types may be possible.

In some embodiments, the additive function applies a multiplicative learning rate to outcomes from each of the sequential series of decision trees.

In some embodiments, predicting whether the further cancer patient dies within the threshold number of weeks comprises determining, by using the additive function, a probability that the further cancer patient dies within the threshold number of weeks.

In some embodiments, predicting whether the further cancer patient dies within the threshold number of weeks further comprises based on the probability and a cutoff value, placing the further cancer patient into either a high risk of death category or a low risk of death category. In some embodiments, the cutoff value was selected so that there is no more than a false positive rate of 5-20% when predicting whether the first set of cancer patients die within the threshold number of weeks. In some cases, a cutoff value may be selected so that the false positive rate is 10%.

In some embodiments, cancer patients placed in the high risk of death category are excluded from a clinical trial for treatment of cancer, and wherein cancer patients placed in the low risk of death category are included in the clinical trial for treatment of cancer.

In some embodiments, the stopping condition is that the sequential series of decision trees includes a threshold number of decision trees. Alternatively or additionally, the stopping condition is that the residual values of a particular decision tree in the sequential series of decision trees are all below a threshold value.

In some embodiments, the gradient boosting machine learning model was also trained using model tuning data, wherein the model tuning data involves a second set of cancer patients that underwent cancer treatments, wherein the model tuning data associates (i) results from the laboratory tests as conducted on the second set of cancer patients and tumor types of the second set of cancer patients with (ii) whether the second set of cancer patients died within the threshold number of weeks from initiation of the cancer treatments, and wherein training the gradient boosting machine learning model using the model tuning data comprises: (i) generating two or more variations of the gradient boosting machine learning model by training the sequential series of decision trees for each variation with different sets of hyperparameters; (ii) applying the variations to the model training data and the model tuning data; and (iii) selecting, as the gradient boosting machine learning model, a particular variation from the variations that provides predictions of whether the first set of cancer patients and the second set of cancer patients die within the threshold number of weeks from initiation of the cancer treatments within a threshold degree of accuracy.

The threshold degree of accuracy can be based on a true positive rate or a true negative rate of predictions of whether the first set of cancer patients die within the threshold number of weeks from initiation of the cancer treatments. Alternatively or additionally, the threshold degree of accuracy can be based on a p-value for interaction between: (i) predictions of whether the second set of cancer patients die within the threshold number of weeks from initiation of the cancer treatments, and (ii) PD-L1 positive patients in the second set of cancer patients.

In some embodiments, the hyperparameters include one or more of: maximum depth of the decision trees set to 2, 3, 4, 5, or 6, minimum loss reduction required to split a node in the decision trees set to 0, 1, 2, 3, or 4, minimum sum of weights of all observations required in a child node in the decision trees set between 3.0 and 7.0, fraction of input parameters to be randomly sampled for each of the decision trees set between 0.7 and 1.0, fraction of observations to be randomly sampled for each of the decision trees set between 0.4 and 0.8, number of decision trees in the sequential series of decision trees set between 10 and 25. Other ranges may be used as well.

Conclusion

A novel model has been developed that relies on baseline measures, as opposed to subjective clinical measures like ECOG scores. Based on the evaluation of this index in the MYSTIC and EAGLE studies, this index appears to have clinical utility in identifying patients who may have a relatively more favorable benefit:risk profile compared to the ITT population.

All patents and publications mentioned in this specification are herein incorporated by reference to the same extent as if each independent patent and publication was specifically and individually indicated to be incorporated by reference. Citation or identification of any reference in any section of this application shall not be construed as an admission that such reference is available as prior art to the present invention.

REFERENCES

Arkenau H T, Barriuso J, Olmos D, Ang J E, de Bono J, Judson I, et al. Prospective validation of a prognostic score to improve patient selection for oncology phase I trials. J Clin Oncol. 2009; 27(16):2692-6.

Bellmunt J, de Wit R, Vaughn D J, Fradet Y, Lee J L, Fong L et al. Pembrolizumab as Second-Line Therapy for Advanced Urothelial Carcinoma. N Engl J Med. 2017; 376(11):1015-26.

Bigot F, Castanon E, Baldini C, Hollebecque A, Carmona A, Postel-Vinay S, et al. Prospective validation of a prognostic score for patients in immunotherapy phase I trials: The Gustave Roussy Immune Score (GRIm-Score). Eur J Cancer. 2017; 84:212-8.

Borghaei H, Paz-Ares L, Horn L, Spigel D R, Steins M, Ready N E, et al. Nivolumab versus Docetaxel in Advanced Nonsquamous Non-Small-Cell Lung Cancer. N Engl J Med. 2015; 373(17):1627-39.

Bowen R C, Little N A B, Harmer J R, Ma J, Mirabelli L G, Roller K D, et al. Neutrophil-to-lymphocyte ratio as prognostic indicator in gastrointestinal cancers: a systematic review and meta-analysis. Oncotarget. 2017; 8(19): 32171-89.

Caliskan, A, Bryson J J, and Narayanan A. Semantics derived automatically from language corpora contain human-like biases. Science. 356(6334):183-186, 2017.

Champiat S, Ferrara R, Massard C, Besse B, Marabelle A, Soria J C, et al. Hyperprogressive disease: recognizing a novel pattern to improve patient management. Nat Rev Clin Oncol. 2018; 15(12):748-62.

Chen T, Guestrin C. XGBoost: A Scalable Tree Boosting System. Proceedings of the 22nd ACM SIGKDD International Conference on Knowledge Discovery and Data Mining (KDD). 2016; 785-794. DOI: http://dx.doi.org/10.1145/2939672.2939785.

Chen T, He T, Benesty M, Khotilovich V, Tang Y, Cho H, Chen K, Mitchell R, Cano I, Shou T, Li M, Xie J, Lin M, Geng Y, Li Y. R Package 'xgboost', Mar. 12, 2019. https://cran.r-project.org/web/packages/xgboost/xgboost-.pdf.

Ding Y, Zhang S, Qiao J. Prognostic value of neutrophil-to-lymphocyte ratio in melanoma: Evidence from a PRISMA-compliant meta-analysis. Medicine (Baltimore). 2018; 97(30):e11446.

Ferris R L, Blumenschein G, Jr., Fayette J, Guigay J, Colevas A D, Licitra L, et al. Nivolumab for Recurrent Squamous-Cell Carcinoma of the Head and Neck. N Engl J Med. 2016; 375(19):1856-67.

Friedman J, Hastie T, Tibshirani R. (2000). Additive logistic regression: a statistical view of boosting (with discussion and a rejoinder by the authors). The annals of statistics. 2000; 28(2), 337-407.

Friedman J H. Greedy function approximation: a gradient boosting machine. Annals of Statistics, pp. 2001; 1189-1232.

Freis P, Graillot E, Rousset P, Hervieu V, Chardon L, Lombard-Bohas C, et al. Prognostic factors in neuroendocrine carcinoma: biological markers are more useful than histomorphological markers. Sci Rep. 2017; 7:40609.

Fukui T, Okuma Y, Nakahara Y, Otani S, Igawa S, Katagiri M, et al. Activity of Nivolumab and Utility of Neutrophil-to-Lymphocyte Ratio as a Predictive Biomarker for Advanced Non-Small-Cell Lung Cancer: A Prospective Observational Study. Clin Lung Cancer. 2019; 20(3):208-14 e2.

Garon E B, Hellmann M D, Rizvi N A, Carcereny E, Leighl N B, Ahn M J, et al. Five-Year Overall Survival for Patients With Advanced NonSmall-Cell Lung Cancer Treated With Pembrolizumab: Results From the Phase I KEYNOTE-001 Study. J Clin Oncol. 2019; JC01900934.

Gupta D, Lis C G. Pretreatment serum albumin as a predictor of cancer survival: a systematic review of the epidemiological literature. Nutr J. 2010; 9:69.

Kazandjian D G, Gong Y, Kazandjian H, Pazdur R, Blumenthal G M. Exploration of baseline derived neutrophil to lymphocyte ratio (dNLR) and lactate dehydrogenase (LDH) in patients (pts) with metastatic non-small cell lung cancer (mNSCLC) treated with immune checkpoint inhibitors (ICI) or cytotoxic chemotherapy (CCT). 2018; 36(15_suppl):3035.

Khunger M, Patil P D, Khunger A, Li M, Hu B, Rakshit S, et al. Post-treatment changes in hematological parameters predict response to nivolumab monotherapy in non-small cell lung cancer patients. PLoS One. 2018; 13(10): e0197743.

Luo M, Sun W, Wu C, Zhang L, Liu D, Li W, et al. High pretreatment serum gamma-glutamyl transpeptidase predicts an inferior outcome in nasopharyngeal carcinoma. Oncotarget. 2017; 8(40):67651-62.

Mezquita L, Auclin E, Ferrara R, Charrier M, Remon J, et al. Association of the Lung Immune Prognostic Index With Immune Checkpoint Inhibitor Outcomes in Patients With Advanced Non-Small Cell Lung Cancer. JAMA Oncol. 2018 Mar. 1; 4(3):351-357.

Minami S, Ihara S, Ikuta S, Komuta K. Gustave Roussy Immune Score and Royal Marsden Hospital Prognostic Score Are Biomarkers of Immune-Checkpoint Inhibitor for Non-Small Cell Lung Cancer. World J Oncol. 2019 April; 10(2):90-100.

Mok T S K, Wu Y L, Kudaba I, Kowalski D M, Cho B C, Turna H Z, et al. Pembrolizumab versus chemotherapy for previously untreated, PD-L1-expressing, locally advanced or metastatic non-small-cell lung cancer (KEYNOTE-042): a randomised, open-label, controlled, phase 3 trial. Lancet. 2019; 393(10183):1819-30.

Mulkey F, By K, Theoret M R, Maher V E, Pazdur R, Sridhara R. Analysis of early mortality in randomized clinical trials evaluating anti-PD-1/PD-L1 antibodies: A systematic analysis by the United States Food and Drug Administration (FDA). 2019; 37(15_suppl):2516-.

Petrelli F, Cabiddu M, Coinu A, Borgonovo K, Ghilardi M, Lonati V, et al. Prognostic role of lactate dehydrogenase in solid tumors: a systematic review and meta-analysis of 76 studies. Acta Oncol. 2015; 54(7):961-70.

Powles T, Duran I, van der Heijden M S, Loriot Y, Vogelzang N J, De Giorgi U et al. Atezolizumab versus chemotherapy in patients with platinum-treated locally advanced or metastatic urothelial carcinoma (IMvigor211): a multicentre, open-label, phase 3 randomised controlled trial. Lancet. 2018; 391(10122):748-57.

Rizvi N, Cho B C, Reinmuth N, Lee K H, Ahn M J, Luft A et al. Durvalumab with or without tremelimumab vs platinum-based chemotherapy as first-line treatment for metastatic non-small cell lung cancer: MYSTIC. ESMO Immuno-Oncology Congress; 2018 Dec. 13-16; Geneva, Switzerland. Abstract LBA6 [oral presentation].

Sacdalan D B, Lucero J A, Sacdalan D L. Prognostic utility of baseline neutrophil-to-lymphocyte ratio in patients receiving immune checkpoint inhibitors: a review and meta-analysis. Onco Targets Ther. 2018; 11:955-65.

Socinski M A, Jotte R M, Cappuzzo F, Orlandi F, Stroyakovskiy D, Nogami N, et al. Atezolizumab for First-Line Treatment of Metastatic Nonsquamous NSCLC. N Engl J Med. 2018; 378(24):2288-301.

Shitara K, Ozguroglu M, Bang Y J, Di Bartolomeo M, Mandala M, Ryu M H, et al. Pembrolizumab versus paclitaxel for previously treated, advanced gastric or gastro-oesophageal junction cancer (KEYNOTE-061): a randomised, open-label, controlled, phase 3 trial. Lancet. 2018; 392(10142):123-33.

Tham T, Bardash Y, Herman S W, Costantino P D. Neutrophil-to-lymphocyte ratio as a prognostic indicator in head and neck cancer: A systematic review and meta-analysis. Head Neck. 2018; 40(11):2546-57.

Varga A, Bernard-Tessier A, Auclin E, Mezquita Perez L. Baldini C, et al. Applicability of the Lung Immune Prognostic Index (LIPI) in patients with metastatic solid tumors when treated with Immune Checkpoint Inhibitors (ICI) in early clinical trials. Ann Oncol. 2019 Feb. 1; 30(Supplement 1).

Wheler J, Tsimberidou A M, Hong D, Naing A, Falchook G, Piha-Paul S, et al. Survival of 1,181 patients in a phase I clinic: the MD Anderson Clinical Center for targeted therapy experience. Clin Cancer Res. 2012; 18(10):2922-9.

Winquist E K S, Nichols A C, Lenehan J G, Macneil S D, Palma D A; Early mortality with immune checkpoint inhibitors (IOs) in solid tumors: An inconvenient truth? J Clin Oncol. 2018; 36 (suppl; abstr 12121).

Yu Y, Wang H, Yan A, Wang H, Li X, Liu J, et al. Pretreatment neutrophil to lymphocyte ratio in determining the prognosis of head and neck cancer: a meta-analysis. BMC Cancer. 2018; 18(1):383.

What is claimed is:

1. A computing system comprising:
computer memory configured to store model training data, wherein the model training data involves a first set of cancer patients that underwent cancer treatments, wherein the model training data includes and associates (i) input of results from 20 or more laboratory tests conducted on the first set of cancer patients and tumor types of the first set of cancer patients with (ii) output of whether individuals from the first set of cancer patients died within a threshold number of weeks from initiation of the cancer treatments, wherein the tumor types include two or more of non-small cell lung cancer, urothelial carcinoma, squamous cell carcinoma of head and neck, gastric cancer, renal cell carcinoma, or Hodgkin's lymphoma; and one or more processors in communication with the computer memory and configured to execute program instructions to:
for each respective laboratory test, train a respective variation of a gradient boosting machine learning model on the 20 or more laboratory tests with the respective laboratory test removed;
determine predictive values of each of the 20 or more laboratory tests by comparing accuracies of the variations of the gradient boosting machine learning model;
select a subset of laboratory tests from the 20 or more laboratory tests with the highest predictive values for at least some of the tumor types; and
train a final gradient boosting machine learning model on the subset of laboratory tests, wherein the final gradient boosting machine learning model predicts whether a further cancer patient dies within the threshold number of weeks based on results from the subset of laboratory tests as conducted on the further cancer patient and a tumor type of the further cancer patient, and wherein predicting whether the further cancer patient dies within the threshold number of weeks comprises:
determining a probability that the further cancer patient dies within the threshold number of weeks, and
based on the probability and a cutoff value, placing the further cancer patient into either a high risk of death category or a low risk of death category, wherein the cutoff value is selected so that there is no more than a false positive rate of 5-20% when predicting whether the first set of cancer patients die within the threshold number of weeks.

2. The computing system of claim 1, wherein results of the subset of laboratory tests include: a neutrophil to lymphocyte ratio, a neutrophil level, an albumin level, a lactate dehydrogenase level, an aspartate amino transferase level, and a gamma-glutamyl transferase level.

3. The computing system of claim 1, wherein cancer patients placed in the high risk of death category are excluded from a clinical trial for treatment of cancer, and wherein cancer patients placed in the low risk of death category are included in the clinical trial for treatment of cancer.

4. The computing system of claim 1, wherein the computer memory is further configured to store model tuning data, wherein the model tuning data involves a second set of cancer patients that underwent cancer treatments, wherein the model tuning data associates (i) results from the laboratory tests as conducted on the second set of cancer patients and tumor types of the second set of cancer patients with (ii) whether the second set of cancer patients died within the threshold number of weeks from initiation of the cancer treatments, and
wherein the one or more processors are further configured to execute further program instructions to:
generate two or more further variations of the gradient boosting machine learning model by training a sequential series of decision trees for each further variation with different sets of hyperparameters;
apply the further variations to the model training data and the model tuning data; and
select, as the gradient boosting machine learning model, a particular variation from the further variations that provides predictions of whether the first set of cancer patients and the second set of cancer patients die within the threshold number of weeks from initiation of the cancer treatments within a threshold degree of accuracy.

5. The computing system of claim 4, wherein the hyperparameters include one or more of: maximum depth of the decision trees set to 2, 3, 4, 5, or 6, minimum loss reduction required to split a node in the decision trees set to 0, 1, 2, 3, or 4, minimum sum of weights of all observations required in a child node in the decision trees set between 3.0 and 7.0, fraction of input parameters to be randomly sampled for each of the decision trees set between 0.7 and 1.0, fraction of observations to be randomly sampled for each of the decision trees set between 0.4 and 0.8, number of decision trees in the sequential series of decision trees set between 10 and 25.

6. A computer-implemented method comprising:
obtaining model training data, wherein the model training data involves a first set of cancer patients that underwent cancer treatments, wherein the model training data includes and associates (i) input of results from 20 or more laboratory tests conducted on the first set of cancer patients and tumor types of the first set of cancer patients with (ii) output of whether individuals from the first set of cancer patients died within a threshold number of weeks from initiation of the cancer treatments, wherein the tumor types include two or more of non-small cell lung cancer, urothelial carcinoma, squamous cell carcinoma of head and neck, gastric cancer, renal cell carcinoma, or Hodgkin's lymphoma;
for each respective laboratory test, training a respective variation of a gradient boosting machine learning model on the 20 or more laboratory tests with the respective laboratory test removed;
determining predictive values of each of the 20 or more laboratory tests by comparing accuracies of the variations of the gradient boosting machine learning model;
selecting a subset of laboratory tests from the 20 or more laboratory tests with the highest predictive values for at least some of the tumor types; and
training a final gradient boosting machine learning model on the subset of laboratory tests, wherein the final gradient boosting machine learning model predicts whether a further cancer patient dies within the threshold number of weeks based on results from the subset of laboratory tests as conducted on the further cancer patient and a tumor type of the further cancer patient, and wherein predicting whether the further cancer patient dies within the threshold number of weeks comprises:
determining a probability that the further cancer patient dies within the threshold number of weeks, and
based on the probability and a cutoff value, placing the further cancer patient into either a high risk of death category or a low risk of death category, wherein the cutoff value is selected so that there is no more than a false positive rate of 5-20% when predicting whether the first set of cancer patients die within the threshold number of weeks.

7. The computer-implemented method of claim 6, wherein result of the subset of laboratory tests include a neutrophil to lymphocyte ratio, a neutrophil level, an albumin level, a lactate dehydrogenase level, an aspartate amino transferase level, and a gamma-glutamyl transferase level.

8. The computer-implemented method of claim 6, wherein cancer patients placed in the high risk of death category are excluded from a clinical trial for treatment of cancer, and wherein cancer patients placed in the low risk of death category are included in the clinical trial for treatment of cancer.

9. A computer-implemented method comprising:
obtaining a gradient boosting machine learning model, wherein the gradient boosting machine learning model was trained on model training data, wherein the model training data involves a first set of cancer patients that underwent cancer treatments, wherein the model training data includes and associates (i) input of results from 20 or more laboratory tests conducted on the first set of cancer patients and tumor types of the first set of cancer patients with (ii) output of whether individuals from the first set of cancer patients died within a threshold number of weeks from initiation of the cancer treatments, wherein training the gradient boosting machine learning model involved: (i) for each respective laboratory test, training a respective variation of a gradient boosting machine learning model on the 20 or more laboratory tests with the respective laboratory test removed, (ii) determining predictive values of each of the 20 or more laboratory tests by comparing accuracies of the variations of the gradient boosting machine learning model, (iii) selecting a subset of laboratory tests from the 20 or more laboratory tests with the highest predictive values for at least some of the tumor types, and (iv) training a final gradient boosting machine learning model on the subset of laboratory tests, wherein the tumor types include two or more of non-small cell lung cancer, urothelial carcinoma, squamous cell carcinoma of head and neck, gastric cancer, renal cell carcinoma, or Hodgkin's lymphoma;
obtaining results from the subset of laboratory tests as conducted on a further cancer patient;
obtaining a tumor type of the further cancer patient;
applying the final gradient boosting machine learning model to results from the subset of laboratory tests as conducted on the further cancer patient and the tumor type of the further cancer patient; and
receiving, from the final gradient boosting machine learning model, a prediction of whether the further cancer patient dies within the threshold number of weeks, wherein predicting whether the further cancer patient dies within the threshold number of weeks comprises:
determining a probability that the further cancer patient dies within the threshold number of weeks, and
based on the probability and a cutoff value, placing the further cancer patient into either a high risk of death category or a low risk of death category, wherein the cutoff value is selected so that there is no more than a false positive rate of 5-20% when predicting whether the first set of cancer patients die within the threshold number of weeks.

10. The computer-implemented method of claim 9, wherein results of the subset of laboratory tests include a neutrophil to lymphocyte ratio, a neutrophil level, an albumin level, a lactate dehydrogenase level, an aspartate amino transferase level, and a gamma-glutamyl transferase level.

11. The computer-implemented method of claim 9, wherein cancer patients placed in the high risk of death category are excluded from a clinical trial for treatment of cancer, and wherein cancer patients placed in the low risk of death category are included in the clinical trial for treatment of cancer.

* * * * *